United States Patent
Bennett et al.

(10) Patent No.: US 11,433,137 B2
(45) Date of Patent: Sep. 6, 2022

(54) COMPOUNDS FOR TREATING CANCER

(71) Applicant: BicycleRD Limited, Cambridge (GB)

(72) Inventors: Gavin Bennett, Cambridge (GB); Daniel Paul Teufel, Cambridge (GB)

(73) Assignee: BICYCLERD LIMITED, Cambridge (GB)

( * ) Notice: Subject to any disclaimer, the term of this patent is extended or adjusted under 35 U.S.C. 154(b) by 0 days.

(21) Appl. No.: 16/714,938

(22) Filed: Dec. 16, 2019

(65) Prior Publication Data

US 2020/0215199 A1 Jul. 9, 2020

Related U.S. Application Data

(62) Division of application No. 15/862,964, filed on Jan. 5, 2018, now Pat. No. 10,624,968.

(60) Provisional application No. 62/443,508, filed on Jan. 6, 2017.

(51) Int. Cl.
| | | |
|---|---|---|
| A61K 47/64 | (2017.01) |
| A61P 35/00 | (2006.01) |
| A61K 47/65 | (2017.01) |
| A61K 38/08 | (2019.01) |
| C07K 7/64 | (2006.01) |
| C07K 7/50 | (2006.01) |

(52) U.S. Cl.
CPC .......... *A61K 47/64* (2017.08); *A61K 38/08* (2013.01); *A61K 47/65* (2017.08); *A61P 35/00* (2018.01); *C07K 7/64* (2013.01); *C07K 7/50* (2013.01)

(58) Field of Classification Search
CPC ...... A61K 47/64; A61K 31/195; A61K 51/08; A61K 38/00; A61K 47/6415; A61K 38/12; A61K 49/0056; A61K 49/14; A61P 35/00; C07K 14/001; C07K 14/81; C07K 16/40; C07K 7/50
See application file for complete search history.

(56) References Cited

U.S. PATENT DOCUMENTS

| | | | |
|---|---|---|---|
| 6,552,065 B2 | 4/2003 | Remiszewski et al. |
| 7,390,799 B2 | 6/2008 | Bruncko et al. |
| 8,138,347 B2 | 3/2012 | Knight et al. |
| 8,906,682 B2 | 12/2014 | June et al. |
| 10,441,663 B2 | 10/2019 | Bennett et al. |
| 10,532,106 B2 * | 1/2020 | Teufel .................... A61K 47/64 |
| 10,792,368 B1 | 10/2020 | Teufel et al. |
| 10,994,019 B2 | 5/2021 | Teufel et al. |
| 11,103,591 B2 | 8/2021 | Teufel et al. |
| 2013/0064791 A1 * | 3/2013 | Poelstra ............... A61K 38/21 424/85.5 |
| 2013/0072598 A1 | 3/2013 | Yang et al. |
| 2018/0200378 A1 | 7/2018 | Bennett et al. |
| 2019/0389907 A1 | 12/2019 | Teufel et al. |
| 2020/0129630 A1 | 4/2020 | Koehler et al. |
| 2020/0354456 A1 | 11/2020 | Bennett et al. |

FOREIGN PATENT DOCUMENTS

| | | | | |
|---|---|---|---|---|
| GB | WO2016067035 A1 * | 5/2016 | ............... C07K 7/08 |
| WO | WO-2001042246 A2 | 6/2001 |
| WO | WO-2002088112 A1 | 11/2002 |
| WO | WO-2003063794 A2 | 8/2003 |
| WO | WO-2004019973 A1 | 3/2004 |
| WO | WO-2004077062 A2 | 9/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006078161 A1 | 7/2006 |
| WO | WO-2006078846 A1 | 7/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2009098450 A2 | 8/2009 |
| WO | WO-2009114512 A1 | 9/2009 |
| WO | WO-2010089115 A1 | 8/2010 |
| WO | WO-2011090760 A1 | 7/2011 |
| WO | WO-2013050615 A1 | 4/2013 |
| WO | WO-2016067035 A1 | 5/2016 |
| WO | WO-2017191460 A1 | 11/2017 |
| WO | WO-2018/096365 A1 | 5/2018 |
| WO | WO-2018/115204 A1 | 6/2018 |
| WO | WO-2018127699 A1 | 7/2018 |
| WO | WO-2020/089627 A1 | 5/2020 |
| WO | WO-2020/178574 A1 | 9/2020 |
| WO | WO-2020/229803 A1 | 11/2020 |
| WO | WO-2021/074647 A1 | 4/2021 |

OTHER PUBLICATIONS

Seiki et al. Membrane-type 1 matrix metalloproteinase: a key enzyme for tumor invasion. Cancer Letters. 2003; 194: 1-11. (Year: 2003).*

Paul Polakis. Antibody Drug Conjugates for Cancer Therapy. Pharmacol Rev. Jan. 1, 2016; 68(1):3-19. (Year: 2016).*

Berge et al., "Pharmaceutical Salts," Journal of Pharmaceutical Sciences, vol. 66, No. 1, Jan. 1977 (pp. 1-19).

(Continued)

*Primary Examiner* — Aradhana Sasan
*Assistant Examiner* — Jia-Hai Lee
(74) *Attorney, Agent, or Firm* — Dechert LLP; Andrea L. C. Reid; Gang Wang

(57) ABSTRACT

The present invention provides compounds, compositions thereof, and methods of using the same.

28 Claims, 17 Drawing Sheets

Specification includes a Sequence Listing.

(56) References Cited

OTHER PUBLICATIONS

ClinicalTrials.gov identified NCT02488759, "An Investigational Immuno-therapy Study to Investigate the Safety and Effectiveness of Nivolumab, and Nivolumab Combination Therapy in Virus-associated Tumors (CheckMate358)," first received date Jul. 2, 2015; https://clinicaltrials.gov/ct2/show/study/NCT02488759 (7 pages).
ClinicalTrials.gov identifier NCT02426892, "Nivolumab and HPV-16 Vaccination in Patients with HPV-16 Positive Incurable Solid Tumors," first received date Apr. 27, 2015; https://clinicaltrials.gov/ct2/show/study/NCT02426892 (8 pages).
Eder, "A phage display derived stabilised bicyclic peptide targeting MMP-14 shows high imaging contrast in small animal PET imaging," European Journal of Nuclear Medicine and Molecular Imaging, vol. 42, suppl. 1, Oct. 2015 (3 pages).
Gu et al., "The influence of the penetrating peptide iRGD on the effect of paclitaxel-loaded MT1-AF7p-conjugated nanoparticles on glioma cells," Biomaterials, vol. 34, Jul. 2013 (pp. 5138-5148).
Heinis et al., "Phage-encoded combinatorial chemical libraries based on bicyclic peptides," Nature Chemical Biology, vol. 5, No. 7, Jul. 2009 (pp. 502-507).
International Search Report and Written Opinion issued by the European Patent Office as International Searching Authority for International Application No. PCT/GB2018/050017, dated Mar. 23, 2018 (11 pages).
Okazaki et al., "A rheostat for immune responses: the unique properties of PD-1 and their advantages for clinical application," Nature Immunology, vol. 14, No. 12, Dec. 2013 (pp. 1212-1218).
Polakis, "Antibody Drug Conjugates for Cancer Therapy," Pharmacological Reviews, vol. 68, No. 1, Jan. 2016 (pp. 3-19).
Sounni et al., "MT1-MMP expression promotes tumor growth and angiogenesis through an up-regulation of vascular endothelial growth factor expression," FASEB Journal, vol. 16, No. 6, Apr. 2002 (pp. 555-564).
Zou et al., "PD-L1 (B7-H1) and PD-1 Pathway Blockade for Cancer Therapy: Mechanisms, Response Biomarkers and Combinations," Science Translational Medicine, vol. 8, No. 328, Mar. 2016 (34 pages).

* cited by examiner

A

B

COMPOUNDS FOR TREATING CANCER

CROSS-REFERENCE TO RELATED APPLICATION

This application claims the benefit under 35 U.S.C. § 119(e) of U.S. Provisional Application No. 62/443,508, filed Jan. 6, 2017, the content of which is incorporated herein in its entirety by reference.

BACKGROUND OF THE INVENTION

MT1-MMP is a transmembrane metalloprotease that plays a major role in the extracellular matrix remodelling, directly by degrading several of its components and indirectly by activating pro-MMP2. MT1-MMP is crucial for tumor angiogenesis (Sounni et al (2002) FASEB J. 16(6), 555-564) and is over-expressed on a variety of solid tumors. Accordingly, there remains a high unmet need in developing inhibitors of MT1-MMP for the treatment of cancer

DETAILED DESCRIPTION OF CERTAIN EMBODIMENTS OF THE INVENTION

1. Compound

Figure 1:
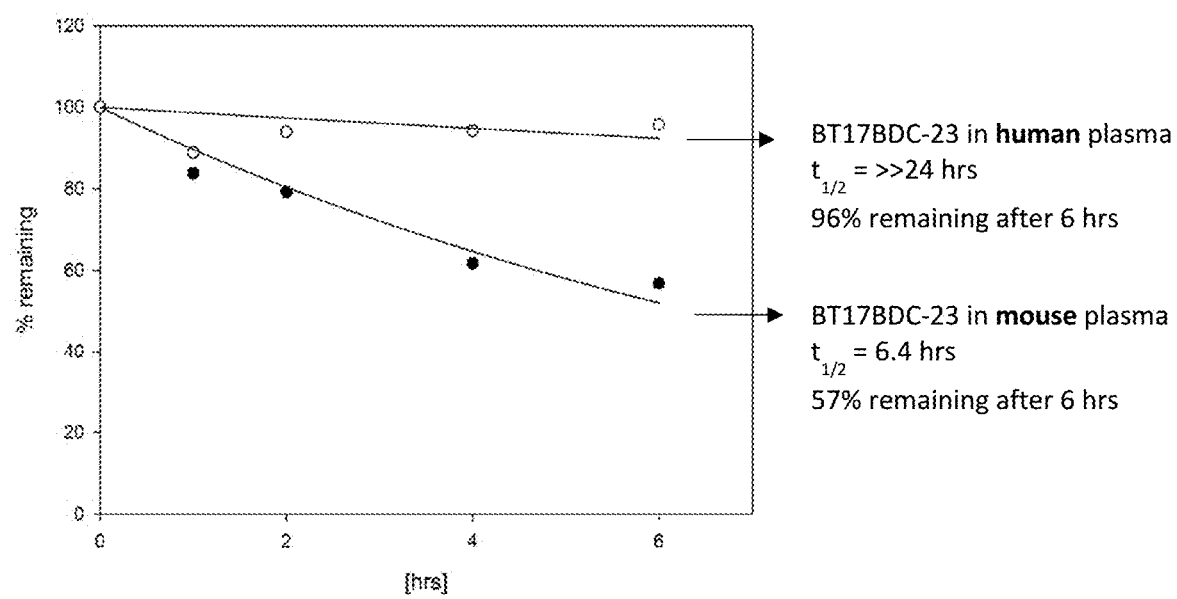
FIG. 1 depicts the plasma stability of I-1a in human and mouse.

A proprietary phage display and cyclic peptide technology (Bicycle technology) was utilized to identify high affinity binding peptides to the membrane type 1-matrix metalloproteinase (MT1-MMP/MMP14). MT1-MMP (MT1) is a cell surface membrane protease normally involved in tissue remodeling which has been found to be over-expressed in many solid tumors. Overexpression of MT1 has been linked to cancer invasiveness and poor prognosis. While attempts to target the proteolytic activity of MT1 and other MMPs in cancer were unsuccessful in clinical trials largely due to toxicity caused by insufficient selectivity, MT1-MMP remains an attractive cancer target for targeted cytotoxic delivery approaches.

Diverse selection phage libraries containing $10^{11}$ to $10^{13}$ unique peptide sequences which are post-translationally cyclized with thiol-reactive scaffolds were used to identify small (1.5-2 kDa) constrained bicyclic peptides binders (Bicycles) to the hemopexin domain of MT1. Initial binders were subject to affinity maturation by directed screens and stabilization by chemical optimization.

A bicyclic constrained peptide binder (Bicycle) was identified that binds to the hemopexin domain of MT1 with an apparent Kd of approximately 2 nM. The Bicycle peptide (N241) binds with similar affinity to the entire ectodomain of the protease but shows no binding to the catalytic domain. N241 also shows no binding toward any of the closely related MMP family members tested (MMP15, MMP16, MMP24, MMP1, Pro-MMP1, MMP2). Characterization of the pharmacologic effect of N241 on MT1 in vitro shows that the peptide has no direct impact on the catalytic activity of the protease, nor related MMP catalytic activity (MMP1, MMP2 and MMP9) nor cell migration or invasion. However, binding of fluorescently-tagged N241 to MT1 on HT1080 fibrosarcoma cells results in the rapid internalization and subsequent lysosomal localization of the compound. In addition, $^{177}$Lu-loaded N241 demonstrates rapid tumor localization when injected IV into mice bearing MT1-positive tumor xenografts, with levels as high as 15-20% injected dose per gram of tumor in less than 60 minutes. In contrast, a non-binding Bicycle peptide shows no tumor localization. These properties suggest that N241 may be a good delivery vehicle for cytotoxic payloads targeting MT1-postive tumor cells. Bicycle drug conjugates (BDCs) with a variety of linkers and cytotoxic payloads were prepared which retained binding to MT1. The anti-tumor activity of select BDCs was demonstrated in MT1-positive human tumor cell xenografts in mice.

I-1a is a Bicycle drug conjugate (BDC) comprising a constrained bicyclic peptide that binds with high affinity and specificity to membrane type 1-matrix metalloprotease (MT1-MMP; MMP14) covalently linked via a Spacer-AA$^1$-AA$^2$-Linker to monomethyl auristatin E (MMAE), a potent antimitotic agent. MT1-MMP is naturally involved in tissue remodeling, however overexpression of the cell-surface protease has been tied to tumor aggressiveness and invasiveness, as well as poor patient prognosis for many cancer indications. The Bicycle binder for I-1a (N241) was identified using a proprietary phage display peptide technology consisting of highly diverse phage libraries of linear amino acid sequences constrained into two loops by a central chemical scaffold. While binding with similar affinity and specificity to that observed with monoclonal antibodies, the small size of a Bicycle peptide (1.5-2 kDa) aids in its rapid extravasation and tumor penetration making it an ideal format for the targeted delivery of cytotoxic payloads.

One advantage of the $AA^1$-$AA^2$ linker is the specificity of toxin targeting and release. Non-specific release of toxin is known and has been termed bystander activity. For example, antibody drug conjugates (ADCs) have been shown to be mostly activated through internalization and degradation of the antibody in the lysosome and release of activated metabolite that can kill tumor cells. Depending on the type of payload (toxin) and linker, activated metabolites can have bystander activity (the ability to penetrate to neighboring cells) and kill neighboring tumor cells. For example, the toxins DM1 and MMAE (the metabolite of Brentuximab vedotin, trade name Adcetris) have bystander activity while DM1-SMCC-lysine (the metabolite of Trastuzumab emtasine, trade name Kadcyla) and MMAF do not. Most of the BDC activity is not mediated by target-mediated internalization and degradation of BDC into active metabolites. Without being bound by any particular theory, it is believed that BDCs are mostly activated outside of the cells through disulfide reduction for BDCs utilizing a disulfide linker and protease cleavage by cathepsin B expressed on the tumor cell surface for BDCs utilizing a $AA^1$-$AA^2$ linker such as I-1a, which is consistent with the observed half-life of BDCs. Utilizing cleavage by cathepsin B has the potential for a more selective release of toxin as cathepsin B activity has been found to be elevated in a variety of human tumors and tumor cell lines. An alternative hypothesis is that BDCs deliver toxin via a non-targeted mechanism inside the cell through pinocytosis and lysosome degradation. A further hypothesis is that BDCs deliver toxin via a combination of both internal and external activation.

A series of Bicycle-spacer-$AA^1$-$AA^2$-linker-Toxin BDCs were prepared, with varying spacer format to adjust the presentation of the Bicycle and evaluated for their antitumor activity in an MT1-positive tumor xenograft model. The BDC selected for further assessment (I-1a) was evaluated for efficacy in an array of tumor xenograft models.

An $AA^1$-$AA^2$ linker-MMAE construct (I-1a) was among the most active constructs against MT1-positive EBC-1 lung tumor xenografts. Dosing I-1a on a 3× weekly schedule for two weeks, significant reduction in tumor growth was seen at 1 mg/kg, with 3 mg/kg and 10 mg/kg causing complete regressions in this model. The therapeutic efficacy of I-1a at 10 mg/kg is accompanied by brief body weight loss which is reversible upon discontinuation of treatment.

I-1a, a Bicycle drug conjugate (BDC), shows potent antitumor activity in human tumor xenograft models of lung cancer. Without wishing to be bound by any particular theory, it is believed that the small size of the BDC may offer a significant advantage to other targeted cytotoxic approaches such as antibody-drug conjugates due to rapid extravasation and improved tumor penetration.

In certain aspects, the present invention provides a method of treating certain cancers in a subject, comprising administering to the subject an effective amount of a drug conjugate comprising a high affinity binder of MT1-MMP, such as I-1, or a pharmaceutically acceptable salt or composition thereof. In certain aspects, the present invention provides a method of treating certain cancers in a subject, comprising administering to the subject an effective amount of a drug conjugate comprising a high affinity binder of MT1-MMP, such as I-1a, or a pharmaceutically acceptable salt or composition thereof.

In some embodiments, the present invention provides a Bicycle Drug Conjugate ("BDC") of formula I:

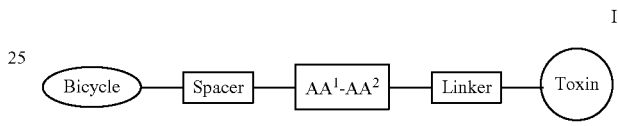

I wherein:

Bicycle is a polypeptide which is covalently bound to a molecular scaffold such that two or more peptide loops are subtended between attachment points to the scaffold;

Spacer is a bivalent moiety that connects the Bicycle moiety with the $AA^1$-$AA^2$ moiety; $AA^1$-$AA^2$ is a bivalent moiety comprising at least one citrulline moiety that connects the Spacer moiety with the Linker moiety wherein each of $AA^1$ and $AA^2$ is an independently selected natural or unnatural amino acid moiety; Linker is a bivalent spacer moiety that connects the $AA^1$-$AA^2$ moiety with the Toxin moiety and Toxin is a chemotherapeutic agent.

In certain embodiments, the present invention provides a compound of formula I-a or I-b:

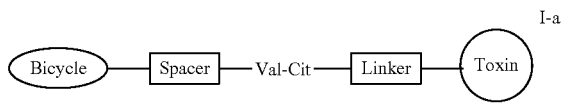

I-a

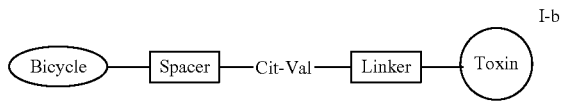

I-b or a pharmaceutically acceptable salt thereof, wherein each of Bicycle, Spacer, Linker and Toxin is as defined and described herein.

In certain embodiments, the present invention provides a compound of formula I-c or I-d:

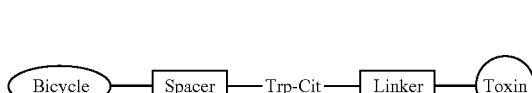

or a pharmaceutically acceptable salt thereof, wherein each of Bicycle, Spacer, Linker and Toxin is as defined and described herein.

In certain embodiments, the present invention provides a compound of formula I-e or I-f:

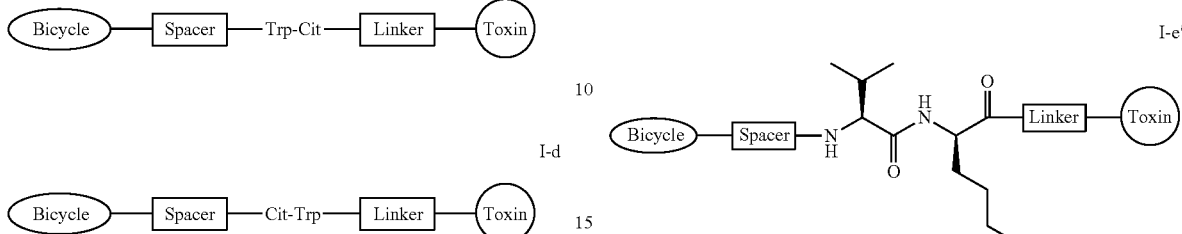

or a pharmaceutically acceptable salt thereof, wherein each of Bicycle, Spacer, Linker and Toxin is as defined and described herein.

In certain embodiments, the present invention provides a compound of formula I-e', I-e", or I-e''':

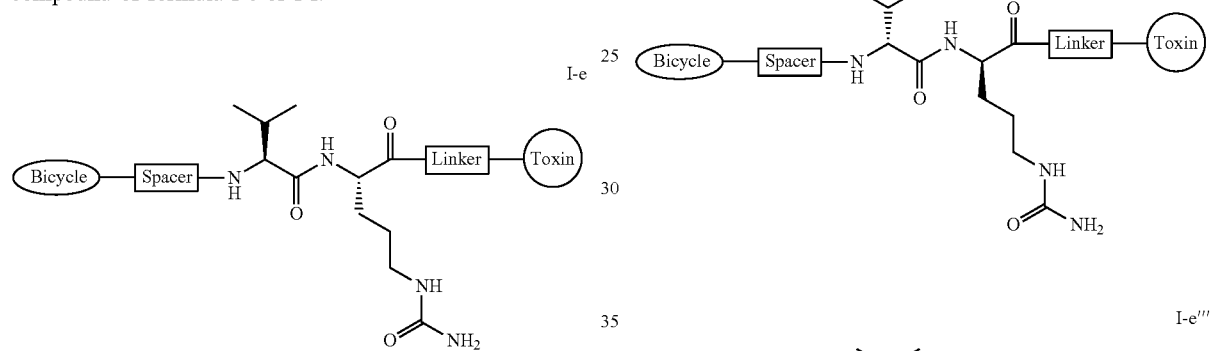

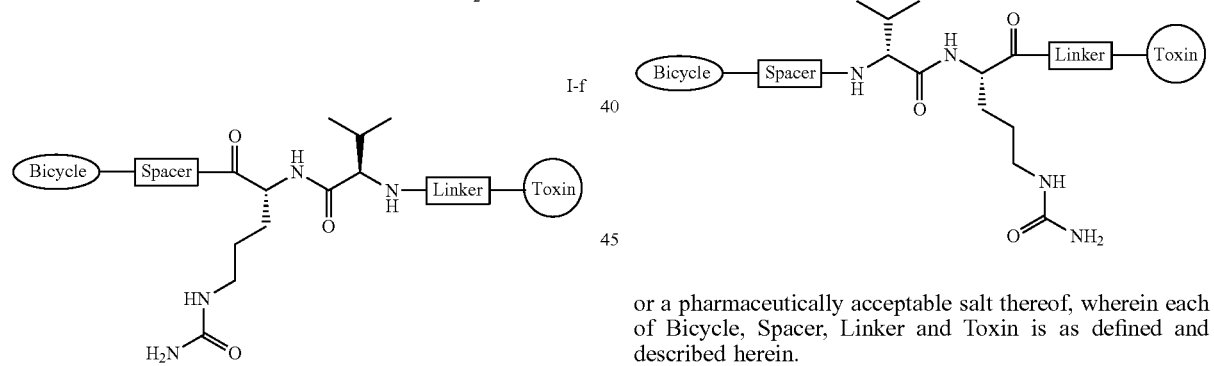

or a pharmaceutically acceptable salt thereof, wherein each of Bicycle, Spacer, Linker and Toxin is as defined and described herein.

In certain embodiments, the present invention provides a compound of formula I-f', I-f", or I-f''':

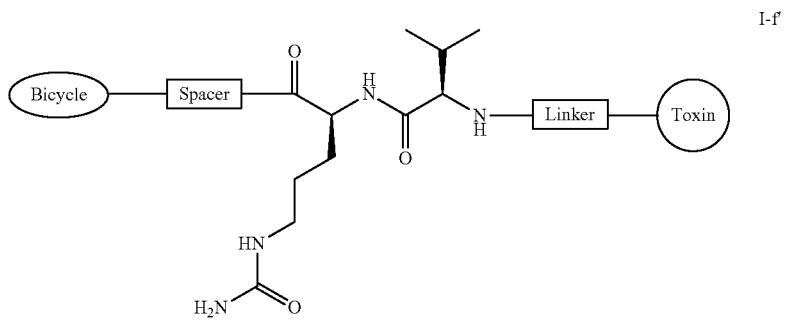

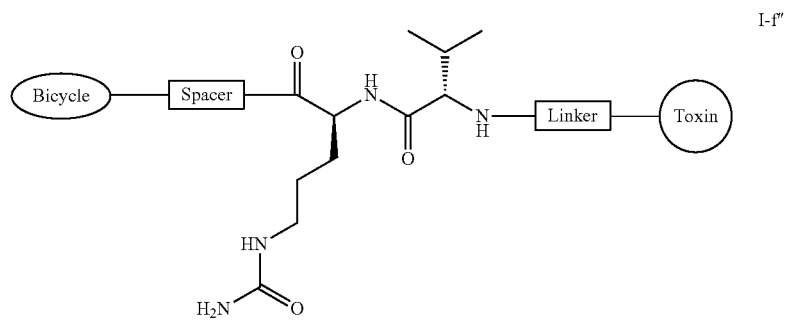
I-f″
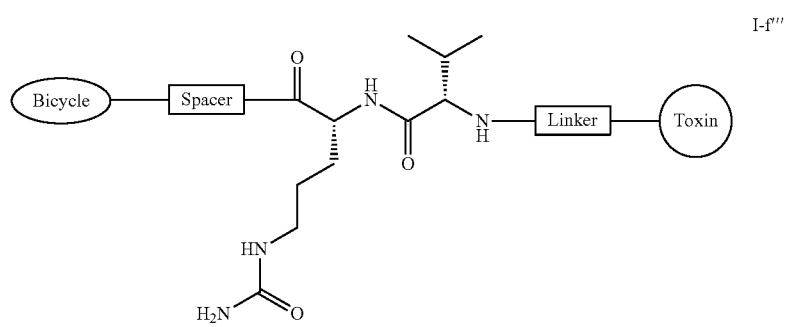
I-f‴
or a pharmaceutically acceptable salt thereof, wherein each of Bicycle, Spacer, Linker and Toxin is as defined and described herein.
In certain embodiments, the present invention provides a compound of formula I-g or I-h:
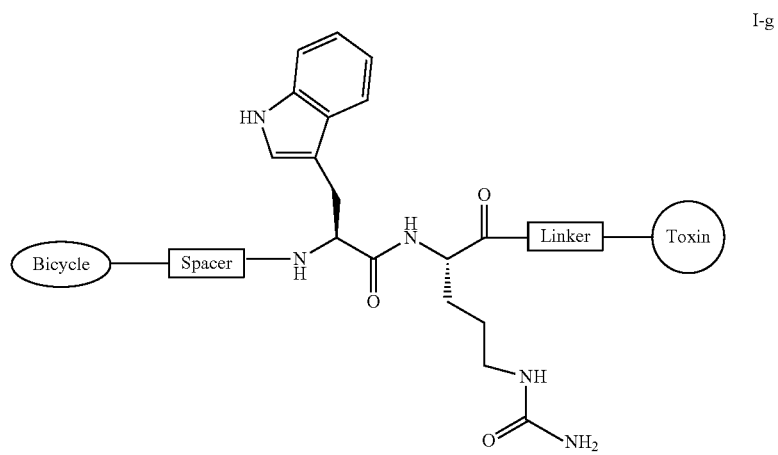
I-g I-h

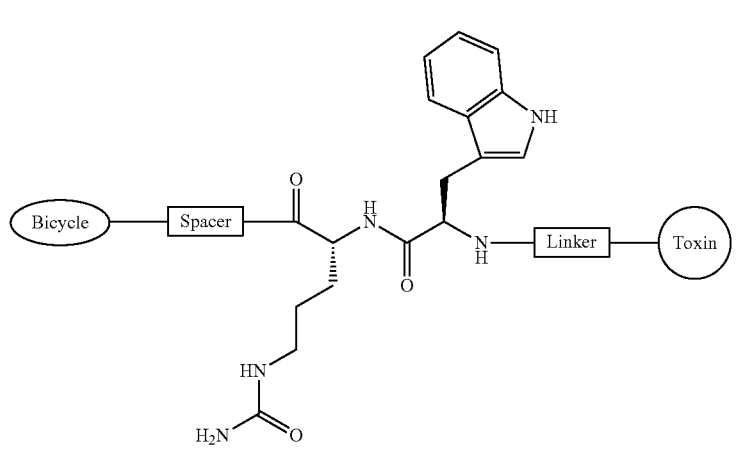

or a pharmaceutically acceptable salt thereof, wherein each of Bicycle, Spacer, Linker and Toxin is as defined and described herein.

In certain embodiments, the present invention provides a compound of formula I-g', I-g", or I-g''':

I-g'

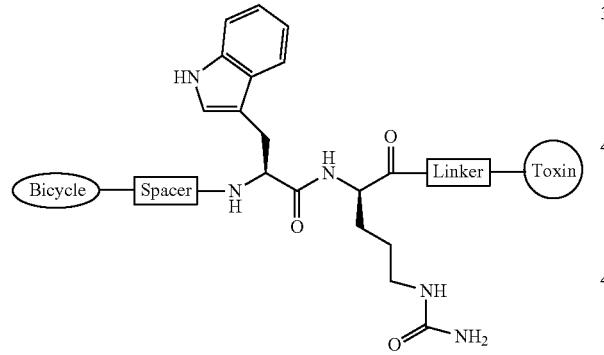

I-g'''

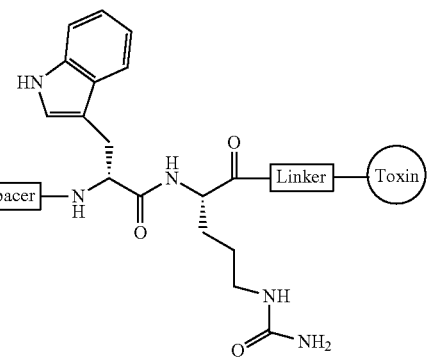

or a pharmaceutically acceptable salt thereof, wherein each of Bicycle, Spacer, Linker and Toxin is as defined and described herein.

In certain embodiments, the present invention provides a compound of formula I-h', I-h", or I-h''':

I-g"

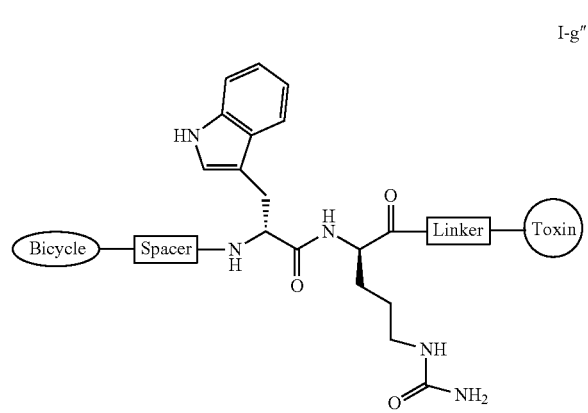

I-h'

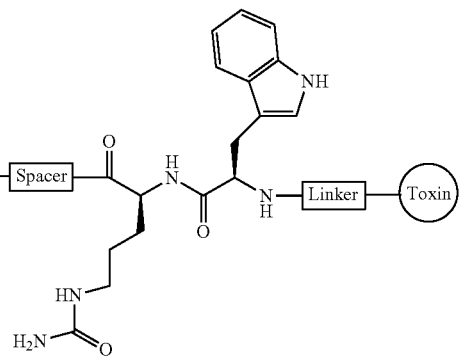

-continued

I-h″

[Structure: Bicycle—Spacer—[amino acid with indole sidechain and urea-containing ornithine]—Linker—Toxin]

I-h‴

[Structure: Bicycle—Spacer—[amino acid with indole sidechain and urea-containing ornithine]—Linker—Toxin]

or a pharmaceutically acceptable salt thereof, wherein each of Bicycle, Spacer, Linker and Toxin is as defined and described herein.

The amino acid sequences described herein are written N-terminus to C-terminus, except where it is described differently.

I. Bicycle Moieties

As described generally above, the present invention provides a BDC comprising a Bicycle moiety, a Spacer moiety, a $AA^1$-$AA^2$ moiety, a Linker moiety and a Toxin moiety.

As used herein, the term Bicycle moiety refers to a bicyclic peptide covalently bound to a molecular scaffold.

As defined above and described herein, a bicyclic peptide is a polypeptide which is covalently bound to a molecular scaffold such that two or more peptide loops are subtended between attachment points to the scaffold.

In some embodiments, the polypeptide is a high affinity binder of membrane type 1 metalloprotease (MT1-MMP, also known as MMP14). In some embodiments, the polypeptide is fully cross-reactive with murine, dog, cynomolgus and human MT1-MMP. In some embodiments, the polypeptide is selective for MT1-MMP, but does not cross-react with MMP-1, MMP-2, MMP-15 and MMP-16. In some embodiments, the polypeptide is specific for human MT1-MMP. In some embodiments, the polypeptide is specific for mouse MT1-MMP. In some embodiments, the polypeptide is specific for human and mouse MT1-MMP. In some embodiments, the polypeptide is specific for human, mouse and dog MT1-MMP. In some embodiments, the polypeptide is a high affinity binder of MT1-MMP Hemopexin domain (PEX).

In some embodiments, the polypepetide is a peptide described in WO 2016/067035, the content of which is incorporated herein by reference in its entirety.

In some embodiments, the polypeptide is -C-X-U/O-X-X-G-C-E-D-F-Y-X-X-C-(SEQ ID NO: 17) wherein X represents any amino acid residue; U represents a polar, uncharged amino acid residue selected from N, C, Q, M, S and T; and O represents a non-polar aliphatic amino acid residue selected from G, A, I, L, P and V. In some embodiments, the polypeptide is -C-X-U/O-X-X-G-C-E-D-F-Y-X-X-C-(SEQ ID NO: 1) wherein X represents any amino acid residue; U represents a polar, uncharged amino acid residue selected from N, C, Q, M, S and T; and O represents a non-polar aliphatic amino acid residue selected from G, A, I, L, P and V. In some embodiments, the polypeptide is -CYNEFGCEDFYDIC- (SEQ ID NO: 2). In some embodiments, the polypeptide is βAla-Sar10-A-CYN-EFGCEDFYDIC- (SEQ ID NO: 3). In some embodiments, the polypeptide is -C(D-Ala)NEFGCEDFYDIC- (SEQ ID NO: 4). In some embodiments, the polypeptide is -C(D-Ala)NE(1Nal)(D-Ala)CEDFYD(tBuGly)C- (SEQ ID NO: 5). In some embodiments, the polypeptide is -C-Y/M/F/V-U/O-U/Z-J-G-C-E-D-F-Y-Z-O-C- (SEQ ID NO: 6). In some embodiments, the polypeptide is -C-Y/M/F/V-N/G-E/Q-F-G-C-E-D-F-Y-D-I-C- (SEQ ID NO: 7). In some embodiments, the polypeptide is -C-Y/M/F-N/G-E/Q-F-G-C-E-D-F-Y-D-I-C-(SEQ ID NO: 8). In some embodiments, the polypeptide is -C-Y/M-N-E/Q-F-G-C-E-D-F-Y-D-I-C- (SEQ ID NO: 9). In some embodiments, the polypeptide is -C-M-N-Q-F-G-C-E-D-F-Y-D-I-C-(SEQ ID NO: 10). In some embodiments, the polypeptide is -C-F-G-E-F-G-C-E-D-F-Y-D-I-C-(SEQ ID NO: 11). In some embodiments, the polypeptide is -C-V-N-E-F-G-C-E-D-F-Y-D-I-C-(SEQ ID NO: 12). In some embodiments, the polypeptide is -C-F-N-E-F-G-C-E-D-F-Y-D-I-C-(SEQ ID NO: 13). In some embodiments, the polypeptide is -C-Y-N-E-Y-G-C-E-D-F-Y-D-I-C-(SEQ ID NO: 14). In some embodiments, the polypeptide is -C-Y-N-E-W-G-C-E-D-F-Y-D-I-C-(SEQ ID NO: 15). In some embodiments, the polypeptide is -CKNRGFGCEDFYDIC- (SEQ ID NO: 16). As described in WO 2016/067035, the content of which is incorporated herein by reference in its entirety, Z represents a polar, negatively charged amino acid residue selected from D or E, and J represents a non-polar aromatic amino acid residue selected from F, W and Y. As also described in WO 2016/067035, D-Ala represents D-alanine, 1Nal represents 1-naphthylalanine; and tBuGly represents tert-butylglycine.

In some embodiments, the polypeptide comprises L amino acids. In some embodiments, the polypeptide comprises D amino acids. In some embodiments, the polypeptide comprises a mixture of D and L amino acids.

In some embodiments, the polypeptide is selected from those depicted in Table 1, below.

In some embodiments, the polypeptide is selected from those depicted in Table 1a, below.

In some embodiments, the polypeptide is selected from those depicted in Table 1b, below.

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment the molecular scaffold may be, or may be based on, natural monomers such as nucleosides, sugars, or steroids. For example the molecular scaffold may comprise a short polymer of such entities, such as a dimer or a trimer. In one embodiment the molecular scaffold is a compound of known toxicity, for example of low toxicity.

Examples of suitable compounds include cholesterols, nucleotides, steroids, or existing drugs such as tamazepam.

In one embodiment the molecular scaffold may be a macromolecule. In one embodiment the molecular scaffold is a macromolecule composed of amino acids, nucleotides or carbohydrates.

In one embodiment the molecular scaffold is formed via a molecular scaffold reagent which comprises the molecular scaffold and reactive groups that are capable of reacting with functional group(s) of the polypeptide to form covalent bonds.

The molecular scaffold reagent may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold reagent may comprise or may consist of tris(bromomethyl)benzene, especially 1,3,5-tris(bromomethyl)benzene (TBMB)

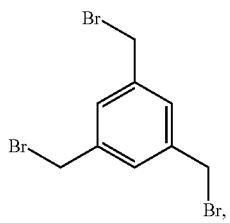

or a derivative thereof.

In one embodiment, the molecular scaffold may be formed by treatment of the polypeptide with a molecular scaffold reagent which comprise or may consist of tris (bromomethyl)benzene, especially 1,3,5-tris(bromomethyl) benzene (TBMB),

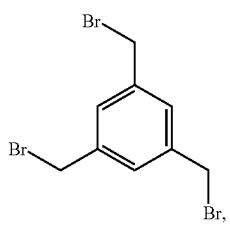

or a derivative thereof, wherein treatment with a polypeptide affords the molecular scaffold

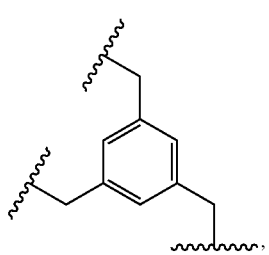 [SMILES: *Cc1cc(C*)cc(C*)c1]

or a derivative thereof, via bromide displacement.

In one embodiment, the molecular scaffold reagent is 2,4,6-tris(bromomethyl)mesitylene

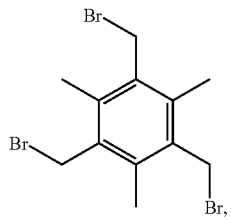

wherein treatment with a polypeptide affords the molecular scaffold

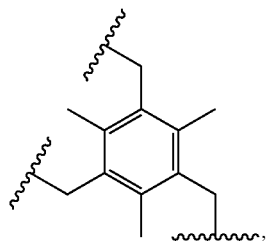 [SMILES: *Cc1c(C)c(C*)c(C)c(C*)c1C]

via bromide displacement. This molecular scaffold reagent is similar to 1,3,5-tris(bromomethyl)benzene but contains three additional methyl groups attached to the benzene ring. This has the advantage that the additional methyl groups may form further contacts with the polypeptide and hence add additional structural constraint.

In one embodiment, the molecular scaffold reagent may comprise or may consist of N,N',N''-(benzene-1,3,5-triyl)-tris(2-bromoacetamide),

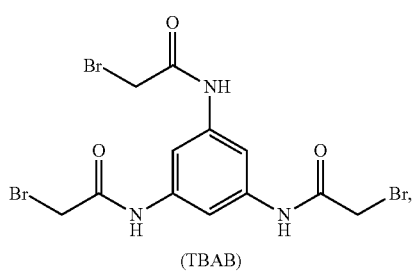 [SMILES: O=C(CBr)Nc1cc(NC(=O)CBr)cc(NC(=O)CBr)c1]

(TBAB)

wherein treatment with a polypeptide affords the molecular scaffold

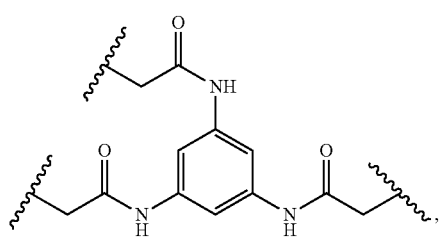 [SMILES: *CC(=O)Nc1cc(NC(=O)C*)cc(NC(=O)C*)c1]

via bromide displacement. In one embodiment, the molecular scaffold may comprise or may consist of triacrylformal,

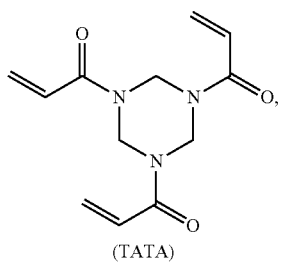
(TATA)

wherein treatment with a polypeptide affords the molecular scaffold

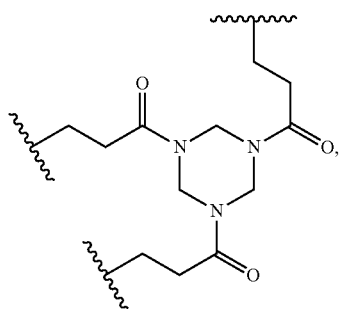 [SMILES: *CCC(=O)N1CN(C(=O)CC*)CN(C(=O)CC*)C1]

via Michael addition.

In some embodiments, the molecular scaffold is selected from those depicted in Table 1, below.

In some embodiments, the molecular scaffold is selected from those depicted in Table 1a, below.

In some embodiments, the molecular scaffold is selected from those depicted in Table 1b, below.

The molecular scaffold reagent of the invention contains chemical groups that allow functional groups of the polypeptide of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used in the molecular scaffold reagent to react with thiol groups of cysteines are alkyl halides (or also named halogenoalkanes or haloalkanes).

Examples include bromomethylbenzene (the scaffold reactive group exemplified by TBMB) or iodoacetamide. Other scaffold reactive groups that are used to selectively couple compounds to cysteines in proteins are maleimides. Examples of maleimides which may be used as molecular scaffold reagents in the invention include: tris-(2-maleimidoethyl)amine

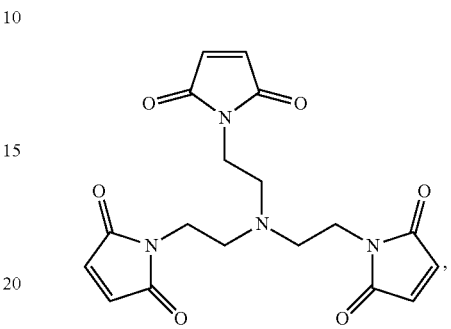

wherein treatment with a polypeptide affords the molecular scaffold

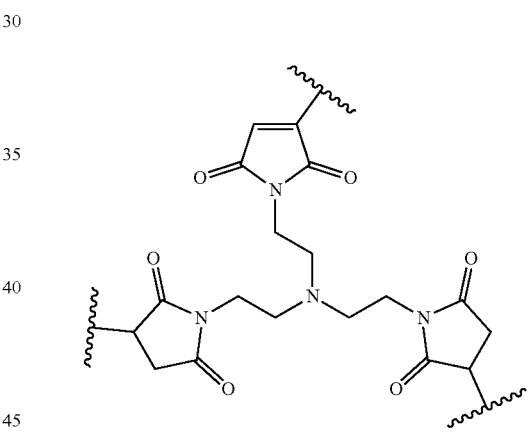

via Michael addition; tris-(2-maleimidoethyl)benzene

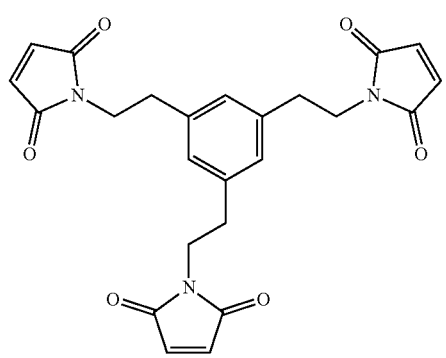

wherein treatment with a polypeptide affords the molecular scaffold

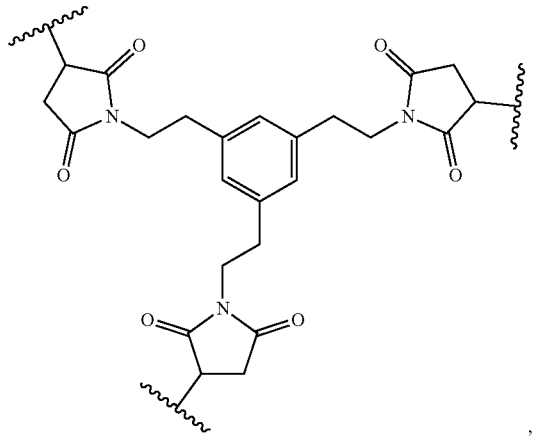 [SMILES: *C1CC(=O)N(CCc2cc(CCN3C(=O)CC(*)C3=O)cc(CCN3C(=O)CC(*)C3=O)c2)C1=O]

via Michael addition; and tris-(maleimido)benzene

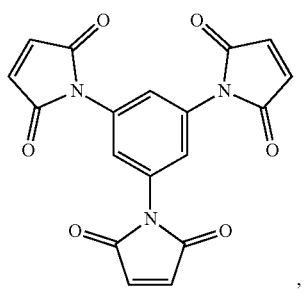 [SMILES: O=C1C=CC(=O)N1c1cc(N2C(=O)C=CC2=O)cc(N2C(=O)C=CC2=O)c1]

wherein treatment with a polypeptide affords the molecular scaffold

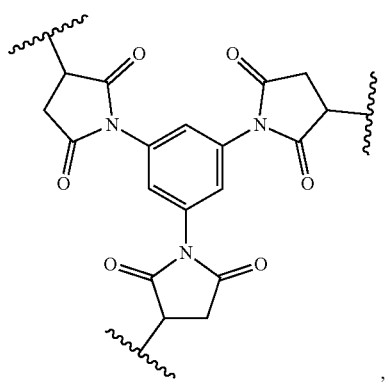 [SMILES: *C1CC(=O)N(c2cc(N3C(=O)CC(*)C3=O)cc(N3C(=O)CC(*)C3=O)c2)C1=O]

via Michael addition. Selenocysteine is also a natural amino acid which has a similar reactivity to cysteine and can be used for the same reactions. Thus, wherever cysteine is mentioned, it is typically acceptable to substitute selenocysteine unless the context suggests otherwise.

In some embodiments, a Bicycle is of formula II:

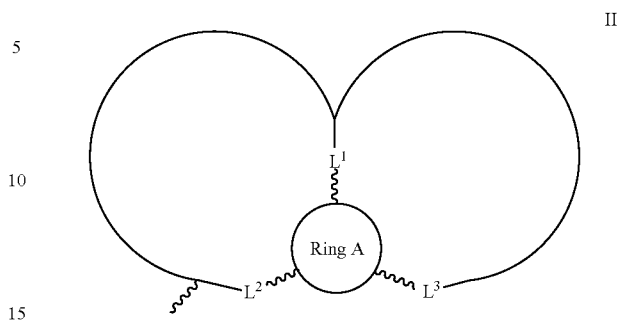

wherein:

each of $L^1$, $L^2$, and $L^3$ is independently a $C_{1-6}$ bivalent straight or branched saturated or unsaturated hydrocarbon chain wherein 1-2 methylene units of the chain are independently and optionally replaced with —S—, —N(R$^2$)—, —C(O)—, —C(O)N(R$^2$)—, —N(R$^2$)C(O)—;

each R is independently hydrogen or $C_{1-4}$ alkyl;

Ring A is a 6-membered saturated, partially unsaturated, or aromatic ring having 0-3 heteroatoms independently selected from nitrogen, oxygen, or sulfur;

each "loop" comprises a peptide targeting MT1-MMP;

and ⸹ indicates the site of attachment to the Spacer.

In some embodiments, a Bicycle is of formula II':

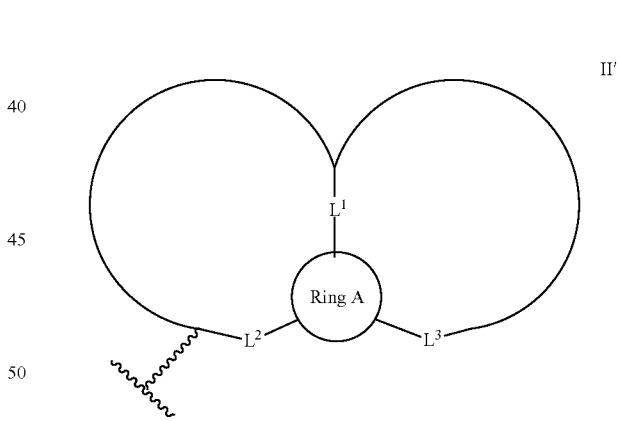

wherein:

each of $L^1$, $L^2$, and $L^3$ is independently a $C_{1-6}$ bivalent straight or branched saturated or unsaturated hydrocarbon chain wherein 1-2 methylene units of the chain are independently and optionally replaced with —S—, —N(R)—, —C(O)—, —C(O)N(R)—, or —N(R)C(O)—;

each R is independently hydrogen or $C_{1-4}$ alkyl;

Ring A is a 6-membered saturated, partially unsaturated, or aromatic ring having 0-3 heteroatoms independently selected from nitrogen, oxygen, and sulfur;

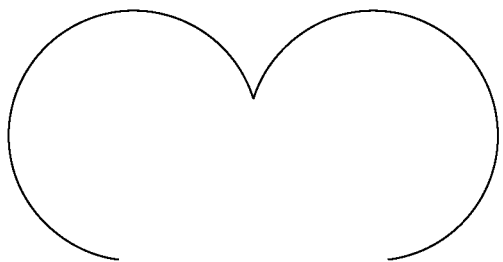

comprises a polypeptide targeting MT1-MMP; and

indicates the site of attachment to the Spacer.

As defined above and described herein, each of $L^1$, $L^2$, and $L^3$ is independently a $C_{1-6}$ bivalent straight or branched saturated or unsaturated hydrocarbon chain wherein 1-2 methylene units of the chain are independently and optionally replaced with —S—, —N($R^2$)—, —C(O)—, —C(O)N($R^2$)—, —N($R^2$)C(O)—.

In some embodiments, each of $L^1$, $L^2$, and $L^3$ is independently a $C_{1-6}$ bivalent straight or branched saturated or unsaturated hydrocarbon chain wherein 1-2 methylene units of the chain are independently and optionally replaced with —S—, —N(R)—, or —C(O)—. In some embodiments, each of $L^1$, $L^2$, and $L^3$ is independently a $C_{1-6}$ bivalent straight or branched saturated or unsaturated hydrocarbon chain wherein 1 methylene unit of the chain is independently and optionally replaced with —S—, —N(R)—, or —C(O)—. In some embodiments, each of $L^1$, $L^2$, and $L^3$ is independently a $C_{1-6}$ bivalent straight or branched saturated or unsaturated hydrocarbon chain wherein 1 methylene unit of the chain is optionally replaced with —S—. In some embodiments, each of $L^1$, $L^2$, and $L^3$ is independently a $C_{1-6}$ bivalent straight or branched saturated or unsaturated hydrocarbon chain wherein 1 methylene unit of the chain is optionally replaced with —N(R)—. In some embodiments, each of $L^1$, $L^2$, and $L^3$ is independently a $C_{1-6}$ bivalent straight or branched saturated or unsaturated hydrocarbon chain wherein 1 methylene unit of the chain is optionally replaced with —C(O)—.

In some embodiments, each of $L^1$, $L^2$, and $L^3$ is -$CH_2$—.

In some embodiments, each of $L^1$, $L^2$, and $L^3$ is —C(O)$CH_2CH_2$—.

In some embodiments, each of $L^1$, $L^2$, and $L^3$ is -$CH_2SCH_2$—.

In some embodiments, $L^1$ is -$CH_2$—. In some embodiments, $L^1$ is —C(O)$CH_2CH_2$—. In some embodiments, $L^1$ is -$CH_2SCH_2$—. In some embodiments, $L^1$ is -$CH_2NHCH_2$—. In some embodiments, $L^1$ is -$CH_2N(CH_3)CH_2$—. In some embodiments, $L^1$ is -$CH_2SCH_2C(O)NH$—. In some embodiments, $L^1$ is -$CH_2NHCH_2C(O)NH$—. In some embodiments, $L^1$ is -$CH_2N(CH_3)CH_2C(O)NH$—. In some embodiments, $L^1$ is -$CH_2SCH_2CH_2C(O)$—. In some embodiments, $L^1$ is -$CH_2NHCH_2CH_2C(O)$—. In some embodiments, $L^1$ is -$CH_2N(CH_3)CH_2CH_2C(O)$—. In some embodiments, $L^1$ is selected from those depicted in Table 1, below. In some embodiments, $L^1$ is selected from those depicted in Table 1a, below. In some embodiments, $L^1$ is selected from those depicted in Table 1b, below.

In some embodiments, $L^2$ is -$CH_2$—. In some embodiments, $L^2$ is —C(O)$CH_2CH_2$—. In some embodiments, $L^2$ is -$CH_2SCH_2$—. In some embodiments, $L^2$ is -$CH_2NHCH_2$—. In some embodiments, $L^2$ is -$CH_2N(CH_3)CH_2$—. In some embodiments, $L^2$ is -$CH_2SCH_2C(O)NH$—. In some embodiments, $L^2$ is -$CH_2NHCH_2C(O)NH$—. In some embodiments, $L^2$ is -$CH_2N(CH_3)CH_2C(O)NH$—. In some embodiments, $L^2$ is -$CH_2SCH_2CH_2C(O)$—. In some embodiments, $L^2$ is -$CH_2NHCH_2CH_2C(O)$—. In some embodiments, $L^2$ is -$CH_2N(CH_3)CH_2CH_2C(O)$—. In some embodiments, $L^2$ is selected from those depicted in Table 1, below. In some embodiments, $L^2$ is selected from those depicted in Table 1a, below. In some embodiments, $L^2$ is selected from those depicted in Table 1b, below.

In some embodiments, $L^3$ is —$CH_2$—. In some embodiments, $L^3$ is —C(O)$CH_2CH_2$—. In some embodiments, $L^3$ is —$CH_2SCH_2$—. In some embodiments, $L^3$ is —$CH_2NHCH_2$—. In some embodiments, $L^3$ is —$CH_2N(CH_3)CH_2$—. In some embodiments, $L^3$ is —$CH_2SCH_2C(O)NH$—. In some embodiments, $L^3$ is —$CH_2NHCH_2C(O)NH$—. In some embodiments, $L^3$ is —$CH_2N(CH_3)CH_2C(O)NH$—. In some embodiments, $L^3$ is —$CH_2SCH_2CH_2C(O)$—. In some embodiments, $L^3$ is —$CH_2NHCH_2CH_2C(O)$—. In some embodiments, $L^3$ is —$CH_2N(CH_3)CH_2CH_2C(O)$—. In some embodiments, $L^3$ is selected from those depicted in Table 1, below. In some embodiments, $L^3$ is selected from those depicted in Table 1a, below. In some embodiments, $L^3$ is selected from those depicted in Table 1b, below.

As defined above and described herein, each R is independently hydrogen or $C_{1-4}$ alkyl.

In some embodiments, R is hydrogen. In some embodiments, R is $C_{1-4}$ alkyl. In some embodiments, R is methyl. In some embodiments, R is ethyl.

In some embodiments, R is selected from those depicted in Table 1, below. In some embodiments, R is selected from those depicted in Table 1a, below. In some embodiments, R is selected from those depicted in Table 1b, below.

As defined above and described herein, Ring A is a 6-membered saturated, partially unsaturated, or aromatic ring having 0-3 heteroatoms independently selected from nitrogen, oxygen, or sulfur.

In some embodiments, Ring A is

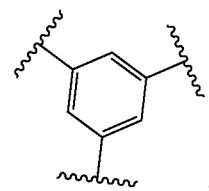

In some embodiments, Ring A is

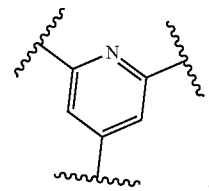

In some embodiments, Ring A is

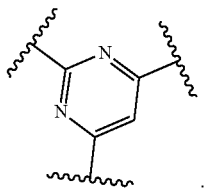 [SMILES: *c1cc(*)nc(*)n1]

In some embodiments, Ring A is

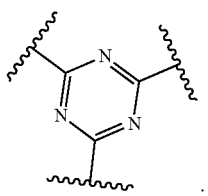 [SMILES: *c1nc(*)nc(*)n1]

In some embodiments, Ring A is

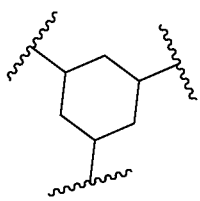

In some embodiments, Ring A is

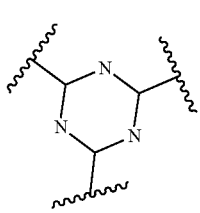

In some embodiments, Ring A is selected from those depicted in Table 1, below. In some embodiments, Ring A is selected from those depicted in Table 1a, below. In some embodiments, Ring A is selected from those depicted in Table 1b, below.

As defined above and described herein,

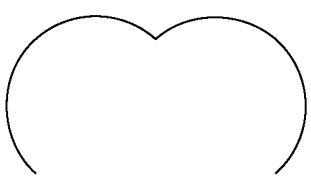

comprises a polypeptide targeting MT1-MMP.

In some embodiments,

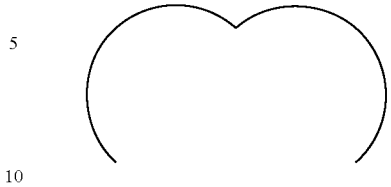

comprises a polypeptide selected from SEQ ID NOS. 1-17 as described herein.

In some embodiments,

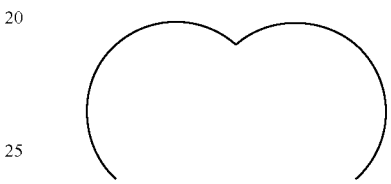

is a polypeptide selected from those depicted in Table 1, below. In some embodiments,

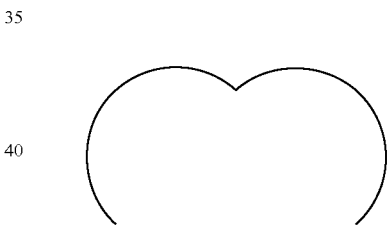

is a polypeptide selected from those depicted in Table 1a, below. In some embodiments,

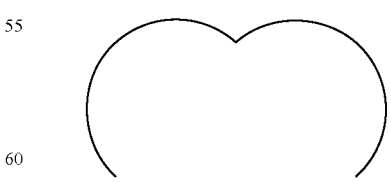

is a polypeptide selected from those depicted in Table 1b, below.

23
In some embodiments, a Bicycle is:
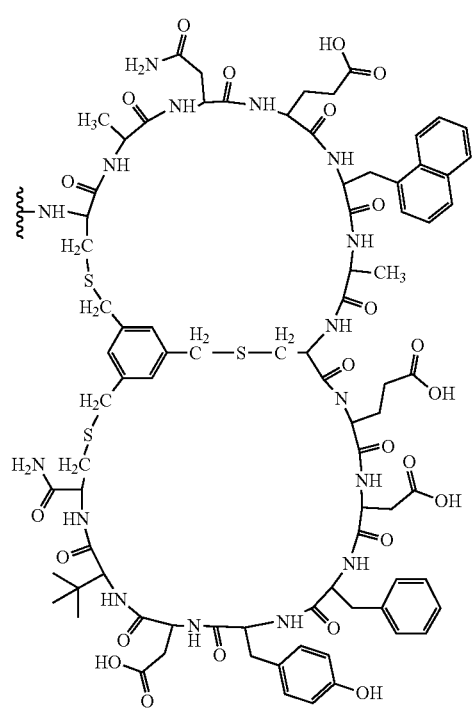
24
In some embodiments, a Bicycle is:
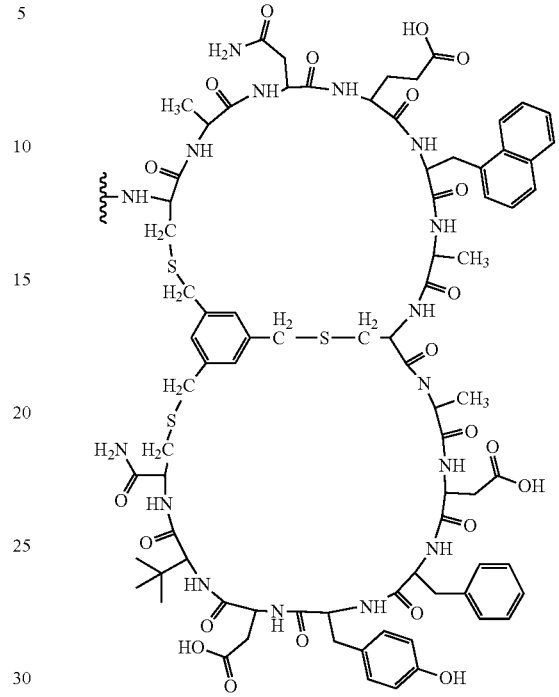
In some embodiments, a Bicycle is:
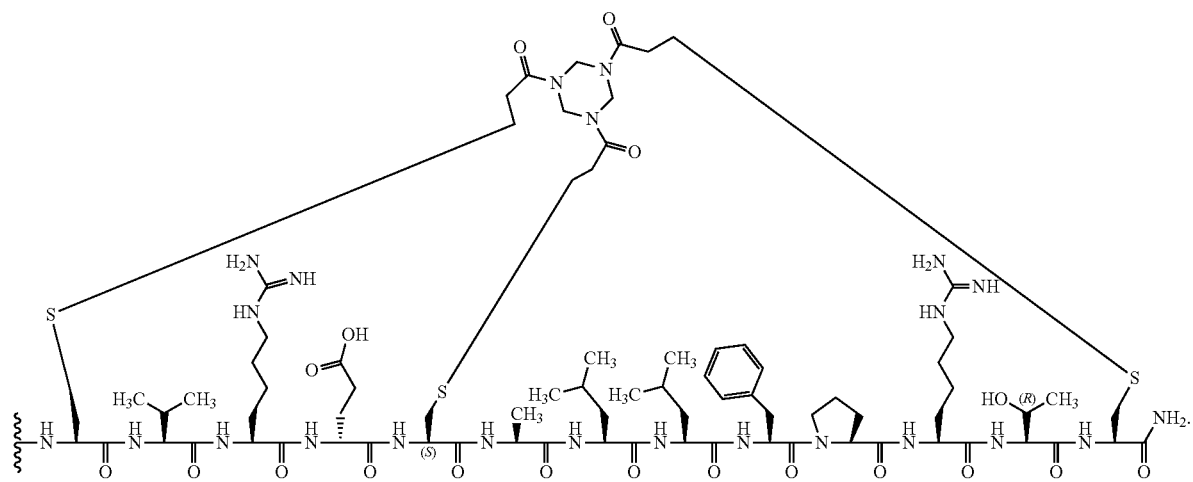

In some embodiments, a Bicycle is:

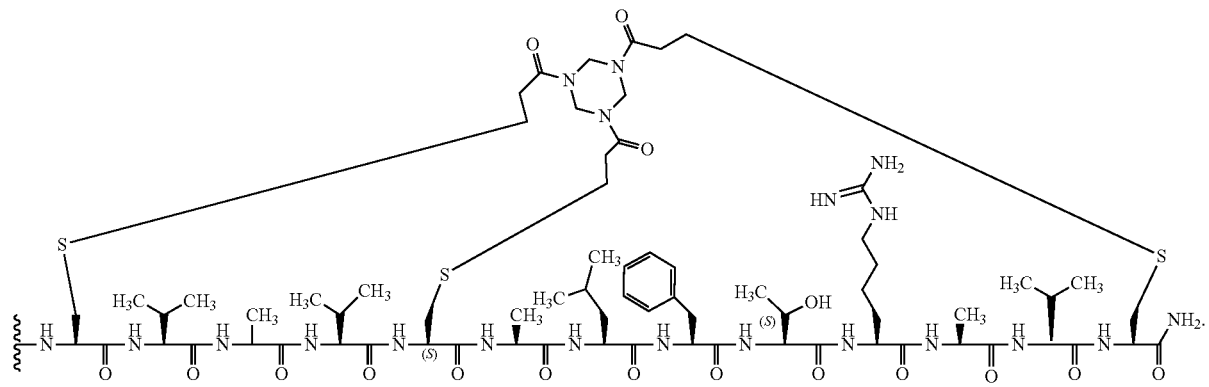

In some embodiments, a Bicyle is selected from those depicted in Table 1, below. In some embodiments, a Bicycle is selected from those depicted in Table 1a, below. In some embodiments, a Bicycle is selected from those depicted in Table 1b, below.

II. Spacer Moieties

As used herein Spacer refers to a bivalent moiety that connects the Bicycle moiety with the $AA^1$-$AA^2$ moiety.

One of ordinary skill in the art will appreciate that a variety of Spacer moieties are amenable to achieve connection of the Bicycle with the $AA^1$-$AA^2$ moiety.

In certain embodiments, the Spacer moiety is a bivalent moiety comprising an alanine, a polysarcosine domain, a beta-alanine and a glutaryl moiety. In some embodiments, the polysarcosine domain is a 5-15 membered bivalent polysarcosine moiety. In some embodiments, the polysarcosine domain is a 5 membered bivalent polysarcosine moiety. In some embodiments, the polysarcosine domain is a 6 membered bivalent polysarcosine moiety. In some embodiments, the polysarcosine domain is a 7 membered bivalent polysarcosine moiety. In some embodiments, the polysarcosine domain is a 8 membered bivalent polysarcosine moiety. In some embodiments, the polysarcosine domain is a 9 membered bivalent polysarcosine moiety. In some embodiments, the polysarcosine domain is a 10 membered bivalent polysarcosine moiety. In some embodiments, the polysarcosine domain is a 11 membered bivalent polysarcosine moiety. In some embodiments, the polysarcosine domain is a 12 membered bivalent polysarcosine moiety. In some embodiments, the polysarcosine domain is a 13 membered bivalent polysarcosine moiety. In some embodiments, the polysarcosine domain is a 14 membered bivalent polysarcosine moiety. In some embodiments, the polysarcosine domain is a 15 membered bivalent polysarcosine moiety.

In some embodiments, the Spacer moiety is

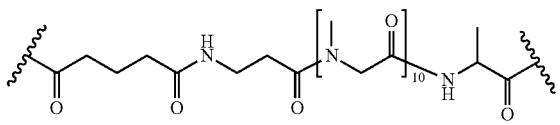

In certain embodiments, the Spacer moiety is a bivalent thiopropanoyl maleimido caproyl moiety. In other embodiments, the Spacer moiety is selected from:

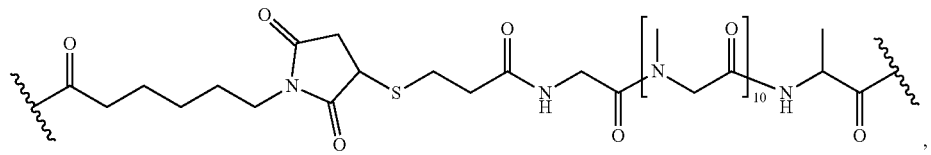

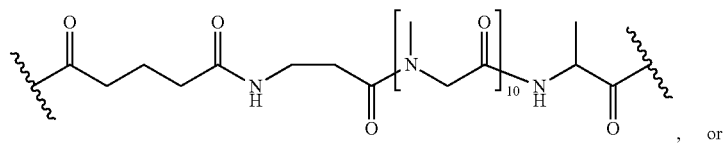
, or

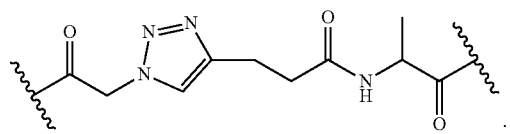
.

In some embodiments, the Spacer moiety is

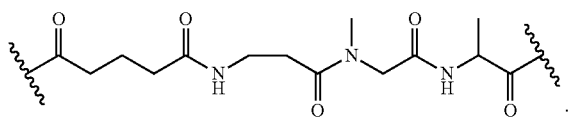 [SMILES: *C(=O)CCCC(=O)NCCC(=O)N(C)CC(=O)NC(C)C(*)=O]

In some embodiments, the Spacer moiety is

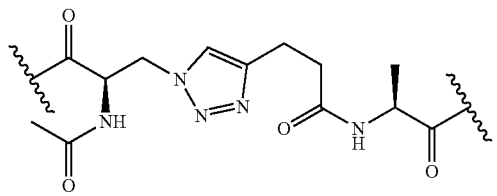

In some embodiments, the Spacer moiety is

In some embodiments, the Spacer moiety is selected from those depicted in Table 1, below.

In some embodiments, the Spacer moiety is selected from those depicted in Table 1a, below.

In some embodiments, the Spacer moiety is selected from those depicted in Table 1b, below.

III. $AA^1$-$AA^2$ Moieties

As used herein $AA^1$-$AA^2$ is a bivalent moiety at least one citrulline moiety that connects the Spacer moiety with the Linker moiety, wherein $AA^1$ and $AA^2$ represent amino acids and the bond between them can be selectively cleaved by enzymes expressed on tumor cells. In some embodiments, $AA^1$-$AA^2$ is a bivalent moiety at least one citrulline moiety and is selectively cleaved by cathepsin.

In some embodiments, each of $AA^1$ and $AA^2$ is an L amino acid. In some embodiments, each of $AA^1$ and $AA^2$ is a D amino acid. In some embodiments, one of $AA^1$ and $AA^2$ is an L amino acid, and the other one is a D amino acid.

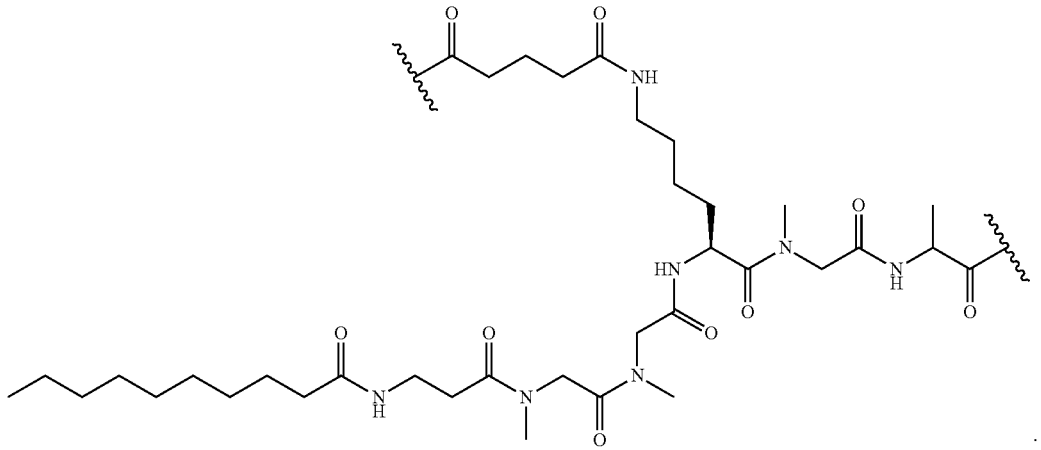 [SMILES: *C(=O)CCCC(=O)NCCCC[C@H](NC(=O)CN(C)C(=O)CN(C)C(=O)CCNC(=O)CCCCCCCCC)C(=O)N(C)CC(=O)NC(C)C(*)=O]

In some embodiments, the Spacer moiety is

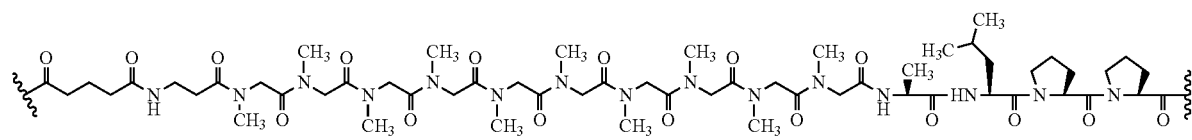

In some embodiments, the Spacer moiety is

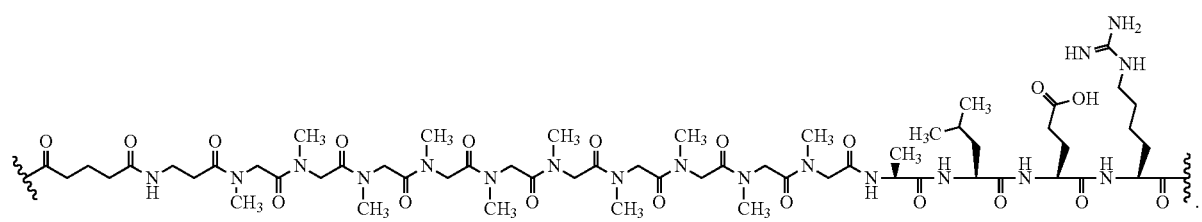 [SMILES: *C(=O)CCCC(=O)NCCC(=O)N(C)CC(=O)N(C)CC(=O)N(C)CC(=O)N(C)CC(=O)N(C)CC(=O)N(C)CC(=O)N(C)CC(=O)N(C)CC(=O)N(C)CC(=O)N(C)CC(=O)N[C@H](C)C(=O)N[C@H](CC(C)C)C(=O)N[C@H](CCC(=O)O)C(=O)N[C@H](CCCCNC(=N)N)C(*)=O]

In some embodiments, AA¹-AA² is -Val-Cit-. In some embodiments, AA¹-AA² is -Cit-Val-. In some embodiments, AA¹-AA² is
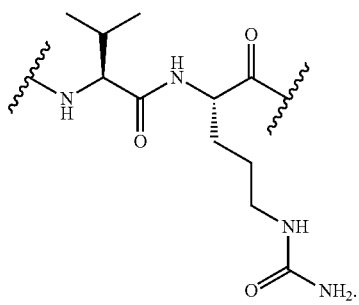 [SMILES: *N[C@H](C(=O)N[C@@H](CCCNC(N)=O)C(*)=O)C(C)C]
In some embodiments, AA¹-AA² is
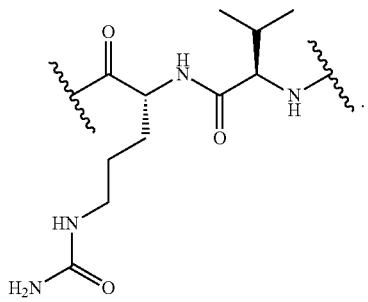 [SMILES: *N[C@@H](C(=O)N[C@H](CCCNC(N)=O)C(*)=O)C(C)C]
In some embodiments, AA¹-AA² is
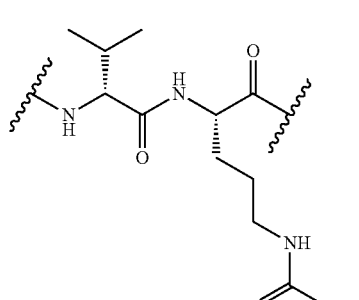
In some embodiments, AA¹-AA² is
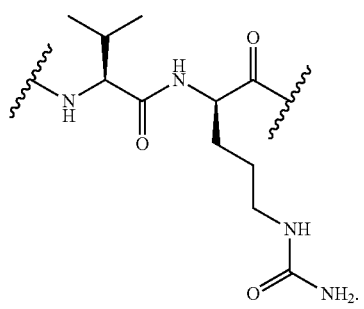 [SMILES: *N[C@H](C(=O)N[C@H](CCCNC(N)=O)C(*)=O)C(C)C]
In some embodiments, AA¹-AA² is
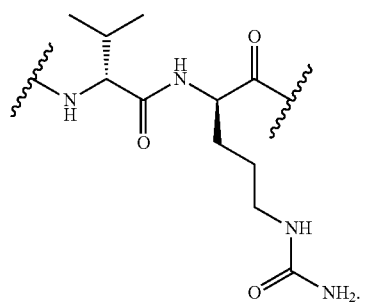 [SMILES: *N[C@@H](C(=O)N[C@H](CCCNC(N)=O)C(*)=O)C(C)C]
In some embodiments, AA¹-AA² is
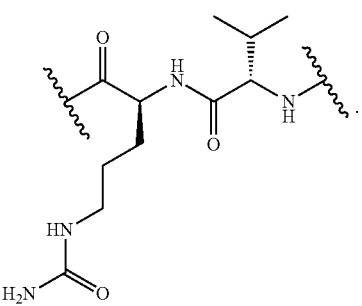 [SMILES: *N[C@H](C(=O)N[C@@H](CCCNC(N)=O)C(*)=O)C(C)C]
In some embodiments, AA¹-AA² is
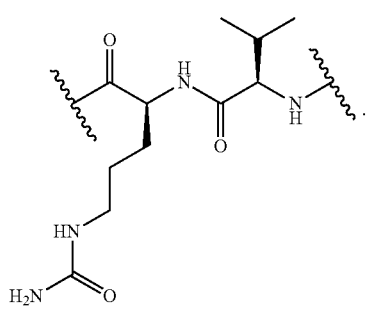 [SMILES: *N[C@@H](C(=O)N[C@@H](CCCNC(N)=O)C(*)=O)C(C)C]
In some embodiments, AA¹-AA² is
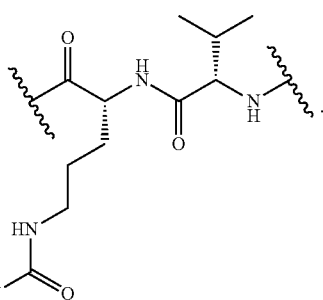

In some embodiments, AA$^1$-AA$^2$ is -Trp-Cit-. In some embodiments, AA$^1$-AA$^2$ is -Cit-Trp-. In some embodiments, AA$^1$-AA$^2$ is
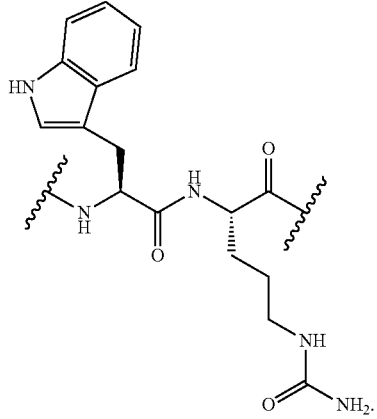 [SMILES: *N[C@@H](Cc1c[nH]c2ccccc12)C(=O)N[C@@H](CCCNC(N)=O)C(*)=O]
In some embodiments, AA$^1$-AA$^2$ is
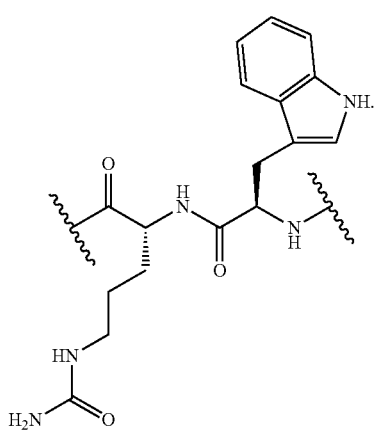 [SMILES: *N[C@H](Cc1c[nH]c2ccccc12)C(=O)N[C@H](CCCNC(N)=O)C(*)=O]
In some embodiments, AA$^1$-AA$^2$ is
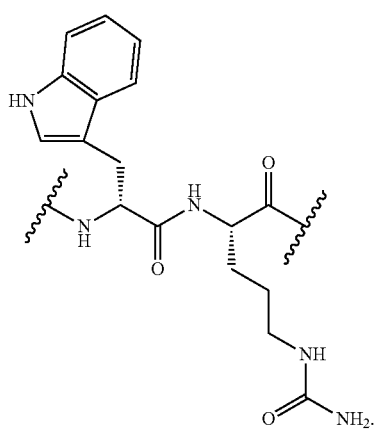 [SMILES: *N[C@H](Cc1c[nH]c2ccccc12)C(=O)N[C@@H](CCCNC(N)=O)C(*)=O]
In some embodiments, AA$^1$-AA$^2$ is
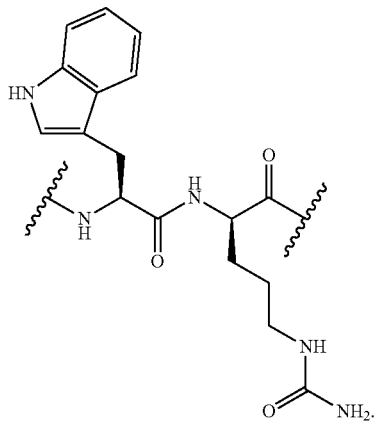 [SMILES: *N[C@@H](Cc1c[nH]c2ccccc12)C(=O)N[C@H](CCCNC(N)=O)C(*)=O]
In some embodiments, AA$^1$-AA$^2$ is
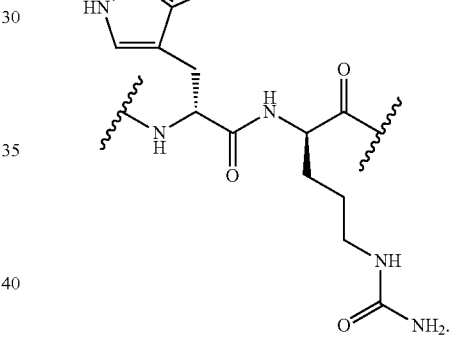
In some embodiments, AA$^1$-AA$^2$ is
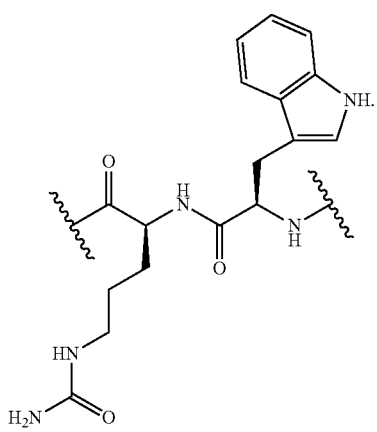 [SMILES: *N[C@H](Cc1c[nH]c2ccccc12)C(=O)N[C@@H](CCCNC(N)=O)C(*)=O]

In some embodiments, $AA^1$-$AA^2$ is

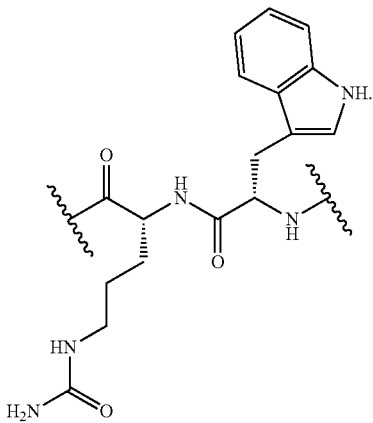 [SMILES: *N[C@@H](Cc1c[nH]c2ccccc12)C(=O)N[C@H](CCCNC(N)=O)C(*)=O]

In some embodiments, $AA^1$-$AA^2$ is

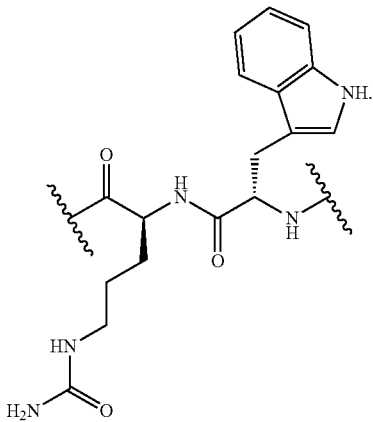 [SMILES: *N[C@@H](Cc1c[nH]c2ccccc12)C(=O)N[C@@H](CCCNC(N)=O)C(*)=O]

In some embodiments, the $AA^1$-$AA^2$ moiety is selected from those depicted in Table 1, below.

In some embodiments, the $AA^1$-$AA^2$ moiety is selected from those depicted in Table 1a, below.

In some embodiments, the $AA^1$-$AA^2$ moiety is selected from those depicted in Table 1b, below.

IV. Linker Moieties

As used herein Linker refers to a bivalent spacer moiety that connects $AA^1$-$AA^2$ moiety with the Toxin moiety. In some embodiments, a Linker is a self-immolative linker.

One of ordinary skill in the art will appreciate that a variety of Linker moieties are amenable to achieve connection of the $AA^1$-$AA^2$ moiety with the Toxin moiety.

In some embodiments, the Linker is a para-aminobenzyl moiety. In some embodiments, the Linker is 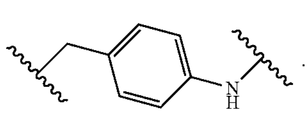 [SMILES: *Cc1ccc(N*)cc1] In some embodiments, the Linker is a bivalent self-immolative spacer moiety. In some embodiments, the Linker is para-aminobenzyl carbamate, 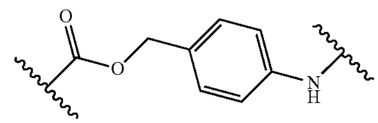 [SMILES: *Nc1ccc(COC(*)=O)cc1] (PABC).

In some embodiments, the Linker moiety is selected from those depicted in Table 1, below.

In some embodiments, the Linker moiety is selected from those depicted in Table 1a, below.

In some embodiments, the Linker moiety is selected from those depicted in Table 1b, below.

V. Toxin Moieties

As used herein Toxin refers to a chemotherapeutic agent.

One of ordinary skill in the art will appreciate that a variety of Toxin moieties are amenable to achieve the chemotherapeutic effects of the present invention.

In some embodiments, the Toxin can be connected at any available position. In some embodiments, the Toxin can be connected at any available —OH, —C(O)OH, —SH, $—NH_2$, or $—NHCH_3$.

In some embodiments, the Toxin is monomethyl auristatin E (MMAE):

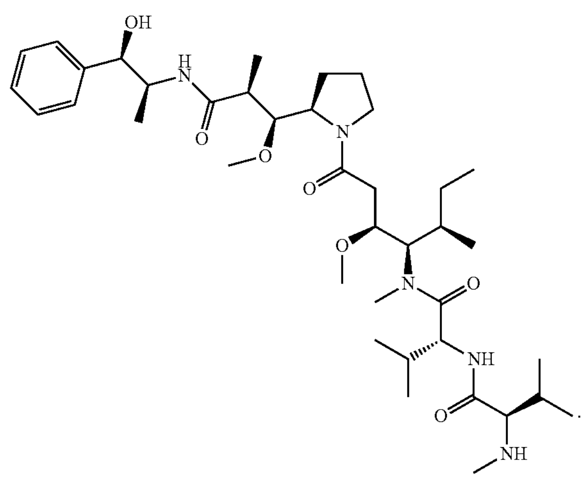 [SMILES: CC[C@@H](C)[C@H]([C@H](CC(=O)N1CCC[C@@H]1[C@@H](OC)[C@H](C)C(=O)N[C@@H](C)[C@H](O)c1ccccc1)OC)N(C)C(=O)[C@H](NC(=O)[C@H](NC)C(C)C)C(C)C]

In some embodiments, the Toxin is monomethyl auristatin F (MMAF):

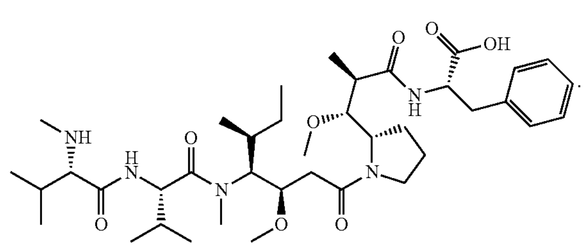 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C]

In some embodiments, the Toxin is DM1:

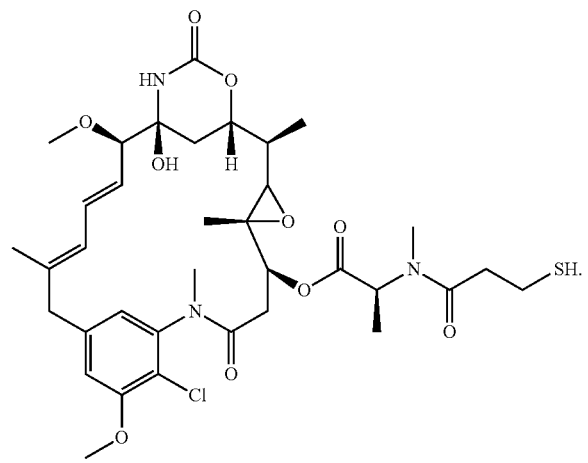 [SMILES: COc1cc2cc(c1Cl)N(C)C(=O)C[C@H](OC(=O)[C@H](C)N(C)C(=O)CCS)[C@@]1(C)OC1[C@H](C)[C@@H]1C[C@@](O)(NC(=O)O1)[C@H](OC)/C=C/C=C(\C)C2]

In some embodiments, the Toxin is DM4:

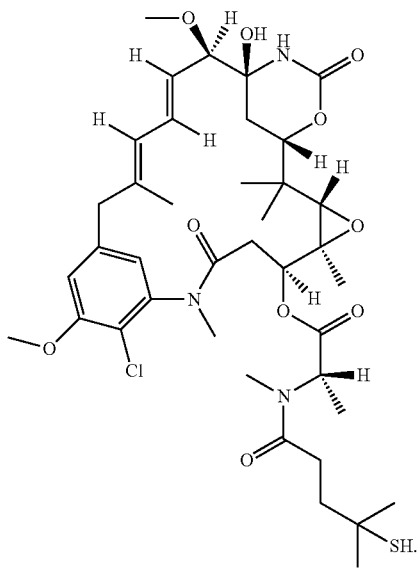 [SMILES: COc1cc2cc(c1Cl)N(C)C(=O)C[C@H](OC(=O)[C@H](C)N(C)C(=O)CCC(C)(C)S)[C@]1(C)O[C@H]1C(C)(C)[C@@H]1C[C@@](O)(NC(=O)O1)[C@H](OC)/C=C/C=C(\C)C2]

In some embodiments, the Toxin is SN38:

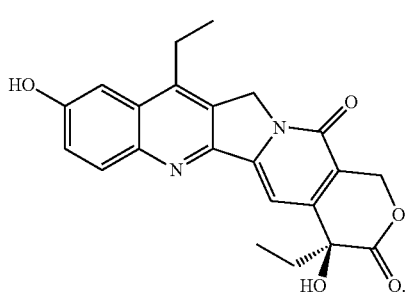 [SMILES: CCc1c2c(nc3ccc(O)cc13)-c1cc3c(c(=O)n1C2)COC(=O)[C@]3(O)CC]

In some embodiments, the Toxin is doxorubicin:

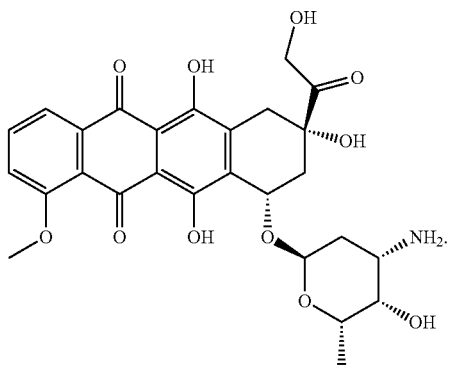 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

In some embodiments, the Toxin is a duocarmycin analog:

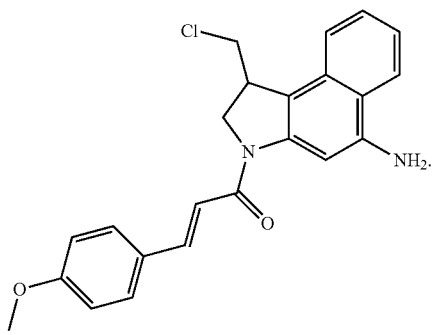 [SMILES: COc1ccc(/C=C/C(=O)N2CC(CCl)c3c2cc(N)c2ccccc32)cc1]

In some embodiments, the Toxin is monomethyl auristatin E (MMAE):

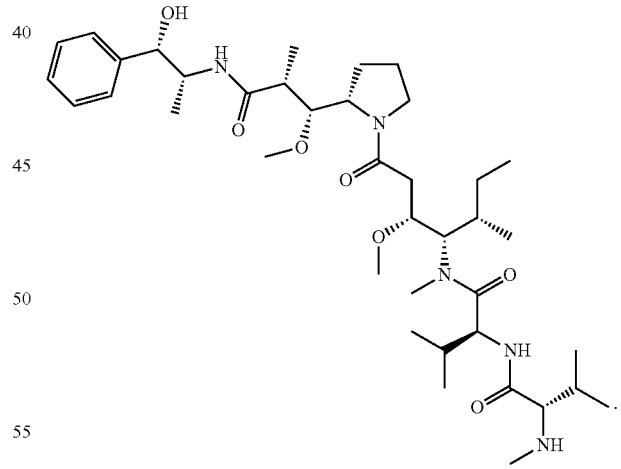

In some embodiments, the toxin moiety is selected from those depicted in Table 1, below.

In some embodiments, the toxin moiety is selected from those depicted in Table 1a, below.

In some embodiments, the toxin moiety is selected from those depicted in Table 1b, below.

Exemplary compounds of the invention are set forth in Table 1, below.

TABLE 1
Exemplary Compounds
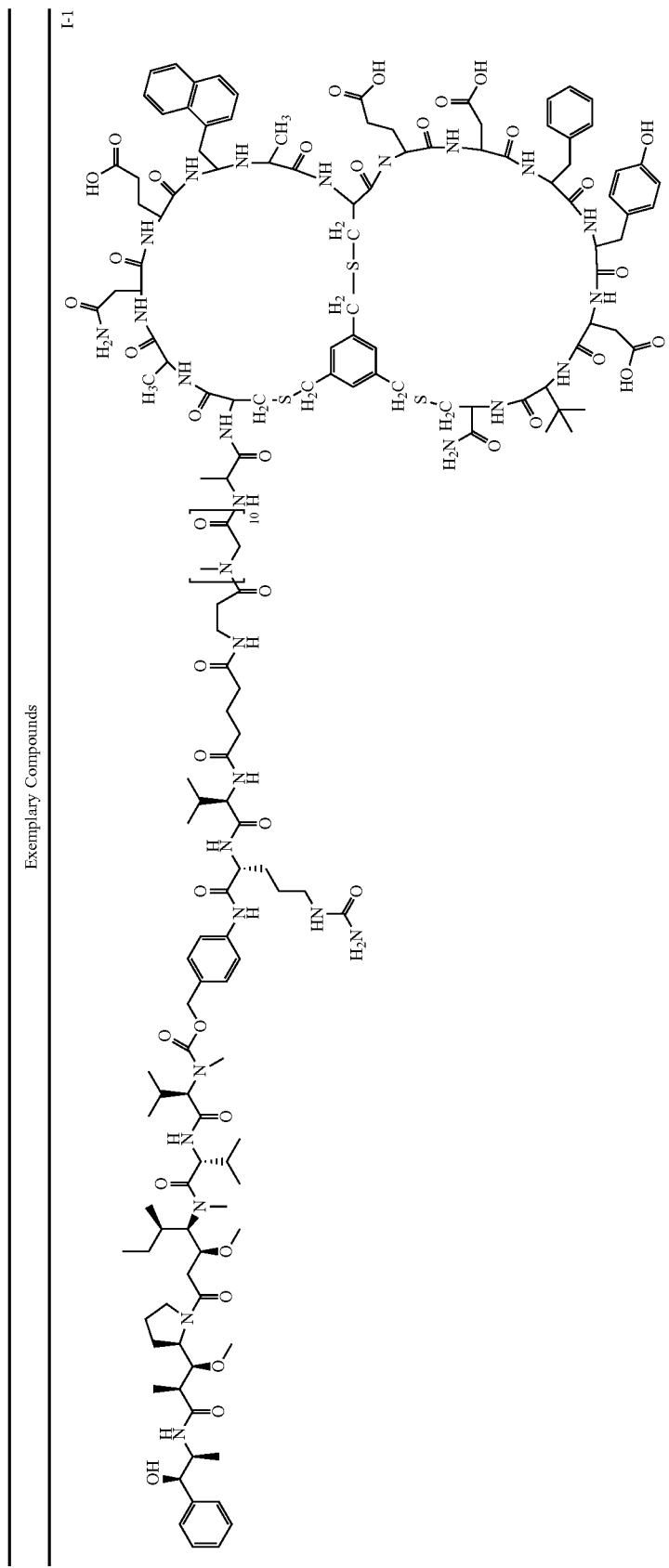
I-1

TABLE 1-continued
Exemplary Compounds
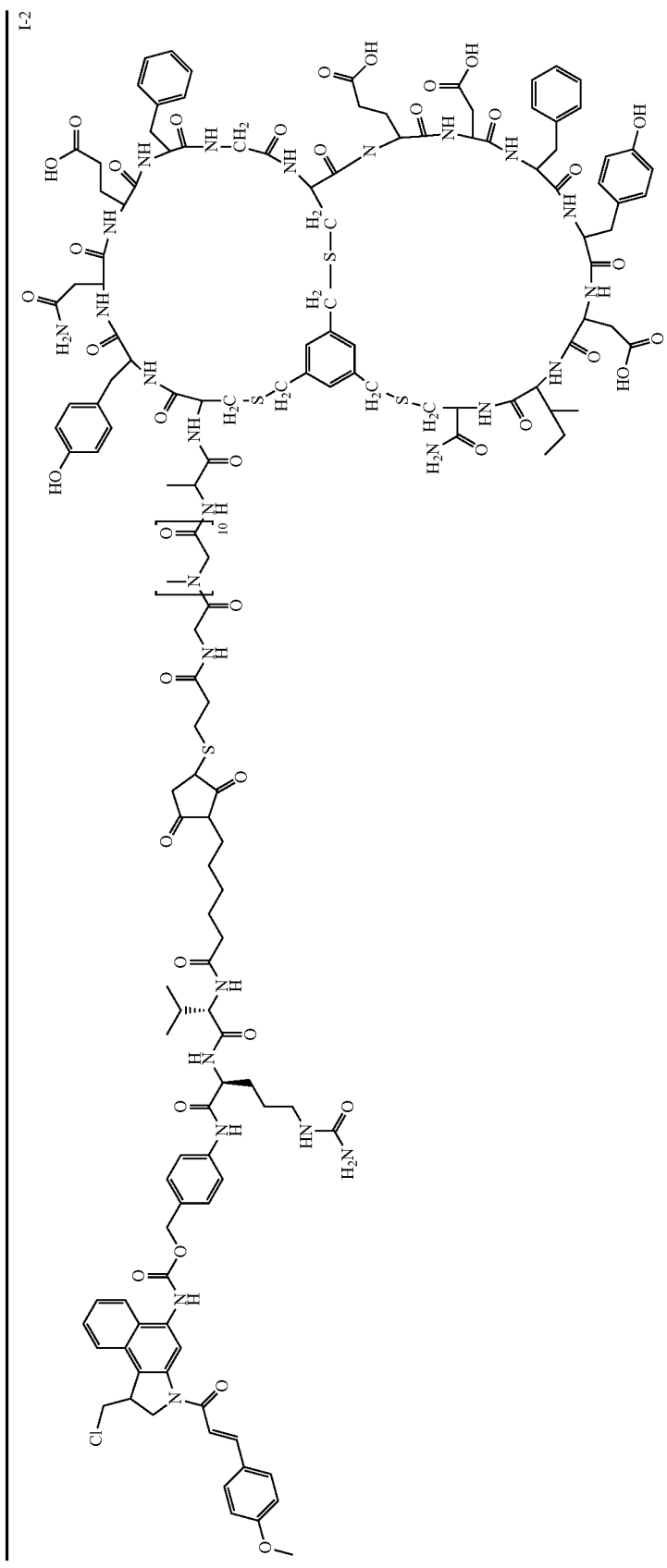
I-2

TABLE 1-continued
Exemplary Compounds
I-3
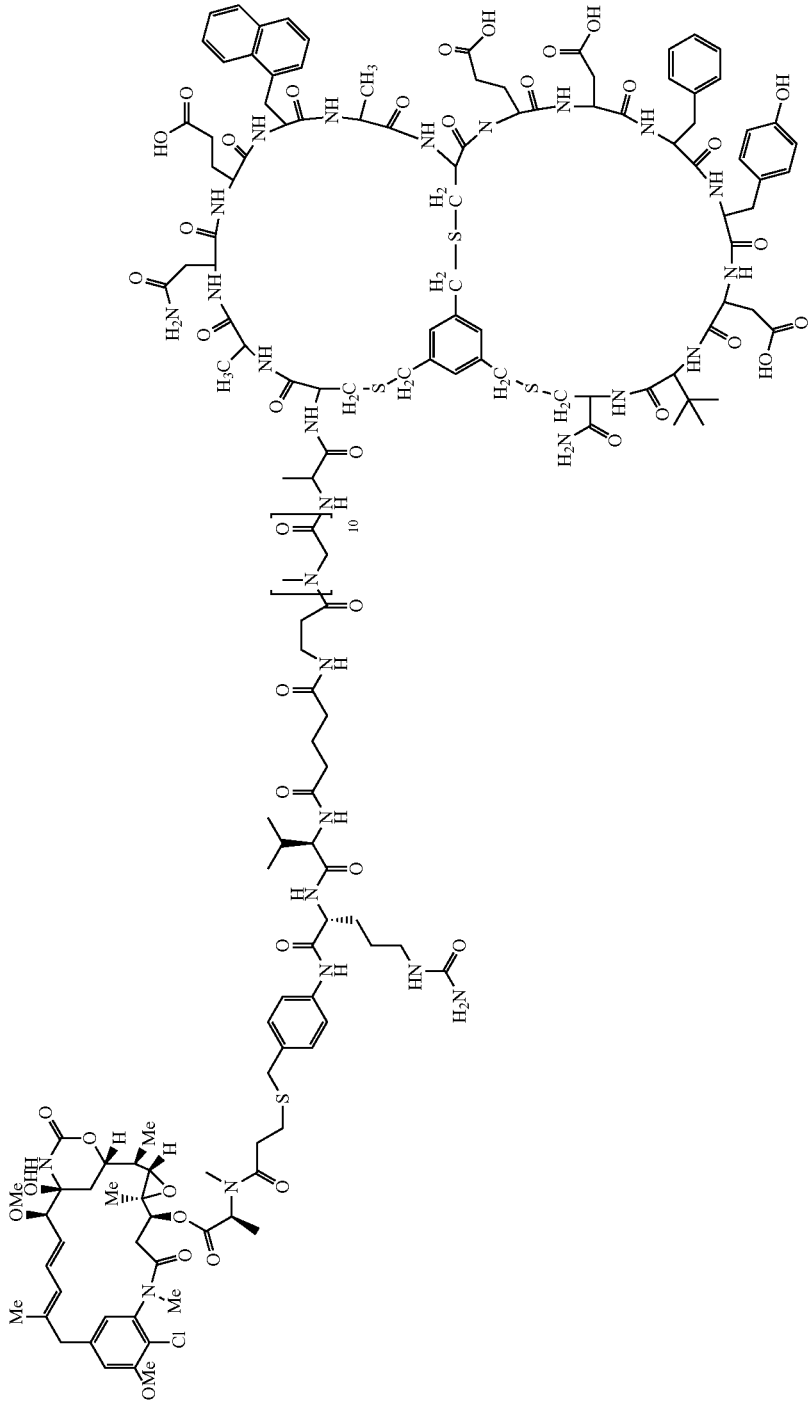

TABLE 1-continued
Exemplary Compounds
I-4
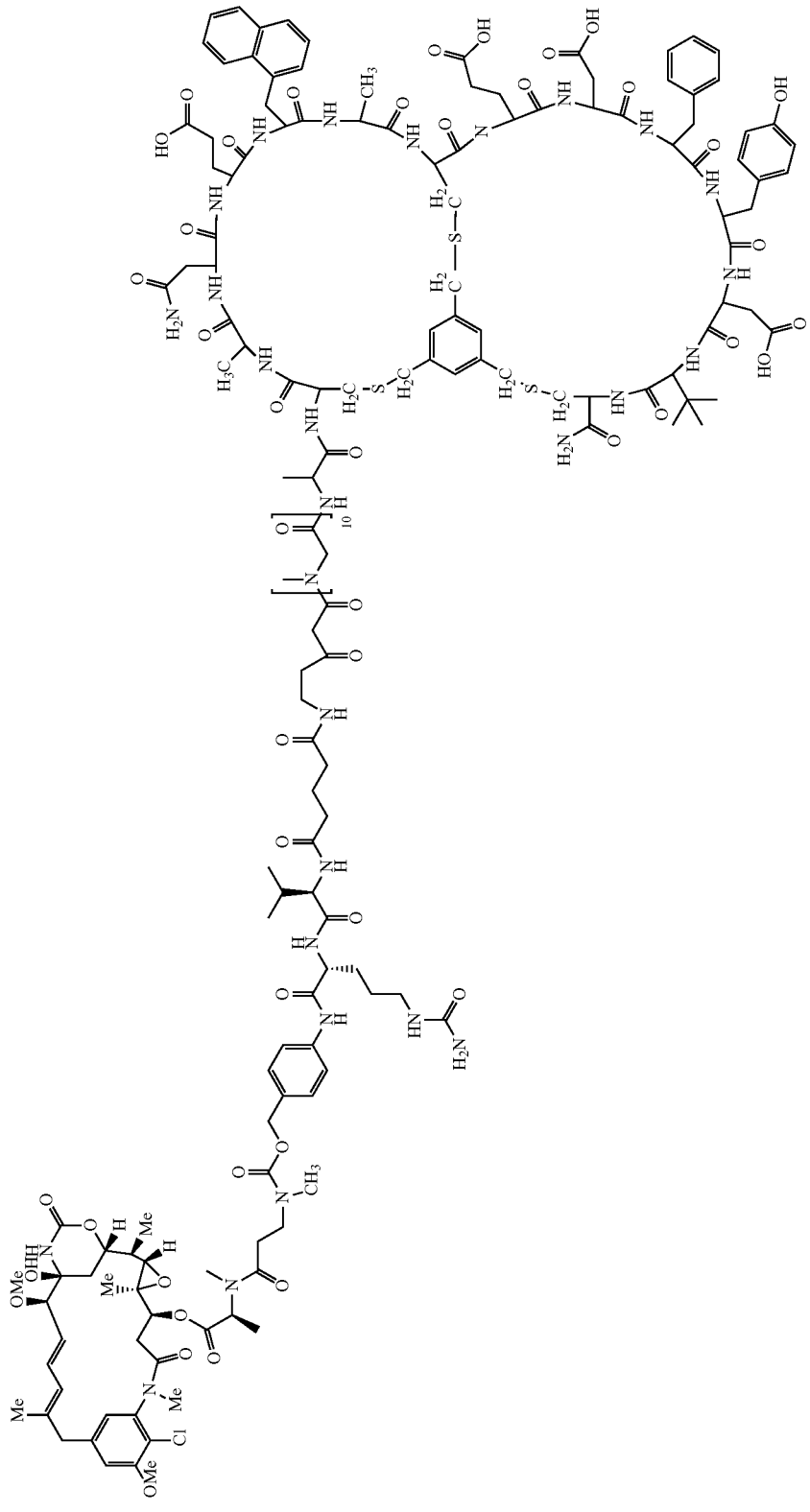

TABLE 1-continued
Exemplary Compounds
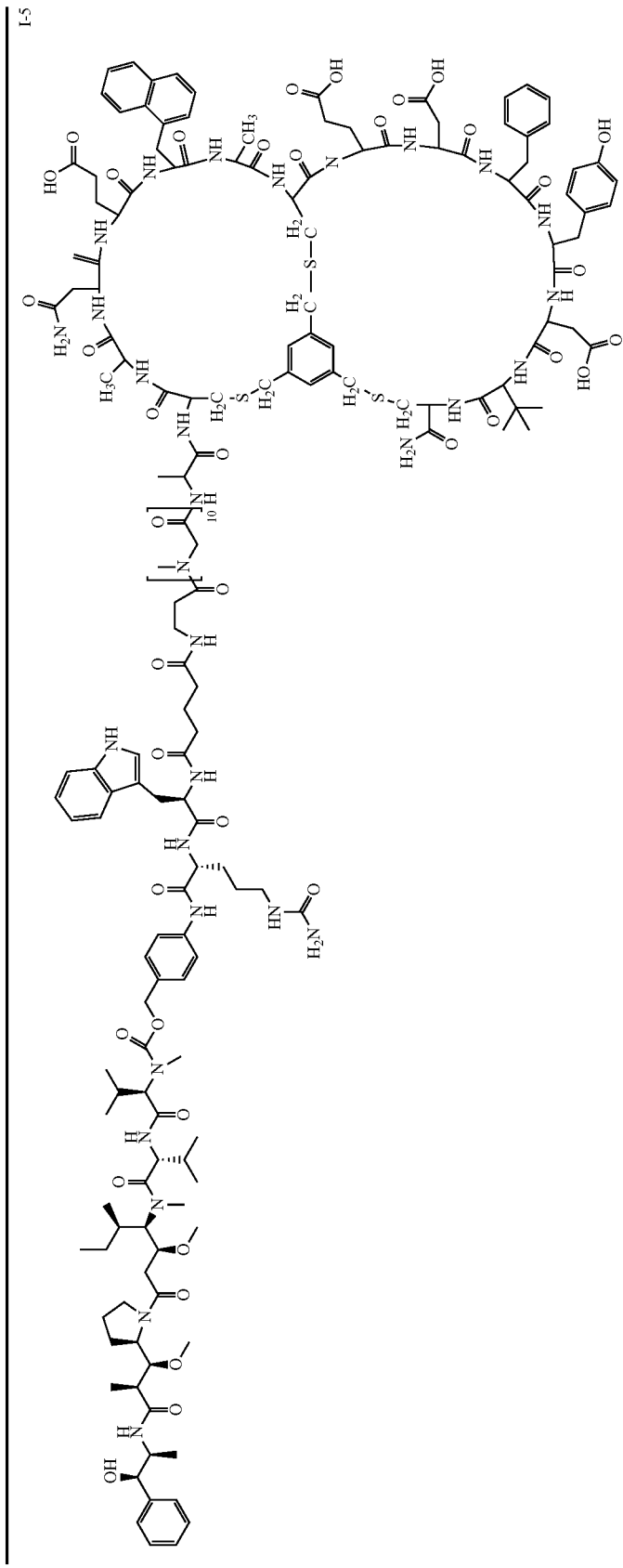
I-5

TABLE 1-continued
Exemplary Compounds
I-6
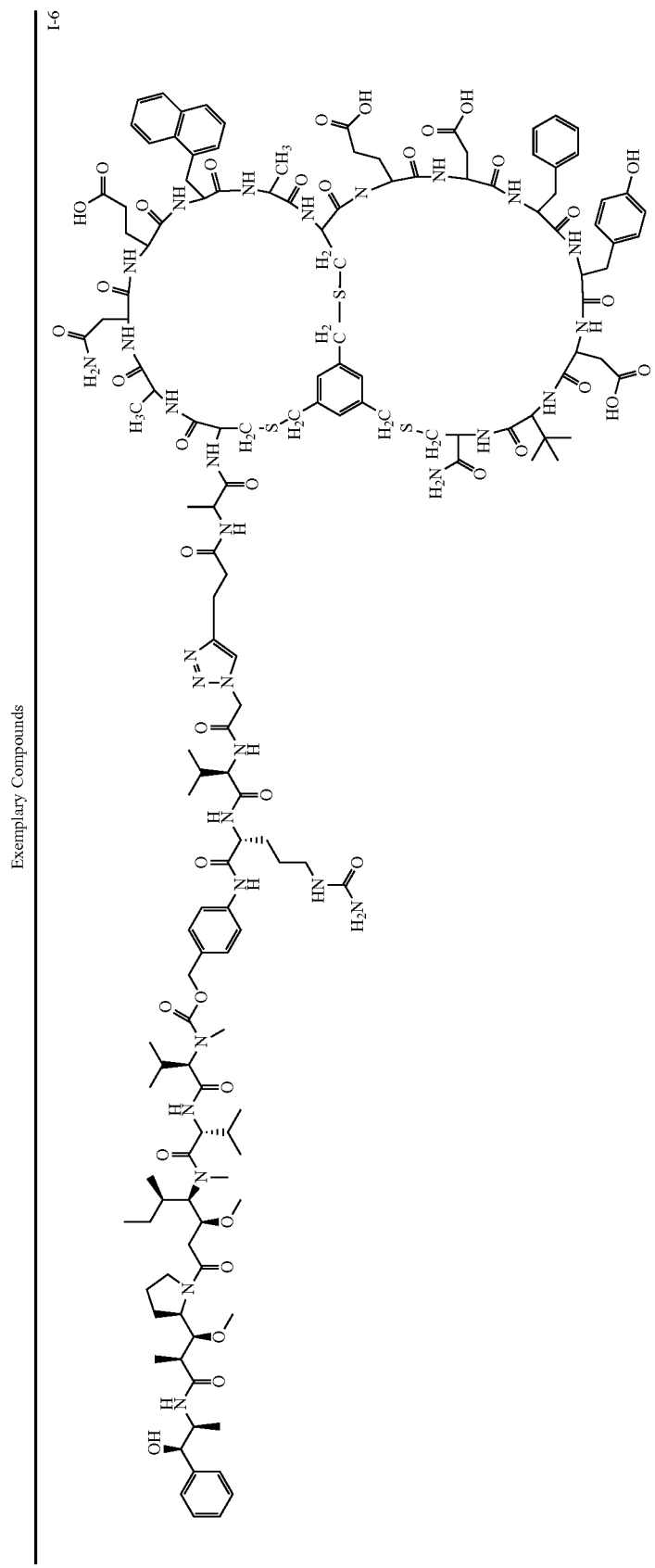

In some embodiments, the present invention provides a compound set forth in Table 1, above, or a pharmaceutically acceptable salt thereof.

Exemplary compounds of the invention are also set forth in Table 1a, below.

TABLE 1a
Exemplary Compounds
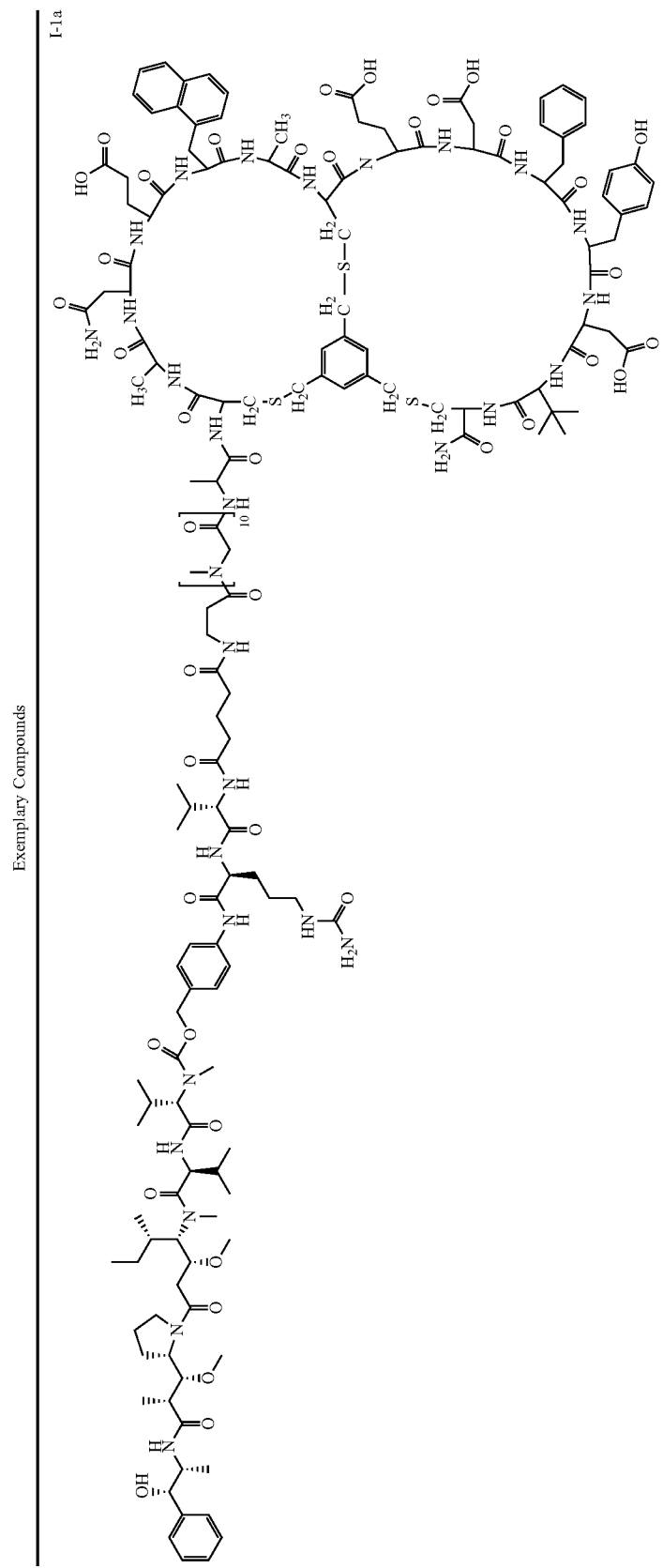
I-1a

TABLE 1a-continued
Exemplary Compounds
I-3a
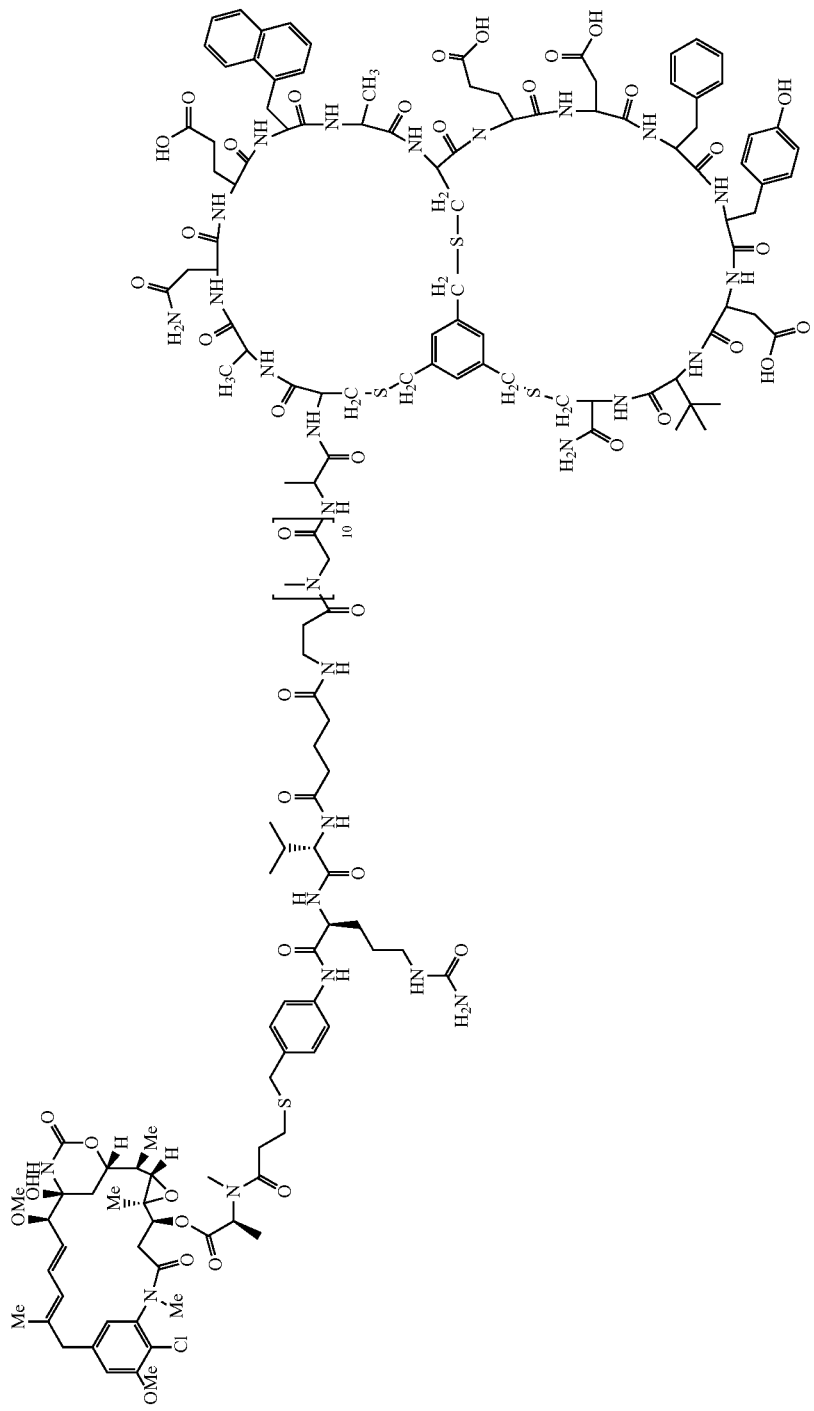

TABLE 1a-continued
Exemplary Compounds
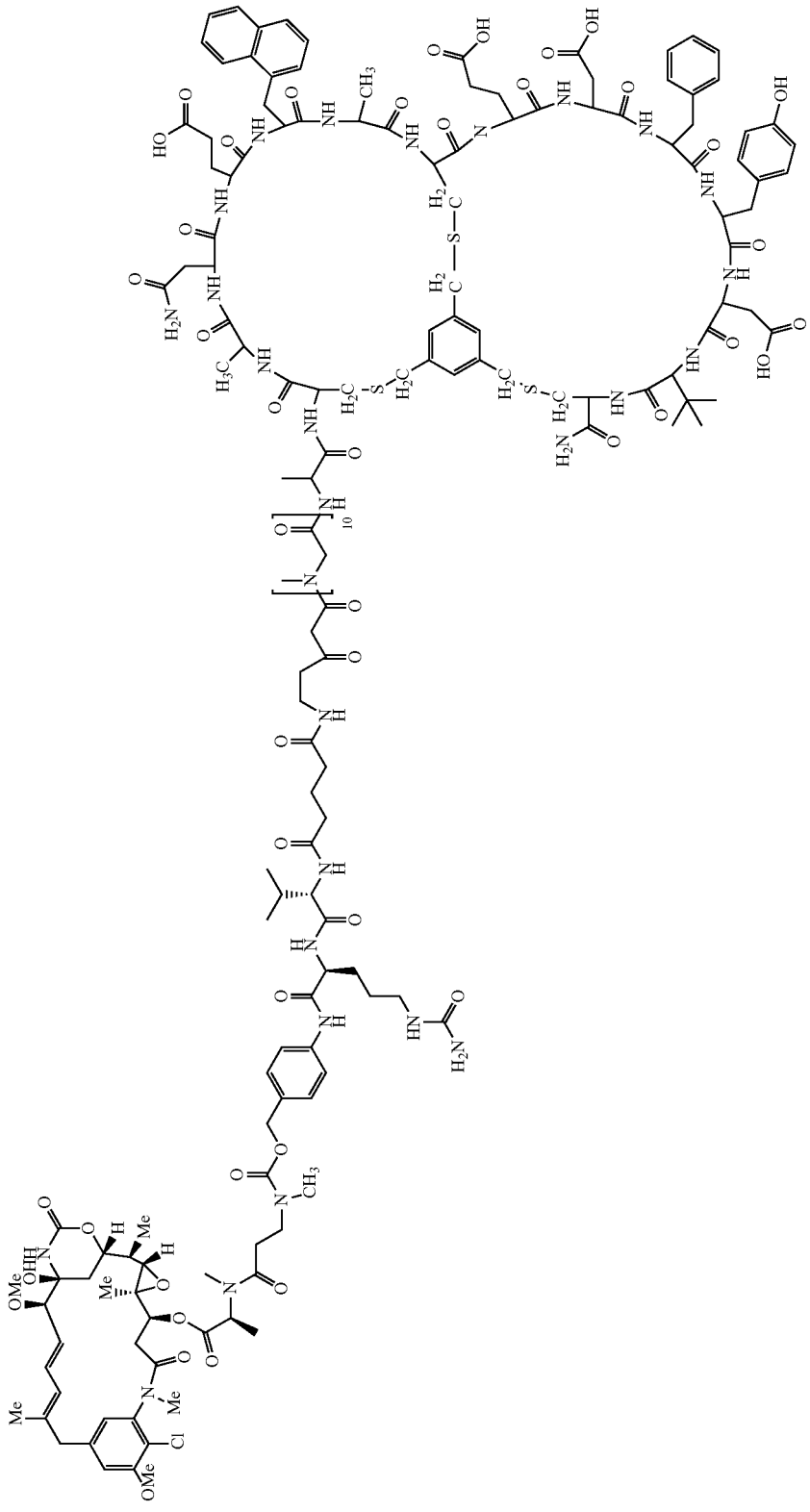
I-4a

TABLE 1a-continued
Exemplary Compounds
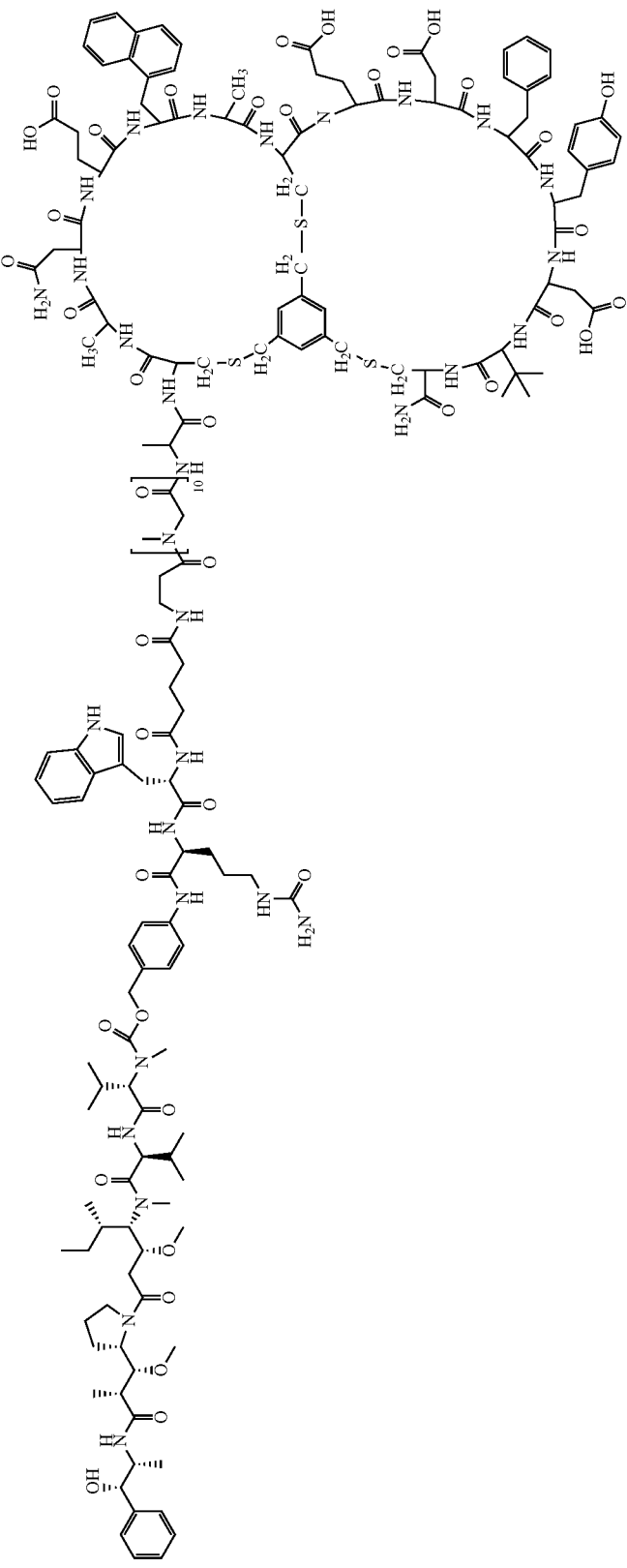
I-5a

TABLE 1a-continued
Exemplary Compounds
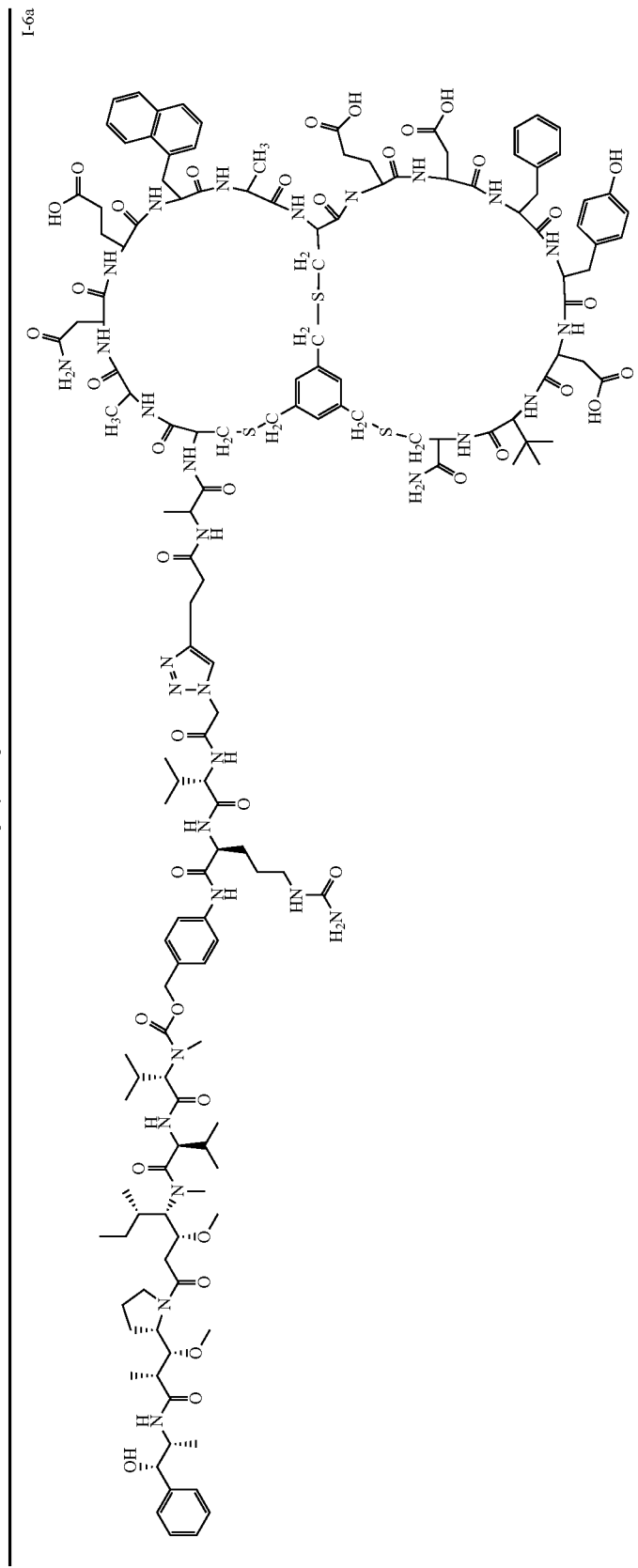
I-6a

In some embodiments, the present invention provides a compound set forth in Table 1a, above, or a pharmaceutically acceptable salt thereof.

Exemplary compounds of the invention are also set forth in Table 1b, below.

TABLE 1b
Exemplary Compounds
I-7
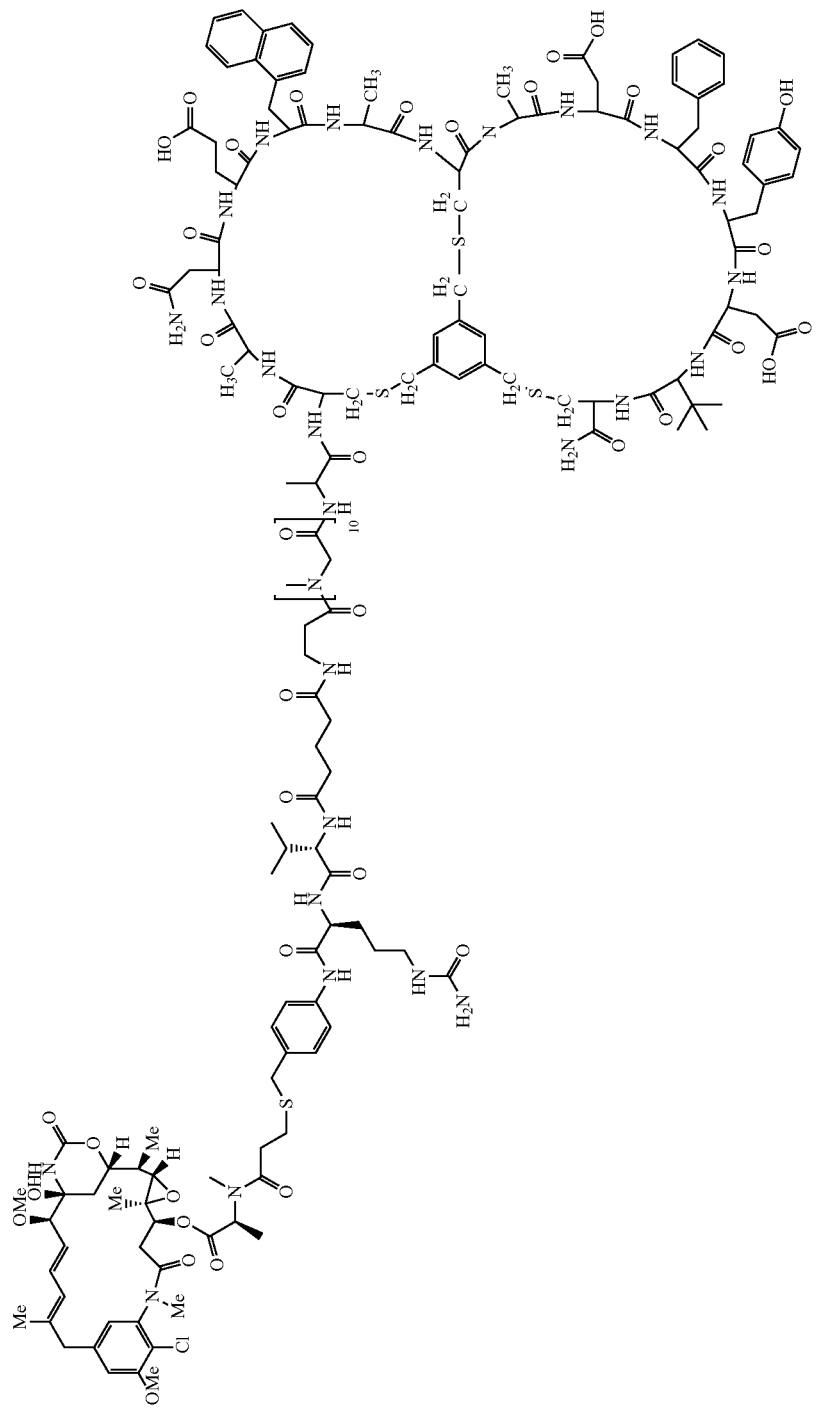

TABLE 1b-continued
Exemplary Compounds
I-8
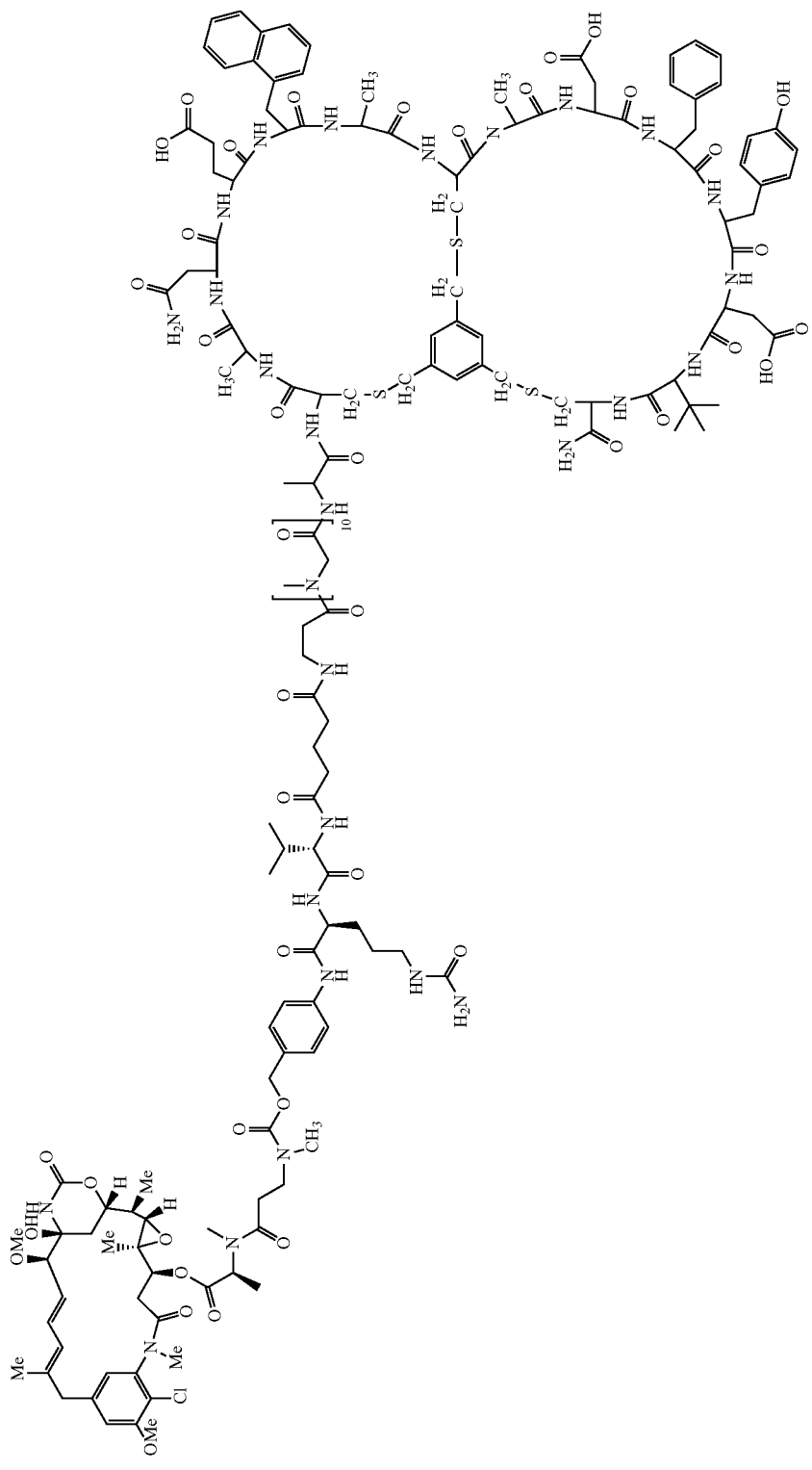

TABLE 1b-continued
Exemplary Compounds
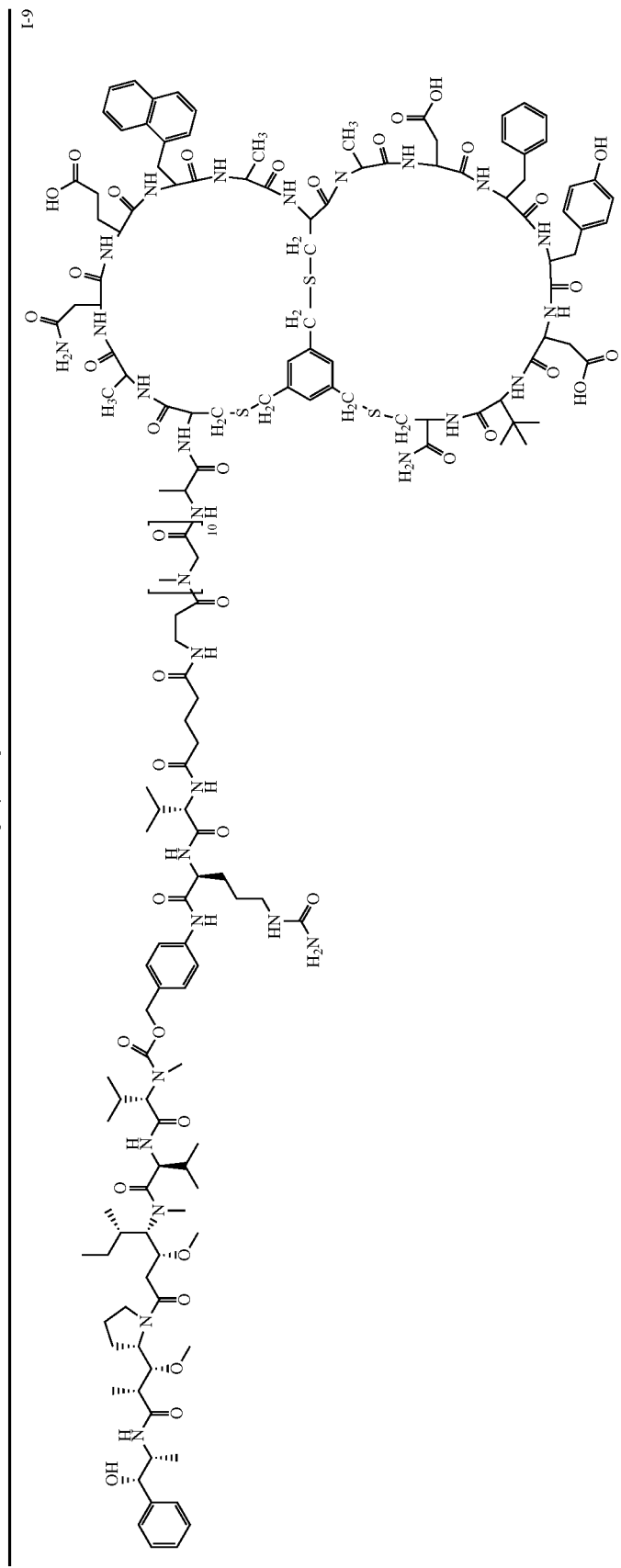
I-9

TABLE 1b-continued
Exemplary Compounds
I-10
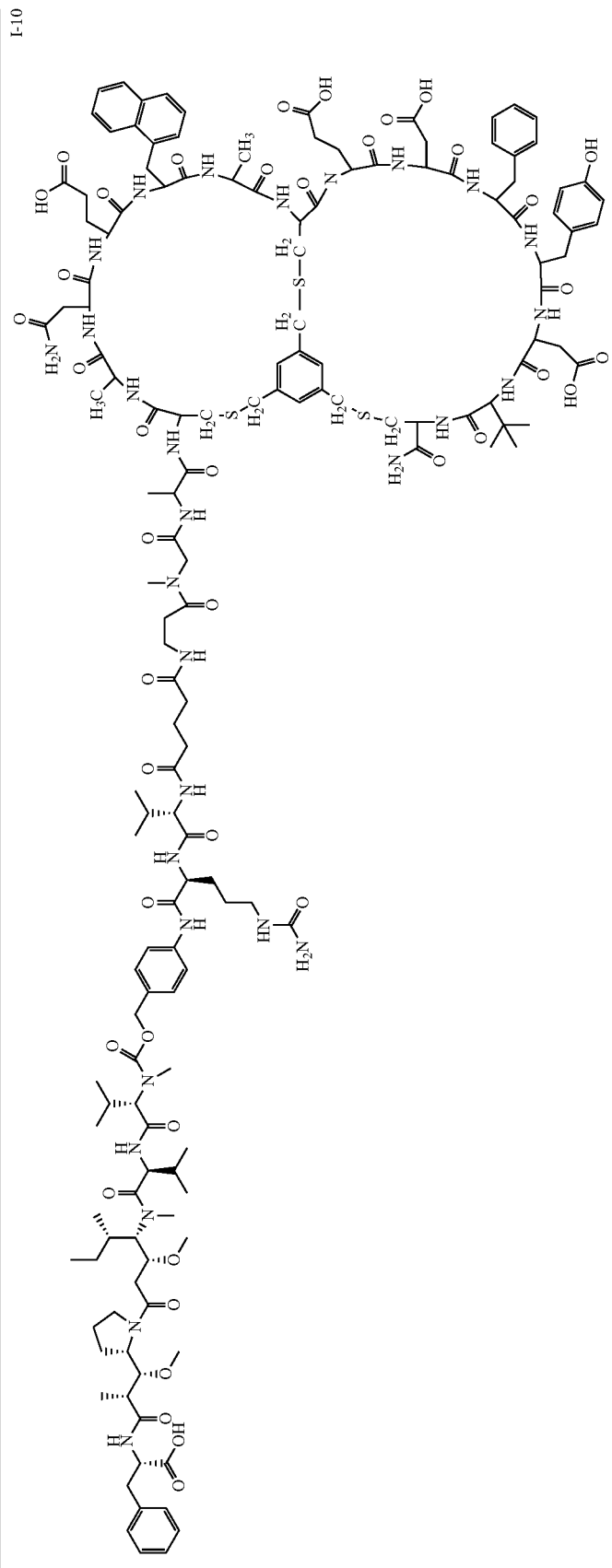

TABLE 1b-continued
Exemplary Compounds
I-11
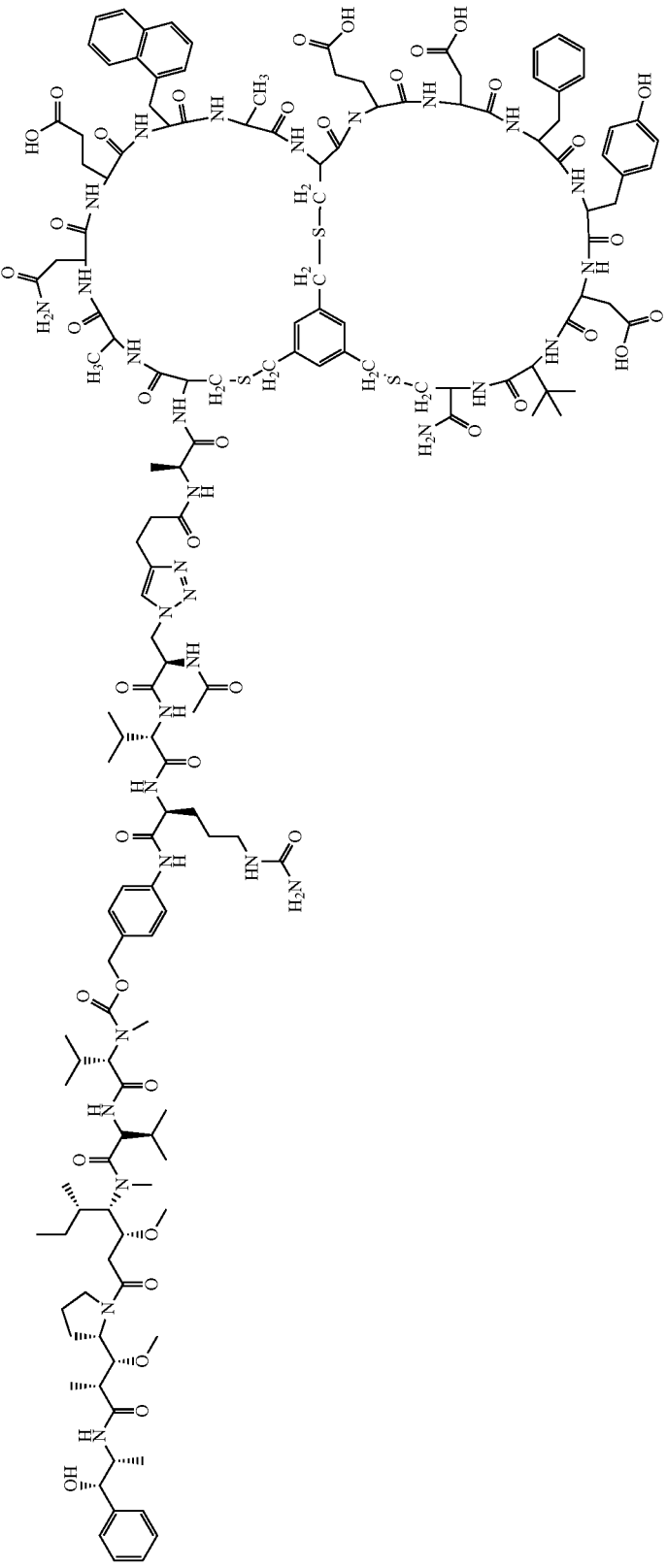

TABLE 1b-continued
Exemplary Compounds
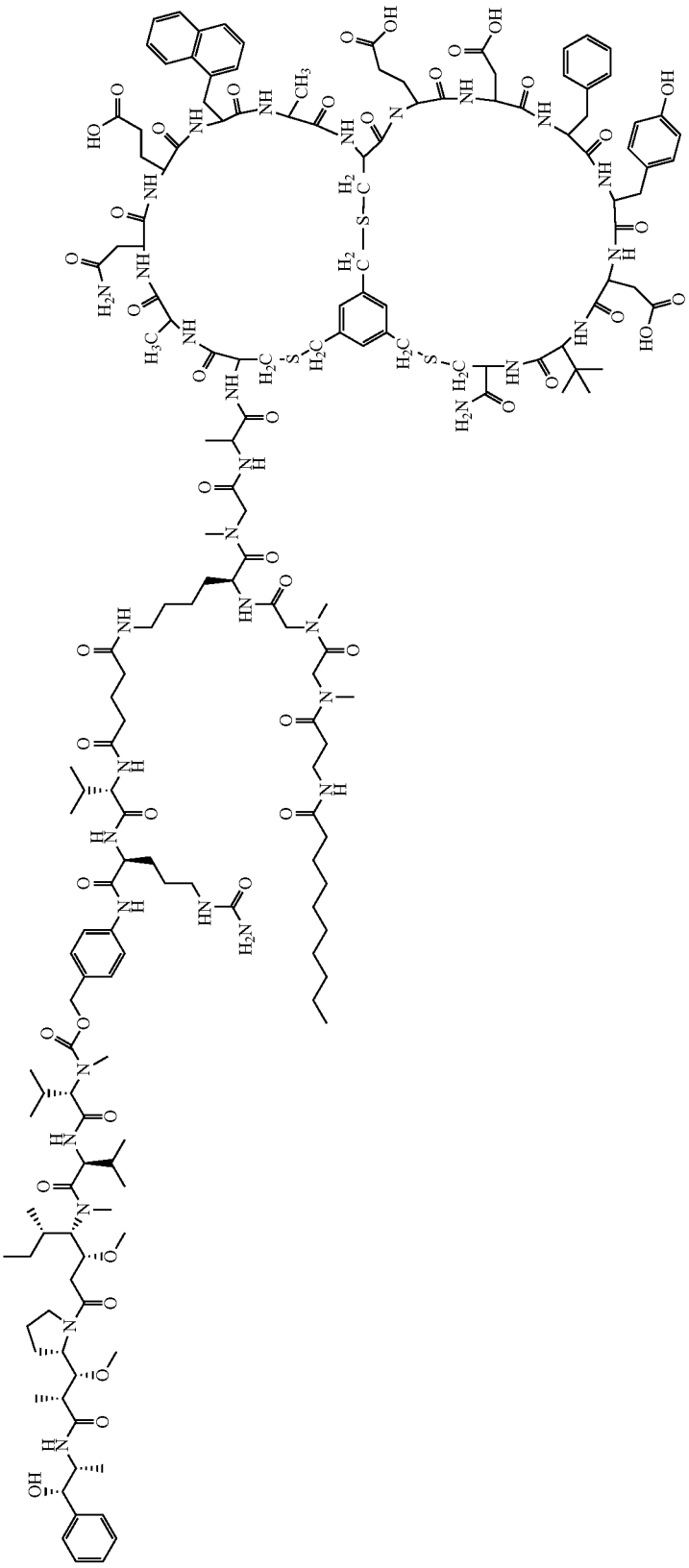
I-12

TABLE 1b-continued
Exemplary Compounds
I-13
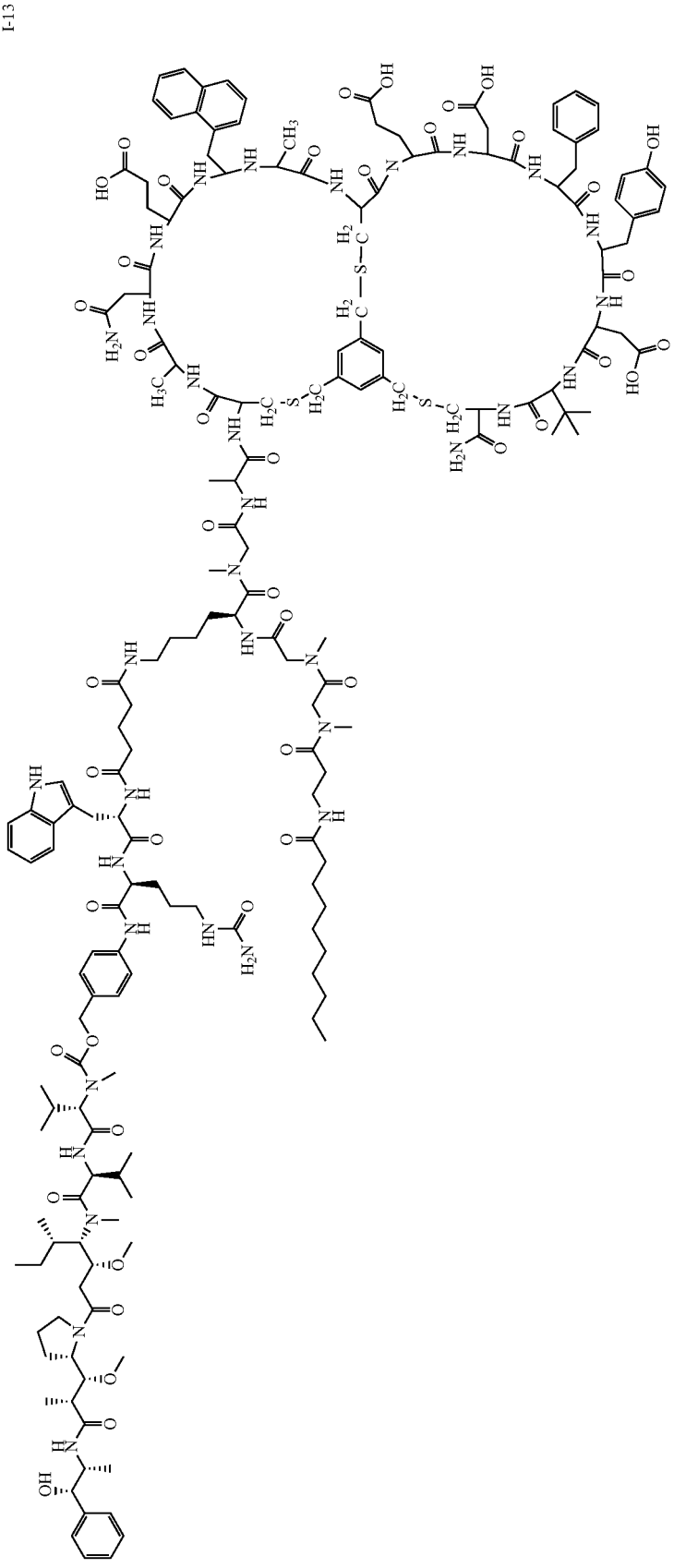

TABLE 1b-continued
Exemplary Compounds
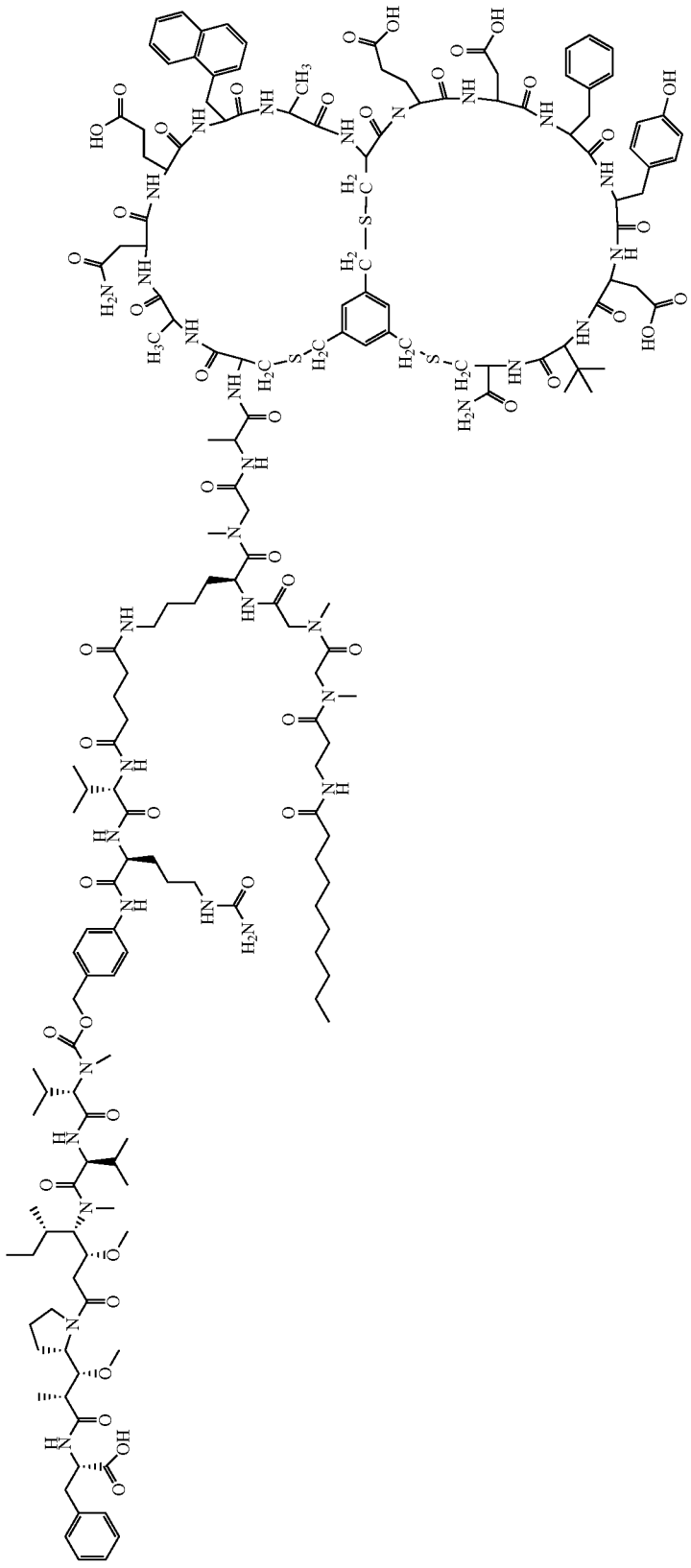
I-14

TABLE 1b-continued
Exemplary Compounds
I-15
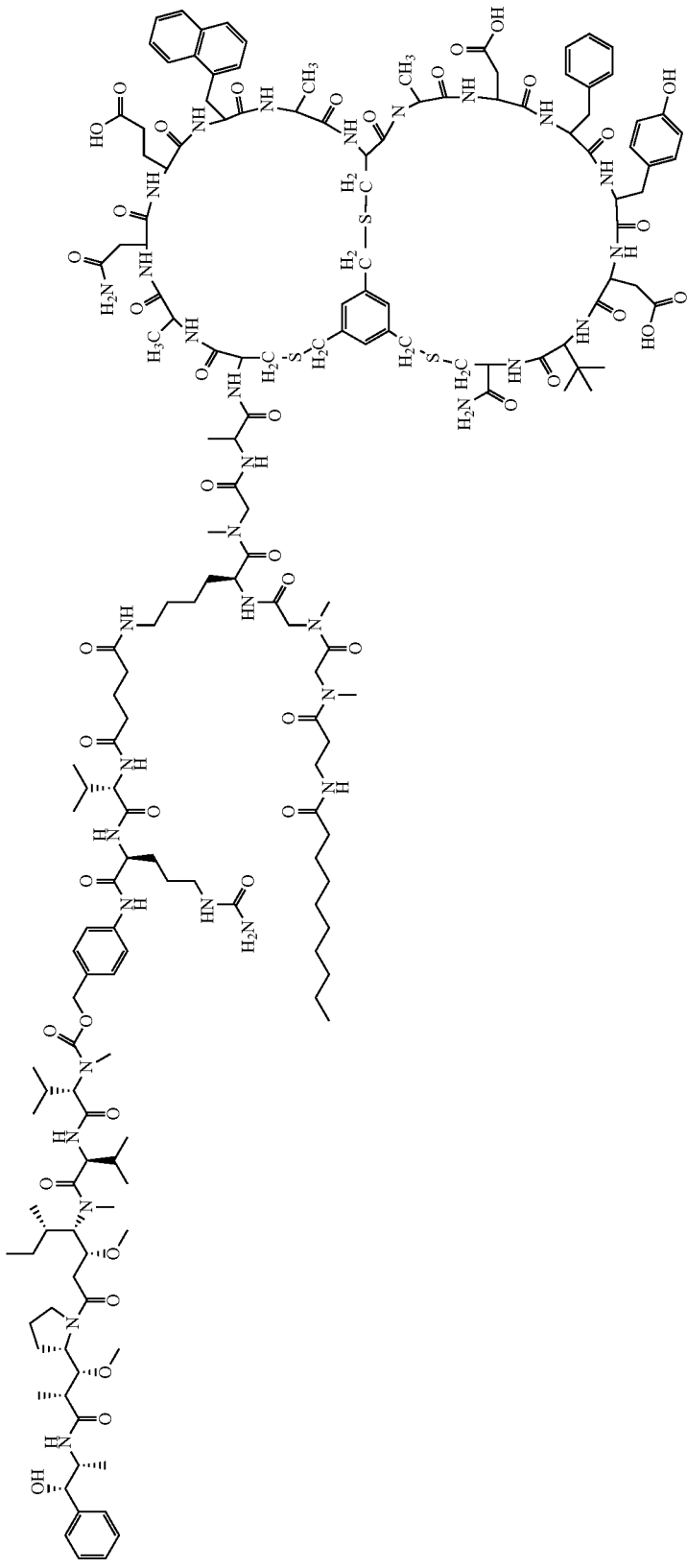
I-16
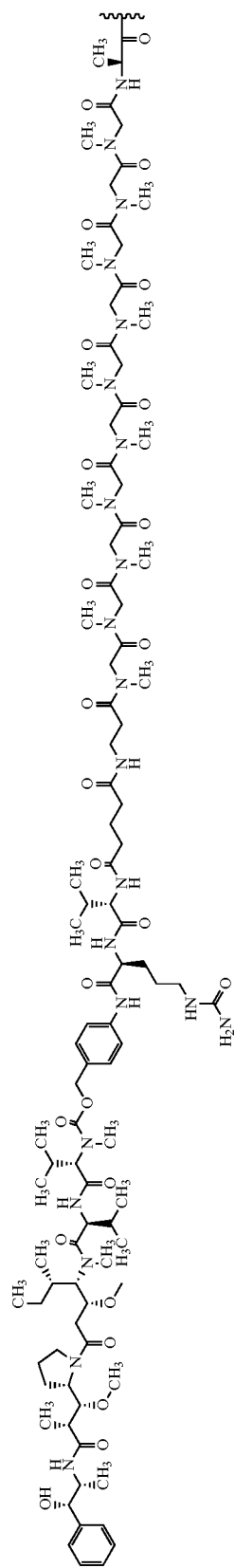

TABLE 1b-continued
Exemplary Compounds
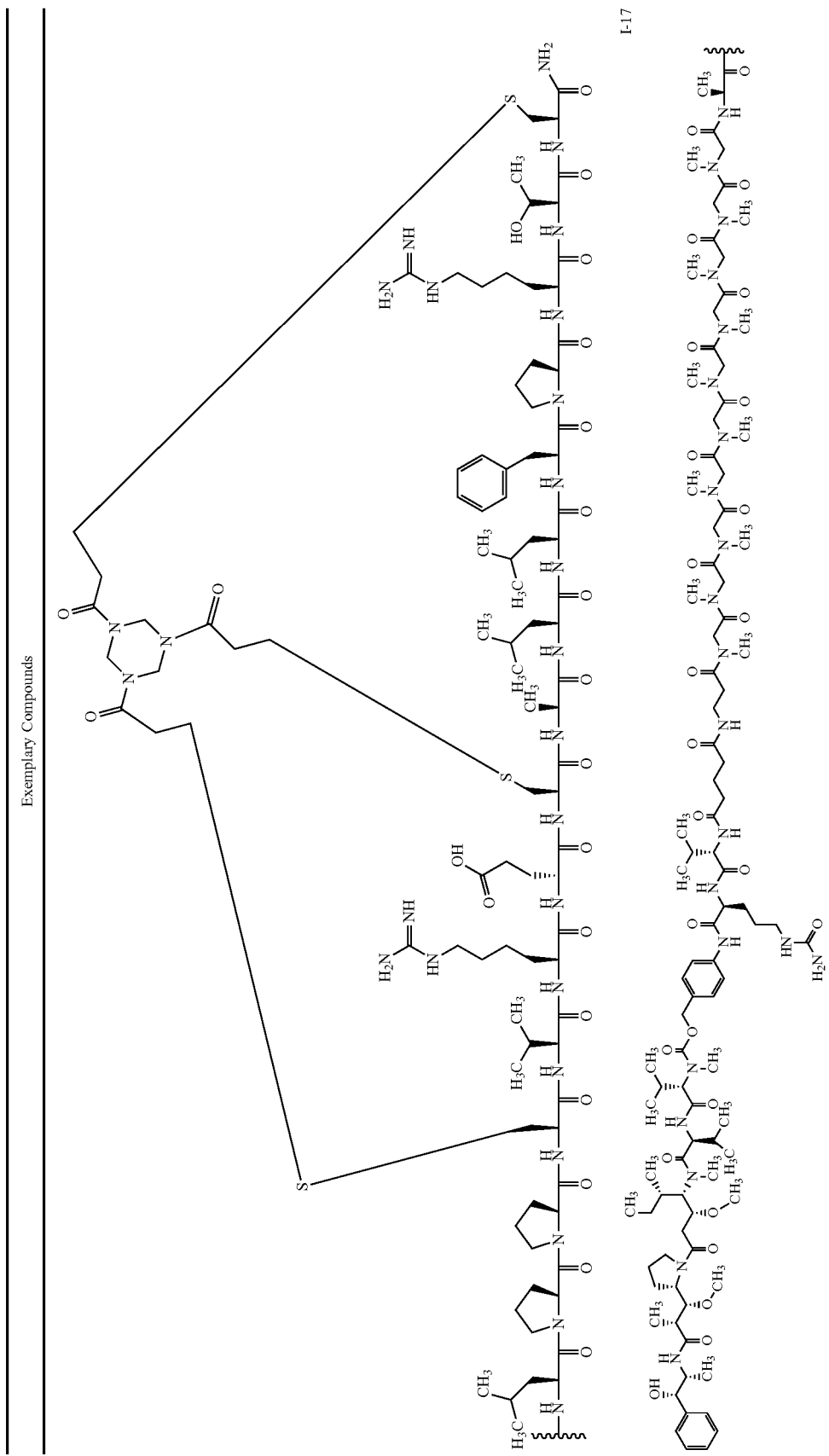
I-17

TABLE 1b-continued
Exemplary Compounds
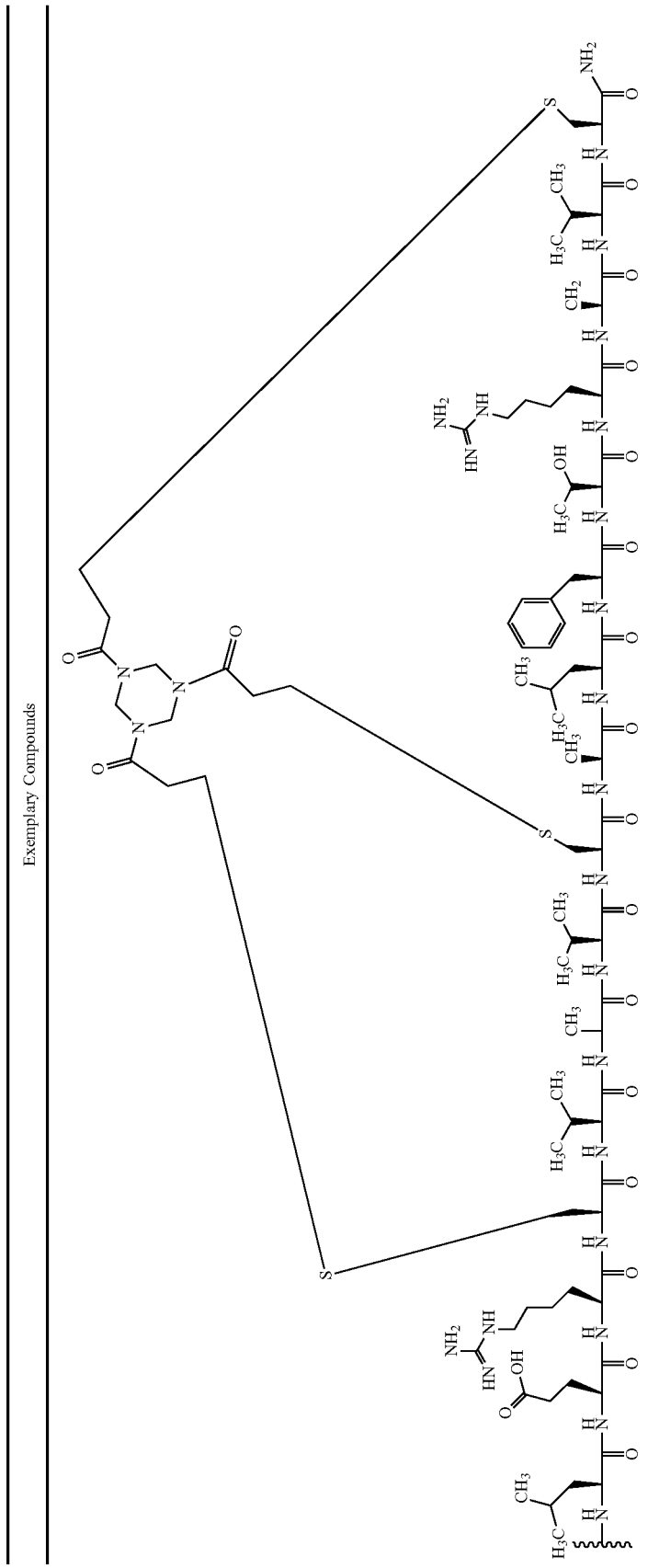

In some embodiments, the present invention provides a compound set forth in Table 1b, above, or a pharmaceutically acceptable salt thereof.

2. Pharmaceutically Acceptable Compositions

According to another embodiment, the invention provides a composition comprising a compound of the present invention, or a pharmaceutically acceptable salt thereof, and a pharmaceutically acceptable carrier, adjuvant, or vehicle.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

A compound of the present invention, or a pharmaceutically acceptable salt thereof, can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

3. Uses of Compounds and Pharmaceutically Acceptable Compositions

Compounds and compositions described herein are generally useful for treatment of cancer.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the present invention provides a method for treating cancer as described herein.

Cancer

Cancer includes, in one embodiment, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the present invention provides a method for treating a cancer that presents as a solid tumor, such as a sarcoma, carcinoma, or lymphoma, comprising the step of administering a disclosed compound, or a pharmaceutically acceptable salt thereof, to a patient in need thereof. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

The present invention further features methods and compositions for the diagnosis, prognosis and treatment of viral-associated cancers, including human immunodeficiency virus (HIV) associated solid tumors, human papilloma virus (HPV)-16 positive incurable solid tumors, and adult T-cell leukemia, which is caused by human T-cell leukemia virus type 1 (HTLV-I) and is a highly aggressive form of CD4+ T-cell leukemia characterized by clonal integration of HTLV-I in leukemic cells (See https://clinicaltrials.gov/ct2/show/study/NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.gov/ct2/show/study/NCT02488759; see also https://clinicaltrials.gov/ct2/show/study/NCT0240886; https://clinicaltrials.gov/ct2/show/NCT02426892)

In some embodiments, the present invention provides a method for treating a tumor in a patient in need thereof, comprising administering to the patient any of the compounds, salts or pharmaceutical compositions described herein. In some embodiments, the tumor comprises any of the cancers described herein. In some embodiments, the tumor comprises melanoma cancer. In some embodiments, the tumor comprises breast cancer. In some embodiments, the tumor comprises lung cancer. In some embodiments the tumor comprises small cell lung cancer (SCLC). In some embodiments the the tumor comprises non-small cell lung cancer (NSCLC).

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

The compounds and compositions, according to the method of the present invention, may be administered using any amount and any route of administration effective for treating or lessening the severity of cancer. The exact amount required will vary from subject to subject, depending on the species, age, and general condition of the subject, the severity of the disease or condition, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, the invention relates to a method of treating MT1-positive cancer in a patient comprising the step of administering to said patient a compound of the present invention, or a composition comprising said compound. In some embodiments, a cancer is as described in detail herein.

In some embodiments, the invention relates to a method of treating cancer in a patient comprising the step of administering to said patient a compound of the present invention, or a composition comprising said compound, wherein the cancer is selected from colorectal cancer, non-small cell lung cancer, breast cancer, gastric cancer, sarcoma, myeloma, nasalpharyngeal/laryngeal/oesophageal cancer, ovarian cancer, epithelial cancer, melanoma, glioma, astrocytoma, glioblastoma, neuroblastoma, mesothlioma, bladder cancer, hepatocellular carcinoma, and prostate cancer. In some embodiments, the cancer is colorectal cancer. In some embodiments, the cancer is non-small cell lung cancer. In some embodiments, the cancer is breast cancer. In some embodiments, the cancer is gastric cancer. In some embodiments, the cancer is sarcoma. In some embodiments, the cancer is myeloma. In some embodiments, the cancer is nasalpharyngeal/laryngeal/oesophageal cancer. In some embodiments, the cancer is ovarian cancer. In some embodiments, the cancer is epithelial cancer. In some embodiments, the cancer is melanoma. In some embodiments, the cancer is glioma. In some embodiments, the cancer is astrocytoma. In some embodiments, the cancer is glioblastoma. In some embodiments, the cancer is neuroblastoma. In some embodiments, the cancer is mesothelioma. In some embodiments, the cancer is bladder cancer. In some embodiments, the cancer is hepatocellular carcinoma. In some embodiments, the cancer is prostate cancer.

In some embodiments, the cancer is triple negative breast cancer. In some embodiments, the cancer is Her2 positive breast cancer. In some embodiments, the cancer is lung adenocarcinoma. In some embodiments, the cancer is lung squamous cell carcinoma. In some embodiments, the cancer is fibrosarcoma. In some embodiments, the cancer is leiomyosarcoma. In some embodiments, the cancer is rhabdomyosarcoma. In some embodiments, the cancer is Osteosarcoma. In some embodiments, the cancer is esophageal squamous cell carcinoma. In some embodiments, the cancer is intestinal adenocarcinoma. In some embodiments, the cancer is hepatocellular carcinoma. In some embodiments, the cancer is uterine squamous cell carcinoma.

Co-Administration of Additional Therapeutic Agents

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

In some embodiments, the additional therapeutic agent is selected from an immunostimulatory therapeutic compound. In some embodiments, the immunostimulatory therapeutic compound is selected from elotuzumab, mifamurtide, an agonist or activator of a toll-like receptor, or an activator of RORγt.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, an immunostimulatory therapeutic compound, and an immune checkpoint inhibitor.

Other checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Other checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Other checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Other checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Other checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Other checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Other checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Other checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Other checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Other checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Other checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

In another aspect, the present invention provides a method of treating cancer in a patient in need thereof, wherein said method comprises administering to said patient a compound disclosed herein or a pharmaceutically acceptable salt thereof in combination with one or more additional therapeutic agents selected from an indoleamine (2,3)-dioxygenase (IDO) inhibitor, a Poly ADP ribose polymerase (PARP) inhibitor, a histone deacetylase (HDAC) inhibitor, a CDK4/CDK6 inhibitor, or a phosphatidylinositol 3 kinase (PI3K) inhibitor.

In some embodiments, the IDO inhibitor is selected from epacadostat, indoximod, capmanitib, GDC-0919, PF-06840003, BMS:F001287, Phy906/KD108, or an enzyme that breaks down kynurenine.

In some embodiments, the PARP inhibitor is selected from olaparib, rucaparib, or niraparib.

In some embodiments, the HDAC inhibitor is selected from vorinostat, romidepsin, panobinostat, belinostat, entinostat, or chidamide.

In some embodiments, the CDK 4/6 inhibitor is selected from palbociclib, ribociclib, abemaciclib or trilaciclib.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, a second therapeutic agent selected from an indoleamine (2,3)-dioxygenase (IDO) inhibitor, a Poly ADP ribose polymerase (PARP) inhibitor, a histone deacetylase (HDAC) inhibitor, a CDK4/CDK6 inhibitor, or a phosphatidylinositol 3 kinase (PI3K) inhibitor, and a third therapeutic agent selected from an immune checkpoint inhibitor. In some embodiments, the immune checkpoint inhibitor is selected from nivolumab, pembrolizumab, ipilimumab, avelumab, durvalumab, atezolizumab, or pidilizumab.

Another immunostimulatory therapeutic that may be used in the present invention is recombinant human interleukin 15 (rhIL-15). rhIL-15 has been tested in the clinic as a therapy for melanoma and renal cell carcinoma (NCT01021059 and NCT01369888) and leukemias (NCT02689453). Another immunostimulatory therapeutic that may be used in the present invention is recombinant human interleukin 12 (rhIL-12). Another suitable IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). Recombinant human interleukin 12 (rhIL-12) has been tested in the clinic for many oncological indications, for example, as a therapy for lymphoma (NM-IL-12, Neumedicines, Inc.), (NCT02544724 and NCT02542124).

In some embodiments, the PI3K inhibitor is selected from idelalisib, alpelisib, taselisib, pictilisib, copanlisib, duvelisib, PQR309, or TGR1202.

In another aspect, the present invention provides a method of treating cancer in a patient in need thereof, wherein said method comprises administering to said patient a compound disclosed herein or a pharmaceutically acceptable salt thereof in combination with one or more additional therapeutic agents selected from a platinum-based therapeutic, a taxane, a nucleoside inhibitor, or a therapeutic agent that interferes with normal DNA synthesis, protein synthesis, cell replication, or will otherwise inhibit rapidly proliferating cells.

In some embodiments, the platinum-based therapeutic is selected from cisplatin, carboplatin, oxaliplatin, nedaplatin, picoplatin, or satraplatin.

In some embodiments, the taxane is selected from paclitaxel, docetaxel, albumin-bound paclitaxel, cabazitaxel, or SID530.

In some embodiments, the therapeutic agent that interferes with normal DNA synthesis, protein synthesis, cell replication, or will otherwise interfere with the replication of rapidly proliferating cells is selected from trabectedin, mechlorethamine, vincristine, temozolomide, cytarabine, lomustine, azacitidine, omacetaxine mepesuccinate, asparaginase *Erwinia chrysanthemi*, eribulin mesylate, capacetrine, bendamustine, ixabepilone, nelarabine, clorafabine, trifluridine, or tipiracil.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, a second therapeutic agent selected from a platinum-based therapeutic, a taxane, a nucleoside inhibitor, or a therapeutic agent that interferes with normal DNA synthesis, protein synthesis, cell replication, or will otherwise inhibit rapidly proliferating cells, and a third therapeutic agent selected from an immune checkpoint inhibitor.

In some embodiments, the immune checkpoint inhibitor is selected from nivolumab, pembrolizumab, ipilimumab, avelumab, durvalumab, atezolizumab, or pidilizumab.

In some embodiments, any one of the foregoing methods further comprises the step of obtaining a biological sample from the patient and measuring the amount of a disease-related biomarker.

In some embodiments, the biological sample is a blood sample.

In some embodiments, the disease-related biomarker is selected from circulating CD8+ T cells or the ratio of CD8+ T cells:Treg cells.

In one aspect, the present invention provides a method of treating an advanced cancer, comprising administering a compound disclosed herein or a pharmaceutically acceptable salt thereof or pharmaceutical composition thereof, either as a single agent (monotherapy), or in combination with a chemotherapeutic, a targeted therapeutic, such as a kinase inhibitor, and/or an immunomodulatory therapy, such as an immune checkpoint inhibitor. In some embodiments, the immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the additional therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); B cr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaecuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547, 632 (Pfizer); foretinib (Exelexis, GlaxoSmithKline); quizartinib (Daiichi Sankyo) and motesanib (Amgen/Takeda).

In some embodiments, the additional therapeutic agent is an mTOR inhibitor, which inhibits cell proliferation, angiogenesis and glucose uptake. Approved mTOR inhibitors useful in the present invention include everolimus (Afinitor®, Novartis); temsirolimus (Torisel®, Pfizer); and sirolimus (Rapamune®, Pfizer).

In some embodiments, the additional therapeutic agent is a Poly ADP ribose polymerase (PARP) inhibitor. Approved PARP inhibitors useful in the present invention include olaparib (Lynparza®, AstraZeneca); rucaparib (Rubraca®, Clovis Oncology); and niraparib (Zejula®, Tesaro). Other PARP inhibitors being studied which may be used in the present invention include talazoparib (MDV3800/BMN 673/LT00673, Medivation/Pfizer/Biomarin); veliparib (ABT-888, AbbVie); and BGB-290 (BeiGene, Inc.).

In some embodiments, the additional therapeutic agent is a phosphatidylinositol 3 kinase (PI3K) inhibitor. Approved PI3K inhibitors useful in the present invention include idelalisib (Zydelig®, Gilead). Other PI3K inhibitors being studied which may be used in the present invention include alpelisib (BYL719, Novartis); taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, the additional therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In some embodiments, the additional therapeutic agent is a histone deacetylase (HDAC) inhibitor. Approved HDAC inhibitors useful in the present invention include vorinostat (Zolinza®, Merck); romidepsin (Istodax®, Celgene); panobinostat (Farydak®, Novartis); and belinostat (Beleodaq®, Spectrum Pharmaceuticals). Other HDAC inhibitors being studied which may be used in the present invention include entinostat (SNDX-275, Syndax Pharmaceuticals) (NCT00866333); and chidamide (Epidaza®, HBI-8000, Chipscreen Biosciences, China).

In some embodiments, the additional therapeutic agent is a CDK inhibitor, such as a CDK 4/6 inhibitor. Approved CDK 4/6 inhibitors useful in the present invention include palbociclib (Ibrance®, Pfizer); and ribociclib (Kisqali®, Novartis). Other CDK 4/6 inhibitors being studied which may be used in the present invention include abemaciclib (Ly2835219, Eli Lilly); and trilaciclib (G1T28, G1 Therapeutics).

In some embodiments, the additional therapeutic agent is an indoleamine (2,3)-dioxygenase (IDO) inhibitor. IDO inhibitors being studied which may be used in the present invention include epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); and an enzyme that breaks down kynurenine (Kynase, Kyn Therapeutics).

In some embodiments, the additional therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In some embodiments, the additional therapeutic agent is an aromatase inhibitor. Approved aromatase inhibitors which may be used in the present invention include exemestane (Aromasin®, Pfizer); anastazole (Arimidex®, AstraZeneca) and letrozole (Femara®, Novartis).

In some embodiments, the additional therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, the additional therapeutic agent is a folic acid inhibitor. Approved folic acid inhibitors useful in the present invention include pemetrexed (Alimta®, Eli Lilly).

In some embodiments, the additional therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, the additional therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, the additional therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, the additional therapeutic agent is a glutaminase inhibitor. Glutaminase inhibitors being studied which may be used in the present invention include CB-839 (Calithera Biosciences).

In some embodiments, the additional therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, the additional therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, the additional therapeutic agent is a nucleoside inhibitor, or other therapeutic that interfere with normal DNA synthesis, protein synthesis, cell replication, or will otherwise inhibit rapidly proliferating cells. Such nucleoside inhibitors or other therapeutics include trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, the additional therapeutic agent is a platinum-based therapeutic, also referred to as platins. Platins cause cross-linking of DNA, such that they inhibit DNA repair and/or DNA synthesis, mostly in rapidly reproducing cells, such as cancer cells. Approved platinum-based therapeutics which may be used in the present invention include cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); and nedaplatin (Aqupla®, Shionogi). Other platinum-based therapeutics which have undergone clinical testing and may be used in the present invention include picoplatin (Poniard Pharmaceuticals); and satraplatin (JM-216, Agennix).

In some embodiments, the additional therapeutic agent is a taxane compound, which causes disruption of microtubules, which are essential for cell division. Approved taxane compounds which may be used in the present invention include paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), and cabazitaxel (Jevtana®, Sanofi-Aventis). Other taxane compounds which have undergone clinical testing and may be used in the present invention include SID530 (SK Chemicals, Co.) (NCT00931008).

In some embodiments, the additional therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, the present invention provides a method of treating prostate cancer comprising administering to a patient in need thereof an effective amount of a compound disclosed herein or a pharmaceutically acceptable salt thereof or pharmaceutical composition thereof in combination with an additional therapeutic agent that interferes with the synthesis or activity of androgens. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, the additional therapeutic agent is a selective estrogen receptor modulator (SERM), which interferes with the synthesis or activity of estrogens. Approved SERMs useful in the present invention include raloxifene (Evista®, Eli Lilly).

In some embodiments, the additional therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, the additional therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, the additional therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap."

Additional Co-Administered Therapeutic Agents—Targeted Therapeutics and Immunomodulatory Drugs In some embodiments, the additional therapeutic agent is selected from a targeted therapeutic or immunomodulatory drug. Adjuvant therapies with targeted therapeutics or immunomodulatory drugs have shown promising effectiveness when administered alone but are limited by the development of tumor immunity over time or evasion of the immune response.

In some embodiments, the present invention provides a method of treating cancer, such as a cancer described herein, comprising administering to a patient in need thereof an effective amount of a compound disclosed herein or a pharmaceutically acceptable salt thereof or pharmaceutical composition thereof in combination with an additional therapeutic agent such as a targeted therapeutic or an immunomodulatory drug. In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In other embodiments, the immunomodulatory therapeutic is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, the additional therapeutic agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, the additional therapeutic agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8$^+$ T cell response.

In some embodiments, the present invention comprises administering to said patient a compound disclosed herein or a pharmaceutically acceptable salt thereof in combination with a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

Additional Co-Administered Therapeutic Agents—Immunostimulatory Drugs

In some embodiments, the additional therapeutic agent is an immunostimulatory drug. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the present invention provides a method of treating cancer, such as a cancer described herein, comprising administering to a patient in need thereof an effective amount of a compound disclosed herein or a pharmaceutically acceptable salt thereof or pharmaceutical composition thereof in combination with an additional therapeutic agent such as a immunostimulatory drug, such as an immune checkpoint inhibitor. In some embodiments, the compound and the checkpoint inhibitor are administered simultaneously or sequentially. In some embodiments, a compound disclosed herein is administered prior to the initial dosing with the immune checkpoint inhibitor. In certain embodiments, the immune checkpoint inhibitor is administered prior to the initial dosing with the compound disclosed herein.

In certain embodiments, the immune checkpoint inhibitor is selected from a PD-1 antagonist, a PD-L1 antagonist, or a CTLA-4 antagonist. In some embodiments, a compound disclosed herein or a pharmaceutically acceptable salt thereof is administered in combination with nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); or atezolizumab (anti-PD-L1 antibody, Tecentriq®, Genentech).

Other immune checkpoint inhibitors suitable for use in the present invention include REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; and PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

Another paradigm for immune-stimulation is the use of oncolytic viruses. In some embodiments, the present invention provides a method for treating a patient by administering a compound disclosed herein or a pharmaceutically acceptable salt thereof or pharmaceutical composition thereof in combination with an immunostimulatory therapy such as oncolytic viruses. Approved immunostimulatory oncolytic viruses which may be used in the present invention include talimogene laherparepvec (live, attenuated herpes simplex virus, Imlygic®, Amgen).

In some embodiments, the additional therapeutic agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. An activator of RORγt, that is being studied which may be used in the present invention is LYC-55716 (Lycera), which is currently being evaluated in clinical trials for the treatment of solid tumors (NCT02929862).

In some embodiments, the additional therapeutic agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other checkpoint inhibitors that may be used in the present invention include inhibitors of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

Other checkpoint inhibitors that may be used in the present invention include inhibitors of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

Checkpoint inhibitors that may be used in the present invention also include inhibitors of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Other immune-oncology agents that may be used in the present invention in combination with a compound disclosed herein include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

Other additional therapeutic agents that may be used in the present invention include glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

A compound of the current invention may also be used to advantage in combination with other antiproliferative compounds. Such antiproliferative compounds include, but are not limited to checkpoint inhibitors; aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from Astra-Zeneca, PD181461 from Pfizer and leucovorin.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signalling processes should proceed.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl)2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; Zd$_6$474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01
1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

The following Examples illustrate the invention described above; they are not, however, intended to limit the scope of the invention in any way. The beneficial effects of the pharmaceutical compounds, combinations, and compositions of the present invention can also be determined by other test models known as such to the person skilled in the pertinent art.

List of Common Abbreviations Used in the Experimental Section

DMA: N,N-dimethylacetamide
DMSO: dimethyl sulfoxide
EDCI: 1-(3-dimethylaminopropyl)-3-ethylcarbodiimide hydrochloride
eqv.: equivalents
HPLC: high performance liquid chromatography
LCMS: liquid chromatography-mass spectrometry
M: molar
mg: milligrams
min: minutes
mL: milliliters
mM: millimolar
mmol: millimoles
NETS: N-hydroxysuccinimide
° C.: degrees Celsius
PBS: phosphate buffered saline
RP-HPLC: reverse phase high performance liquid chromatography
RP-HPLC-MS: reverse phase high performance liquid chromatography mass spectrometry
rt: room temperature
TFA: trifluoracetic acid Example 1

Evaluation of I-1A, DM1-Sme, MMAE and SN38 Against a Panel of 11 Cancer Cell Lines The procedure for the cancer cell line panel is provided in Table 2.

DM1-Sme is DM1 wherein the free thiol is covalently attached to methanethiol via a disulfide bond.

TABLE 2

Procedure

| Day | Protocol Description |
|---|---|
| Day −1 | Adjust the cell density to the recommend information. Detailed information for each seeding cell line can be found in Table 3. Add 90 μL cells to two plates as the cells seeding plate-map. Add 100 μL media and 100 μL PBS to the plates as the cells seeding plate-map. |
| Day 0 | Toxins preparation: Diluted I-1a with DMSO and adjusted the stock concentration to 10 mM. DM1-Sme & SN-38 stock concentration is 10.6 mM and 10 mM, respectively. MMAE stock concentration is 10 mM. The stock concentration of the reference compound Paclitaxel is 10 mM. Prepare the stock plate of test compounds: For Paclitaxel, the starting concentration is 1 mM, 3-fold dilution in DMSO, 10 doses. For I-1a, the starting concentration is 5 mM, 5-fold dilution in DMSO, 10 doses. For DM1-Sme, MMAE and SN-38, the starting concentration is 500 uM, 5-fold dilution in DMSO, 10 doses. For all compounds, 100-fold dilution of the dose compounds from the compound stock plate by the complete medium in the mid plate (2 μL compound + 198 μL medium). Transfer 10 μL diluted compounds to the assay plate. The final paclitaxel concentration starts at 1 uM, 3-fold dilution and 10 doses. The final I-1a concentration starts at 5 uM, 5-fold dilution and 10 doses. The final DM1-Sme, MMAE and SN-38 concentration starts at 0.5 uM, 5-fold dilution and 10 doses. Toxins treat cells for 72 hours. |
| Day 3 | Equilibrate the assay plate to room temperature for nearly 30 minutes. Add 50 μL CellTiter Glo reagent to each well. Detect the plate after 10 mins by EnVision (luminescence). |

Details of the initial cell plating procedure are described in Table 3. All cell lines met the criteria that the viability of adhere/mixed cells >90% and the viability of suspension cells >85% during the initial cell plating. All cell plates in this assay met the criteria that Max CV<10%. The reference compound paclitaxel worked well on all the tested cell lines and the data of paclitaxel were consistent with the historical data as shown in Table 5, below.

TABLE 3

Cell Plating Details

| Cell Line Name | Tumor Types | Cell Type | Media | Seed Density | Initial cell plating Passage | Viability |
|---|---|---|---|---|---|---|
| HCT15 | Colorectal | adherent | RPMI 1640 + 10% FBS | 1500 | P8 | 89.9% |
| HT29 | Colorectal | adherent | RPMI 1640 + 10% FBS | 4000 | P19 | 96.7% |
| NCI-H292 | Lung(Non-small cell) | adherent | RPMI 1640 + 10% FBS | 2000 | P10 | 95.6% |
| MDA-MB-231 | Breast | adherent | RPMI 1640 + 10% FBS | 3000 | P15 | 98.4% |
| HCC1806 | Breast | adherent | RPMI 1640 + 10% FBS | 3000 | P10 | 97.7% |
| EBC-1 | Lung(Non-small cell) | adherent | RPMI 1640 + 10% FBS | 3000 | P22 | 96.5% |
| SNU-16 | Gastric | suspension | RPMI 1640 + 10% FBS | 5000 | P15 | 89.0% |
| HT1080 | Sarcoma | adherent | RPMI 1640 + 10% FBS | 2000 | P17 | 97.2% |
| MOLP-8 | Myeloma | suspension | RPMI 1640 + 20% FBS | 10000 | P13 | 86.5% |
| PC-3 | Prostate | adherent | RPMI 1640 + 10% FBS | 2000 | P21 | 98.0% |
| NCI-H1975 | Lung(Non-small cell) | adherent | RPMI 1640 + 10% FBS | 4000 | P25 | 98.6% |

Tested cell lines were evaluated for expression of MT1-MMP. Results are shown in Table 4. Although the relationship between expression and efficacy in the cytotoxicity assay is not linear, there is the potential of a threshold level of MT1 expression for efficacy despite the range of tumor types, growth rates and model formats present in the 11 cell line panel.

TABLE 4

Expression of MT1-MMP in Tested Cell Lines

| Cell Line Name | Expression of MT1-MMP (>~5 implies expression) |
|---|---|
| HT1080 | 8.7 |
| PC-3 | 7.6 |
| MDA-MB-231 | 7.1 |
| NCI-H292 | 7.0 |
| NCI-H1975 | 6.7 |
| HCC1806 | 6.6 |
| EBC-1 | 6.5 |
| SNU-16 | 6.2 |
| HCT15 | 5.8 |
| HT29 | 5.7 |
| MOLP-8 | 5.6 |

The $IC_{50}$ results and top inhibition percentage for I-1a and the reference compound paclitaxel is shown in Table 5.

TABLE 5

11 Cell Line Panel Cytotoxicity Testing Results for I-1a and Paclitaxel (Reference Compound)

| | I-1a | | Paclitaxel | |
|---|---|---|---|---|
| Cell Line Name | Re $IC_{50}$ (nM) | Top inhibition % | $IC_{50}$ (nM) | $IC_{50}$* (nM) |
| HT1080 | 21.4 | 82 | 6.6 | 1 |
| PC-3 | 102 | 59 | 9.2 | 12 |
| MDA-MB-231 | 211 | 71 | 4.8 | 9 |
| NCI-H292 | 56.2 | 82 | 2.9 | 2 |
| NCI-H1975 | 24.2 | 60 | 7.2 | 5 |
| HCC1806 | 15.2 | 88 | 2.7 | 2 |
| EBC-1 | 35.7 | 70 | 4.1 | 4 |
| SNU-16 | 63.3 | 96 | 2.5 | 2 |
| HCT15 | >5000 | <50 | 112 | 128 |
| HT29 | 219 | 81 | 4.1 | 2 |
| MOLP-8 | 197 | 89 | 6.9 | 4 |

*Historical $IC_{50}$ observed for paclitaxel.

The $IC_{50}$ results and top inhibition percentage for DM1-Sme, MMAE and SN38 are shown in Table 6.

TABLE 6

11 Cell Line Panel Cytotoxicity Testing Results for DM1-Sme, MMAE and SN38

| Cell Line Name | DM1-Sme | | MMAE | | SN38 | |
|---|---|---|---|---|---|---|
| | Re IC50(nM) | Top inhibition % | Re IC50(nM) | Top inhibition % | Re IC50(nM) | Top inhibition % |
| HT1080 | 0.22 | 99 | 0.68 | 97 | 1.35 | 96 |
| PC-3 | 0.18 | 54 | 0.85 | 58 | 48.7 | 78 |
| MDA-MB-231 | 0.79 | 49 | 0.62 | 61 | 25.1 | 78 |
| NCI-H292 | 0.27 | 77 | 0.34 | 86 | 3.48 | 92 |
| NCI-H1975 | 1.52 | 64 | 0.38 | 65 | 272 | 116 |
| HCC1806 | 0.62 | 88 | 0.26 | 91 | 4.69 | 96 |
| EBC-1 | 0.32 | 65 | 0.35 | 67 | 2.34 | 87 |
| SNU-16 | 0.77 | 98 | 0.18 | 99 | 2.14 | 76 |
| HCT15 | 0.94 | 94 | 21.4 | 100 | 11.5 | 80 |
| HT29 | 0.68 | 82 | 0.42 | 81 | 23.7 | 98 |
| MOLP-8 | 0.21 | 92 | 0.65 | 93 | 3.59 | 88 |

Three toxins (DM1-Sme, MMAE and SN38) work well on all 11 tumor cell lines ($IC_{50}$<300 nM). I-1a works well on all cell lines except HCT-15. I-1a has elevated HCT-15 $IC_{50}$'s ($IC_{50}$>5000 nM).

Data Details for Tables 5 and 6.

Inhibition %=(Max-Sample value)/(Max-Min)*100.

The $IC_{50}$ curves were generated by 4 Parameter Logistic Model-Sigmoidal Dose-Response Model as follows: Y=Bottom+(Top-Bottom)/(1+10^((log $EC_{50}$-x)*Hill-Slope)).

Example 2

Evaluation of the Efficacy of I-1A in EBC-1 Xenograft Model in Female BALB/C Nude Mice Study Objective The objective of this study was to evaluate the anti-tumor efficacy of I-1a, in EBC-1 xenograft model in female BALB/c nude mice. The experimental design is shown in Table 7.

TABLE 7

Experimental Design

| Gr[a] | n[b] | Treatment | Dose (mg/kg) | Dose volume (ml/kg) | Conc. (mg/ml) | Dosing Route | Schedule |
|---|---|---|---|---|---|---|---|
| 1 | 3 | Vehicle | — | 10 | — | IV | 3x weekly for 2 weeks (D 0, 2, 4, 7, 9, 11, 14) |
| 2 | 3 | I-1a | 1 | 10 | 0.1 | IV | 3x weekly for 2 weeks (D 0, 2, 4, 7, 9, 11, 14) |
| 3 | 3 | I-1a | 3 | 10 | 0.3 | IV | 3x weekly for 2 weeks (D 0, 2, 4, 7, 9, 11, 14) |
| 4 | 3 | I-1a | 10 | 10 | 1 | IV | 3x weekly for 2 weeks (D 0, 2, 4, 7, 9, 11, 14) |

[a]group,
[b]number

Materials

Animals and Housing Conditions

Animals
  Species: *Mus Musculus*.
  Strain: BALB/c nude.
  Age: 6-8 weeks.
  Sex: Female.
  Body weight: 18-22 g.
  Number of animals: 42 mice.

Housing Conditions

The mice were kept in individual ventilation cages at constant temperature and humidity with 3 animals in each cage.
  Temperature: 20-26° C.
  Humidity 40-70%.
  Cages: Made of polycarbonate. The size is 300 mm×180 mm×150 mm. The bedding material is corn cob, which is changed twice per week.
  Diet: Animals had free access to irradiation sterilized dry granule food during the entire study period.
  Water: Animals had free access to sterile drinking water.
  Cage identification: The identification labels for each cage contained the following information: number of animals, sex, strain, date received, treatment, study number, group number and the starting date of the treatment.
  Animal identification: Animals were marked by ear coding.

Test and Positive Control Articles
  Testing article
  Product identification: I-1a
  Physical description: Clear solution (in DMSO)
  Purity: >95%
  Package and storage condition: stored at −80° C.

Experimental Methods and Procedures

Cell Culture

The EBC-1 tumor cells were maintained as a monolayer culture in RPMI1640 medium supplemented with 10% fetal calf serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

Tumor Inoculation

Each mouse was inoculated subcutaneously at the right flank with the EBC-1 tumor cells ($5 \times 10^6$) in 0.2 ml of PBS for tumor development. The treatments were started on Day 7 after the tumor inoculation when the average tumor size reached approximately 152 mm$^3$. Each group consisted of 3 tumor-bearing mice. The testing articles were administrated to the mice according to the predetermined regimen as shown in Table 7.

effectiveness; T and C are the mean volumes of the treated and control groups.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of vehicle control group on the same day with Ti, and V0 is the average tumor volume of vehicle group on the day of treatment start.

TABLE 8

Testing Article Formulation Preparation

| Compound | Preparation | Concentration (mg/ml) | Storage |
|---|---|---|---|
| Vehicle | 50 mM Hepes pH 7.0, 20% PEG 400 | — | −80° C. |
| I-1a, 1 mg/kg | Dilute 14 μl 100 mg/ml I-1a stock into 1386 μl formulation buffer to make the 1 mg/ml mother solution. Dilute 100 μl mother solution into 900 μl formulation buffer, mix immediately with the pipette/gentle vortexing. The solution should be completely clear to the eye and free of particulates. | 0.1 | Do not store |
| I-1a, 3 mg/kg | Dilute 300 μl mother liquid into 700 μl formulation buffer, mix immediately with the pipette/gentle vortexing. The solution should be completely clear to the eye and free of particulates. | 0.3 | Do not store |
| I-1a, 10 mg/kg | The remaining mother liquid | 1 | Do not store |

Observations

All the procedures related to animal handling, care and the treatment in the study were performed according to the guidelines of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss(body weights were measured every day), eye/hair matting and any other abnormal effect as stated in the protocol. Death and observed clinical signs were recorded on the basis of the numbers of animals within each subset. Animals that were observed to be in a continuing deteriorating condition or their tumor size exceeding 2000 mm$^3$ were euthanized prior to death or before reaching a comatose state.

Tumor Measurements and the Endpoints

The major endpoint was to see if the tumor growth could be delayed or mice could be cured. Tumor sizes were measured three times per week in two dimensions using a caliper, and the volume was expressed in mm$^3$ using the formula: V=0.5 a×b$^2$ where a and b were the long and short diameters of the tumor, respectively.

The tumor size was used for calculations of T/C values. The T/C value (in percent) is an indication of antitumor Sample Collection Plasma was collected from all the mice 5 min, 15 min, 30 min, 1 h and 2h after dosing on day 14. Study end blood sample (30-50 μl) was taken via orbital sinus vein puncture with EDTA-2K as anticoagulant (1.5 μl 0.5 M EDTA-2K). 10 μl plasma was pipetted to a new tube for PK analysis.

Statistical Analysis

Summary statistics, including mean and the standard error of the mean (SEM), were provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using Prism. $P<0.05$ was considered to be statistically significant Results Mortality, Morbidity, and Body Weight Gain or Loss Animal body weight was monitored regularly as an indirect measure of toxicity. Body weight change in female BALB/c nude mice bearing EBC-1 dosed with I-1a is shown in Table 9.

TABLE 9

| | | Body Weight (g) | | | | | | |
|---|---|---|---|---|---|---|---|---|
| | | Days after the start of treatment | | | | | | |
| Group | Treatment | 0 | 2 | 4 | 7 | 9 | 11 | 14 |
| 1 | Vehicle i.v. tiw* x2 w | 22.0 ± 0.2 | 22.0 ± 0.3 | 22.7 ± 0.1 | 22.9 ± 0.2 | 23.9 ± 0.1 | 23.7 ± 0.1 | 23.9 ± 0.0 |

TABLE 9-continued

| | | Body Weight (g) | | | | | | |
|---|---|---|---|---|---|---|---|---|
| | | Days after the start of treatment | | | | | | |
| Group | Treatment | 0 | 2 | 4 | 7 | 9 | 11 | 14 |
| 2 | I-1a 1 mg/kg i.v. tiw x2 w | 23.4 ± 1.4 | 23.3 ± 1.3 | 23.6 ± 1.6 | 23.8 ± 1.8 | 24.0 ± 1.9 | 24.0 ± 1.7 | 23.8 ± 1.8 |
| 3 | I-1a 3 mg/kg i.v. tiw x2 w | 21.9 ± 1.1 | 21.4 ± 1.0 | 21.7 ± 1.1 | 22.3 ± 1.0 | 22.4 ± 1.1 | 22.0 ± 1.1 | 22.0 ± 1.3 |
| 4 | I-1a 10 mg/kg i.v. tiw x2 w | 23.1 ± 0.8 | 21.8 ± 0.7 | 20.8 ± 0.7 | 19.3 ± 1.0 | 22.0 ± 0.9 | 20.6 ± 1.2 | 22.4 ± 1.0 |

*tiw = 3 times per week.

Tumor Volume Trace

Mean tumor volumes over time in female BALB/c nude mice bearing EBC-1 xenografts dosed with I-1a are shown in Table 10.

TABLE 10

| | Tumor Volume Trace over Time | | | | | | |
|---|---|---|---|---|---|---|---|
| Tumor volume | Days | | | | | | |
| $(mm^3)^a$ | 0 | 2 | 4 | 7 | 9 | 11 | 14 |
| Vehicle tiw[b] | 146 ± 24 | 309 ± 3 | 443 ± 18 | 730 ± 56 | 925 ± 35 | 1061 ± 118 | 1195 ± 91 |
| I-1a 1 mg/kg tiw | 162 ± 41 | 239 ± 92 | 308 ± 78 | 427 ± 188 | 395 ± 174 | 380 ± 171 | 271 ± 99 |
| I-1a 3 mg/kg tiw | 144 ± 15 | 126 ± 22 | 105 ± 8 | 63 ± 3 | 22 ± 6 | 0 ± 0 | 0 ± 0 |
| I-1a 10 mg/kg tiw | 165 ± 33 | 110 ± 8 | 74 ± 17 | 28 ± 6 | 5 ± 3 | 0 ± 0 | 0 ± 0 |

Note:
[a]Mean ± SEM,
[b]tiw = 3 times per week

Tumor Growth Curve

Tumor growth curves are shown in Table 11.

TABLE 11

| | Tumor Growth Inhibition | | | |
|---|---|---|---|---|
| Treatment | Tumor Size $(mm^3)^a$ at Day 14 | TGI (%) | T/C (%) | p value |
| Vehicle | 1195 ± 91 | — | — | — |
| I-1a, 1 mg/kg TIW | 271 ± 99 | 90 | 23 | *** |
| I-1a, 3 mg/kg TIW | 0 ± 0 | 114 | 0 | *** |
| I-1a, 10 mg/kg TIW | 0 ± 0 | 116 | 0 | *** |

[a]Mean ± SEM.

Tumor Growth Inhibition Analysis

Tumor Growth Inhibition is calculated by dividing the group average tumor volume for the treated group by the group average tumor volume for the control group (T/C). For a test article to be considered to have anti-tumor activity, T/C must be 50% or less. Dunnett's One-way ANOVA was conducted to analysis the statistical differences of compound-treatment groups vs Vehicle group on day 14, *** indicates p<0.001.

Results Summary and Discussion

In this study, the therapeutic efficacy of I-1a in the EBC-1 xenograft model was evaluated. The measured body weight is shown in Table 9. Tumor sizes of all treatment groups at various time points are shown in Table 10.

As shown in Table 10, the mean tumor size of vehicle treated mice reached 1195 mm³ on Day 14, mice treated I-1a at 1 mg/kg (TGI=90%), 3 mg/kg (TGI=114%),10 mg/kg (TGI=116%) showed significant tumor growth inhibition effect.

Example 3

Specificity of Toxin Release

I-1a, which possesses a $AA^1$-$AA^2$ linker, is more resistant to non-specific release of toxin versus BDCs with disulfide linkers, as demonstrated by a reduced susceptibility to blocking with bacitracin, a protein disulfide isomerase (PDI) inhibitor. Measurement of cytotoxicity in HT 1080 cells after 24 hours incubation with I-1a showed a 1.4-fold shift in $IC_{50}$ when comparing no bacitracin versus 1 mM bacitracin as shown in Table 12. The $AA^1$-$AA^2$ linker chemistry results in less non-specific toxin release.

TABLE 12

Cytotoxicity in HT1080 cells in the presence and absence of 1 mM bacitracin

| | No block | +1 mM bacitracin (PDI inhibitor) |
|---|---|---|
| I-1a | $IC_{50}$ = 5.3 nM | $IC_{50}$ = 7.3 nM (1.4x shift) |

Example 4

Plasma Stability of I-1a (LC-MS/MS Assay)

I-1a plasma stability studies were conducted in human and mouse plasma.

Background

In vitro plasma stability assay measures the extent of degradation of compounds in plasma.

Determination of the stability of new chemical entities in plasma is important in drug discovery, as compounds which rapidly degrade in plasma generally show poor in vivo efficacy.

Peptides or BDCs are incubated at 37° C. in plasma (mouse or human) at low micromolar concentrations for several hours. The stability is quantitatively measured by LC-MS/MS.

Preparation of DMSO Stock Solutions

The preparation of stock solutions for the plasma stability assay is as follows.

Prepare a 160 μM DMSO stock of a standard peptide (containing all D-AAs) to use as an internal standard.

Prepare DMSO (CC grade, hybrimax) stock for each peptide or BDC at 1 mM.

Dilute the 1 mM DMSO stock for each peptide at 160 μM (64 μL of 1 mM stock+168*2 μL of DMSO (CC grade, hybrimax)).

Prepare scalar dilutions from 160 μM to 5 μM (160 μM, 80 μM, 40 μM, 20 μM, 10 μM, 5 μM).

80 μM stock: 100 μL of 160 μM+100 uL of DMSO (CC grade, hybrimax),

40 μM stock: 100 μL of 80 μM+100 uL of DMSO (CC grade, hybrimax),

20 μM stock: 100 μL of 40 μM+100 uL of DMSO (CC grade, hybrimax)

10 μM stock: 100 μL of 20 μM+100 uL of DMSO (CC grade, hybrimax)

5 μM stock: 100 μL of 10 μM+100 μL of DMSO (CC grade, hybrimax)

For each stock solution, mix thoroughly with pipette and gently vortex.

Plasma Stability Experiment—Time Course

Add 8 μL of the 160 μM DMSO stock of peptide or BDC and add 8 μL of 160 μM DMSO stock of 06-34-18-N182 as internal standard to 304 μL of plasma (152 μL*2) for a final concentration of 4 μM (5% DMSO).

Incubate at 37° C. in 100% humidity.

Pipette out 40 μL for 7 timepoints: time 0, 1 h, 2 h, 4 h, 6h, 8 h, 24 h into a 1.5 mL Eppendorf. Store at −80° C. immediately. (total volume of samples 7×40=280 μL).

Plasma Stability Experiment—Standard Curve

Add 5 μL of each DMSO stock to 95 μL of plasma. For each sample, mix thoroughly with pipette and gently vortex.

Store at −80° C.

The concentrations of the standard curve samples are shown in Table 13, below.

TABLE 13

Concentrations of the Standard Curve Samples

| Dilution | DMSO Stock (μM) | Prespike (μM) | Extract Concentration (1:4 dilution) μM |
|---|---|---|---|
| 80 | 80 | 4 | 1 |
| 40 | 40 | 2 | 0.5 |
| 20 | 20 | 1 | 0.25 |
| 10 | 10 | 0.5 | 0.125 |
| 5 | 5 | 0.25 | 0.0625 |

Preparation for LCMS Experiments

Thaw the plasma samples in a water bath at room temperature.

Add to the sample the extraction solvent. The extraction solvent contains 1 part of water, 3 parts of methanol, and 3 parts of acetonitrile.

To the time course samples add 120 μL of extraction solvent, mix thoroughly with pipette and gently vortex.

To the standard curve samples add 2*150 μL, mix thoroughly with pipette and gently vortex.

Centrifuge for 40 minutes at 14000 rpm at 4° C.

Transfer the supernatant to the LC-MS vials and run the experiment immediately afterwards.

LC-MS/MS Experiments

It is recommend to follow one transition for the peptide of BDCs to study, and one transition for the internal standard 06-34-18-N182 at the same time. The most relevant Selected Ion Reaction (SIR) and Multiple Reaction Monitoring (MRM) transitions were determined for each peptide or BDC. The recommended transitions for the study is shown in Table 14, below.

TABLE 14

Recommended Transitions for the Standard, I-1a and MMAE

| Compound Name | Parent (m/z) | Daughter (m/z) | Dwell (s) | Cone (V) | Collision (V) |
|---|---|---|---|---|---|
| Standard | 871 | 871.1 | 0.160 | 35 | 10 |
| I-1a | 1293.1 | 213 | 0.160 | 30 | 60 |
| I-1a | 1293.1 | 1293.7 | 0.160 | 30 | 10 |
| MMAE | 718 | 506.5 | 0.160 | 10 | 20 |
| MMAE | 718 | 718 | 0.160 | 10 | 10 |

The recommended gradients as shown in Tables 15 and 16, below.

TABLE 15

Recommended Gradient 1

| Time (min) | Flow Rate (mL/min) | A % | B % |
|---|---|---|---|
| Initial | | 95 | 5 |
| 1.50 | 0.6 | 95 | 5 |
| 5.50 | 0.6 | 40 | 60 |
| 6.00 | 0.6 | 5 | 95 |

TABLE 15-continued

Recommended Gradient 1

| Time (min) | Flow Rate (mL/min) | A % | B % |
|---|---|---|---|
| 6.50 | 0.6 | 5 | 95 |
| 6.70 | 0.6 | 95 | 5 |
| 8.00 | 0.6 | 95 | 5 |

TABLE 16

Recommended Gradient 2

| Time (min) | Flow Rate (mL/min) | C % | D % |
|---|---|---|---|
| Initial |  | 95 | 5 |
| 1.50 | 0.6 | 95 | 5 |
| 5.50 | 0.6 | 40 | 60 |
| 6.00 | 0.6 | 5 | 95 |
| 6.50 | 0.6 | 5 | 95 |
| 6.70 | 0.6 | 95 | 5 |
| 8.00 | 0.6 | 95 | 5 |

Where the mobile phase A through D is as follows: A=0.1% HCOOH in water; B=0.1% HCOOH in MeCN; C=5 mM ammonium bicarbonate in water; D=5 mM ammonium bicarbonate 10% water in acetonitrile The recommended injection volume is 5 uL Sample temperature should be set up at 21° C.

The column temperature is 40° C.

The LC-MS method is called "Default" and has the following settings:
Polarity: ES+
CalibrationDynamic 1
Capillary (kV): 2.51
Cone (V): 20.00
Extractor (V): 3.00
RF (V): 0.10
Source Temperature (° C.): 150
Desolvation Temperature (° C.): 400
Cone Gas Flow (L/Hr): 2
Desolvation Gas Flow (L/Hr): 800
Collision Gas Flow (mL/Min): 0.20
LM 1 Resolution: 12.00
HM 1 Resolution: 12.00
Ion Energy 1: 1.00
MS Mode Entrance: 50.00
MS Mode Collision Energy: 3.00
MS Mode Exit: 50.00
MSMS Mode Entrance: 1.00
MSMS Mode Collision Energy: 20.00
MSMS Mode Exit: 0.50
LM 2 Resolution: 14.00
HM 2 Resolution: 14.00
Ion Energy 2: 1.00
Gain: 1.00

The suggested order of the samples is: from time course 7 (24h) to time course 0 to reduce carrying over of the samples; and from dilution 5 μM to 80 μM for the standard curve samples for the same reason.

The analysis of the data has been performed using "QuanLynks" and "Sigmaplot" software.

Figure 2:
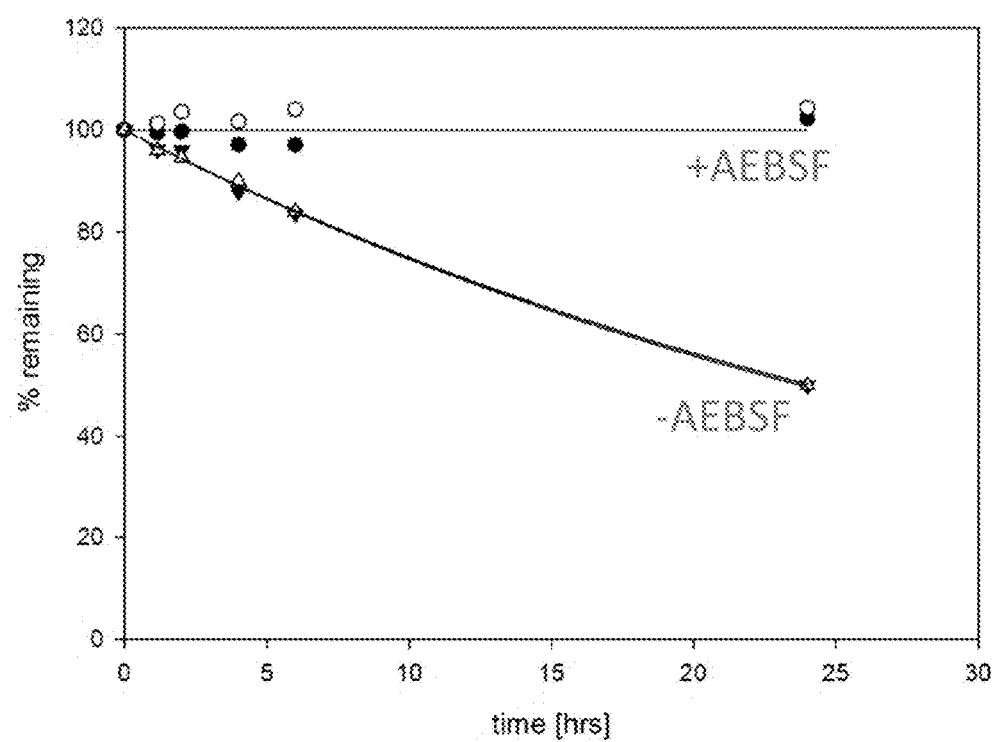
FIG. 2 depicts the plasma stability of I-1a with and without AEBSF.
Figure 3:
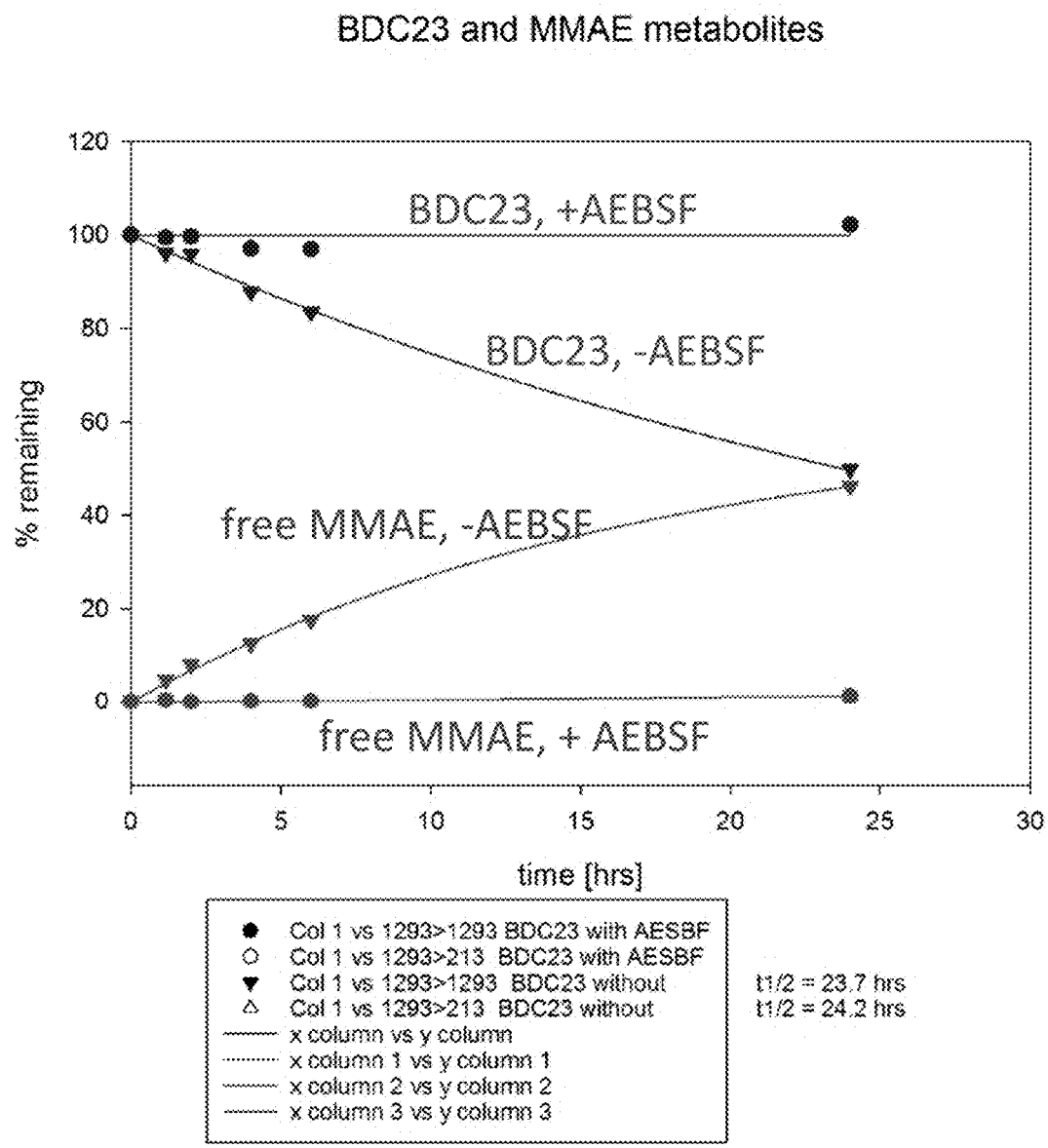
FIG. 3 depicts the plasma stability of I-1a in mouse and the formation of the MMAE metabolite.

Results for the plasma stability testing in mouse and human plasma are shown in FIGS. 1-3.

For the studies depicted in FIGS. 1-3, the following conditions were used.

Column: Waters ACQUITY CSH Phenyl-Hexyl 1.7 μm 2.1×50 mm

Mobile Phase: C=5 mM ammonium bicarbonate in water; B=5 mM ammonium bicarbonate 10% water in acetonitrile.

Gradient: 5 to 60% B in 4 minutes at 0.6 mL/min flow.

FIG. 1 shows plasma stability curves for I-1a in mouse and human plasma (1 μM in plasma, pH 7.4 at 37° C.). After 24 hours incubation in human plasma, 96% I-1a remained which corresponds to a $t_{1/2}$=>>24 h. After 24 hours incubation in mouse plasma, 57% I-1a remained which corresponds to a $t_{1/2}$=6.4 h.

Without being bound to any particular theory, it is believed that the lower stability observed in mouse is likely due to mouse carboxyesterase 1c (Ces1c) and the generally more aggressive proteolytic environment found in mouse.

To test the hypothesis that plasma instability in mouse was due to Ces1c, I-1a was incubated in mouse plasma both in the presence and absence of AEBSF,

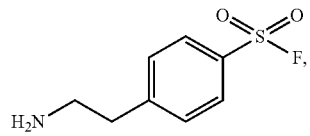 [SMILES: NCCc1ccc(S(=O)(=O)F)cc1]

a serine protease inhibitor that is cross-reactive with Ces1c.

FIG. 2 shows plasma stability curves for I-1a in mouse plasma (4 μM in plasma, pH 7.4 at 37° C.). After 24 hours incubation in mouse plasma without AEBSF, 50% I-1a remained which corresponds to a $t_{1/2}$=24 h. After 24 hours incubation in mouse plasma+AEBSF, 100% I-1a remained which corresponds to a $t_{1/2}$=>>24 h.

Additionally, formation of the MMAE metabolite in mouse plasma (release of the toxin) was monitored both in the presence and absence of AEBSF. As shown in FIG. 3, in the presence of AEBSF, degradation of I-1a is inhibited as shown by the lack of formation of free MMAE. In the absence of AEBSF, I-1a degradation tracks with the appearance of free MMAE.

Example 5

Target Specificity of In Vitro Cytotoxicity of I-1a

The target dependence of cytotoxicity of I-1a in cell lines expressing or lacking MT1-MMP was assessed by measuring ATP levels in an endpoint assay after 24 hours exposure to toxin, in the presence or absence of an excess of binding peptide or non-binding control peptide.

The structure of the binding peptide, which is the Bicycle+Spacer of I-1a, is

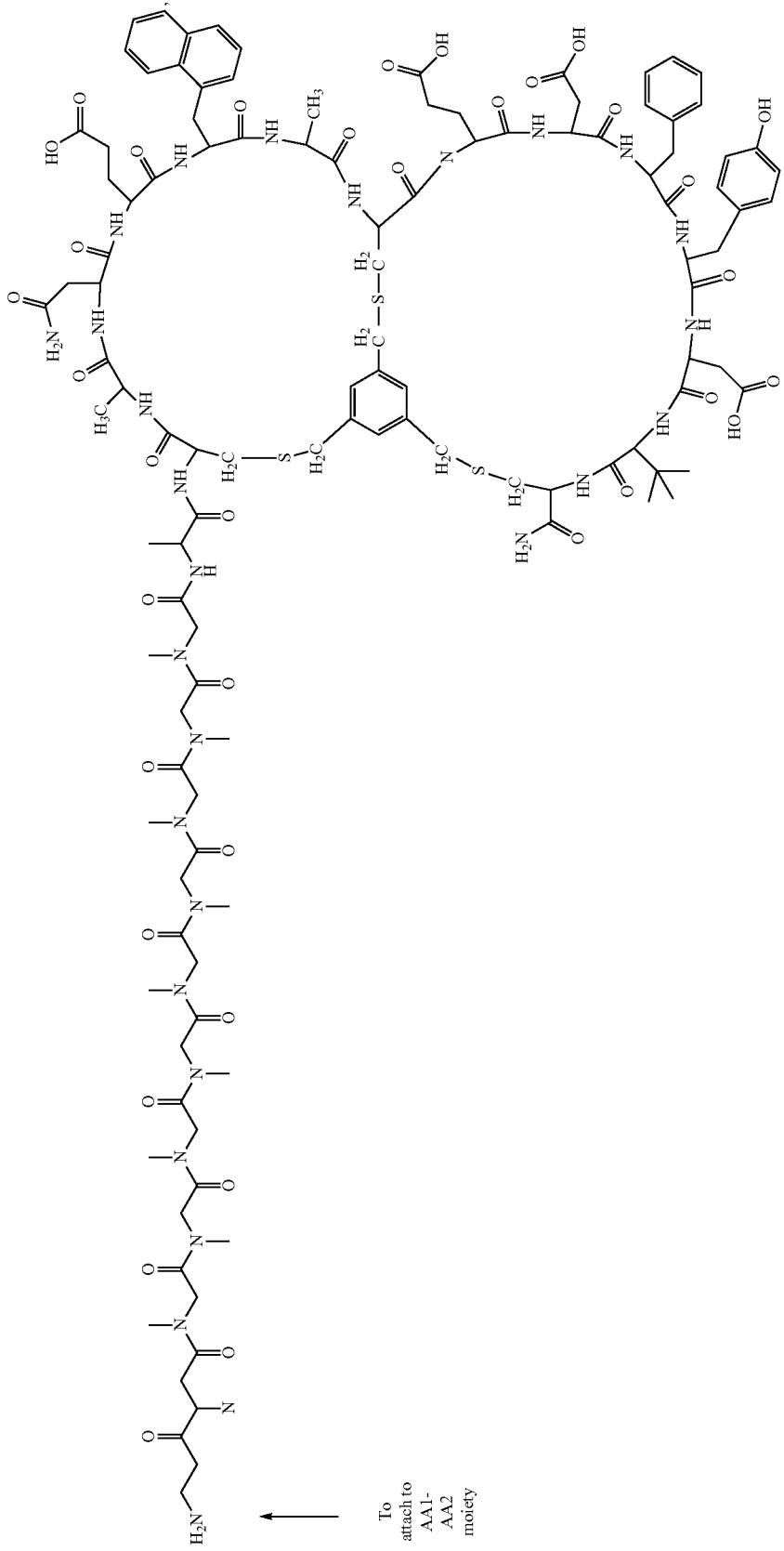

where all amino acids are in the natural L-form except the two alanines which are in the D-form.

The non-binding peptide is (B-Ala)-Sar10-ACVP-CADFPIWYC (SEQ ID NO: 17). The non-binding peptide showed no inhibition in MT1-MMP fluorescent polarization competition experiments up to 20 µM.

Methods

HT1080 cells were seeded in 96 well plates (75 µL/well) and incubated overnight at 37° C.+5% $CO_2$. The next day, peptides were prepared in buffer from a DMSO stock. 10 µL of buffer or peptide was added to the cells and incubated for 1 hour. Toxins were diluted in cell culture media and 15 µL/well was added to the cells (<0.5% final DMSO). Cells were approximately 30-50% confluent upon dosing. Plates were sealed with gas permeable seals and incubated for 24 hours at 37° C.+5% $CO_2$. After 24 hours, media was removed, cells were washed with PBS and 100 µL fresh media was added per well. Cells were incubated for a further 48 hours at 37° C.+5% $CO_2$.

ATPLite reagent (Perkin Elmer) was equilibrated to room temperate and reconstituted in buffer as per the manufacturer's instructions. 100 µL reagent was added per well. Plates were sealed and shaken gently for 20 minutes to ensure complete cell lysis before luminescence was read using a BMG Pherastar. Luminescence counts correlate with ATP levels and hence cell viability. Data was analyzed using GraphPad Prism. Non-linear regression fit was used to calculate an $IC_{50}$ for each toxic agent: Y=Bottom+(Top-Bottom)/(1+10^((Log $IC_{50}$-X)*Hill Slope)).

Results are shown in Table 17, below. A shift in the cytotoxicity $IC_{50}$ of 13-fold was observed for I-1a in the presence of 250 µM binding peptide, whereas the presence of 250 µM non-binding peptide resulted in only a 2-fold shift, indicating that I-1a can be competed with the binding peptide but not an unrelated peptide. These results demonstrate the specificity of I-1a binding in targeting HT1080 cells. The toxin MMAE shows a 1.2-fold shift in the cytotoxicity $IC_{50}$ in the presence of 250 µM binding peptide and no shift in $IC_{50}$ in the presence of 250 µM non-binding peptide consistent with its lack of a MT1-MMP binding moiety.

TABLE 17

HT1080 Cytotoxicity $IC_{50}$ shift in the presence and absence of binding peptide

| | I-1a | | | MMAE | | |
|---|---|---|---|---|---|---|
| | $IC_{50}$ (nM) | Maximum kill (%) | Shift in $IC_{50}$ | $IC_{50}$ (nM) | Maximum kill (%) | Shift in $IC_{50}$ |
| No block | 13.7 ± 5.5 | 95% | | 0.06 ± 0.07 | 95% | |
| +250 µM binding peptide | 160.7 ± 83.4 | 95% | x12.5 ± 7.6 | 0.05 ± 0.06 | 95% | x1.2 ± 0.5 |
| +250 µM non-binding peptide | 18.7 ± 9.9 | 95% | x1.7 ± 1.2 | 0.05 ± 0.07 | 95% | x1.0 ± 0.3 |

Data is represented as mean $IC_{50}$ (nM) ± standard deviation, average maximum cell killing (%) compared to a lysis control and average shift in $IC_{50}$ of I-1a in presence of peptide ± standard deviation compared to no block.

Number of experimental repeats = 3

Example 6

Cell Toxicity of I-1a and Toxins in HT1080 and L540 Cells in the Presence/Absence of Protein Disulphide Isomerase Inhibitors Bacitracin at 1 Mm One advantage of the $AA^1$-$AA^2$ linker is its resistance to cleavage by protein disulphide isomerase which can readily cleave disulfide bonds. This can result in the non-selective release of toxin for BDCs that utilize a disulfide linkage.

As mentioned previously, non-selective delivery of toxin is termed bystander activity. One contributing factor in some BDCs may be the enzyme protein disulphide isomerase (PDI) which can cleave the —S—S— bond to release toxin. In order to determine the effect of PDI in the delivery of toxin, PDI is inhibited with bacitracin, a known inhibitors of PDI.

Bacitracin is a cyclic peptide that interferes with cell wall/peptidoglycan synthesis. It has been used as a PDI inhibitor and has the following structure:

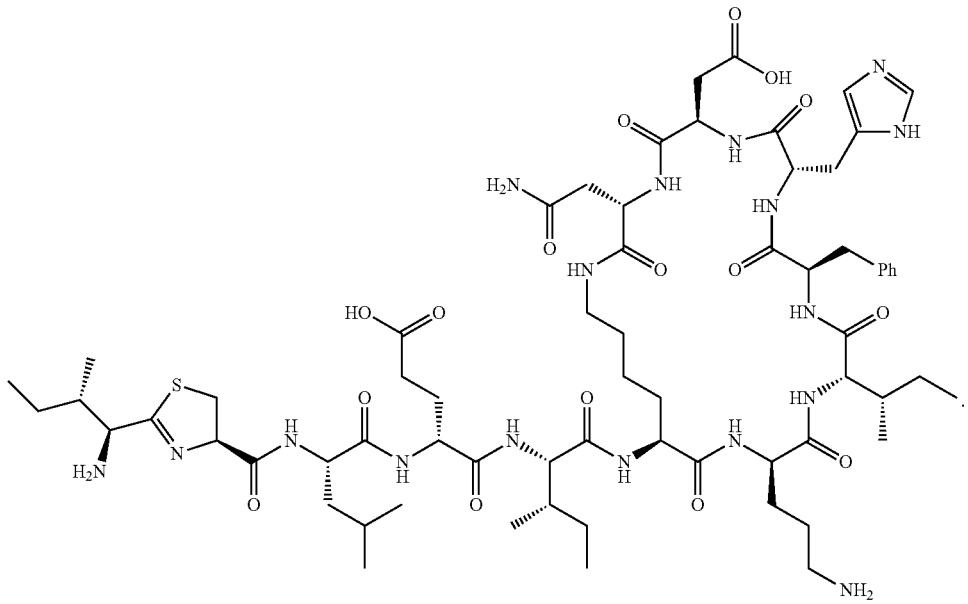 [SMILES: CC[C@H](C)[C@H](N)C1=N[C@H](C(=O)N[C@@H](CC(C)C)C(=O)N[C@H](CCC(=O)O)C(=O)N[C@H](C(=O)N[C@H]2CCCCNC(=O)[C@H](CC(N)=O)NC(=O)[C@@H](CC(=O)O)NC(=O)[C@H](Cc3cnc[nH]3)NC(=O)[C@@H](Cc3ccccc3)NC(=O)[C@H]([C@@H](C)CC)NC(=O)[C@@H](CCCN)NC2=O)[C@@H](C)CC)CS1]

Materials
DM1-SMe, 10.58 mM stock in DMSO.
I-1a, 100 mg/ml, 25.8 mM.
MMAE, 10 mM
ATPlite 1-step kit (Perkin Elmer 6016731)
HT1080 cells (ATCC, via LGC, BIC918) Maintained in EMEM media (Sigma M2279)+10% FBS (Sigma Code F7524)+4 mM L-Glu (Invitrogen Cat 25030-024)
L540 cells (DSMZ #ACC72, BIC5121), maintained in RPMI-1640 medium (Sigma #R8758)+20% heat-inactivated serum
Clear tissue-culture treated 96 well plates
Gas permeable adhesive seal (VWR 732-0077)
X-clear advanced polyolefin starseal (Starlabs E2796-9795)
Staurosporine 1 mM (Sigma 56942-200UL)
Method
I-1a and Toxins with Bacitracin—24 or 72 Hour Exposure in 96 Well Plates
DB seeded cells in normal media, 75 µL in 96 well clear plates, ~24 hours previous.
HT1080—7.5 k cells/well: 50% confluent upon dosing.
L540—20 k cells/well: 40% confluent upon dosing.
Preparation of staurosporine: 1 mM stock in DMSO: Dilute 1:50 (5 µL+245 µL) to 20 µM in media or imaging buffer (4× final conc 5 µM. Final DMSO conc=0.5%).
Lyis reagent made from R&D DYC002: (Final 1% NP40, 20 mM Tris pH8, 137 mM NaCl, 10% glycerol, 2 mM EDTA, 1 mM NaOrthovanadate, 10 ug/ml leupeptin, 10 µg/ml aprotinin). Combine 750 µL water and 750 µL DYC002.

Stock solutions were prepared as shown in Table 18.

TABLE 18

| Stock Solution Preparation | | | | | |
|---|---|---|---|---|---|
| | stock | | Dilution | Amount required for 1428 µM in DMSO | |
| | mM | mg/mL | factor | mM | mg/mL |
| I-1a | 25.8 | 100 | 18.07 | 1.11 | 18.89 |
| | | | | Amount required for 571 µM in DMSO | |
| DM1-SMe | 10.58 | | 18.53 | 1.08 | 18.92 |
| MMAE | 10 | | 17.51 | 1.14 | 18.86 |

Dilute above 1 in 5 by adding 4 mL above to 16 mL DMSO (columns 1-9, DMSO in 10)

HT1080 and L540 Cells
Dilute in media 1:42.85=5 µL DMSO dilute+209 µL media=>use 15 µL per well
This gives a 5 µM top concentration for BDCs in assay
This gives a 2 µM top concentration for DM1-SMe & MMAE in assay
Add 10 µL of media±bacitracin (2 plates of each)—leave for 1 hr
Bacitracin=1 mM final concentration. This requires a 10 mM concentration with no DMSO.
For HT1080 & L540 media this requires 3 ml media+1 ml 40 mM bacitracin to prepare the required concentration.
The solution of 40 mM bacitracin was prepared by dissolving 0.2 g bacitracin in 3514 µL water.

Add 15 μL treatment per well as in Table 19, below.

TABLE 19

Plate Map of Concentrations Tested (nM unless indicated otherwise)

| | | 1 | 2 | 3 | 4 | 5 | 6 | 7 | 8 | 9 | 10 | 11 | 12 |
|---|---|---|---|---|---|---|---|---|---|---|---|---|---|
| I-1a | A | 5000 | 1000 | 200 | 40 | 8 | 1.6 | 0.32 | 0.064 | 0.0128 | 0 | 5 μM | Lysis |
| | B | 5000 | 1000 | 200 | 40 | 8 | 1.6 | 0.32 | 0.064 | 0.0128 | 0 | SS* | |
| DM1- | C | 500 | 100 | 20 | 4 | 0.8 | 0.16 | 0.032 | 0.0064 | 0.00128 | 0 | | |
| SMe | D | 500 | 100 | 20 | 4 | 0.8 | 0.16 | 0.032 | 0.0064 | 0.00128 | 0 | | |
| MMAE | E | 500 | 100 | 20 | 4 | 0.8 | 0.16 | 0.032 | 0.0064 | 0.00128 | 0 | | |
| | F | 500 | 100 | 20 | 4 | 0.8 | 0.16 | 0.032 | 0.0064 | 0.00128 | 0 | | |

*SS = staurosporin

Seal plates with gas permeable membrane and incubate at 37° C.

Washout HT1080 plates with 2×150 μL PBS at 24 h and add 100 μL fresh media

At t=72 h, equilibrate ATPlite reagent to room temperature. Add 10 ml buffer to each vial of lyophilized substrate. Add 100 μL reagent per well. Seal with PCR seal and cover to protect from light. Shake for 20 mins before reading luminescence Luminescence Settings
Endpoint Settings
  Measurement interval time [s]: 1.00
  Optic Settings
  Optic module: LUM plus
  Gain: 3000
  Focal height [mm]: 10.0
  General settings
  Setting time [s]: 0.1
  Target temperature [° C.]: 25

To allow comparison of different kinetic windows all measurement values are normalized to 1 second.

Results

The results are summarized in Table 20, below.

TABLE 20

Summary of I-1a and Toxin $IC_{50}s$ with Bacitracin

| | HT1080 cells, 24 hour exposure (high MT1 expression) | | | L540 cells, 72 hour exposure (low/no MT1 expression) | | |
|---|---|---|---|---|---|---|
| | Standard $IC_{50}$ (nM) | $IC_{50}$ with 1 mM bacitracin (nM) | Fold shift with bacitracin | Standard $IC_{50}$ (nM) | $IC_{50}$ with 1 mM bacitracin (nM) | Fold shift with bacitracin |
| I-1a | 5.3 | 7.3 | x1.4 | 1088 | 2551 | x2.3 |
| DM1-SMe | 0.07 | 0.41 | x5.9 | 9.6 | 12 | x1.2 |
| MMAE | 0.083 | 0.15 | x1.8 | 0.49 | 0.28 | x0.6 |

I-1a $IC_{50}$s were shifted 1.4-fold with bacitracin treatment in HT1080 cells. I-1a $IC_{50}$s were shifted 2.3-fold with bacitracin treatment in L540 cells. These data indicate that cleavage of the $AA^1$-$AA^2$ linker is unaffected by the presence of absence of PDI activity. Similarly MMAE which has no linker shows negligible shifts in the presence of bacitracin in both HT1080 and L540 cells. DM1-SMe which possesses a disulfide linkage to methanethiol shows a small shift of 5.9-fold in HT1080 cells and no shift in L540 cells.

Example 7

Evaluation of the Efficacy of I-1a in HT1080 Xenograft Model

I-1a was evaluated in a HT1080 xenograft model at 1, 3, and 10 mg/kg. Additionally the ability of the binding peptide (the Bicycle+Spacer of I-1a, structure shown in Example 6)

to abrogate activity when dosed at a 100-fold excess immediately before treatment with I-1a in the HT1080 xenograft model was assessed.

Figure 4:
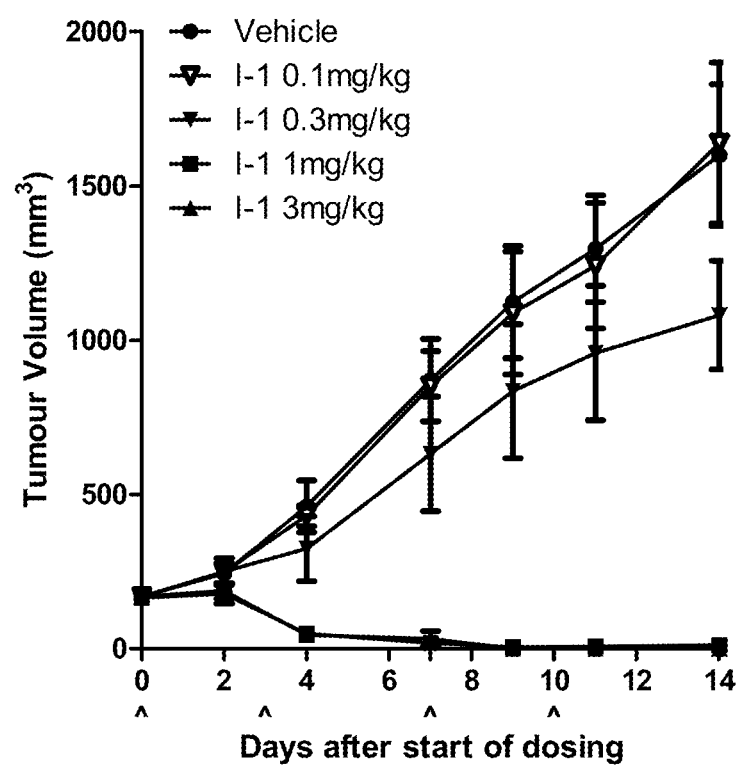
FIG. 4 depicts the efficacy of I-1a in the HT1080 xenograft model.
Figure 5:
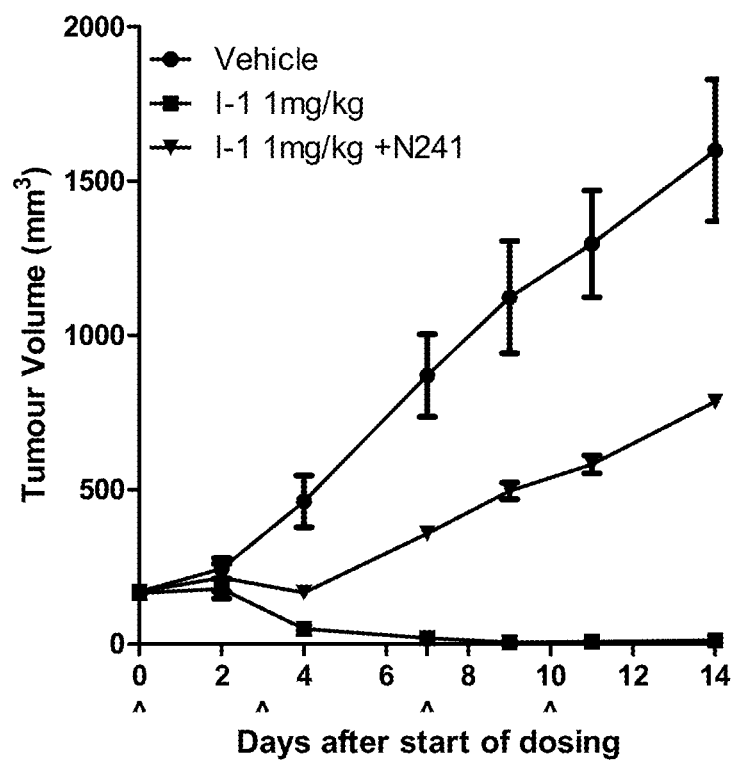
FIG. 5 depicts the displacement of I-1a activity when dosed at 1 mg/kg in the HT1080 xenograft model by the binding peptide.
Figure 6:
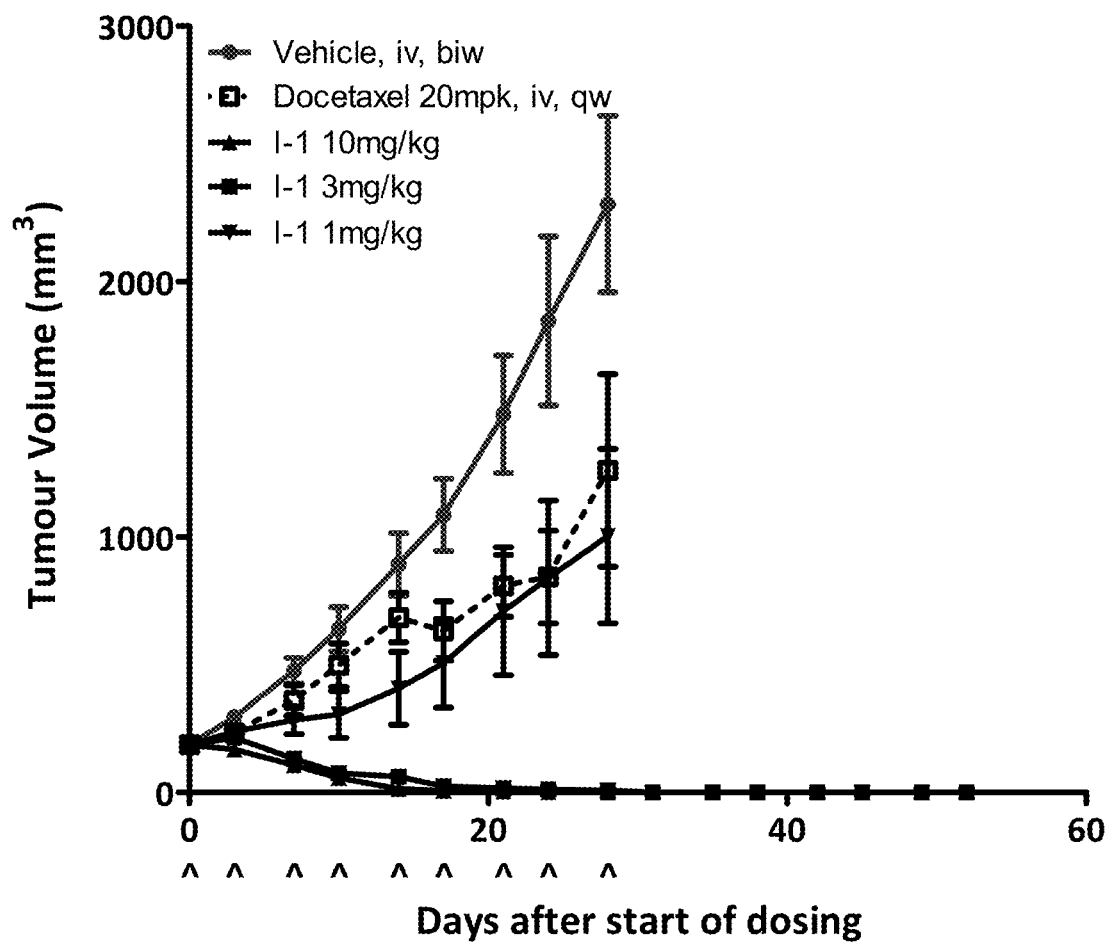
FIG. 6 depicts the efficacy of I-1a in the MT1-MMP expressing non-small cell lung cancer (NSCLC) patient-derived xenograft (PDX) model.

The results of the xenograft studies are shown in FIGS. 4-6.

FIG. 4 shows the efficacy with I-1a in the HT1080 xenograft model. Complete clearance of tumor was observed at 1 mg/kg. No dose-related effects on body weight were observed at any of the doses tested.

FIG. 5 shows the displacement of I-1a activity with 100-fold excess of the binding peptide at 1 mg/kg I-1a. At 1 mg/kg, significant displacement of efficacy is seen with co-dosing of the binding peptide.

Example 8

Synthesis of I-1a

Summary

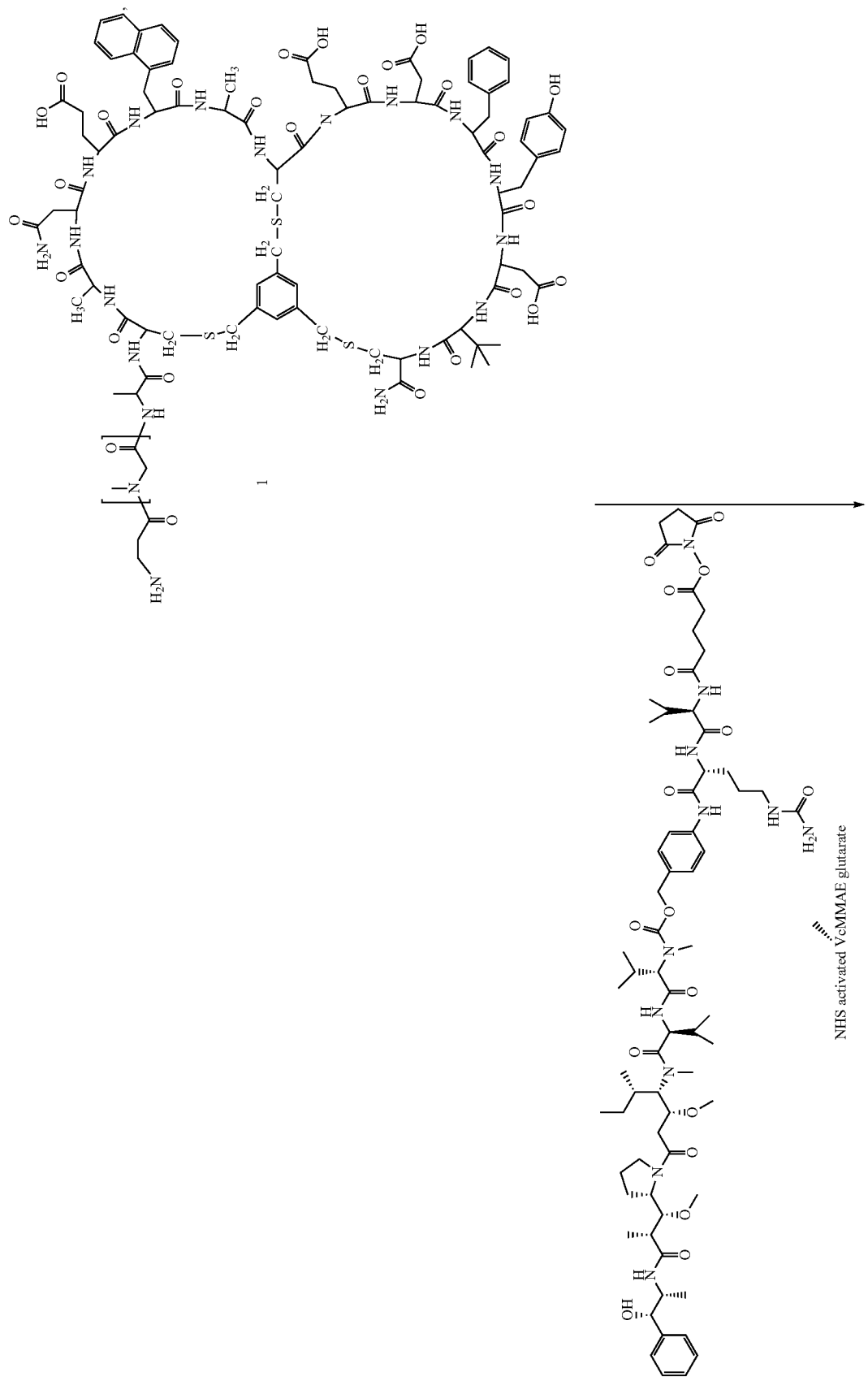

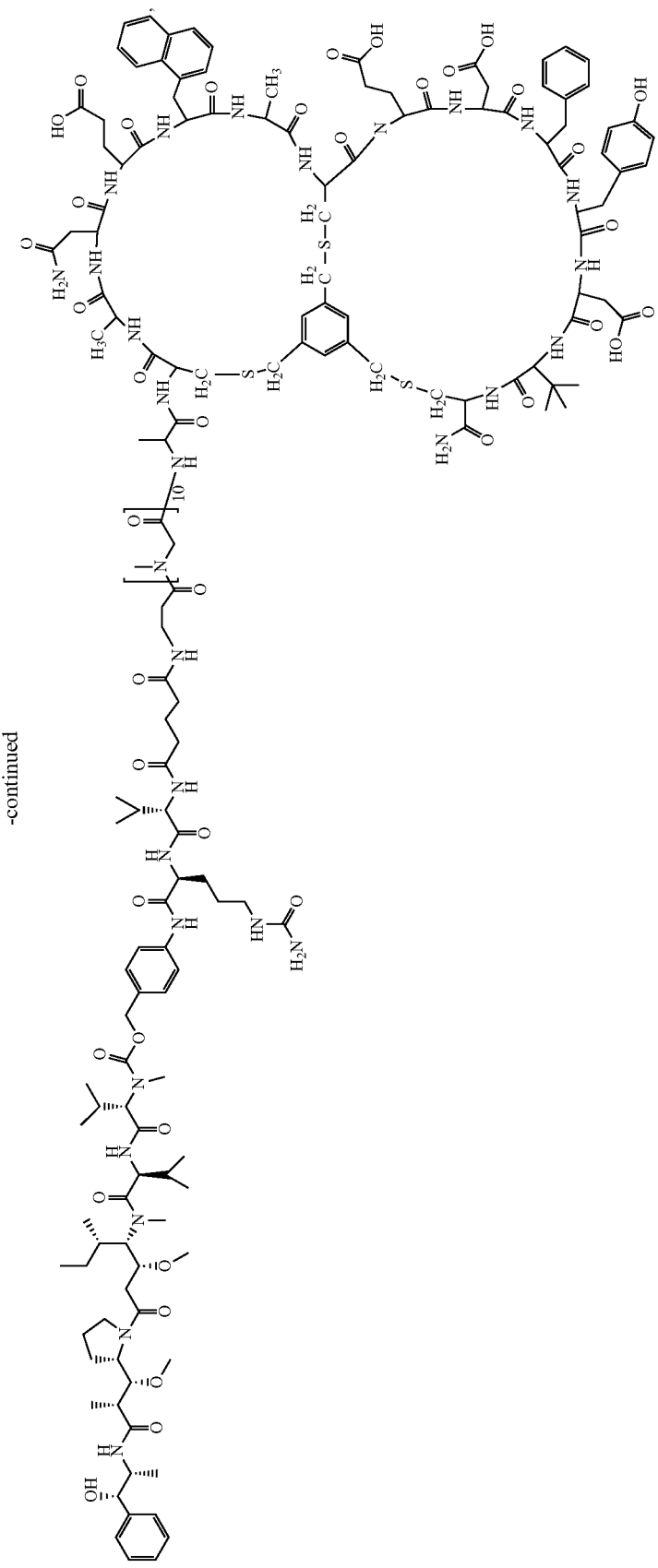
I-1

Bicyclic peptide 1, (MW. 2658.95 Da), was coupled to an auristatin cytotoxic drug linker, monomethyl auristatin E (VcMMAE) via a glutarate linker to give VcMMAE-Bicyclic peptide conjugate (I-1a, MW. 3877.94) after appropriate purification.

An Initial small scale reaction (10 mg of bicyclic peptide) was carried out to confirm suitable conjugation conditions had been selected and to develop an HPLC gradient capable of resolving starting materials/products/by-products.

Two RP-HPLC methods were developed the first using 10 mM ammonium acetate using a Hichrom ACE 3 column (2.1×50 mm, 3 μm, 100 Å, $C_{18}$) and the second using 10 mM ammonium acetate with a waters xselect column (2.1×50 mm, 3.5 μm, peptide CSH™, C18, 130 Å).

Final analysis was carried out on the ACE 3 column using the TFA method.

A single 114 mg preparative conjugation was performed and purified using the Gilson 20:20 preparative HPLC in multiple 20 mg passes after translation from the analytical method using a waters xselect prep column (10×100 mm, 10 μm, peptide CSH™, C18, 130 Å) to yield pure product.

Fractions containing pure product were pooled, lyophilized/reconstituted and quantified gravimetrically before being separated into 5 mg aliquot vials.

A single nominal 5 mg vial (3.4 mg actual) was reconstituted in DMSO for QC analysis The results of the QC tests and product vials supplied are summarized in Table 21, below.

The process from starting materials to final product vials gave 72% yield of I-1a.

TABLE 21

| QC Test Data Summary | | |
|---|---|---|
| QC TEST DATA | | |
| TEST | SPECIFICATION | RESULT |
| Visual | White lyophilized solid | White lyophilized solid |
| Headline Purity (HPLC) | ≥95% | 99.5% |
| | <0.5% | Not detected |
| Salt state from purification | Based on 10 mM $NH_4OAc$ buffer system | $NH_4OAc$ |

TABLE 21-continued

| QC Test Data Summary | | |
|---|---|---|
| PRODUCT SUPPLIED | | |
| Nominal Vial Size | QC Value | No. Vials and Total Mass (mgs) |
| 5 mgs | 5.00 ± 0.5 mgs | 24 × 5.00 |
| TOTAL MASS OF PRODUCT SUPPLIED | | 118.7 mgs |

Materials and Methods
Key Materials
Bicyclic Peptide 1

Bicyclic Peptide 1, (196.74 mg, 73.9 μmol) quantified by UV A280 was provided as a lyophilized powder as follows in Table 22, below.

TABLE 22

| | | Bicyclic Peptide 1 | | | |
|---|---|---|---|---|---|
| Peptide | Tubes | Quantity by A280 (mg) | Quantity by weight (mg) | MW (Average mass) | Extinction coefficient |
| 1 | 1/1 Falcon | 196.74 | 244.47 | 2658.95 | 7290 |
| | TOTAL QUANTITY | 196.74 | 244.47 | | |

VcMMAE

VcMMAE was purchased from Levena Biopharma. Lot no. P15707040144

NHS Activated VcMMAE Glutarate

VcMMAE glutarate was prepared and activated in house with a purity of 80% mid scale and 60% large scale (40% non activated glutarate present).

UV Analysis Buffers 50 mM HEPES, pH7 (for UV measurement, for starting peptide concentration by UV) was used for UV measurements.

The buffer was prepared as follows: HEPES (5.96 g), pH adjustment with 0.5M NaOH to pH 7.0 and made up in ELGA water (500 mL).

Key Methods
Reverse Phase HPLC with UV and/or MSD

Initial quality control data for the peptide was obtained on a Hichrom ACE 3 C18 column with the mass spectrometer on a negative polarity setting. A summary of the HPLC and LCMS methods are described in Table 23, below.

TABLE 23

| HPLC and LCMS Methods | | | | | | |
|---|---|---|---|---|---|---|
| | Method 1 (TFA) | | Method 2 ($NH_4OAc$) | | Method 3 ($NH_4OAC$) | |
| Column | Ace 3 C18, 50 mm × 2.1 mm | | Ace 3 C18, 50 mm × 2.1 mm | | | |
| Buffer A | 0.05% v/v TFA in $H_2O$ | | 10 mM $NH_4OAc$ in $H_2O$ at pH 5.7 | | | |
| Buffer B | 0.05% v/v TFA in MeCN | | Acetonitrile | | | |
| Gradient: | Time (min) | % B | Time (min) | % B | Time (min) | % B |
| | 0 | 1 | 0 | 1 | 0 | 1 |
| | 15 | 99 | 15 | 80 | 5 | 30 |
| | 17 | 1 | 17 | 1 | 25 | 50 |
| | 19 | 1 | 19 | 1 | 26 | 80 |
| | — | — | — | — | 28 | 80 |

TABLE 23-continued

| | HPLC and LCMS Methods | | | |
|---|---|---|---|---|
| | Method 1 (TFA) | Method 2 (NH₄OAc) | Method 3 (NH₄OAC) | |
| | — | — | — — | 30 1 |
| | — | — | — — | 35 1 |
| Flow Rate: | | 0.4 mL/min | | |
| Wavelength: | | 214 nm, 220 nm, 254 nm & 280 nm | | |
| Injection Volume: | | 10 μL (unless otherwise stated) | | |
| HPLC and LCMS system | Agilent 1100 and Agilent G1946D | Agilent 1100 | Agilent 1100 | |
| Column Temperature: | | 25° C. | | |
| MSD | ES Positive unless stated otherwise | N/A | N/A | |

Once qualified the same sample was run on a separate HPLC system with the same mobile phase but using a Waters xselect CSH, C18 column. Analytical monitoring of the reaction progress was again carried out on both columns with the xselect column giving the best peak shape and separation. Final product analysis was carried out using water acetonitrile (0.05 TFA) as this gave the best quality chromatography. The final HPLC conditions developed are described in Table 23.

Biotage Isolera™ Prime

The Biotage Purification RP-HPLC method involved increasing the method duration for the developed methods to 3 or 4 times as described in Table 24.

TABLE 24

| RP-HPLC Method on Biotage Method 1 (TFA) | | |
|---|---|---|
| Gradient | Time (min) | % B |
| | 0 | 5 |
| | 40 | 99 |
| Column | SNAP Ultra C18 12 g/30 g and 60 g | |
| Buffer A | Water (0.05% TFA additive) | |
| Buffer B | Acetonitrile (0.05% TFA additive) | |
| Flow Rate | 12/18 mL/min | |
| Wavelength | 214 nm & 254 nm | |
| Loading onto column | Direct loading via luer lock syringe | |
| System | Biotage Isolera™ Prime | |

Preparative HPLC

Preparative HPLC was conducted on a Gilson 20:20 HPLC system with a Waters xselect, CSH, C18, prep column (10 μm, 130 Å) with 10 mM ammonium acetate (pH 5.7) as this system was capable of resolving the peptide conjugate from other crude reaction components as summarized in Table 25.

TABLE 25

| Preparative HPLC Method Method 1 10 mM NH₄OAC (pH 5.7) | | |
|---|---|---|
| Gradient | Time (min) | % B |
| | 0 | 10 |
| | 12 | 10 |
| | 18 | 20 |
| | 50 | 40 |
| | 60 | 80 |
| | 70 | 80 |
| Column | Waters Xselect CSH ™ peptide column | |
| Buffer A | 10 mM NH₄Ac in H₂O | |
| Buffer B | MeCN | |
| Flow Rate | 4.7 mL/min | |
| Wavelength | 214 nm & 254 nm | |
| System | Gilson 20:20 | |

Freeze Drying (Lyophilization)

Lyophilization used after purification used the conditions described below.

System: Thermo PL3000 HetoPowerdry

Vacuum: 0.80 hPa

Condenser temp: −63° C.

Length of time: 2-4 days

UV Measurements at A280 and A320

The absorbance at both 280 nm and 320 nm was determined for each sample after the instrument had been zeroed with 50 mM HEPES, pH 7.0. The average A280 nm value was then converted into a concentration and the total product per vial was based on the equation below.

Concentration (mg/mL)=(((A280 nm average)×D.F**)/ε*)×molecular weight [where* extinction coefficient and ** is the dilution factor].

Bicyclic peptide 1 has an estimated extinction coefficient of 7290 M⁻¹ cm⁻¹ in aqueous neutral buffered solution.

Reagent and Reaction Characterization

Using both optimized HPLC methods the reagents and conjugation reaction were characterized as listed below.

Bicyclic peptide 1 stock solution.

NHS activated VcMMAE glutarate stock solution.

A trial conjugation reaction between bicyclic peptide 1 and NHS activated VcMMAE glutarate.

Full scale conjugation of bicyclic peptide 1 and NHS activated VcMMAE glutarate.

The preparation of the reagents and conjugation reaction conditions are described below.

Stock solution of bicyclic peptide 1.

Bicyclic peptide 1 (244.47 mg) was provided in a 50 mL falcon tube. The tube was centrifuged at 3900 rpm for 2 minutes. DMA (2.2986 mL) was added to dissolve the peptide giving a 40 mM stock solution which was stored at −80° C. until required.

Synthesis of VcMMAE Glutarate

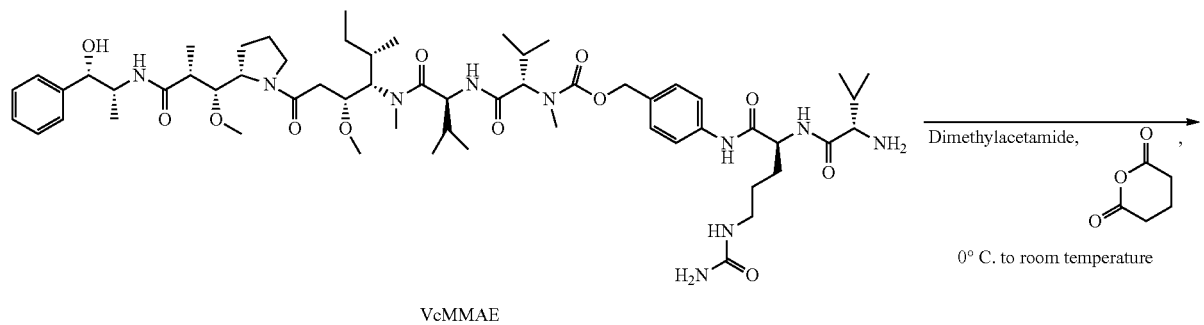

VcMMAE

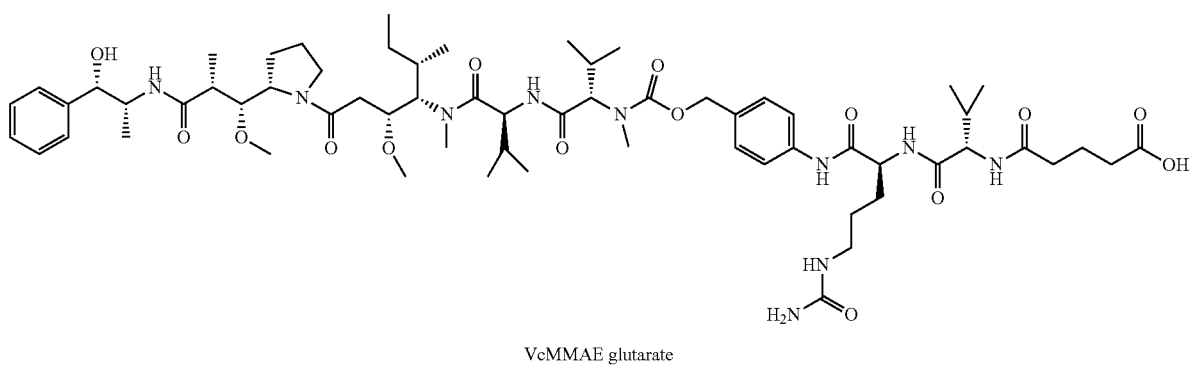

VcMMAE glutarate

A 7 mL screw top vial containing VcMMAE (250 mg) was purged using a nitrogen balloon. 1.72 mL of anhydrous dimethylacetamide was added with stirring and the solution was cooled to 0° C. in an ice water bath. DIPEA (52.24 mg, 0.40 mmol, 2.0 eqv.) was then added as a stock solution in anhydrous dimethyl acetamide (1.05 mL at 50 mg/mL) and the reaction was stirred at 0° C. for 10 minutes.

Glutaric anhydride (46.12 mg, 0.40 mmol, 2.0 eqv.) was then added as a solution in anhydrous dimethyl acetamide (922.4 μL at 50 mg/mL).

The ice bath was then removed and the reaction was stirred to r.t. over the course of 1 h. The progress of the reaction was monitored by LCMS (method 1) and on completion the reaction was quenched with saturated aqueous ammonium sulphate (4 mL) ensuring that the mixture was at a neutral pH before continuing.

Pure water (20 mL) was added causing a precipitate which formed on neutralization to re-dissolve. The aqueous mixture was then transferred into a 100 mL separating funnel rinsing the reaction vessel into the funnel with dichloromethane (25 mL). The layers were separated and the aqueous phase was extracted twice more with fresh dichloromethane (2×25 mL) before drying the combined organic phases by passing through a Biotage® phase separation cartridge into a clean 250 mL round-bottom flask.

The solvent was removed by rotary evaporation with a maximum water bath temperature of 30° C. to give the crude material as a sticky yellow oil which was taken up into 1:5 dimethylacetamide: acetonitrile (4 mL) and loaded as liquid onto a 60 g C18 Biotage cartridge which had been equilibrated into 1% acetonitrile in water with 0.05% TFA buffer.

The cartridge was eluted with 1-99% acetonitrile in water with 0.05% TFA over 40 minutes. Individual fractions were transferred into 50 mL freeze dry vials rinsing the collection tubes with 2 mL 50:50 acetonitrile in water with 0.05% TFA. The vials were then filled to 25 mL using pure water to ensure a solvent content less than 30%. The vials were then frozen at −80° C. overnight before being lyophilized to dryness. Meanwhile pure product containing fractions were identified using LCMS and were combined in a pre-weighed 100 mL round-bottom flask by passing 2×5 mL methanol through pure product containing vials. The methanol was then removed by rotary evaporation with a maximum water bath temperature of 20° C. to give the product as an off white solid (203 mg, 0.18 mmol, 91% yield).

Synthesis of NHS Activated VcMMAE Glutarate (Mid Scale)

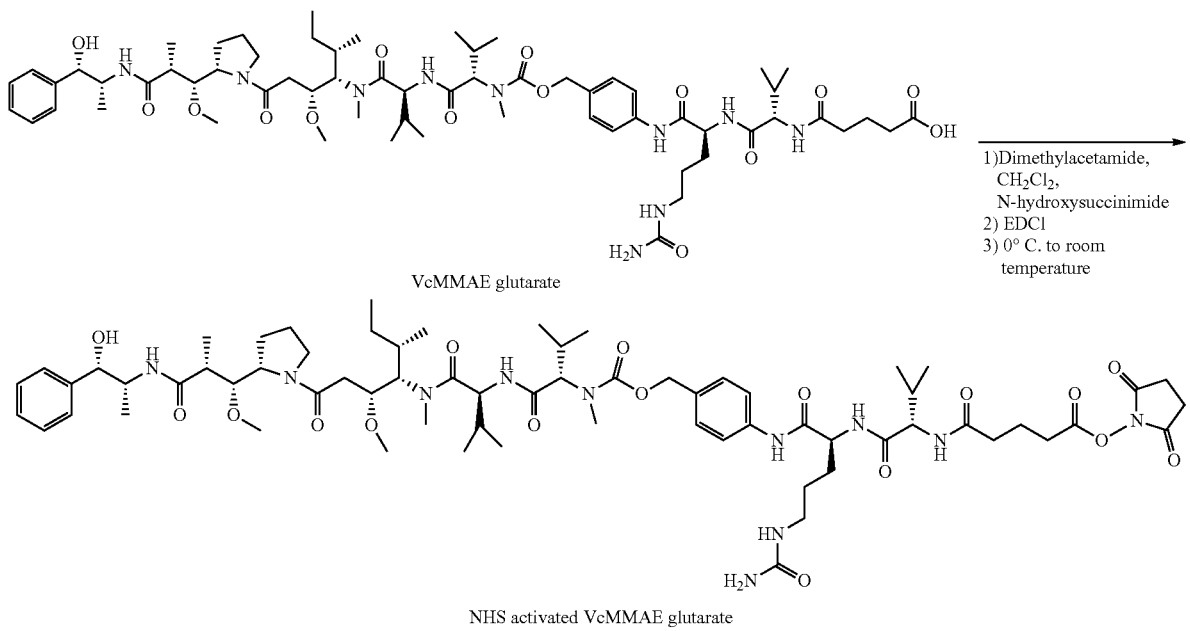

VcMMAE glutarate

1) Dimethylacetamide, CH$_2$Cl$_2$, N-hydroxysuccinimide
2) EDCl
3) 0° C. to room temperature NHS activated VcMMAE glutarate VcMMAE glutarate (50 mg, 0.040 mmol) of the material described above was weighed into a 7 mL screw top vial which was then purged using a nitrogen balloon. Anhydrous dimethylacetamide (1.55 mL) and anhydrous dichloromethane (550 μL) were then added with stirring before adding N-hydroxysuccinimide (5.58 mg, 0.049 mmol, 1.2 eqv.) was then added as a solid and the solution was cooled to 0° C. in an ice water bath.

EDCI (9.30 mg, 0.049 mmol, 1.2 eqv.) was then added as a solid before removing the ice water bath and allowing the reaction to warm to r.t. overnight. Monitoring of the reaction using LCMS (method 1) showed that the reaction had proceeded to approximately 33%. The reaction mixture was cooled to 0° C. and a further 3.0 eqv. of each N-hydroxysuccinimide and EDCI was then added before removing the ice bath and allowing the reaction to warm to r.t. over a further 20 h giving 98% conversion to the product.

Dichloromethane was removed by gentle rotary evaporation before injecting the resulting dimethyl acetamide solution onto a 12 g Biotage® cartridge which had been equilibrated into 5% acetonitrile in water (0.05% TFA buffer) before the cartridge was eluted with 5-99% acetonitrile in water (0.05% TFA) over 40 minutes.

Pure product containing fractions were identified using LCMS and transferred into individual 50 mL freeze dry vials rinsing the collection tubes with 2 mL 50: 50 acetonitrile: water (0.05% TFA) before filling to 25 mL with pure water to ensure an organic content less than 30%.

Vials were then frozen in the −80° C. freezer overnight before being dried by lyophilization. Pure product containing vials were then combined by passing 2×5 mL of 50: 50 acetonitrile: water (0.05% TFA) through all vials into a single pre weighed vial. The vial was then topped up to 25 mL with pure water to give an organic content less than 30% before freezing at −80° C. overnight and drying by lyophilization to give 80% pure material as a free flowing off white solid (33 mg, 0.025 mmol, 61% yield).

Manufacture of NHS Activated VcMMAE Glutarate (Large Scale)

A 50 mL round bottom flask which contained VcMMAE glutarate (136.6 mg, 0.11 mmol) (material described above) was purged using a nitrogen balloon. Anhydrous dimethylacetamide (4.20 mL) and anhydrous dichloromethane (1.5 mL) were then added with stirring before adding N-hydroxysuccinimide (38.4 mg, 0.033 mmol, 3.0 eqv.) was then added as a solid and the solution was cooled to 0° C. in an ice water bath.

EDCI (63.51 mg, 0.33 mmol, 3.0 eqv.) was then added as a solid before removing the ice water bath and allowing the reaction to warm to r.t. overnight. Monitoring of the reaction using LCMS (method 1) showed that the reaction had proceeded to completion.

Dichloromethane was removed by gentle rotary evaporation before injecting the resulting dimethyl acetamide solution onto a 30 g Biotage® cartridge which had been equilibrated into 5% acetonitrile in water (0.05% TFA buffer) before the cartridge was eluted with 5-99% acetonitrile in water (0.1% TFA) over 40 minutes.

Pure product containing fractions were identified using LCMS and transferred into individual 50 mL freeze dry vials rinsing the collection tubes with 2 mL 50: 50 acetonitrile: water (0.1% TFA) before filling to 25 mL with pure water to ensure an organic content less than 30%.

Vials were then frozen in the −80° C. freezer overnight before being dried by lyophilization. Pure product containing vials were then combined by passing 2×5 mL of 50: 50 acetonitrile: water (0.1% TFA) through all vials into a single pre weighed vial. The vial was then topped up to 25 mL with pure water to give an organic content less than 30% before freezing at −80° C. overnight and drying by lyophilization to give 60% pure material as a free flowing off white solid (118 mg, 0.089 mmol, 80% yield).

On freeze drying the ice cake melted on a number of occasions a trace of the pool sample is shown below and indicates that degradation to the acid has taken place during the problematic lyophilization.

Bicyclic Peptide 1

5 µL of the peptide stock solution was added to 195 µL of DMA. The solution was then vortexed and split into two 100 µL HPLC samples. The samples were analyzed with a 5 injection on separate machines fitted with ACE 3 and xselect columns with 10 mM NH$_4$Ac as mobile phase in each case. Analysis of the peptide by LCMS confirmed its purity and identity.

Trial Reaction Analysis

A 10 mg scale trial reaction between the peptide and NHS activated VcMMAE glutarate was carried out to allow for analytical method development.

Stock peptide 1 (32 mM, 116.8 µL in DMA, 3.76 µmol) was transferred to a 1.5 mL vial (septum cap) which had been purged using a nitrogen balloon. DIPEA (3.33 µL, 2.43 mg, 18.8 µmol, 5 eqv.) was then added and the solution was stirred at r.t. for 10 minutes before adding NHS activated VcMMAE glutarate (7.53 mg, 5.64 µL, 1.5 eqv.) in DMA (129.7 µL, 58.02 mM solution). The reaction was stirred at r.t. under a positive nitrogen atmosphere for 18 hours. A 1:100 dilution in 1:1 water:acetonitrile was used to produce a HPLC sample for method development. The reaction mixture was stored at –80° C.

HPLC analysis using method 3 gave 1.3 minutes of separation between product and the closest migrating impurity. The closest impurity to the product at 12.92 mins in 10 mM ammonium acetate (pH 5.7) was identified as the NHS ester.

The analytical method was translated onto the Gilson 20:20 preparative HPLC system to give the preparative HPLC method shown in Table 25.

The material was purified in two 8.77 mg passes by adding 123 µL of the crude reaction mixture carefully to 123 µL of 20% acetonitrile in 10 mM ammonium acetate (pH 5.7) followed by vortex mixing. The full aqueous mixture was then loaded in one portion onto the prep HPLC system running preparative gradient.

Product containing fractions were identified using HPLC method 2 before being transferred to 20 mL lyophilization vials, washing collection tubes with a further 2 mL of 50: 50 acetonitrile: 10 mM ammonium acetate. Vials were then topped up to 10 mL using pure water, then frozen in the –80° C. freezer overnight. Vials were then lyophilized to dryness against a control vial which contained ammonium acetate only.

5 mL of 50: 50 acetonitrile: 10 mM ammonium acetate was then passed through product containing vials in two 2.5 mL portions into a single pre weighed vial. 5 mL of pure water was then added and the mixture was frozen overnight in the –80° C. freezer and lyophilized to dryness to give the pure product as a free flowing white powder (8.7 mg, 2.24×10$^{-3}$ mmol, 60% yield).

Synthesis

166 Mg Scale Up Batch

A 7 mL screw top vial which contained stock peptide solution 1 (32 mM, 1.34 mL in DMA, 42.9 µmol, 114 mg) was purged using a nitrogen balloon. DIPEA (37.4 µL, 27.1 mg, 0.22 mmol, 5 eqv.) was then added and the reaction was stirred at r.t. for 10 minutes. NHS activated VcMMAE glutarate (85.9 mg, 64.4 µmol, 1.5 eqv.) in DMA (1.85 mL, 34.8 mM solution, 60% pure) was then added and the reaction was stirred under a positive nitrogen atmosphere overnight at r.t. Analysis of the reaction showed a similar profile to the 10 mg trial reaction with a trace of peptide remaining. The crude reaction mixture was purified by reverse phase preparative chromatography (8×20 mg passes on the crude material plus 3 re-passed impure material) using the preparative method shown in section 3.2.2. Product containing collection tubes were transferred to individual 50 mL lyophilization vials washing collection tubes with a further 4 mL of 50: 50 acetonitrile: 10 mM ammonium acetate. Vials were then topped up to a volume of 25 mL using pure water, then frozen in the –80° C. freezer overnight. Vials were then lyophilized to dryness against a control vial which contained ammonium acetate only.

10 mL of 50:50 acetonitrile:10 mM ammonium acetate was then passed through product containing vials in two 5 mL portions into a single pre weighed 50 mL lyophilization vial. 15 mL of pure water was then added and the mixture was frozen overnight in the –80° C. freezer and lyophilized to dryness to give the pure product as a free flowing white powder (122.1 mg, by weight). The material was taken back up into 50:50 acetonitrile: 10 mM ammonium acetate (24.42 mL, 5 mg per mL). 1 mL portions of the stock solution were divided between 24 clean, dry 10 mL lyophilization vials (pre weighed) before adding further 50:50 acetonitrile: 10 mM ammonium acetate (24.42 mL) to the parent vial and again portioning between the 10 mL vials in 1 mL portions. 3 mL of water was then added to each vial to give a final of 5 mL per vial (a single vial was not filled to 5 mL; this was used as the analysis vial).

All vials were frozen in the –80° C. freezer overnight then lyophilized to dryness against a control vial which contained ammonium acetate only. After the ice cake has disappeared the vials were lyophilized for a further 48 h to give 23 vials containing 5 mg of product (±0.5 mg) and a single vial which contained 3.4 mg. The total yield was 122.1 mg (32 µmol, 73% yield) of pure product see Table 26.

TABLE 26

| Nominal Vials with Fill Volumes and Amounts | | |
|---|---|---|
| Nominal Vial Size | Quantity of Vials | Fill Volume (mL) |
| 5 mgs | 24 | 5.00 |
| Part filled | 1 | 4.5 |

Product QC Analysis

RP-HPLC and RP-HPLC-MS for I-1a Purity and Identity

A single representative nominal 5 mg vial (actual 3.4 mg) was reconstituted in DMSO (175.5 µL) such that the concentration was at 5 mM, 2 µL of this stock solution was added to 198 of DMSO and the sample analyzed by RP-HPLC and RP-HPLC-MS with a 5 µL to confirm purity and identity respectively. RP-HPLC using method 2 (NH$_4$OAc, method 2) (see Table 23) was used initially as this method gave clear resolution of the product from VcMMAE glutaryl and the VcMMAE glutaryl NHS ester and confirmed that VcMMAE related impurities were not present. A TFA method (method 1, see Table 23) was then used as this method gave the best peak shape compared to NH$_4$OAc.

MS analysis using Method 1 (TFA) (see Table 23) showed the presence of four major m/z ion series. The [M]$^{2+}$ series has the expected mass species of 1939.4 ((2×1939.4)–2=3876.8). The [M]$^{3+}$ series also has the expected mass species of 1293.4 ((3×1293.4)–3=3877.2). Finally, the [M]$^{4+}$ has the mass of 970.2 ((970.2×4)–4=3976.8. The 718 Da adduct which is consistent with MMAE is an artefact of the MS analysis where its intensity is dependent on collision energy.

Discussion and Conclusion

Product Quality

The final product is 99.5% target peptide-VcMMAE conjugate with minimal quantities of unknown impurities as shown in Table 27, below.

TABLE 27

Final QC analysis using Method 1 (TFA) with Hichrom ACE 3

| Peak No. | Ret. Time (min) | Width (min) | Area (mAU) | Height (mAU) | Area % |
|---|---|---|---|---|---|
| 1 | 80749 | 0.0835 | 26.30051 | 5.24981 | 0.4949 |
| 2 | 10.273 | 0.1184 | 5288.19580 | 744.12122 | 99.5051 |

Synthesis

The synthesis of I-1a required little optimization such that the conversion of starting peptide to product was high without the need to add a large excess of VcMMAE glutaryl NHS ester.

Purification

Analytical RP-HPLC resulted in a good separation where all unwanted impurities were resolved from the product peptide. Translation of this method to the Gilson 20:20 preparative HPLC system gave reproducible resolution and separation.

Yield

A total of 1×3.4 mg, 3×4.5 mg, 2×4.6 mg, 4×4.8 mg, 3×4.9 mg, 5×5.0 mg, 1×5.1 mg, 2×5.2 mg, 2×5.3 mg, 1×5.4 mg and 1×5.6 mg product vials were filled. This is a total of 122.1 mgs from 166 mgs achievable from the two starting conjugations. The overall yield from starting materials to vialled product is 73%.

3×4.5 mg, 2×4.6 mg, 4×4.8 mg, 3×4.9 mg, 5×5.0 mg, 1×5.1 mg, 2×5.2 mg, 2×5.3 mg, 1×5.4 mg and 1×5.6 mg were isolated. A vial containing 3.4 mg in DMSO (5 mM) was retained for future QC analysis along with a vial containing 8.7 mg of product from the trial scale.

Summary

The target purity and yield of I-1a was achieved without the presence of MMAE derivatives. Preparative HPLC in 10 mM ammonium acetate (pH 5.7) gave the best separation of compounds, but gave poor product peak shape. HPLC analysis in TFA gave superior peak shape and chromatography quality.

Example 9

Efficacy of I-1a in MT1-MMP Expressing NSCLC PDX Model

Study Objective

The objective of this study was to evaluate the in vivo anti-tumor efficacy of I-1a in the treatment of MT1-MMP high expressing LU-01-0046 PDX model in female Balb/C nude mice.

Materials: Animals and Housing Conditions
Animals
  Species: *Mus Musculus*
  Strain: Balb/C nude
  Age: 6-8 weeks
  Sex: female
  Body weight: 18-22 g
  Number of animals: 18 mice.

Housing Conditions

The mice were kept in individual ventilation cages at constant temperature and humidity with 3 animals in each cage.
  Temperature: 20~26° C.
  Humidity 40-70%.
  Cages: Made of polycarbonate. The size is 300 mm×180 mm×150 mm. The bedding material is corn cob, which is changed twice per week.
  Diet: Animals had free access to irradiation sterilized dry granule food during the entire study period.
  Water: Animals had free access to sterile drinking water.
  Cage identification: The identification labels for each cage contained the following information: number of animals, sex, strain, the date received, treatment, study number, group number and the starting date of the treatment.
  Animal identification: Animals were marked by ear coding.

Tumor Inoculation

Each mouse was inoculated subcutaneously at the right flank with LU-01-0046 of tumor fragment (~30 mm$^3$) for tumor development. The treatment was started when the average tumor volume reaches 163 mm$^3$. The test article administration and the animal numbers in each group were shown in the experimental design table.

Observations

All the procedures related to animal handling, care and the treatment in the study were performed following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured twice weekly), eye/hair matting and any other abnormal effect as stated in the protocol. Death and observed clinical signs were recorded on the basis of the numbers of animals within each subset.

Tumor Measurements and the Endpoints

The major endpoint was to see if the tumor growth could be delayed or mice could be cured. Tumor size was measured two times weekly in two dimensions using a caliper, and the volume was expressed in mm$^3$ using the formula: V=0.5 a×b$^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Sample Collection

Mice in group 2 was re-dosed and plasma was collected at 5 min, 15 min, 30 min, 60 min and 120 min on day 56.

The tumor samples were collected from group 2 and fixed in 10% formalin, then embedded in paraffin and stored at ambient temperature.

Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using Prism. P<0.05 was considered to be statistically significant.

As shown in FIG. 6, the mean tumor size of vehicle-treated animals reached 2304 mm$^3$ on day 28, mice treated with I-1a at 1 mg/kg showed significant growth inhibition, comparable to that seen with the clinically used agent Docetaxel. Mice treated with I-1a at 3 or 10 mg/kg showed significant growth inhibition, greater than that seen with docetaxel.

Example 10

Efficacy & Tolerability of I-1a in MT1-MMP Low-Expressing NSCLC PDX Model

Study Objective

The objective of this study was to evaluate the in vivo anti-tumor efficacy of I-1a in the treatment of MT1-MMP low-expressing LU-01-0486 PDX model in female Balb/C nude mice Materials: Animals and Housing Conditions Animals Species: *Mus Musculus*.

Strain: Balb/C nude.

Age: 6-8 weeks.

Sex: female.

Body weight: 18-22 g.

Number of animals: 18 mice.

Housing Conditions

The mice were kept in individual ventilation cages at constant temperature and humidity with 3 animals in each cage.

Temperature: 20~26° C.

Humidity 40-70%.

Cages: Made of polycarbonate. The size is 300 mm×180 mm×150 mm. The bedding material is corn cob, which is changed twice per week.

Diet: Animals had free access to irradiation sterilized dry granule food during the entire study period.

Water: Animals had free access to sterile drinking water.

Cage identification: The identification labels for each cage contained the following information: number of animals, sex, strain, the date received, treatment, study number, group number and the starting date of the treatment.

Animal identification: Animals were marked by ear coding.

Experimental Methods and Procedures

Tumor Inoculation

Each mouse was inoculated subcutaneously at the right flank with LU-01-0486 of tumor fragment (30 mm$^3$) for tumor development. The treatments was started when the average tumor volume reaches 164 mm$^3$.

Observations

All the procedures related to animal handling, care and the treatment in the study were performed following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured twice weekly), eye/hair matting and any other abnormal effect as stated in the protocol. Death and observed clinical signs were recorded on the basis of the numbers of animals within each subset.

Tumor Measurements and the Endpoints

The major endpoint was to see if the tumor growth could be delayed or mice could be cured. Tumor size was measured two times weekly in two dimensions using a caliper, and the volume was expressed in mm$^3$ using the formula: $V=0.5\ a \times b^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Sample Collection

Mice in group 2, 3 were re-dosed and plasma was collected at 5 min, 15 min, 30 min, 60 min and 120 min on day 24.

The tumor samples were collected and fixed in 10% formalin, then embedded in paraffin and stored at ambient temperature before sending to client.

Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using Prism. P<0.05 was considered to be statistically significant.

Figure 7:
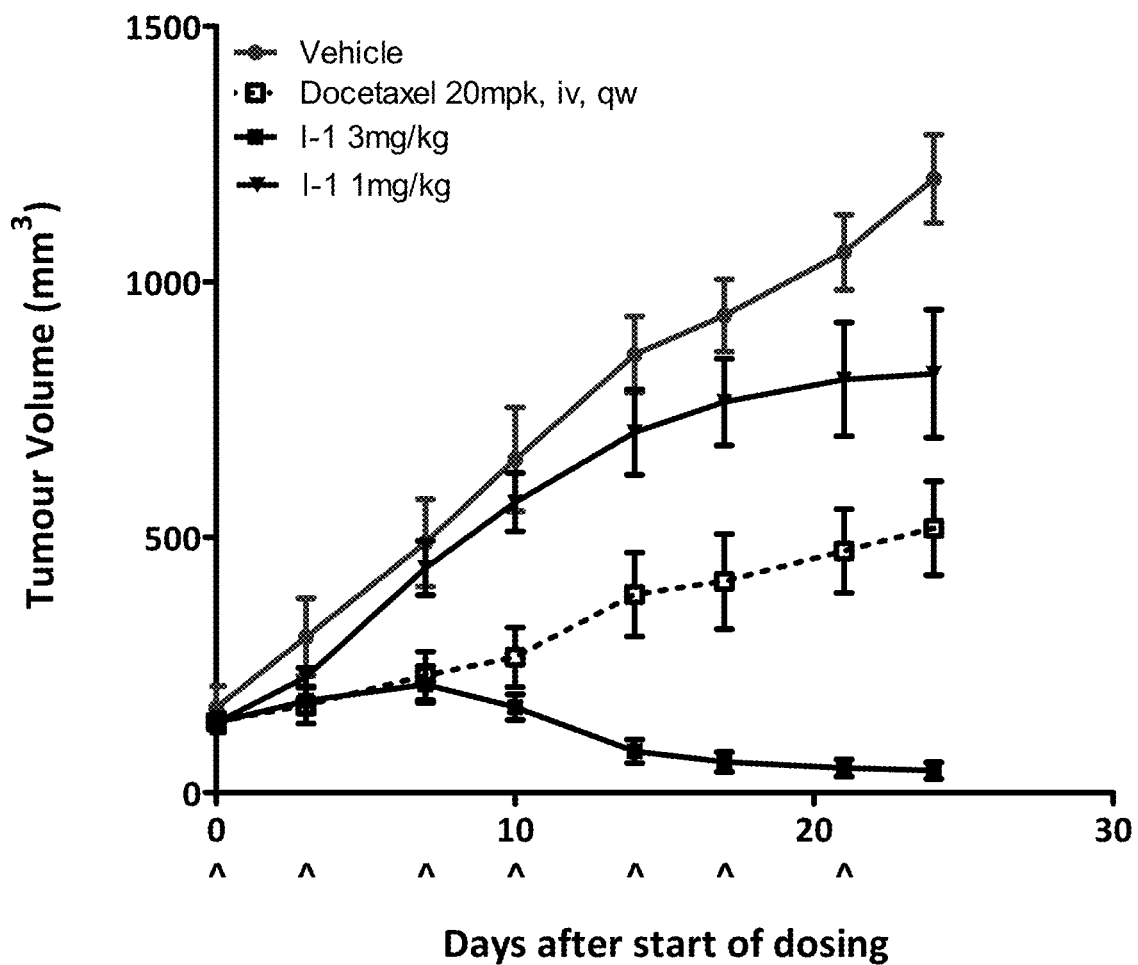
FIG. 7 depicts the efficacy of I-1a in the MT1-MMP low-expressing NSCLC PDX model.
Figure 8:
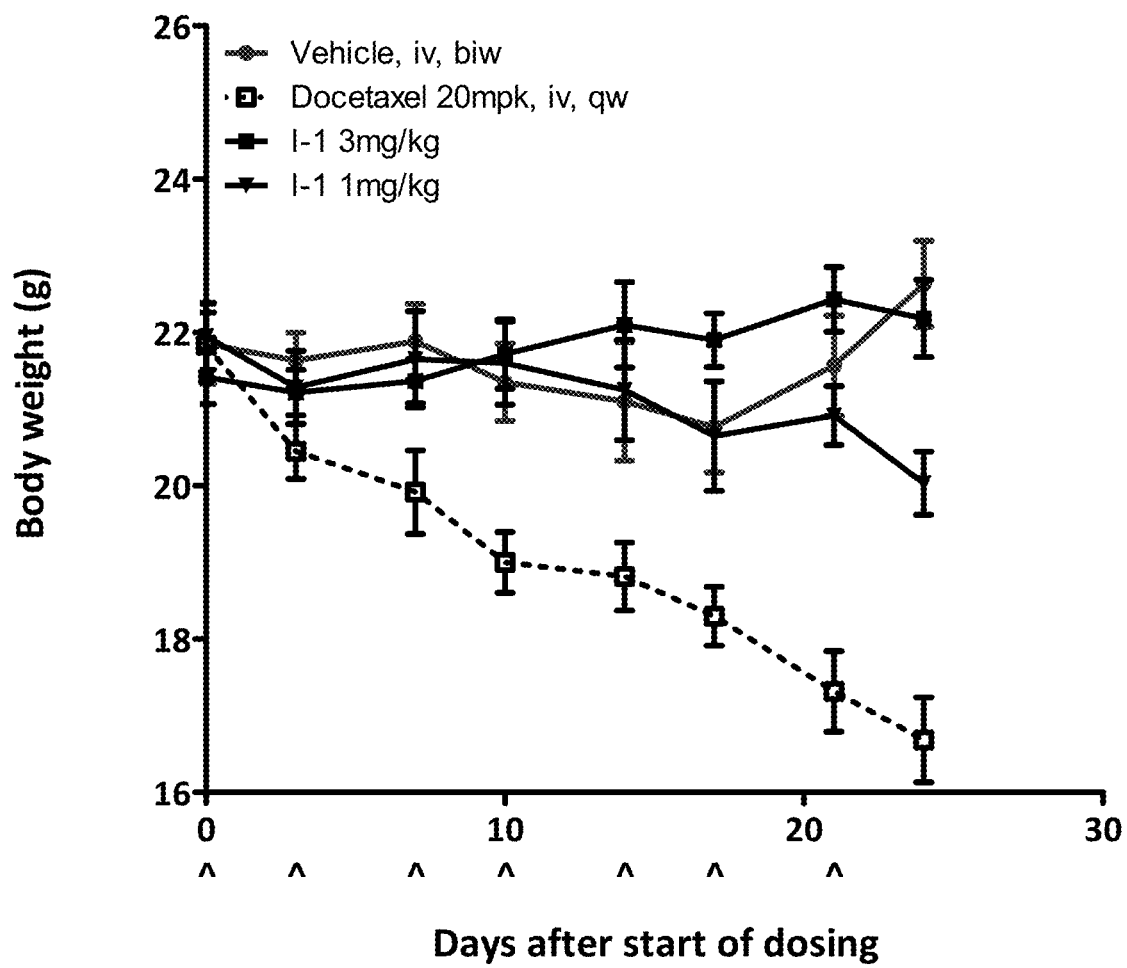
FIG. 8 depicts the tolerability of I-1a in the MT1-MMP low-expressing NSCLC PDX model.

As shown in FIGS. 7 and 8, the mean tumor size of vehicle-treated animals reached 1201 mm$^3$ on day 24, mice treated with the clinically used agent Docetaxel showed significant inhibition of tumor growth, but with severe weight loss, leading to the humane sacrifice of animals at day 24. Mice dosed with I-1a at 3 mg/kg showed greater inhibition of tumor growth without significant effect on body weight. Mice dosed with I-1a at 1 mg/kg showed limited inhibition of tumor growth and no significant effect on body weight.

Example 11

Synthesis of I-10 to I-17

Figure 13:
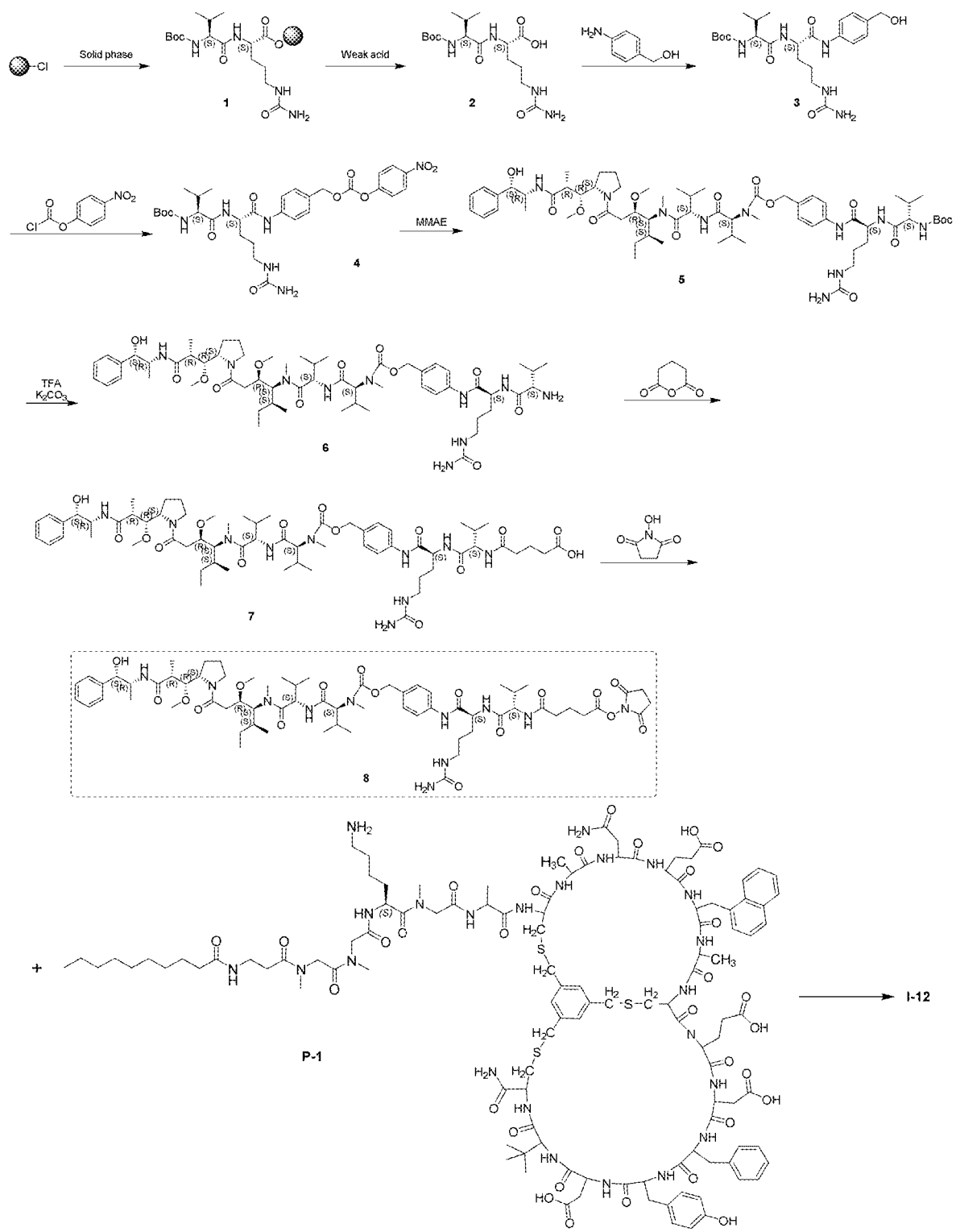
FIG. 13 depicts the reaction scheme of I-12, I-15, I-16 and I-17.
Figure 13:
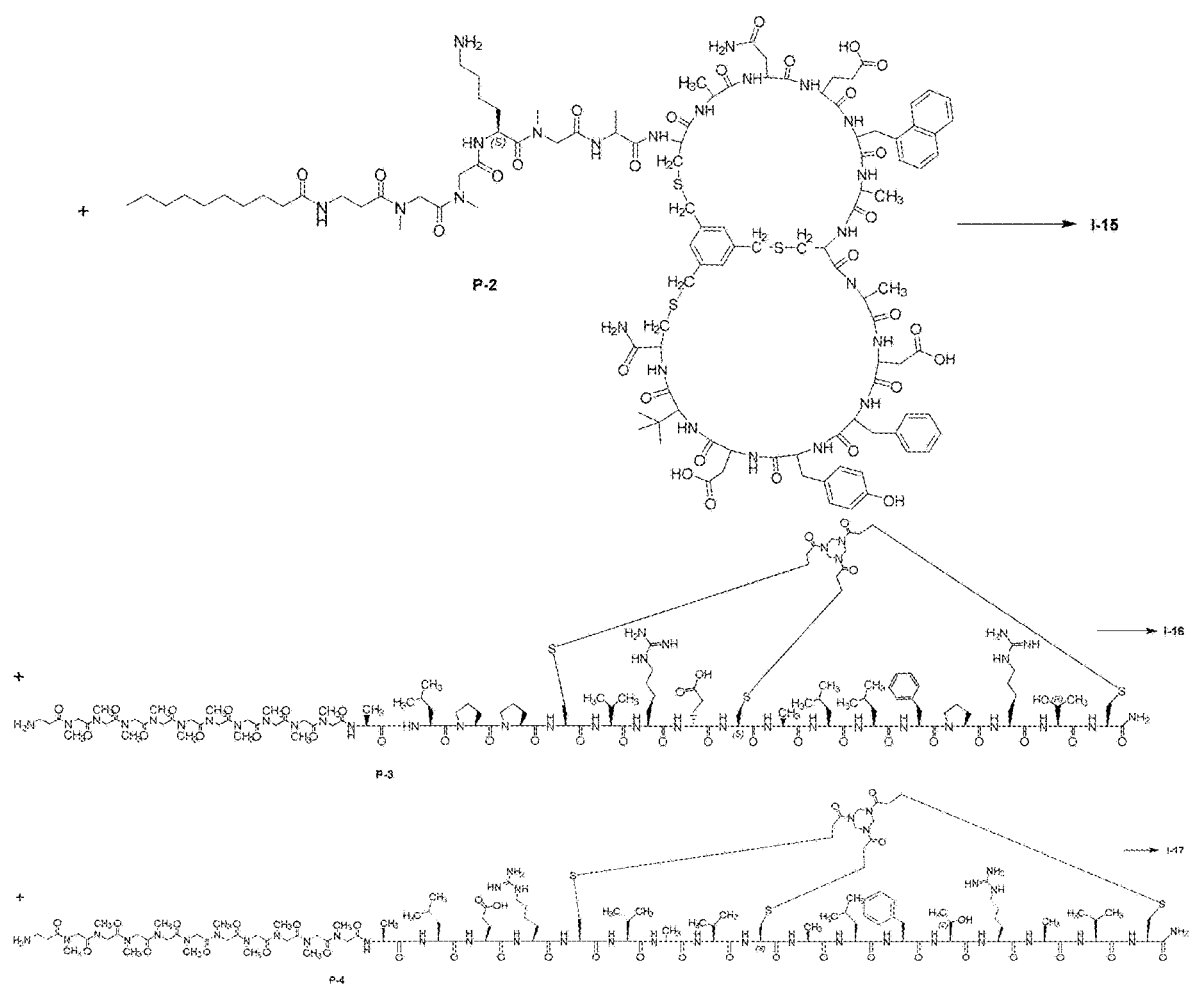

Exemplary synthesis methods are described below.
(1) Separation:
Separation Condition: A phase: 0.075% TFA in H₂O, B phase: MeCN
Separation method: 18-48-55 min, RT=53.5 min
Separation column: Luna 200*25 mm 10 um, C18, 110A and Gemin150*30 mm, $C_{18}$, 5um,
110A, connection, 50° C.
Dissolve method: DMF
Separation purity: 95%
(2) The Reaction Scheme of I-12, I-15, I-16 and I-17 is Shown in FIG. 13.

General Procedure for Preparation of Compound 3

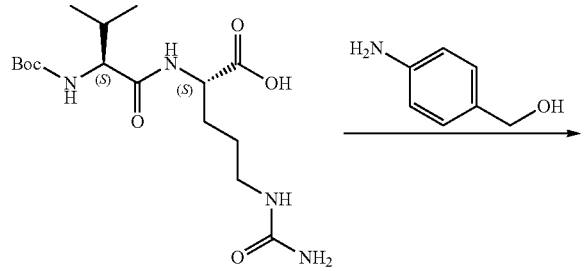

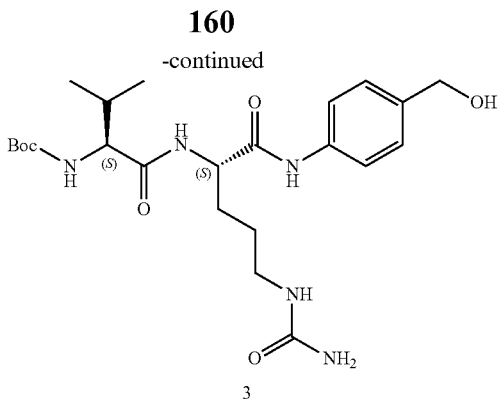

To a solution of Compound 2 (7.00 g, 18.70 mmol, 1.00 eq) in DCM (80.00 mL) and MeOH (40.00 mL) was added (4-aminophenyl)methanol (2.53 g, 20.56 mmol, 1.10 eq) and EEDQ (9.25 g, 37.39 mmol, 2.00 eq) in the dark. And the mixture was stirred at 25° C. for 8 hr. LC-MS showed Compound 2 was consumed completely and one main peak with desired MS was detected. The resulting reaction mixture was concentrated under reduced pressure to remove the solvent to give a residue. The residue was purified by flash silica gel chromatography (ISCO®; 120 g SepaFlash® Silica Flash Column, Eluent of 0~10% MeOH/DCM @ 85 mL/min). Compound 3 (7.00 g, 14.60 mmol, 78.06% yield) was obtained as a white solid.

General Procedure for Preparation of Compound 4

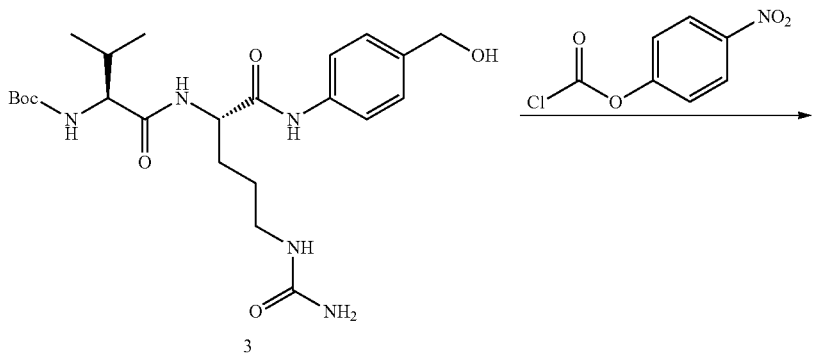

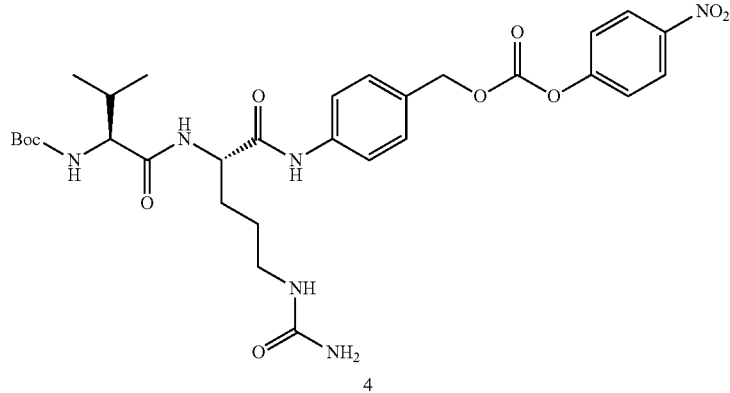

To a solution of Compound 3 (4.00 g, 8.34 mmol, 1.00 eq) and 4-nitrophenyl carbonochloridate (6.72 g, 33.36 mmol, 4.00 eq) in THF (20.00 mL) and DCM (10.00 mL) was added PYRIDINE (2.64 g, 33.36 mmol, 2.69 mL, 4.00 eq). And the reaction mixture was stirred at 25° C. for 5 hr. LC-MS showed Compound 3 was consumed completely and one main peak with desired MS was detected. The reaction mixture was concentrated under reduced pressure to give a residue, which was purified by flash silica gel chromatography (ISCO®; 120 g SepaFlash® Silica Flash Column, Eluent of 0-20% DM/MeOH @ 85 mL/min). Compound 4 (2.20 g, 3.41 mmol, 40.92% yield) was obtained as a white solid.

General Procedure for Preparation of Compound 5

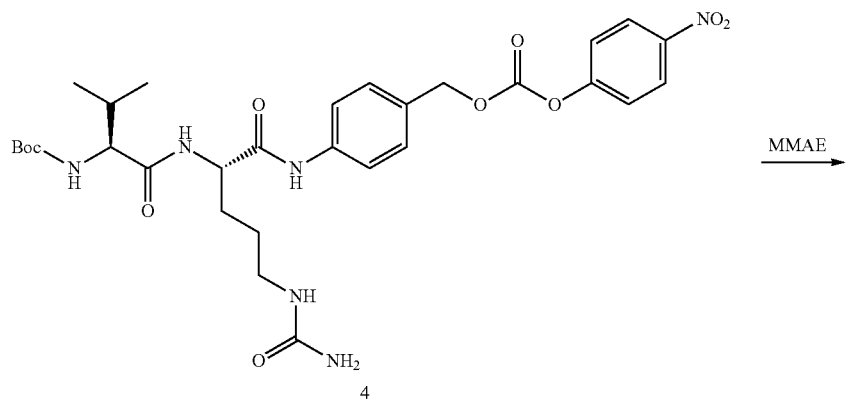

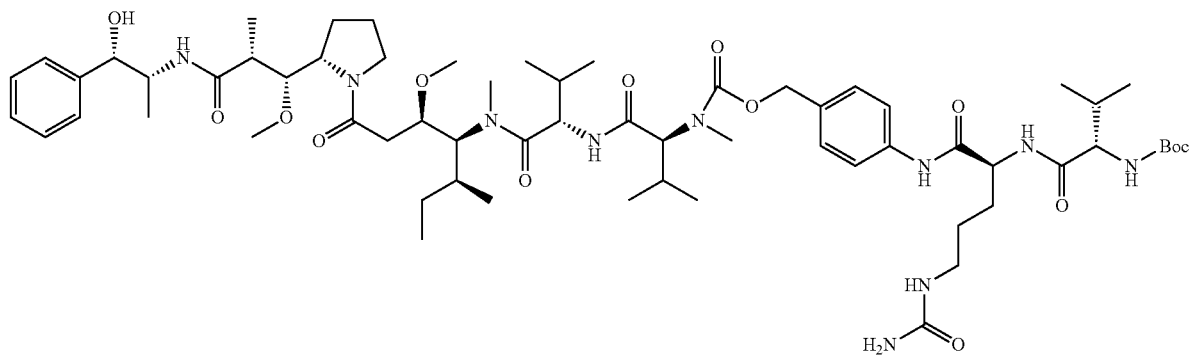

A mixture of Compound 4 (1.10 g, 1.71 mmol, 1.00 eq) and DIEA (2.21 g, 17.06 mmol, 2.98 mL, 10.00 eq) in DMF (10.00 mL) was stirred under nitrogen at 0° C. for 30 mins. MMAE (900.00 mg, 1.25 mmol, 0.73 eq) and HOBt (230.56 mg, 1.71 mmol, 1.00 eq) was added to the mixture and the resulting reaction mixture was stirred under nitrogen at 0° C. for 10 min and at 30° C. for additional 18 hr. LC-MS showed Compound 4 was consumed completely and one main peak with desired MS was detected. The reaction mixture was purified by flash C18 gel chromatography (ISCO®; 120 g SepaFlash® C18 Flash Column, Eluent of 0~50% MeCN/H₂O @ 85 mL/min). Compound 5 (850.00 mg, 694.71 umol, 40.63% yield) was obtained as a white solid.

General Procedure for Preparation of Compound 6

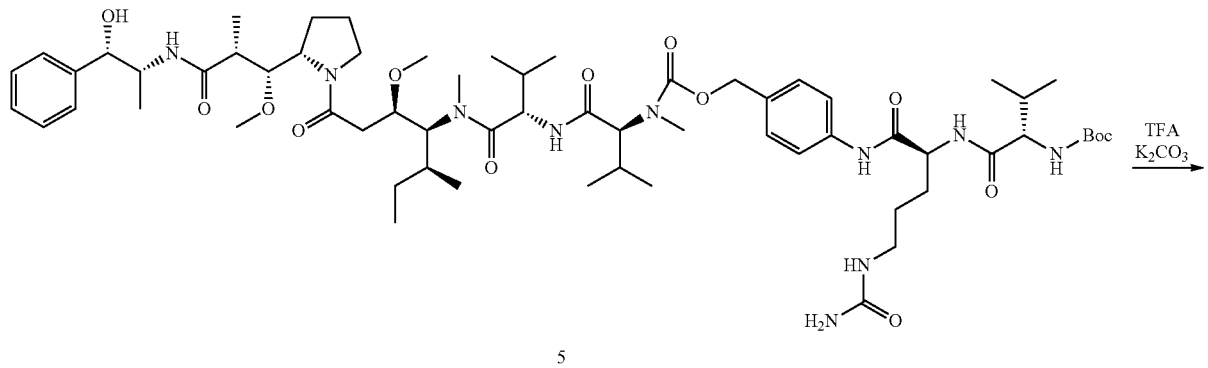

5

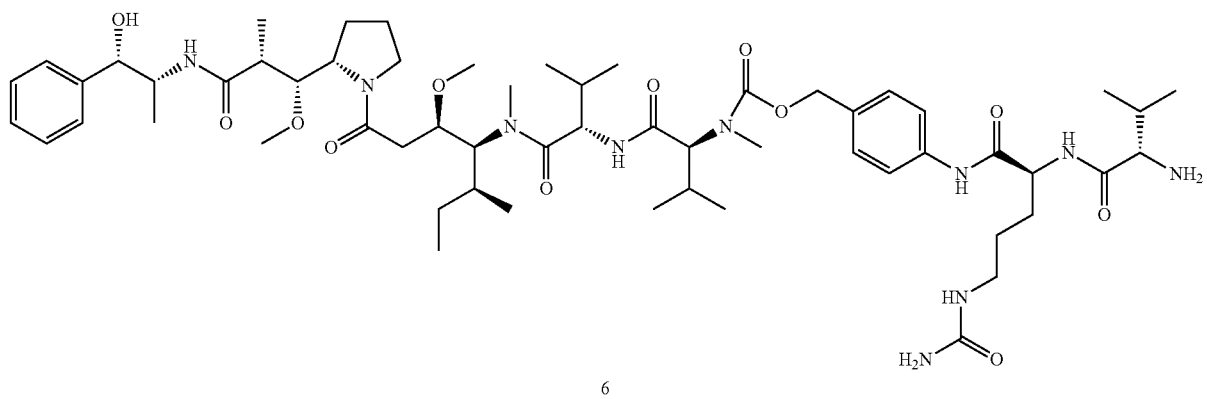

6

To a solution of Compound 5 (850.00 mg, 694.71 umol, 1.00 eq) in DCM (36.00 mL) was added TFA (12.18 g, 106.80 mmol, 7.91 mL, 153.73 eq) and the mixture was stirred at room temperature for 2 hr. The mixture was concentrated under reduced pressure to give a residue, which was dissolved in THF (10.00 mL), and $K_2CO_3$ (2.40 g, 17.37 mmol, 25.00 eq) was added to the mixture. The reaction was stirred at 25° C. for 12 hr. LC-MS showed Compound 5 was consumed completely and one main peak with desired MS was detected. The resulting reaction mixture was purified by flash C18 gel chromatography (ISCO®; 120 g SepaFlash® C18 Flash Column, Eluent of 0~50% MeCN/$H_2O$ @ 85 mL/min). Compound 6 (560.00 mg, 498.48 umol, 71.75% yield) was obtained as a white solid.

General Procedure for Preparation of Compound 7

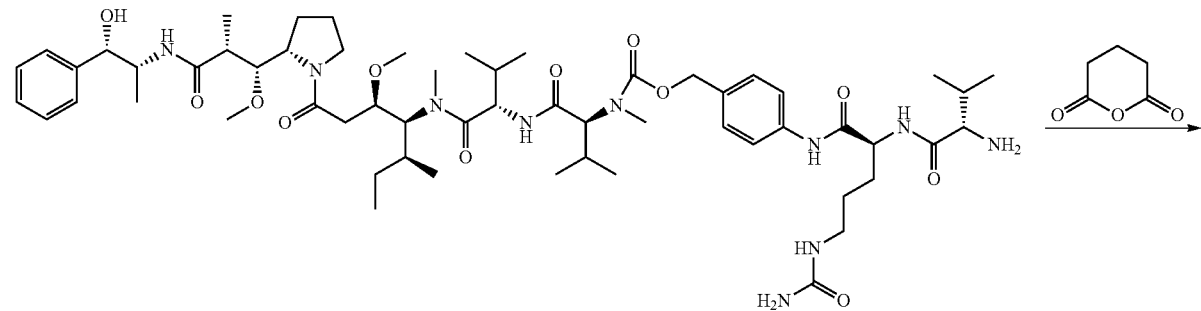

6

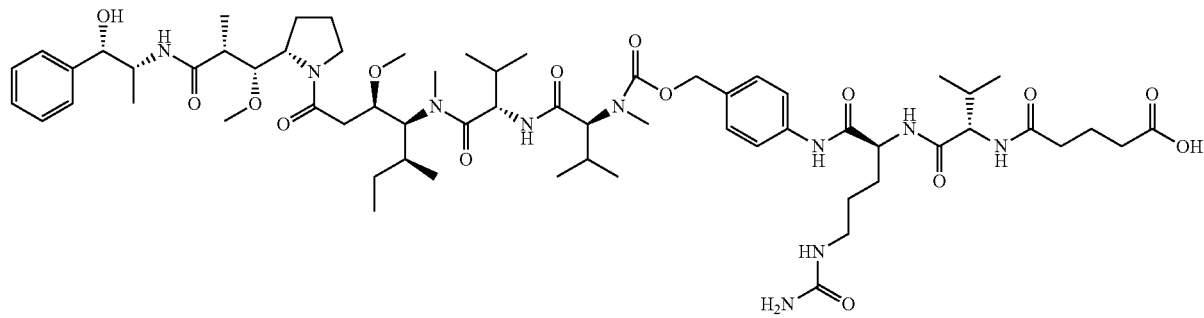

7

A 50 mL round flask containing Compound 7 (400.00 mg, 356.06 umol, 1.00 eq) was purged using a nitrogen balloon. 10 mL of anhydrous DMA was added with stirring and the solution was cooled to 0° C. in an ice water bath. DIEA (92.03 mg, 712.11 umol, 124.37 uL, 2.00 eq) was then added as a stock solution in anhydrous DMA and the reaction was stirred at 0° C. for 10 min. Tetrahydropyran-2,6-dione (81.25 mg, 712.11 umol, 2.00 eq) was added as a solution in DMA. The ice bath was then removed and the reaction was stirred at room temperature over the course of 1 hr. LC-MS showed Compound 6 was consumed completely and one main peak with desired MS was detected. The reaction mixture was purified by flash C18 gel chromatography (ISCO®; 120 g SepaFlash® C18 Flash Column, Eluent of 0~50% MeCN/H$_2$O @ 85 mL/min). Compound 7 (300.00 mg, 242.42 umol, 68.08% yield) was obtainde as a white solid.

General Procedure for Preparation of Compound 8

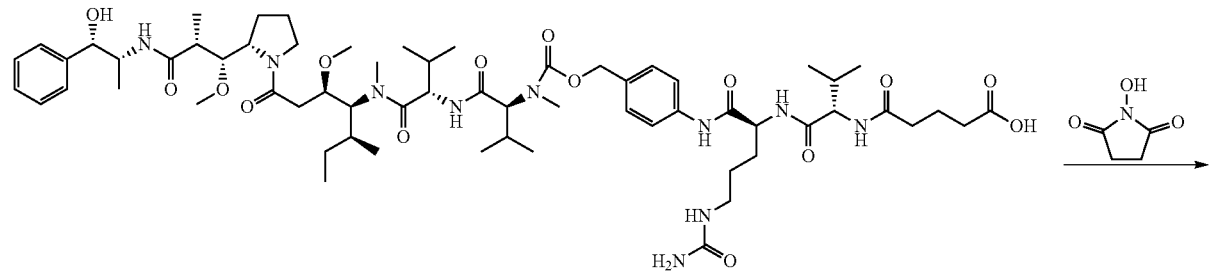

7

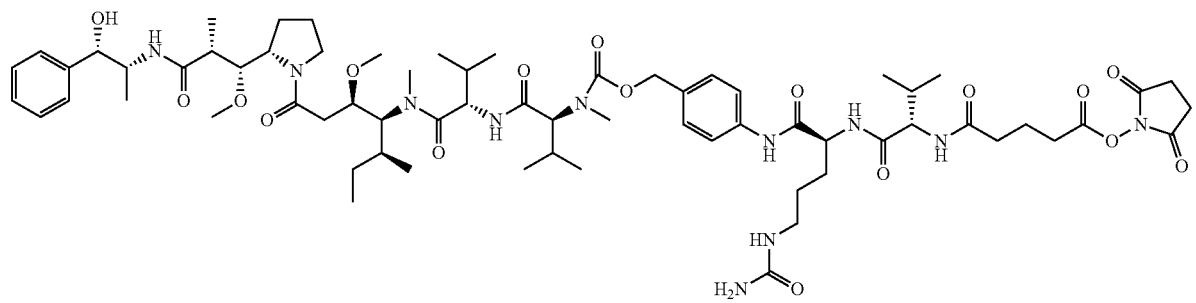

8

A 50 mL round flask containing Compound 7 (300.79 mg, 230.91 umol, 1.00 eq) was purged using a nitrogen balloon. DMA (15.00 mL) and DCM (5.00 mL) were added with stirring and the solution was cooled to 0° C. in an ice water bath. EDCI (132.79 mg, 692.72 umol, 3.00 eq) and 1-hydroxypyrrolidine-2,5-dione (79.72 mg, 692.72 umol, 3.00 eq) were added, and the ice bath was then removed. After that, the reaction was stirred at 25° C. for 16 hr. LC-MS showed Compound 7 was consumed completely and one main peak with desired MS was detected. The reaction mixture was purified by flash C18 gel chromatography (ISCO®; 130 g SepaFlash® C18 Flash Column, Eluent of 0~50% MeCN/H₂O @ 85 mL/min). Compound 7 (155.00 mg, 116.14 umol, 50.30% yield) was obtained as a white solid.

General Procedure for Preparation of I-16

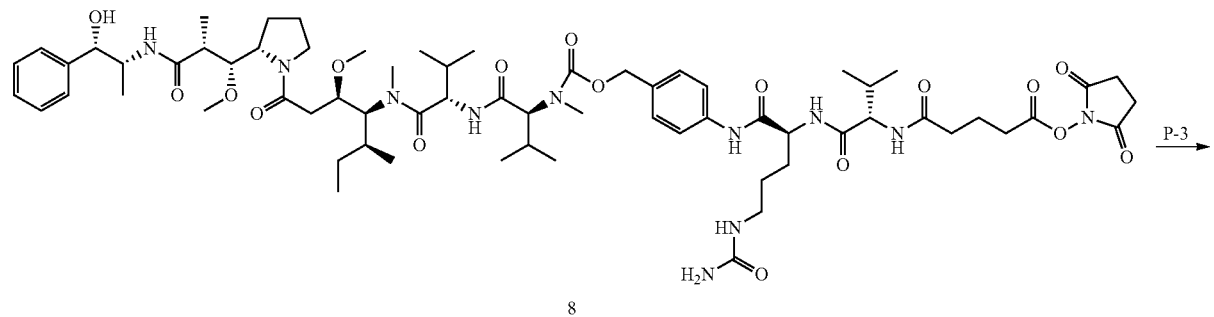

A 50 mL round bottom flask which contained Compound P-3 (66 mg, 22.4 umol, 1.00 eq) in DMA (5 mL) was purged using nitrogen balloon. DIEA (2.91 mg, 112.4 umol, 19.6 uL, 5 eq) was then added with stirring at 25° C. Compound 8 (30.00 mg, 22.48 umol, 1.00 eq) was then added and the reaction was stirred under a positive nitrogen atmosphere at 25° C. for 16 hrs. LC-MS showed Compound 8 was consumed completely and one main peak with desired MS was detected. The resulting reaction mixture was purified by prep-HPLC (TFA condition). Compound I-16 (20.2 mg, 4.85 umol, 21.56% yield) was obtained as a white solid.

General Procedure for Preparation of I-12

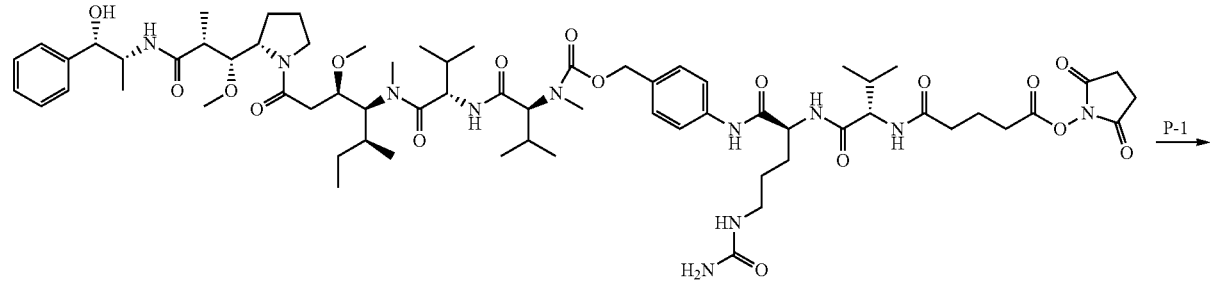

A 50 mL round bottom flask which contained Compound P-1 (75 mg, 22.75 mmol, 1 eq) in DMA (5 mL) was purged using nitrogen balloon. DIEA (2.91 mg, 22.48 umol, 3.92 uL, 1 eq) was then added with stirring. Compound 8 (30.00 mg, 22.48 umol, 1.00 eq) was then added and the reaction was stirred under a positive nitrogen atmosphere 25° C. for 17 hr. LC-MS showed Compound 8 was consumed completely and one main peak with desired MS was detected. The resulting reaction mixture was purified by prep-HPLC (TFA condition). Compound I-12 (29.7 mg, 6.58 umol, 29.25% yield) was obtained as a white solid.

General Procedure for Preparation of I-15

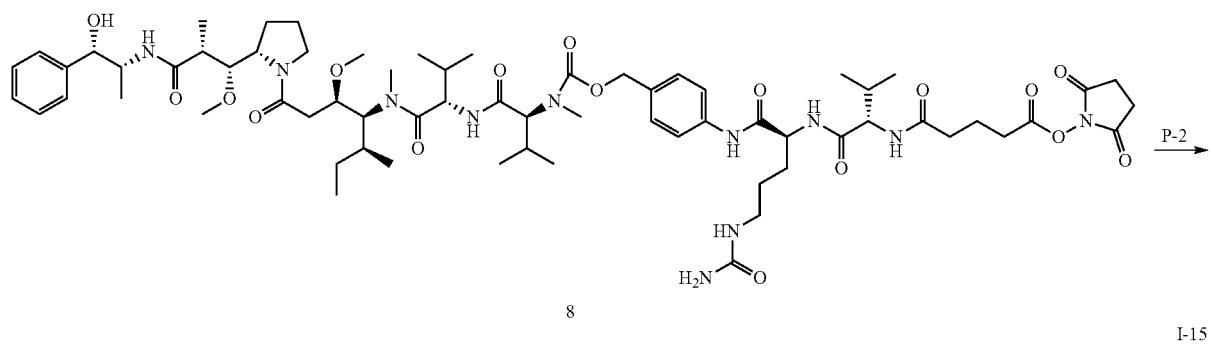

A 50 mL round bottom flask which contained Compound P-2 (72 mg, 22.23 umol, 1 eq) in DMA (5 mL) was purged using nitrogen balloon. DIEA (10.02 mg, 77.56 umol, 13.51 uL, 3.45 eq) was then added with stirring. Compound 8 (30 mg, 22.48 umol, 1.00 eq) was then added and the reaction was stirred under a positive nitrogen atmosphere 25° C. for 16 hr. LC-MS showed Compound 8 was consumed completely and one main peak with desired MS was detected. The resulting reaction mixture was purified by prep-HPLC (TFA condition). Compound I-15 (28.1 mg, 6.31 umol, 28.04% yield) was obtained as a white solid.

General Procedure for Preparation of I-17

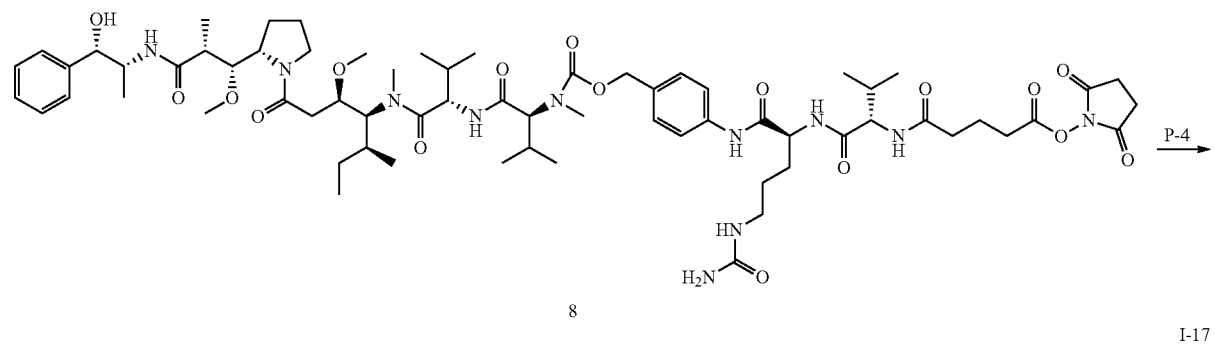

A 50 mL round bottom flask which contained Compound P-4 (40 mg, 13.57 umol, 1.00 eq) in DMA (4 mL) was purged using nitrogen balloon. DIEA (6.6 mg, 51.07 umol, 8.89 uL, 3.79 eq) was then added with stirring at 25° C. Compound 8 (18.00 mg, 13.49 umol, 1.00 eq) was then added and the reaction was stirred under a positive nitrogen atmosphere for 18 hr at 25° C. LC-MS showed Compound 8 was consumed completely and one main peak with desired MS was detected. The resulting reaction mixture was purified by prep-HPLC (TFA condition). Compound I-17 (25.7 mg, 6.17 umol, 34.27% yield) was obtained as a white solid.

(3) The Reaction Scheme of I-11 is Shown Below:

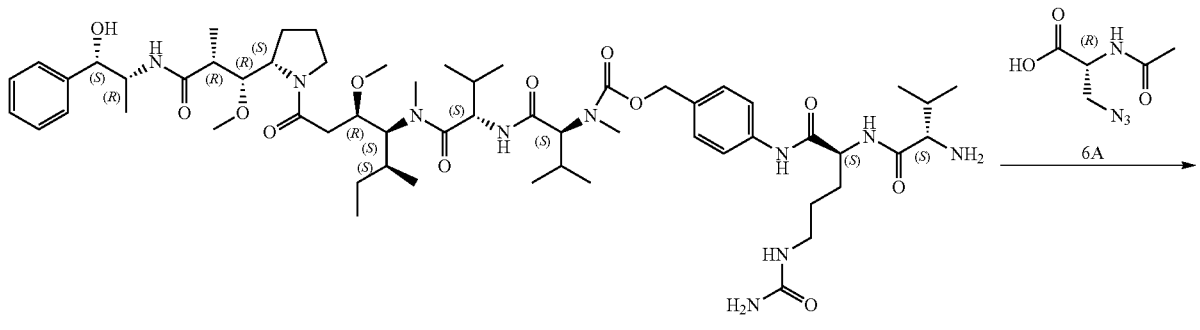

6

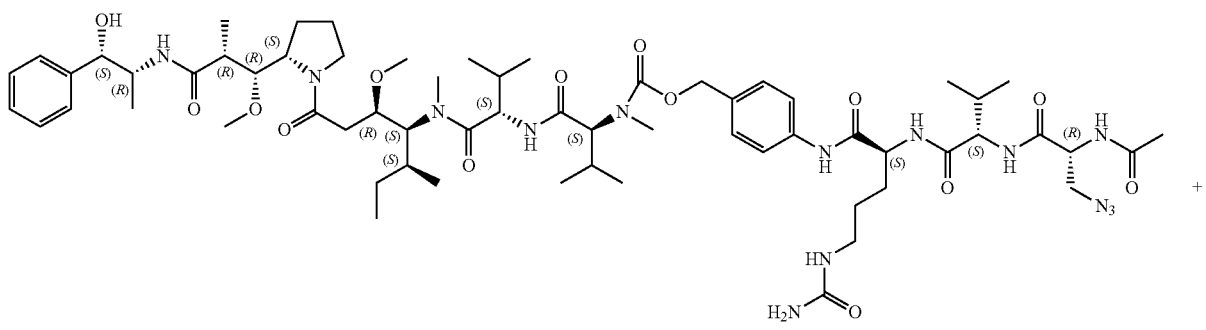

(Ac-Aza)-Val-Cit-PABC-MMAE

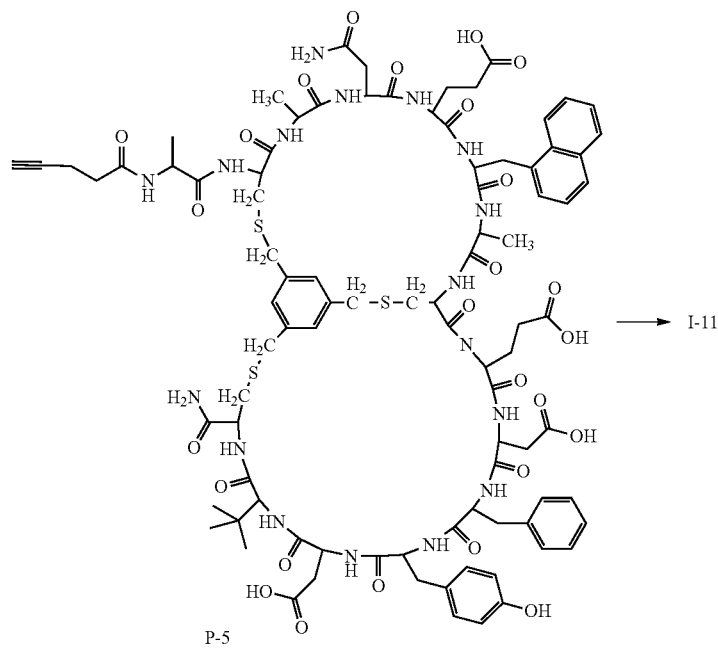

P-5

General Procedure for Preparation of (Ac-Az)-Val-Cit-PABC-MMAE

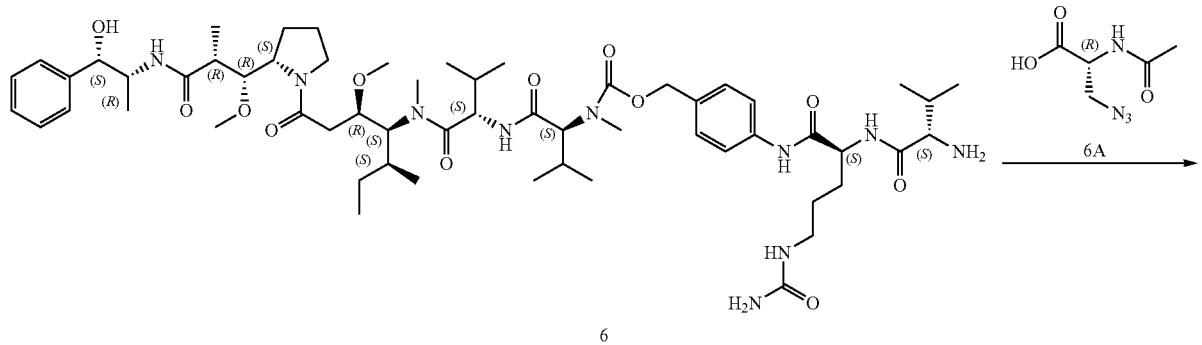

6

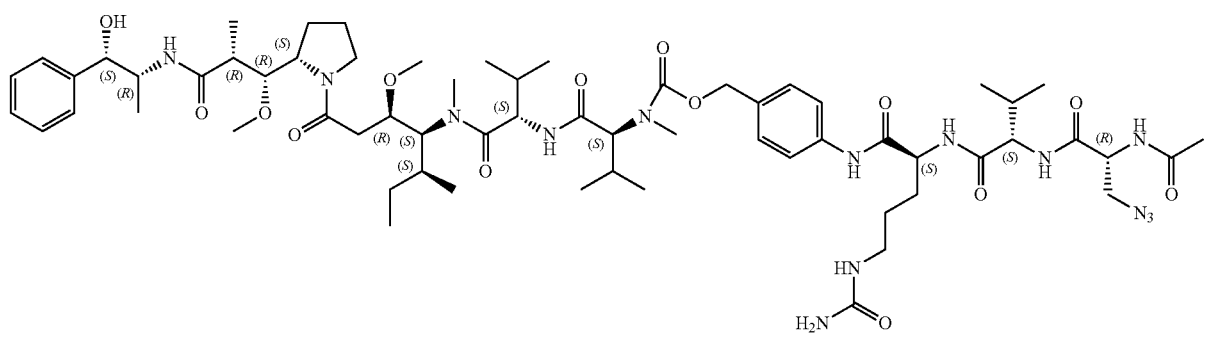

(Ac-Aza)-Val-Cit-PABC-MMAE

To a mixture of Compound 6 (100 mg, 89.01 umol, 1 eq) and Compound 6A (30.65 mg, 178.03 umol, 2 eq) in DMF was added TEA (27.02 mg, 267.04 umol, 37.17 uL, 3 eq), HOBt (24.06 mg, 178.03 umol, 2 eq) and EDCI (34.13 mg, 178.03 umol, 2 eq) at 0° C. under nitrogen. The mixture was stirred at 0° C. for 30 min, and then heated to 25° C. with stirring for 18.5 hr. LC-MS showed Compound 6 was consumed completely and one main peak with desired MS was detected. The resulting reaction mixture was purified by flash C18 gel chromatography (ISCO®; 43 g SepaFlash® C18 Flash Column, Eluent of 0~50% MeCN/DCM @ 40 mL/min). Compound (Ac-Az)-Val-Cit-PABC-MMAE (50 mg, 39.14 umol, 43.97% yield) was obtained as a white solid.

General Procedure for Preparation of I-11

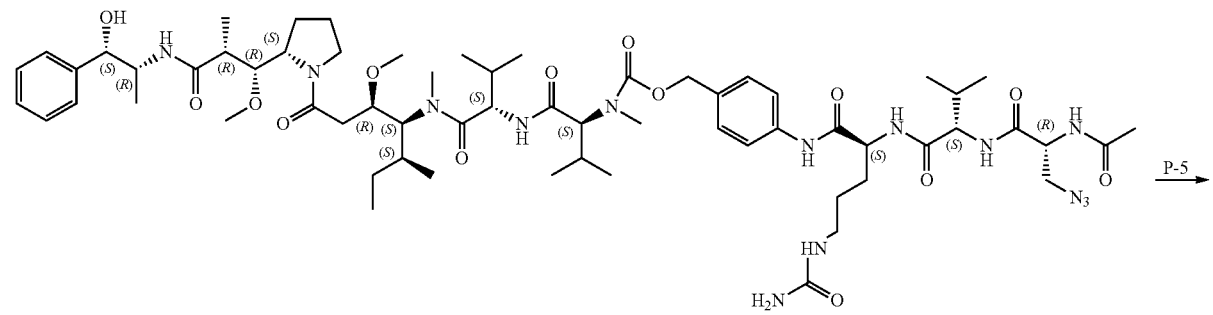

(Ac-Aza)-Val-Cit-PABC-MMAE

I-11

To a mixture of (Ac-Az)-Val-Cit-PABC-MMAE (65 mg, 50.88 umol, 1 eq) and Compound P-5 (90 mg, 45.98 umol, 0.9 eq) in DMF (3 mL) was added a solution of CuSO₄ (24.36 mg, 152.64 umol, 23.43 uL, 3 eq) in Water (0.4 mL) and a solution of Ascorbic Acid (89.61 mg, 508.79 umol, 94.33 uL, 10 eq) in Water (0.4 mL) under nitrogen. Then the mixture was stirred at 25° C. for 1 hr. LC-MS showed Compound (Ac-Az)-Val-Cit-PABC-MMAE was consumed completely and one main peak with desired MS was detected. The resulting reaction mixture was purified by prep-HPLC (TFA condition). I-11 (66.6 mg, 20.59 umol, 44.78% yield) was obtained as a white solid.

Figure 14:
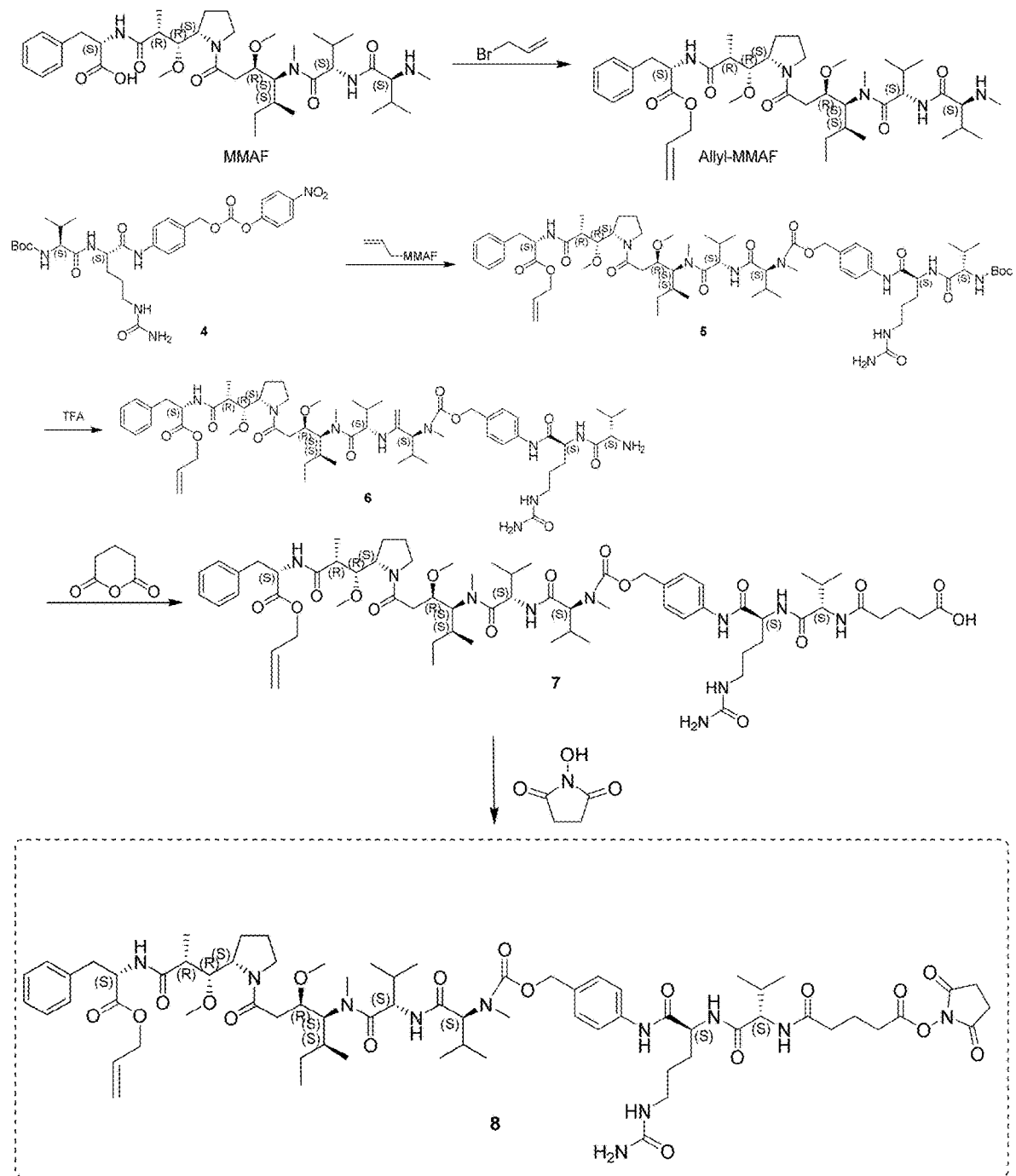
FIG. 14 depicts the reaction scheme of I-10 and I-14.
Figure 14:
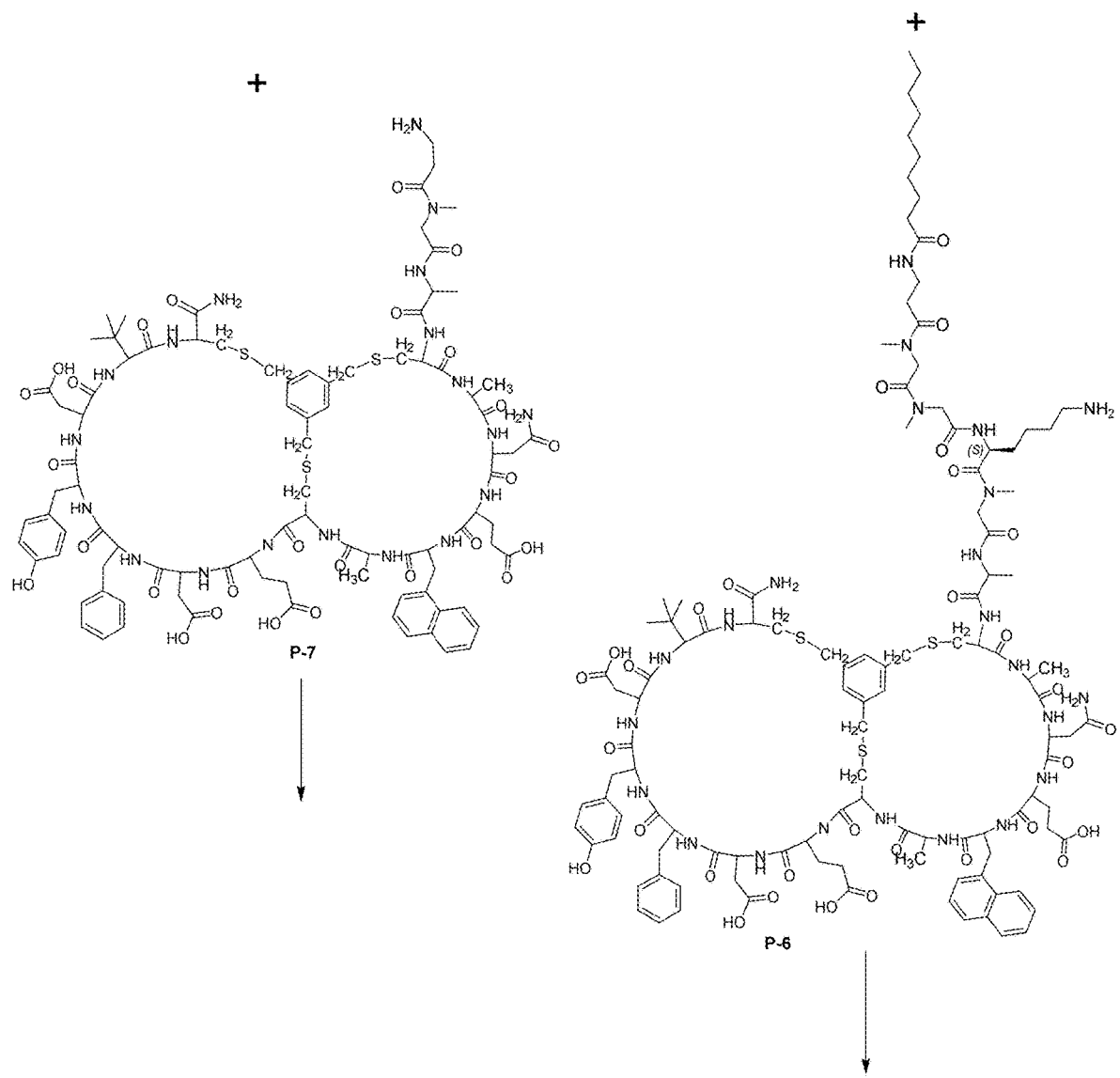
Figure 14:
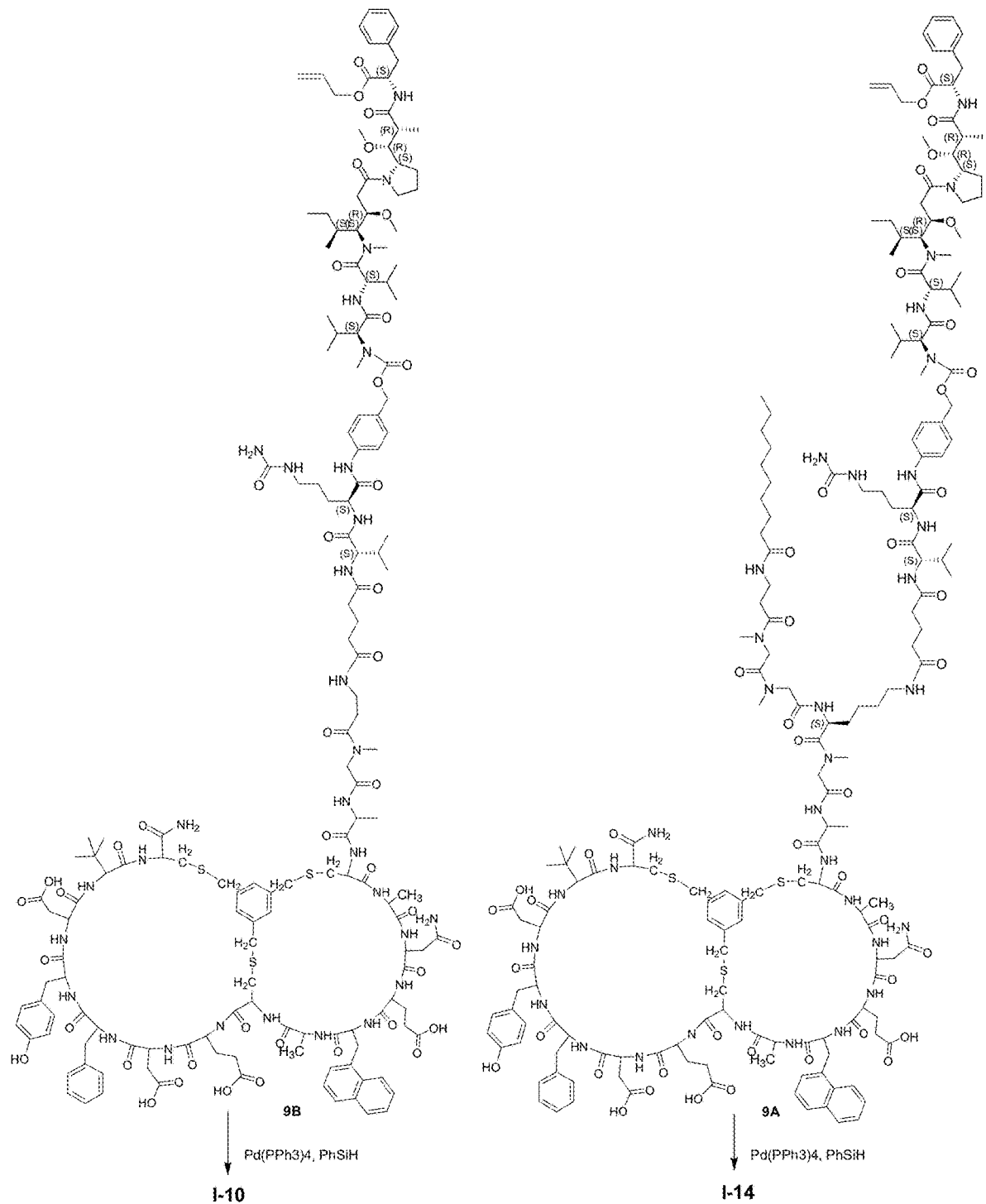

(4) The Reaction Scheme of 1-10 and 1-14 is Shown in FIG. 14.

General Procedure for Preparation of Compound Allyl-MMAF

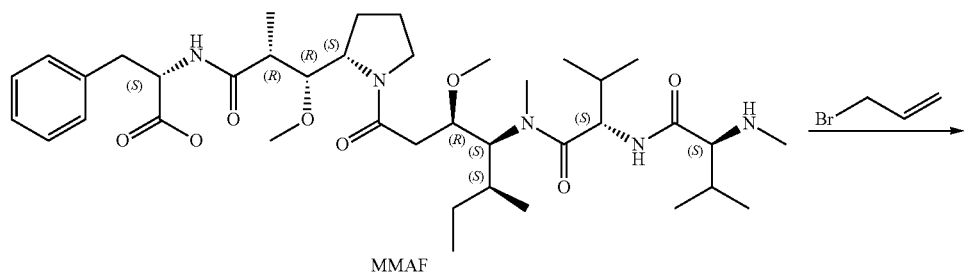

MMAF

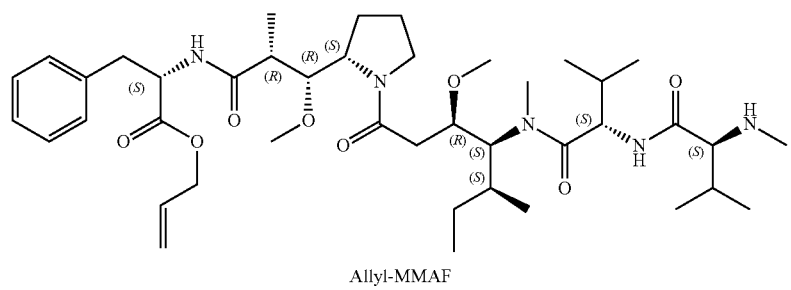

Allyl-MMAF

To a solution of MMAF (300 mg, 409.86 umol, 1 eq) in DMF (10 mL) was added K₂CO₃ (67.97 mg, 491.83 umol, 1.2 eq) and 3-bromoprop-1-ene (49.58 mg, 409.86 umol, 35.42 uL, 1 eq). The mixture was stirred at 25° C. for 17 hr. LC-MS showed MMAF was consumed completely and one main peak with desired MS was detected. The resulting reaction mixture was purified by flash C₁₈ gel chromatography (ISCO®; 130 g SepaFlash® C18 Flash Column, Eluent of 0~60% MeCN/H₂O @ 75 mL/min). Allyl-MMAF (130 mg, 165.38 umol, 40.35% yield) was obtained as a white solid.

General Procedure for Preparation of Compound 5

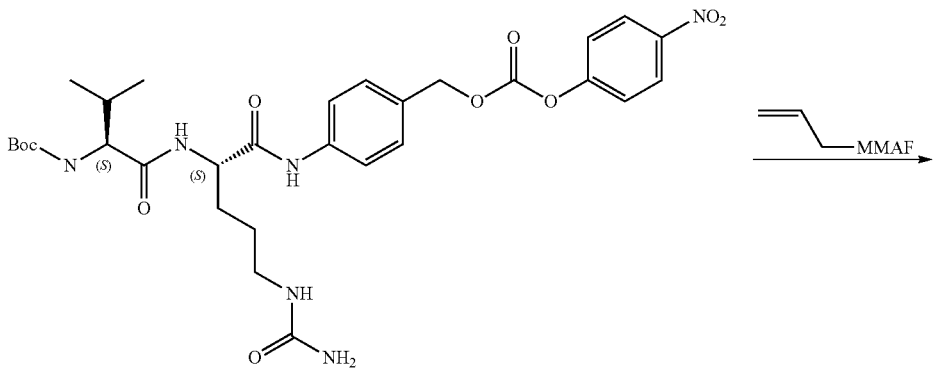

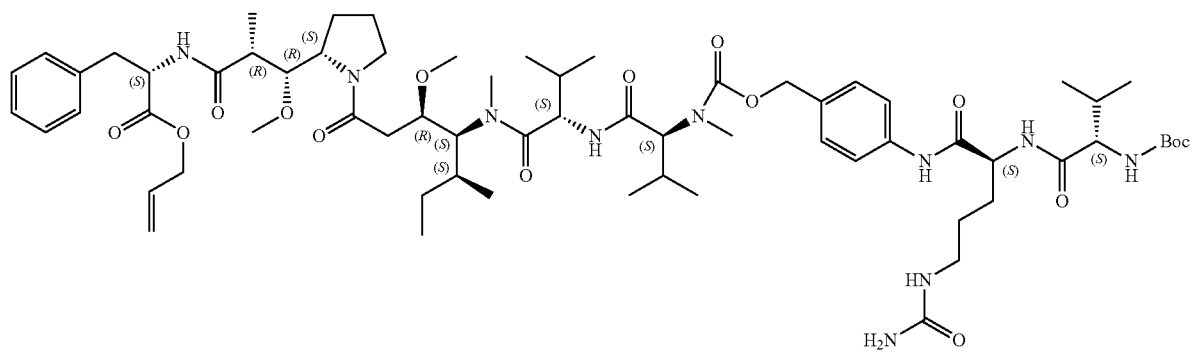

5

To a mixture of Compound 4 (196.83 mg, 305.32 umol, 2 eq) and DIEA (49.33 mg, 381.65 umol, 66.48 uL, 2.5 eq) in DMF (10 mL) was added Allyl-MMAF (120 mg, 152.66 umol, 1 eq) and HOBt (24.75 mg, 183.19 umol, 1.2 eq). The mixture was stirred at 40° C. for 7 hr. LC-MS showed one main peak with desired MS was detected. The resulting reaction mixture was purified by flash C18 gel chromatography (ISCO®; 43 g SepaFlash® C18 Flash Column, Eluent of 0~60% MeCN/H$_2$O @ 40 mL/min). Compound 5 (150 mg, 116.13 umol, 76.07% yield) was obtained as a white solid.

General Procedure for Preparation of Compound 6

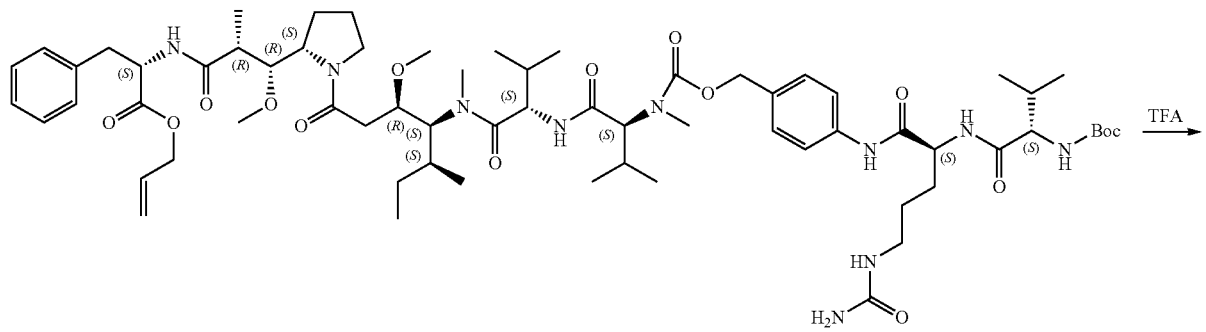

5

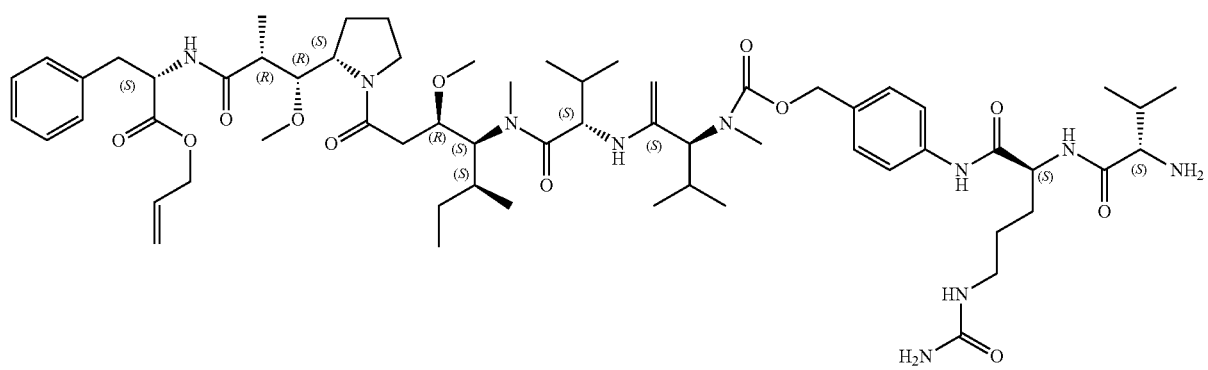

6

To a solution of Compound 5 (110 mg, 85.16 umol, 1 eq) in DCM (18 mL) was added TFA (2.82 g, 24.76 mmol, 1.83 mL, 290.74 eq), and the mixture was stirred at 25° C. for 1 hr. LC-MS showed Compound 5 was consumed completely and one main peak with desired MS was detected. The resulting reaction mixture was concentrated under reduced pressure to give a residue, which was purified by flash C18 gel chromatography (ISCO®; 130 g SepaFlash® C18 Flash Column, Eluent of 0~60% MeCN/H₂O @ 75 mL/min). Compound 6 (60 mg, 50.36 umol, 59.13% yield) was obtained as a white solid.

General Procedure for Preparation of Compound 7

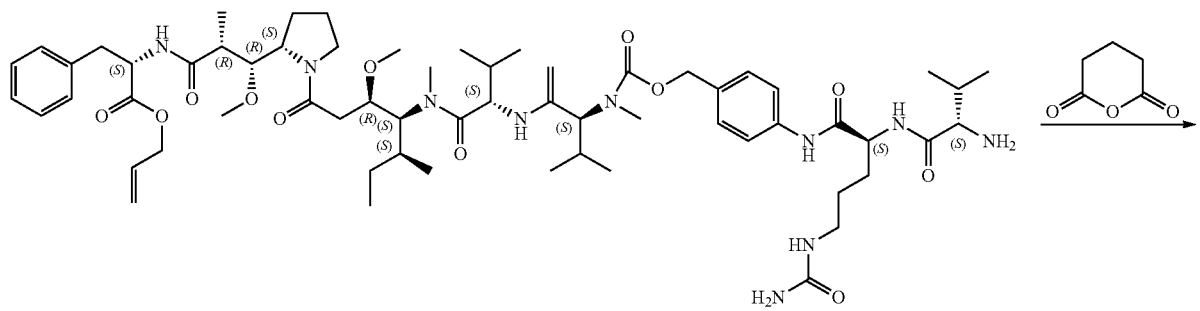

6

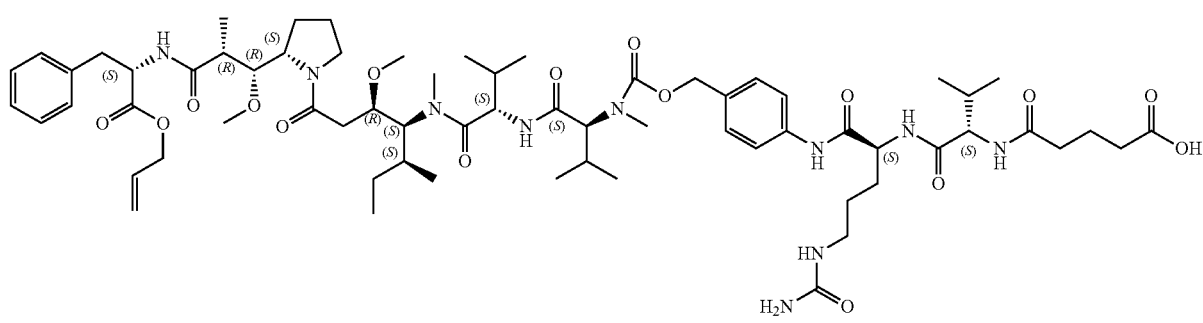

7

To a solution of Compound 6 (60 mg, 50.36 umol, 1 eq) in DMA (5 mL) was added DIEA (13.02 mg, 100.71 umol, 17.54 uL, 2 eq) with stirring at 0° C., followed by adding tetrahydropyran-2,6-dione (11.49 mg, 100.71 umol, 2 eq). The mixture was stirred at 25° C. for 1 hr. LC-MS showed Compound 6 was consumed completely and one main peak with desired MS was detected. The residue was purified by flash C18 gel chromatography (ISCO®; 43 g SepaFlash® C18 Flash Column, Eluent of 0~60% MeCN/H₂O @40 mL/min). Compound 7 (55 mg, 42.13 umol, 83.66% yield) was obtained as a white solid.

General Procedure for Preparation of Compound 8

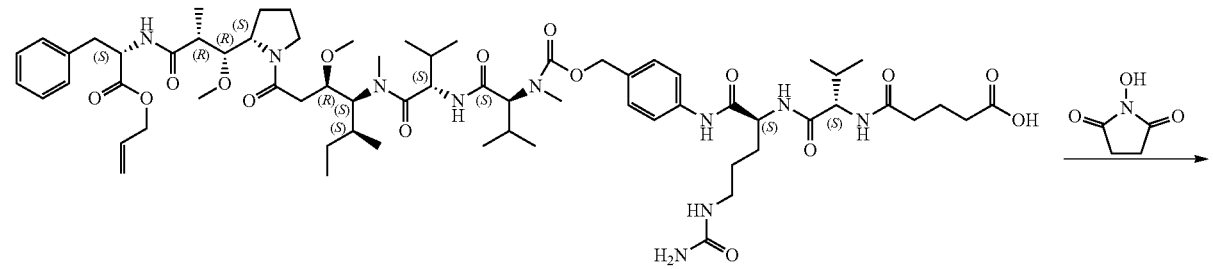

7

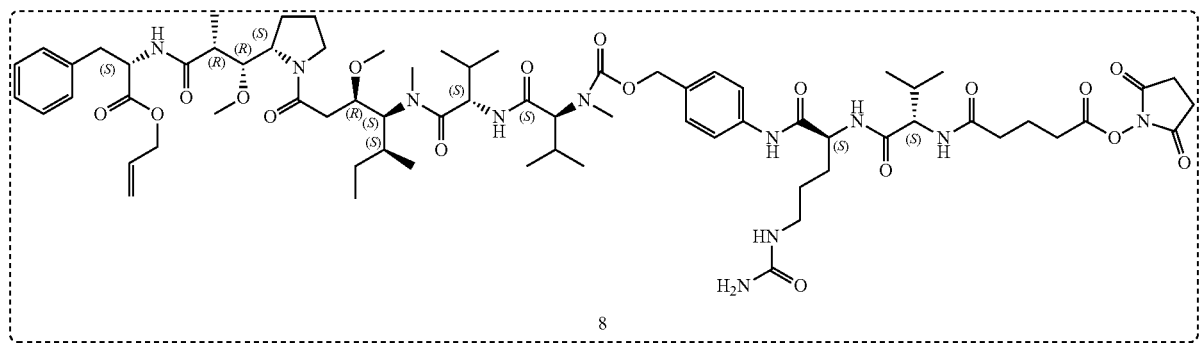

8

To a solution of Compound 7 (55 mg, 42.13 umol, 1 eq) in DMA (4.5 mL) and DCM (1.5 mL) was added 1-hydroxypyrrolidine-2,5-dione (14.54 mg, 126.38 umol, 3 eq) at 0° C. with stirring. followed by adding EDCI (24.23 mg, 126.38 umol, 3 eq). The mixture was stirred at 0° C. for 30 mins at 25° C. for 20 hr. LC-MS showed Compound 7 was consumed completely and one main peak with desired MS was detected. The residue was purified by flash C18 gel chromatography (ISCO®; 43 g SepaFlash® C18 Flash Column, Eluent of 0~60% MeCN/H$_2$O @ 40 mL/min). Compound 8 (45 mg, 32.08 umol, 76.16% yield) was obtained as a white solid.

General Procedure for Preparation of Compound 9A

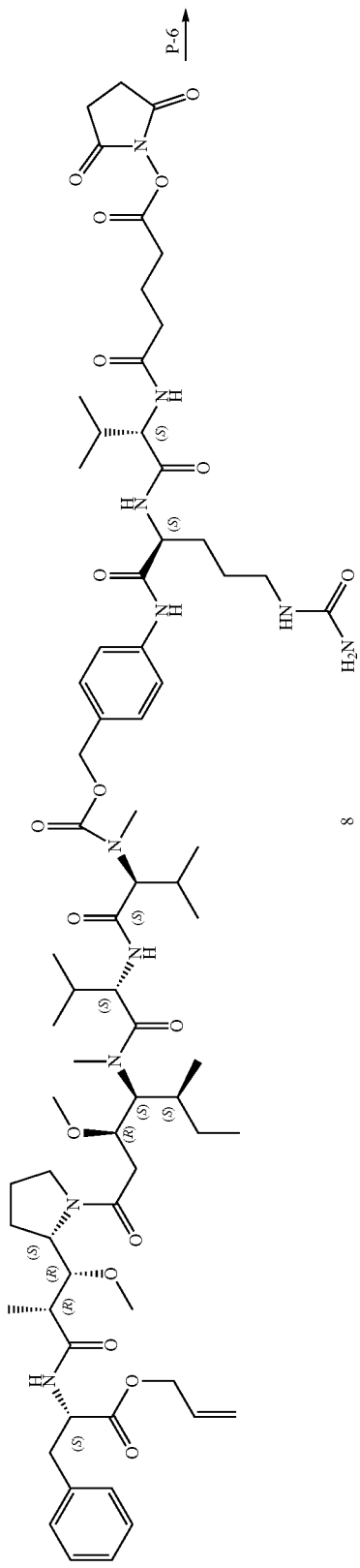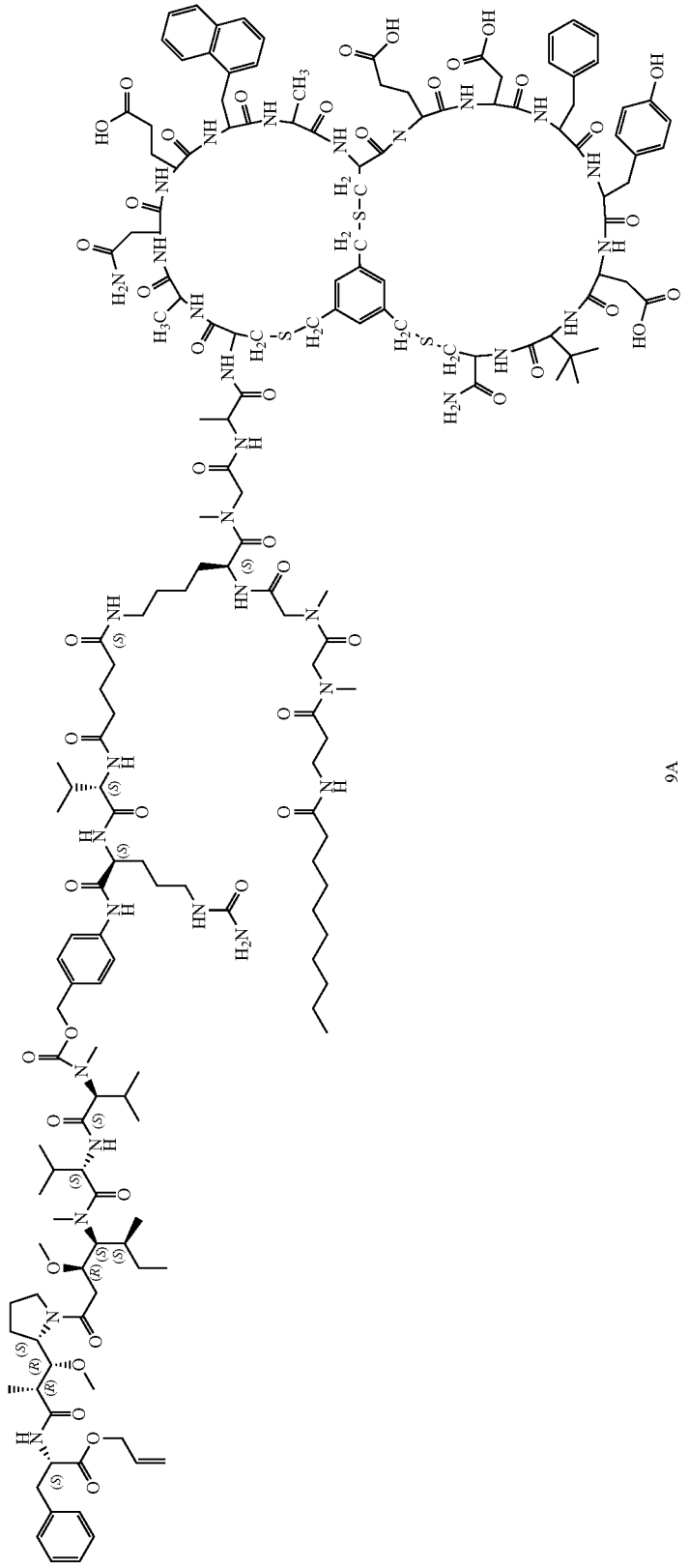

To a solution of Compound P-6 (85 mg, 25.78 umol, 1 eq) in DMA (5 mL) was added DIEA (16.80 mg, 130 umol, 22.64 uL, 5 eq) with stirred under nitrogen, and Compound 8 (45 mg, 32.08 umol, 1.25 eq) was added thereto. The mixture was stirred at 25° C. for 20 hrs. LC-MS showed Compound 8 was consumed completely and one main peak with desired MS was detected. The residue was purified by prep-HPLC (TFA condition). Compound 9A (60 mg, 13.13 umol, 50.92% yield) was obtained as a white solid.

General Procedure for Preparation of I-14

To a solution of Compound 9A (80 mg, 17.50 umol, 1 eq) in DCM (6 mL) and THF (0.5 mL) was added PHENYL-SILANE (9.60 mg, 88.71 umol, 10.95 uL, 5 eq) and $Pd(PPh_3)_4$ (4.40 mg, 3.81 umol, 0.2 eq) under nitrogen. The mixture was stirred at 25° C. for 1 hr. LC-MS showed Compound 9A was consumed completely and one main peak with desired MS was detected. The residue was purified by prep-HPLC (TFA condition). Compound I-14 (52.7 mg, 11.63 umol, 66.46% yield) was obtained as a white solid.

General Procedure for Preparation of Compound 9B

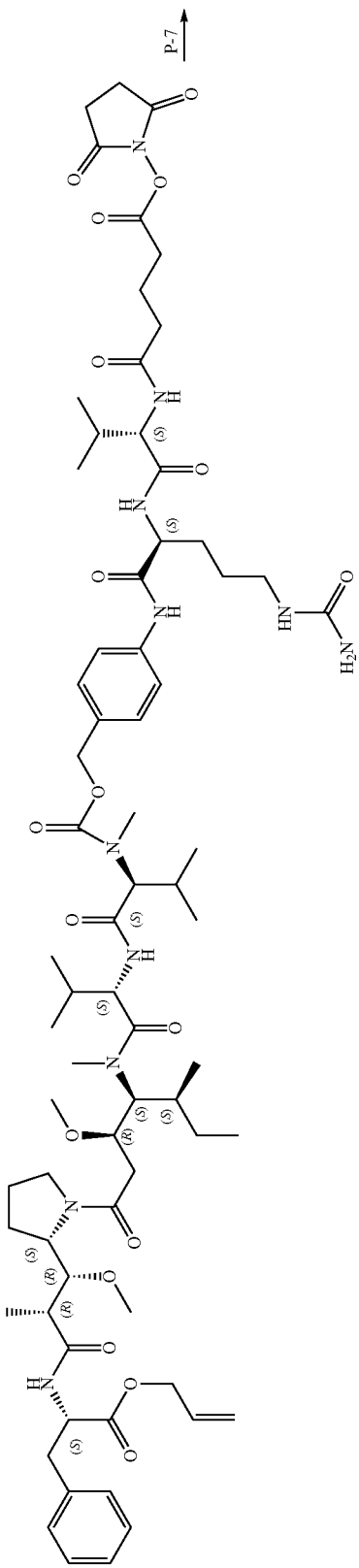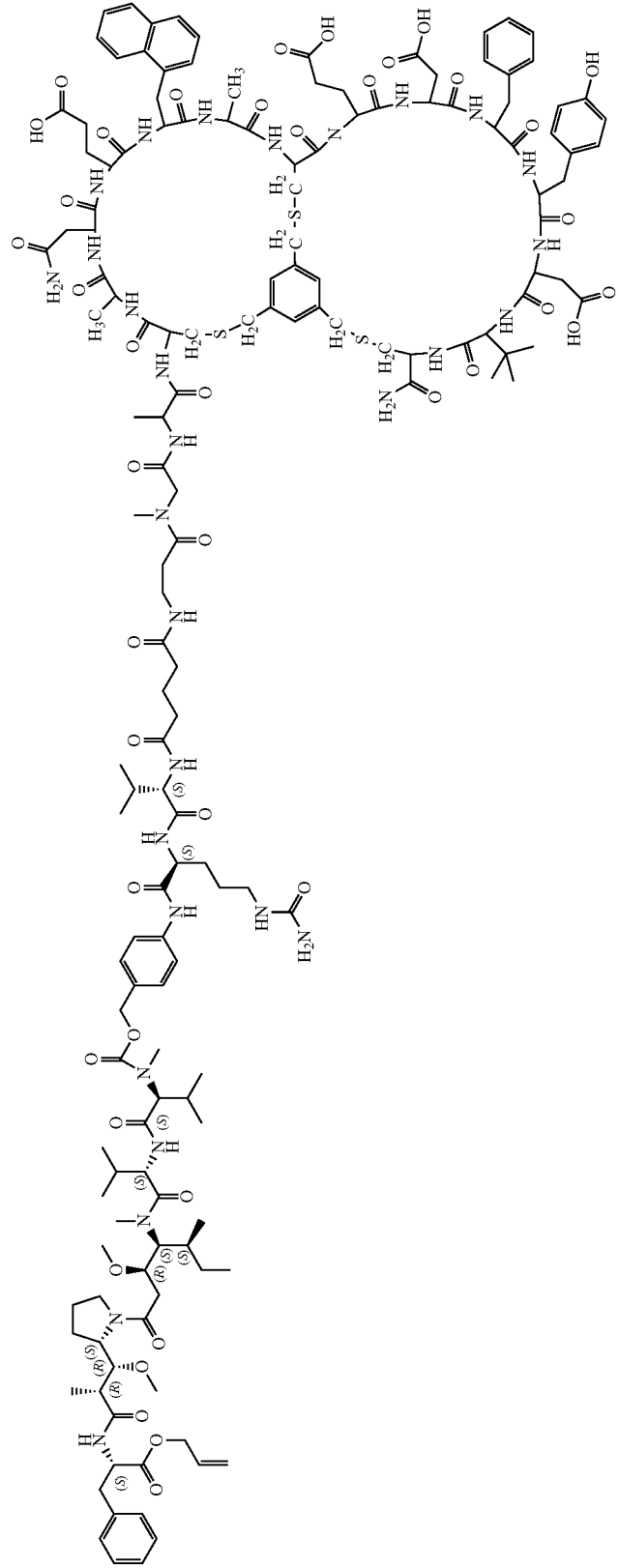

To a mixture of Compound P-7 (85 mg, 31.97 umol, 1 eq) in DMA (5 mL) was added DIEA (20.73 mg, 160.41 umol, 27.94 uL, 5 eq) with stirring under nitrogen, followed by adding compound 8 (45 mg, 32.08 umol, 1 eq). The mixture was stirred at 25° C. for 17 hr. LC-MS showed Compound 8 was consumed completely and one main peak with desired MS was detected. The residue was purified by prep-HPLC (TFA condition). Compound 9B (90 mg, 22.89 umol, 71.58% yield) was obtained as a white solid.

General Procedure for Preparation of I-10

To a solution of Compound 9B (90 mg, 22.89 umol, 1 eq) in DCM (6 mL) and THF (1 mL) was added phenylsilane (35.27 mg, 325.92 umol, 40.21 uL, 14 eq) and Pd(PPh$_3$)$_4$ (15.06 mg, 13.04 umol, 0.56 eq) under nitrogen. The mixture was stirred at 25° C. for 5 hrs. LC-MS showed Compound 9B was consumed completely and one main peak with desired MS was detected. The residue was purified by prep-HPLC (TFA condition). Compound I-10 (26.7 mg, 6.86 umol, 29.97% yield) was obtained as a white solid.

(5) The Reaction Scheme of I-13 is Shown Below:

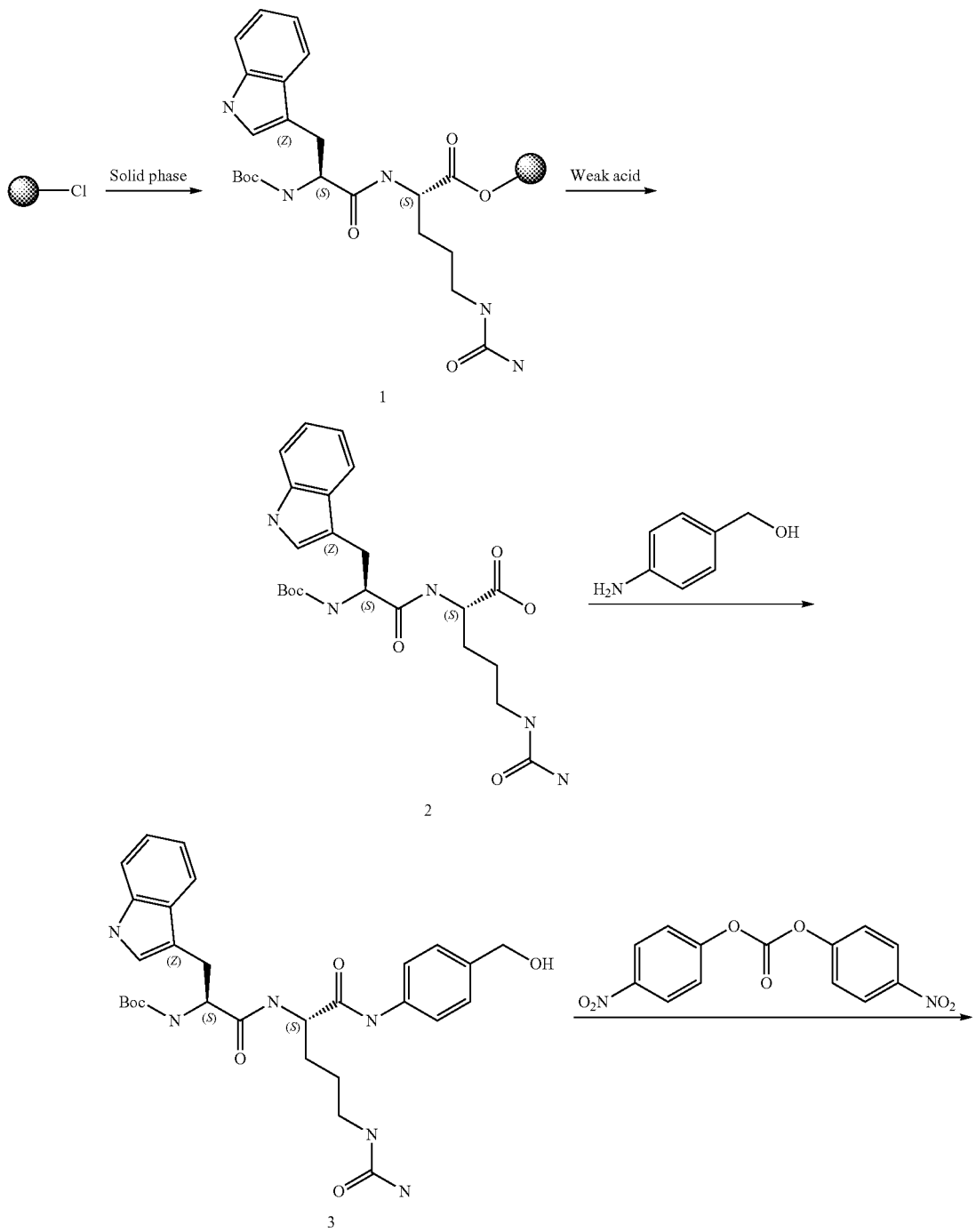

-continued
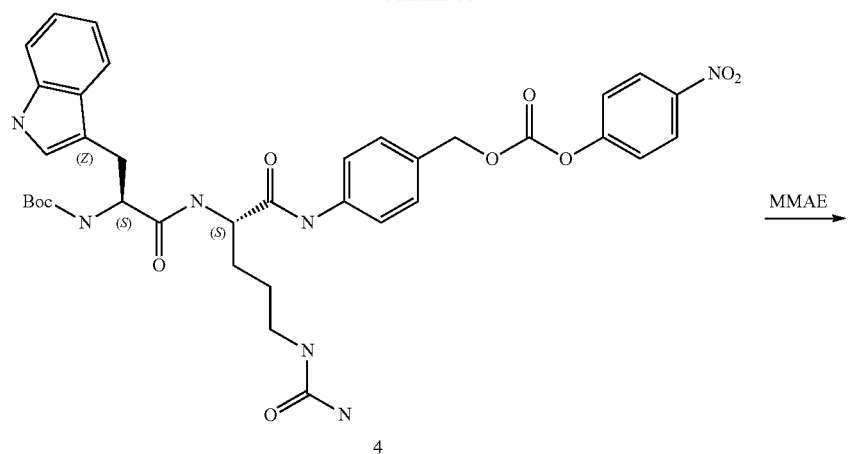
4
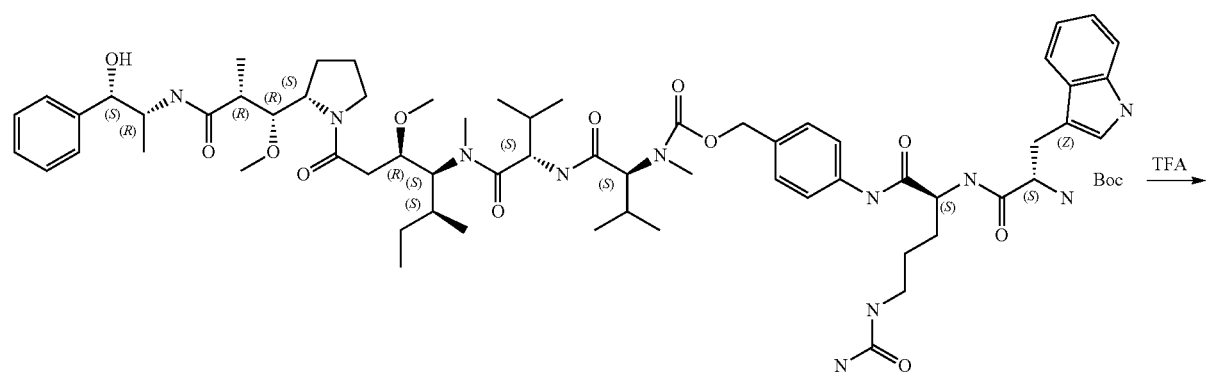
5
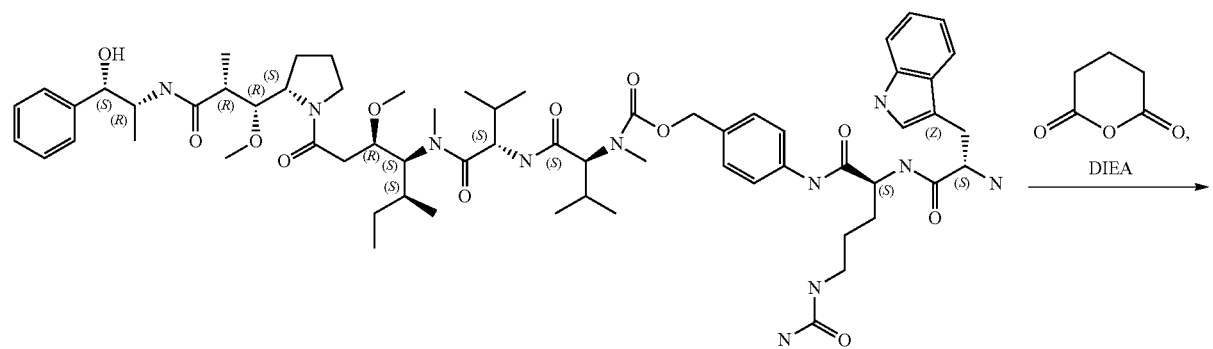
6
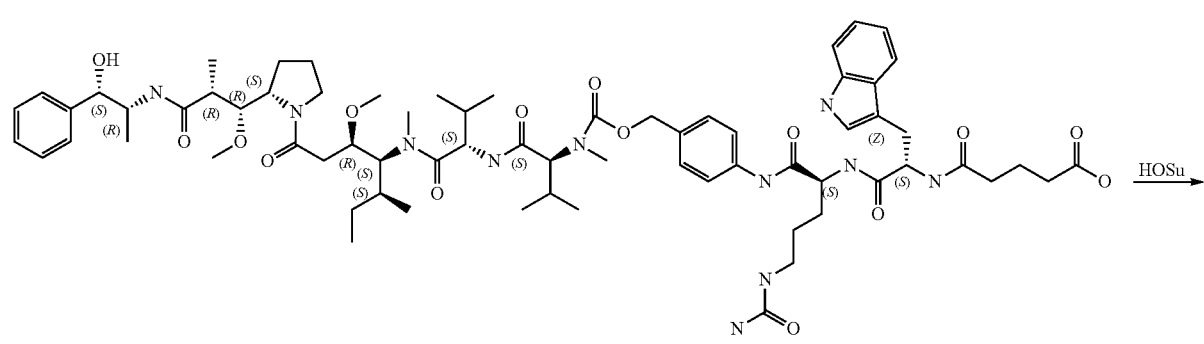
7

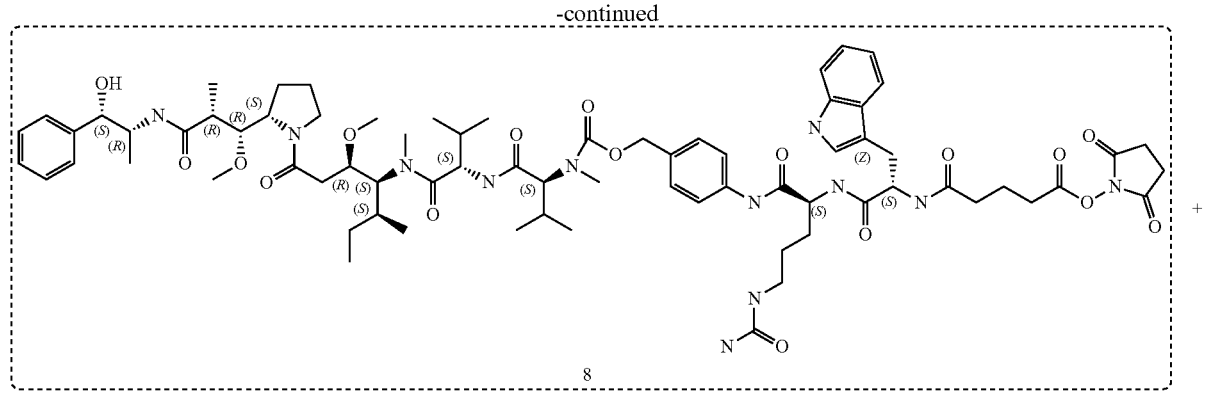
8
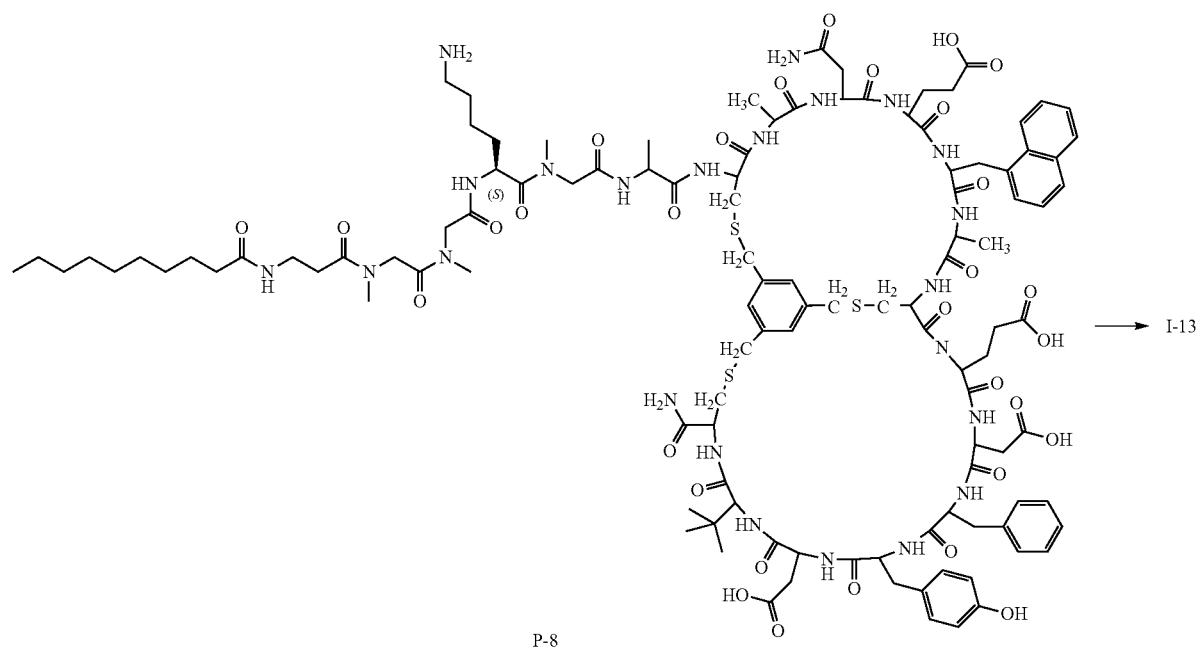
P-8
General Procedure for Preparation of Compound 3
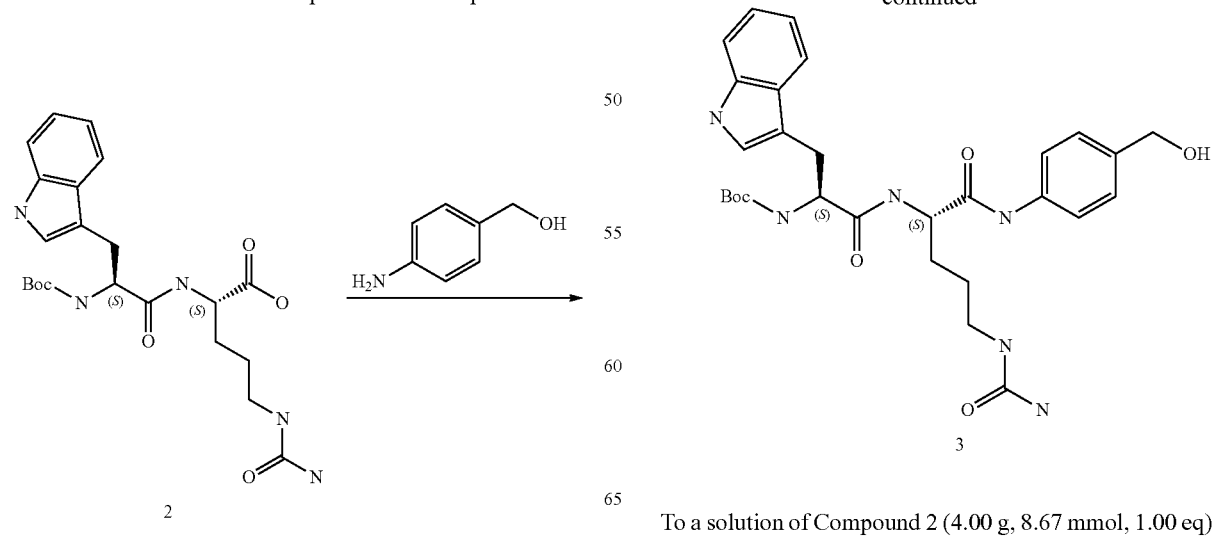
To a solution of Compound 2 (4.00 g, 8.67 mmol, 1.00 eq) in DMF (20.00 mL) was added DIC (9.85 g, 78.03 mmol, 12.01 mL, 9.00 eq) and HOBt (10.54 g, 78.03 mmol, 9.00 eq). The mixture was stirred at 15° C. for 3 hr. TLC indicated Compound 3 was consumed completely and one new spot was formed. The reaction was clean according to TLC. The reaction mixture was concentrated under reduced pressure to remove solvent to give a residue, which was purified by flash silica gel chromatography (ISCO®; 80 g SepaFlash® Silica Flash Column, Eluent of 0~40% Ethylacetate/Petroleum ethergradient @ 60 mL/min). Compound 3 (4.00 g, 7.06 mmol, 81.43% yield) was obtained as a white solid.

General Procedure for Preparation of Compound 4

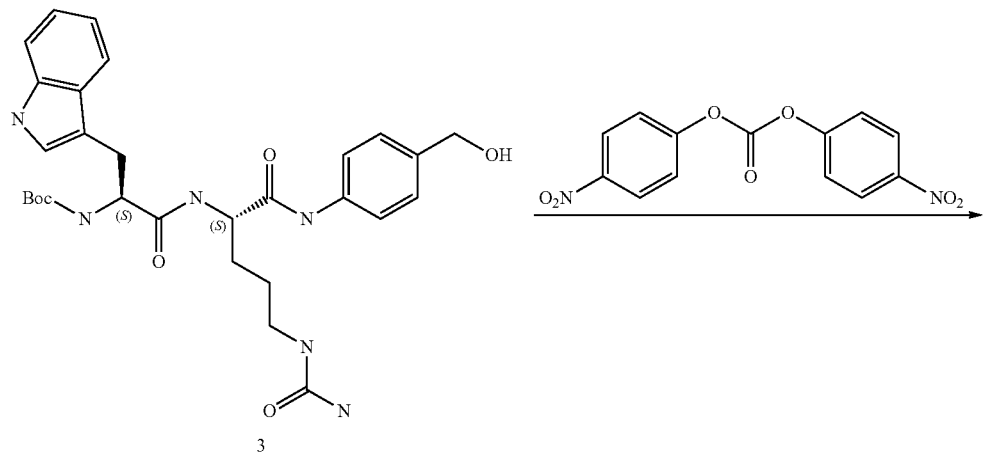

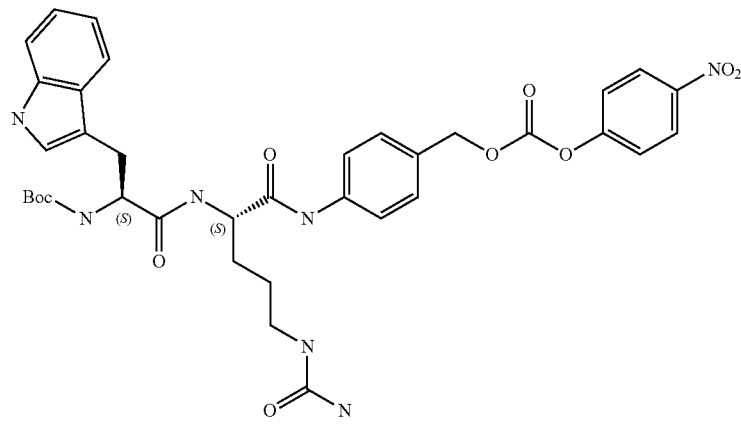

To a solution of Compound 3 (2.00 g, 3.53 mmol, 1.00 eq) in DMF (10.00 mL) was added DIEA (2.74 g, 21.18 mmol, 3.70 mL, 6.00 eq) and bis(4-nitrophenyl) carbonate (6.44 g, 21.18 mmol, 6.00 eq) in one port. The mixture was stirred at 0-15° C. for 1.5 hr. TLC indicated Compound 3 was consumed completely and one new spot was formed. The reaction was clean according to TLC. The reaction mixture was concentrated under reduced pressure to remove solvent to give a residue, which was purified by flash silica gel chromatography (ISCO®; 80 g SepaFlash® Silica Flash Column, Eluent of 0-40% Ethylacetate/Petroleum ethergradient @ 60 mL/min). Compound 4 (2.00 g, 2.73 mmol, 77.43% yield) was obtained as a white solid.

General Procedure for Preparation of Compound 5

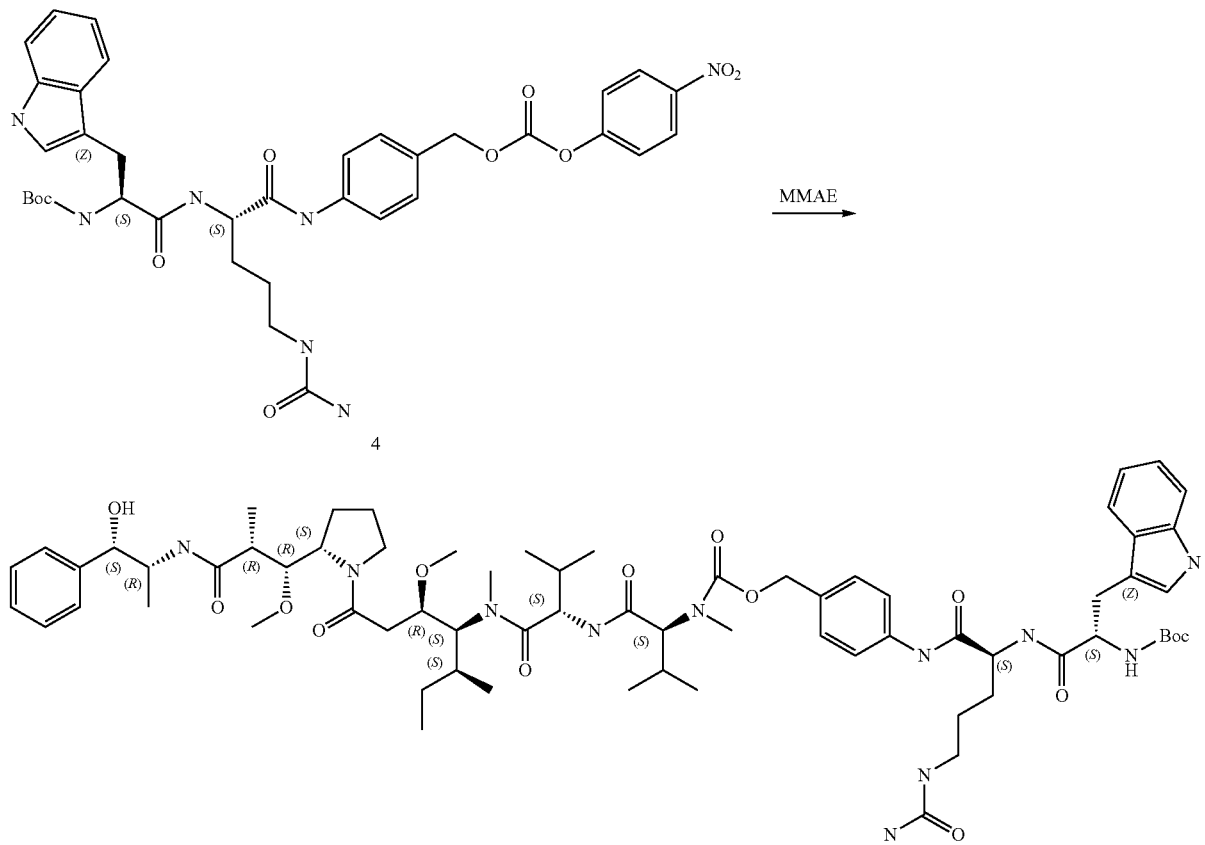

To a solution of Compound 4 (200.00 mg, 240.42 umol, 1.00 eq) in DMF (10.00 mL) was added DIEA (93.22 mg, 721.26 umol, 125.97 uL, 3.00 eq), HOBt (35.73 mg, 264.46 umol, 1.10 eq) and MMAE (172.62 mg, 240.42 umol, 1.00 eq) at 0° C. The mixture was stirred at 30° C. for 16 hr. LC-MS showed Compound 4 was consumed completely and one main peak with desired MS was detected. The resulting reaction mixture was directly purified by prep-HPLC (TFA condition). Compound 5 (180.00 mg, 137.34 umol, 57.12% yield) was obtained as a white solid.

General Procedure for Preparation of Compound 6

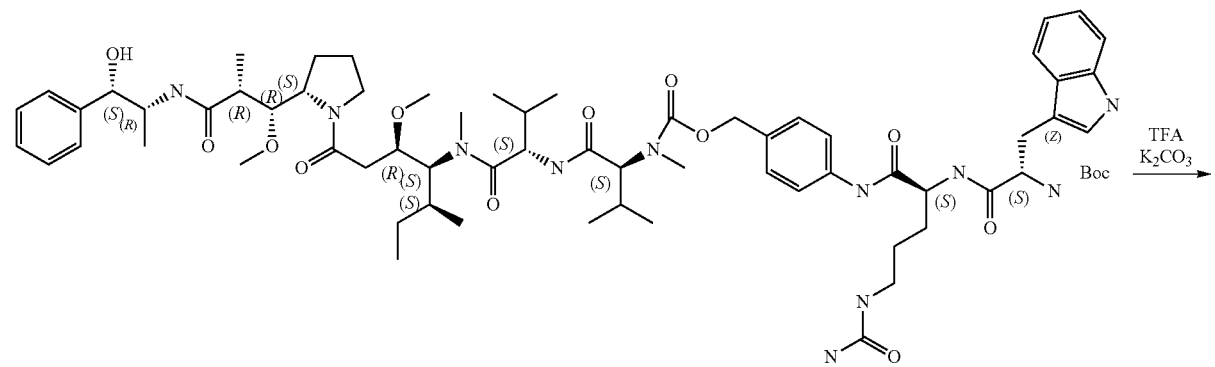

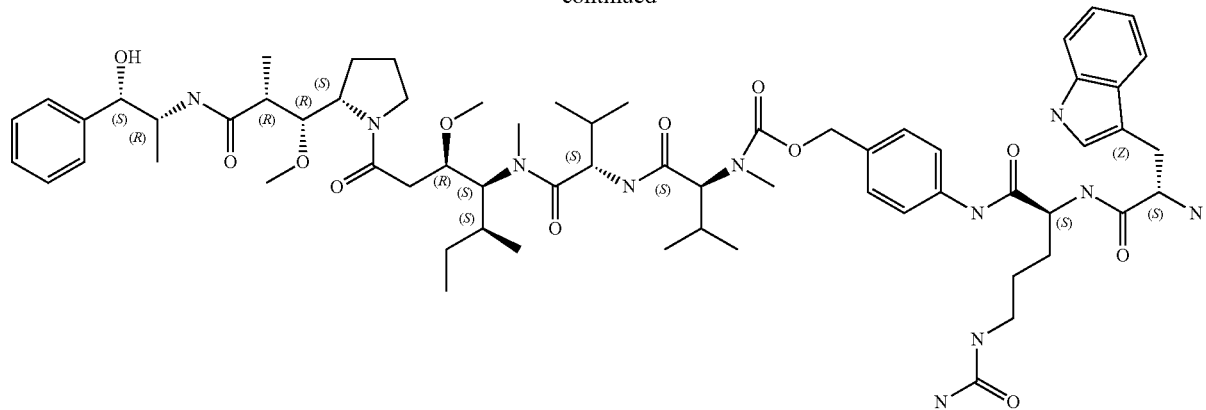

6

To a solution of Compound 5 (180.00 mg, 137.34 umol, 1.00 eq) in DCM (1.00 mL) was added TFA (13.86 g, 121.56 mmol, 9.00 mL, 885.09 eq). The mixture was stirred at 15° C. for 1 hr. LC-MS showed Compound 5 was consumed completely and one main peak with desired MS was detected. The reaction mixture was concentrated under reduced pressure to remove solvent to give a residue, which was purified by prep-HPLC (neutral condition). Compound 6 (80.00 mg, 66.09 umol, 48.12% yield) was obtained as a white solid.

General Procedure for Preparation of Compound 7

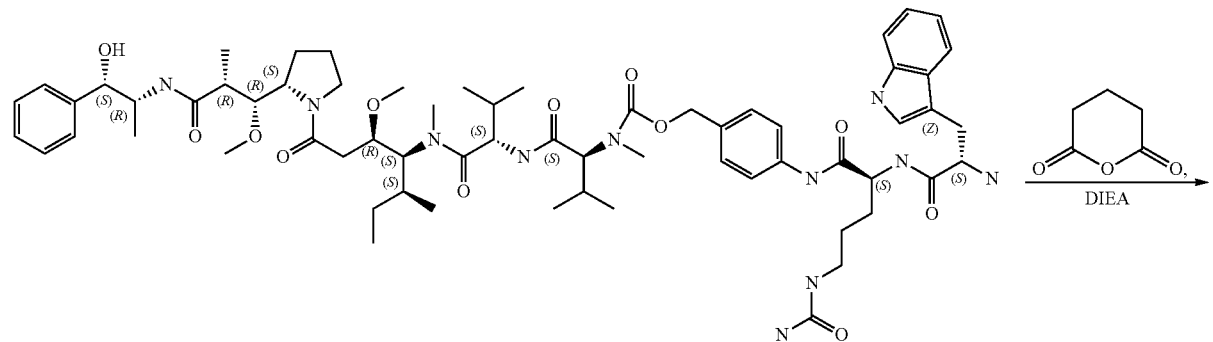

6

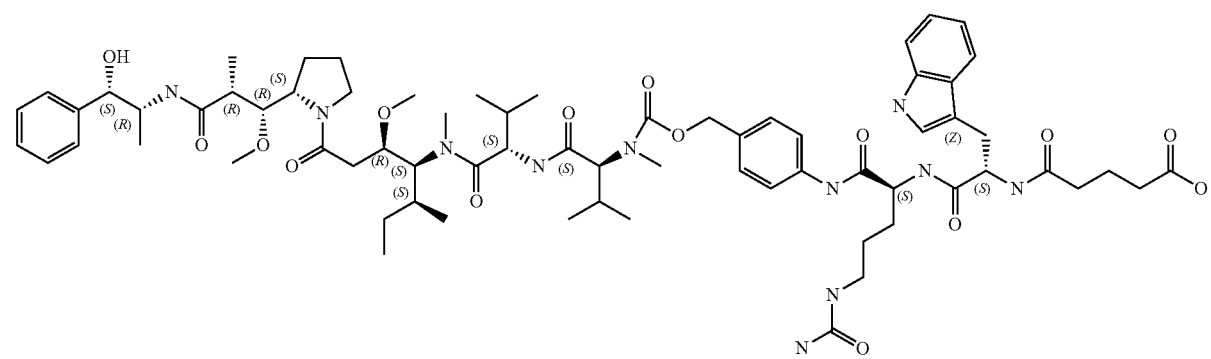

7

To a solution of Compound 6 (80.00 mg, 66.09 umol, 1.00 eq) in DMA (5.00 mL) was added DIEA (17.08 mg, 132.18 umol, 23.08 uL, 2.00 eq) and tetrahydropyran-2,6-dione (15.08 mg, 132.18 umol, 2.00 eq). The mixture was stirred at 15° C. for 16 hr. LC-MS showed Compound 6 was consumed completely and one main peak with desired MS was detected. The resulting reaction mixture was directly purified by prep-HPLC (TFA condition). Compound 7 (65.00 mg, 49.07 umol, 74.25% yield) was obtained as a white solid.

General Procedure for Preparation of Compound 8

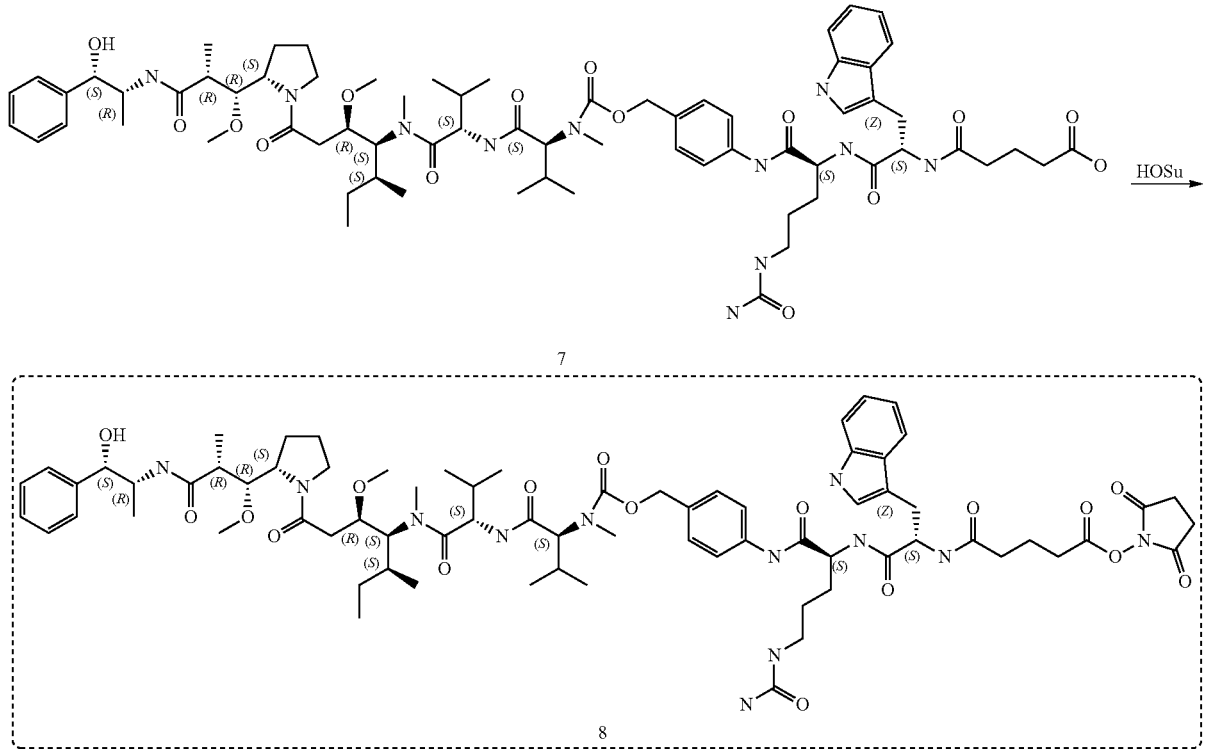

To a solution of Compound 7 (65.00 mg, 49.07 umol, 1.00 eq), 1-hydroxypyrrolidine-2,5-dione (16.94 mg, 147.21 umol, 3.00 eq) in DMA (3.00 mL) and DCM (1.00 mL) was added EDCI (28.22 mg, 147.21 umol, 3.00 eq). The mixture was stirred at 15° C. for 4 hr. LC-MS showed Compound 7 was consumed completely and one main peak with desired MS was detected. The resulting reaction mixture was directly purified by prep-HPLC (TFA condition). Compound 8 (35.00 mg, 24.62 umol, 50.17% yield) was obtained as a white solid.

General Procedure for Preparation of I-13

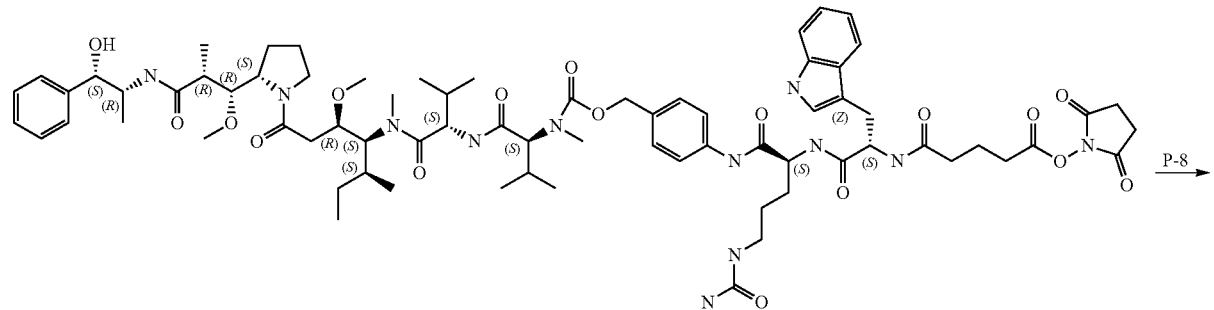

To a solution of Compound P-8 (38 mg, 11.53 umol, 1 eq) in DMA (3 mL) was added DIEA (7.44 mg, 57.65 mmol, 10.03 uL, 5 eq) and Compound 8 (20 mg, 14.07 umol, 1.2 eq). The mixture was stirred at 25° C. for 16 hr. LC-MS showed Compound 8 was consumed completely and one main peak with desired MS was detected. The residue was purified by prep-HPLC (TFA condition). 1-13 (8.1 mg, 1.76 umol, 15.27% yield) was obtained as a white solid. The HPLC and LC/MS data of I-10 to 1-17 are as follows:

| Compound | % area | retention time (min) | Mass found (M/4) |
|---|---|---|---|
| I-16 | 98.62 | 10.06 | 1042.1 |
| I-17 | 98.98 | 12.94 | 1042.2 |
| I-11 | 96.4 | 19.67 | 1078.6 |

-continued

| Compound | % area | retention time (min) | Mass found (M/4) |
|---|---|---|---|
| I-10 | 97.95 | 11.54 | 772.6 |
| I-12 | 96.98 | 14.52 | 1129.9 |
| I-13 | 94.88 | 21.772 | 921.1 |
| I-14 | 98.34 | 13.23 | 900.7 |
| I-15 | 96.75 | 14.14 | 1115.2 |

Example 12

Preparation of I-3a to I-6a, and I-7 to I-9

Compounds P-9, P-10, and P-11, as shown below, were prepared initially as lyophilized solids, and stored at −20° C. until use.

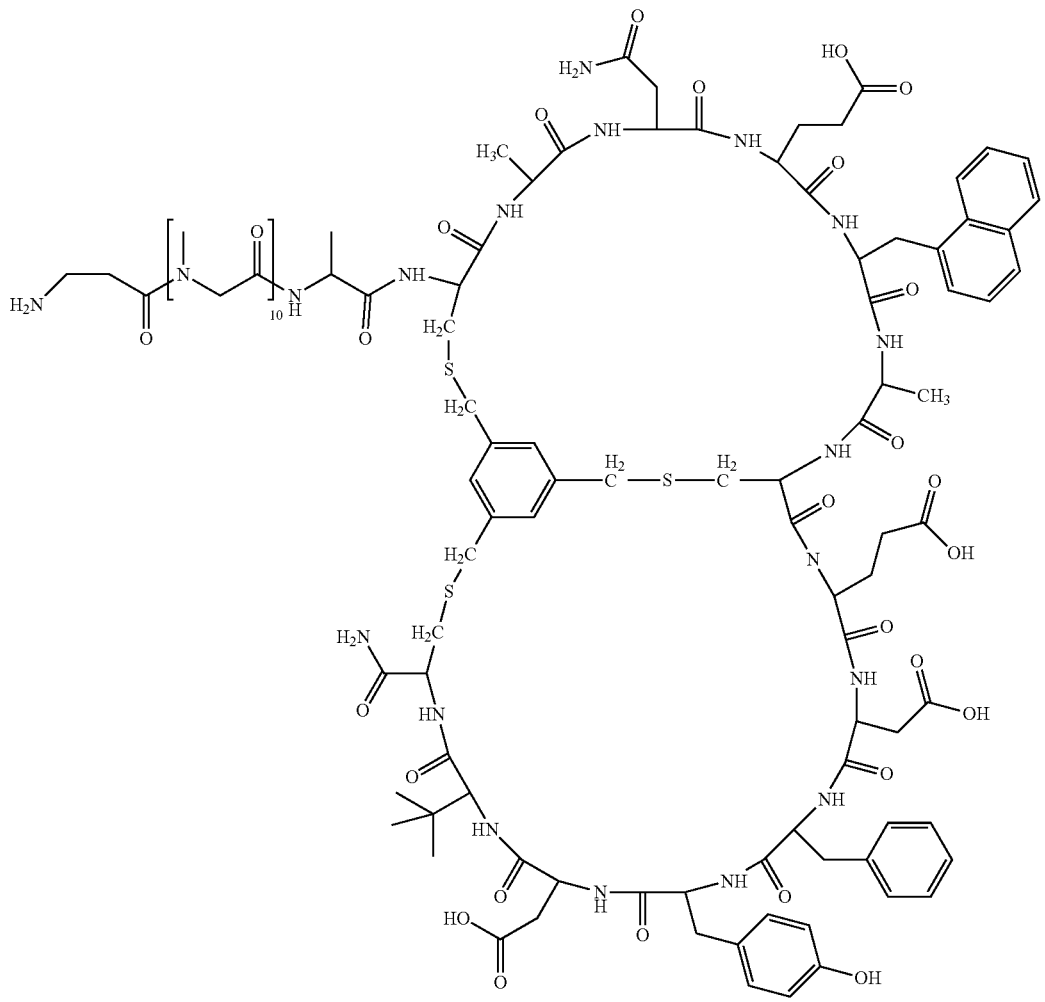

P-9

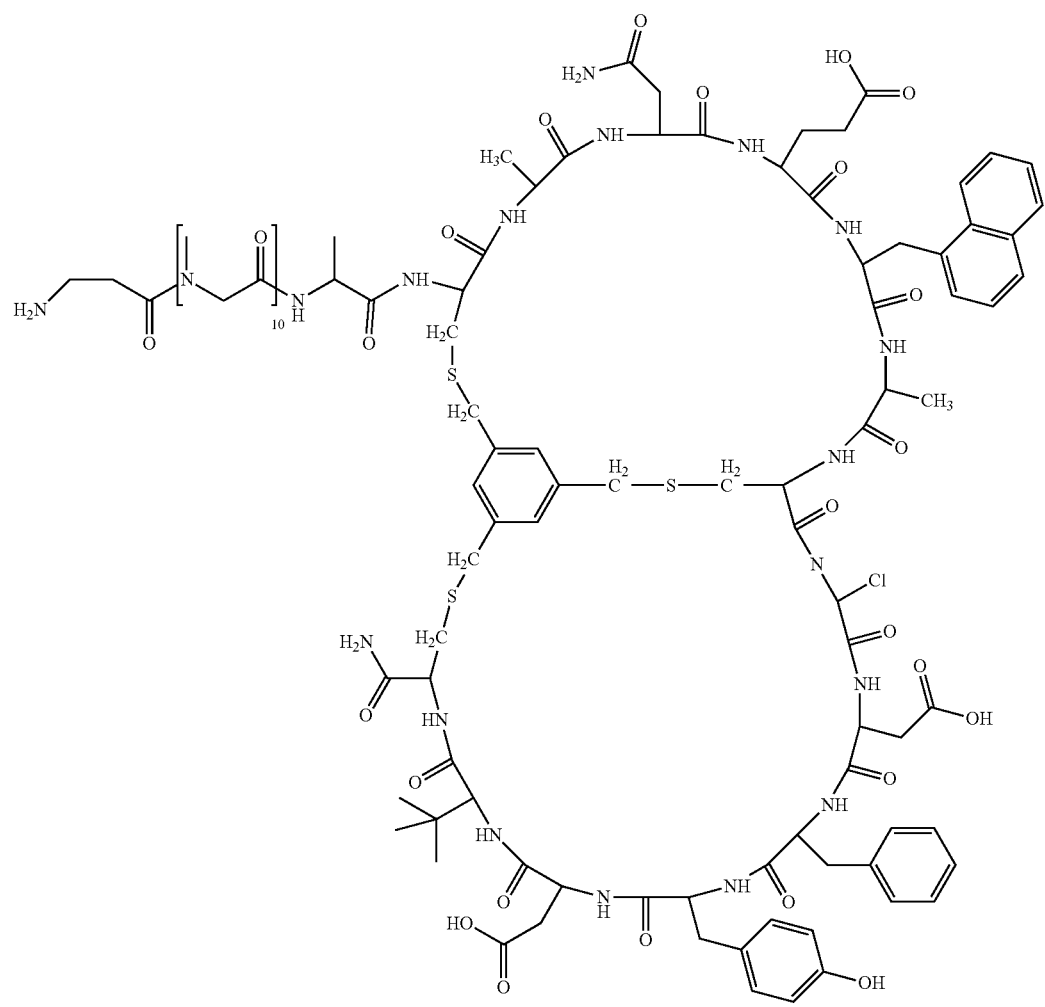
P-10

-continued

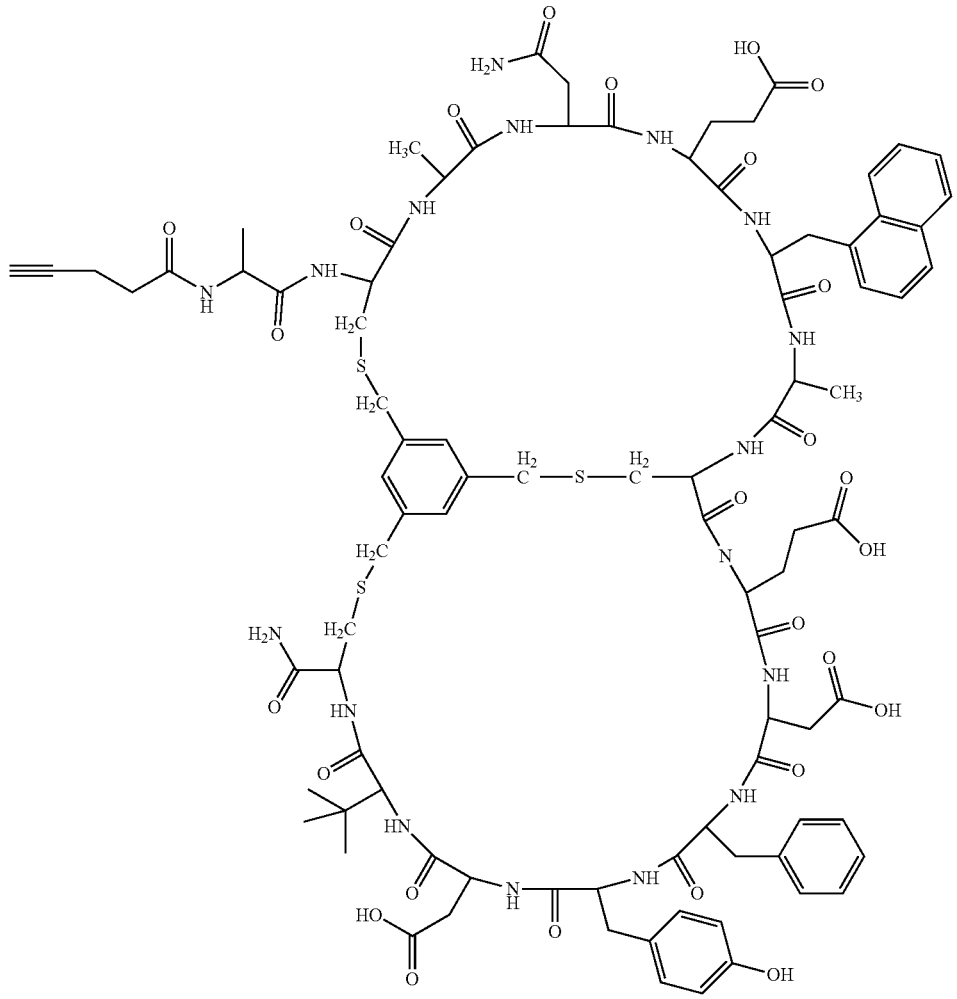

P-11

All the reacting partners containing the cytotoxic payload-linkers were prepared in >95% purity and were used in preparing the conjugates mentioned above.

Results and Discussion

Most of the conjugates specified above are amide derivatives and were prepared via amide coupling reactions except I-6a, which was obtained via a copper catalysed click chemistry. Thus, the starting bicyclic peptides P-9 and P10 contained a free amino group while in peptide P-11 an amino group is derivatized such that it had a single terminal alkyne group to facilitate the cyclization reaction. For the amide coupling reaction, most of the cytotoxic payload-linkers were prepared as the respective N-hydroxysuccinimide (NHS) esters except for the coupling partner to prepare I-4a where a tetrafluorophenyl ester was used as the NHS-ester derivative was observed to be unstable during its preparation. For the preparation of I-6a, the appropriate azide derivative was prepared and used in the click reaction.

Initially, all conjugation reactions for the preparation were carried out at 5-15 mg scale to assess the conditions and were then scaled up. Initially, 3.2 eq. of the NHS (or TFP) esters to 1 eq of peptide was reacted in the presence of 30 eq. of DIEA (i.e., 8 mM peptide+26 mM reactant+230 mM DIEA in 0.5 mL DMF) as the base in DMF was used. However, it was observed that the reactions proceeded well even with 2.3-2.5 eq of the NHS esters. It was also observed that the reactions resulted in less impurities or by-products when carried out in DMSO as the solvent instead of DMF. All reactions were purified by preparative reversed phase chromatography. It was also observed that it was necessary to carry out at least two purifications to obtain the conjugates with desired purity of >95%. The purified fractions were analysed by LC-MS and pure fractions were pooled and lyophilized after each purification cycle to give the conjugates as lyophilized solids. The products were appropriately dissolved subsequently in a mixture of acetonitrile/water and re-lyophilized.

Methods

Reactions were all monitored by LC-MS using Waters Acquity UPLC. Details of the column and method used are given below:

Column: Acquity UPLC BEH C18, 2.1×50 mm, 1.7 µm

Flow Rate: 0.6 mL/min

Wavelength: 254 nm and 220 nm

Solvents: A—HPLC grade water+0.05 v/v acetic acid; B—acetonitrile+0.05% v/v acetic acid

| METHOD | | |
|---|---|---|
| Time (min) | % A | % B |
| 0.0 | 95 | 5 |
| 5.0 | 5 | 95 |
| 5.10 | 95 | 5 |
| 6.50 | 95 | 5 |

Methods for Conjugations

Small scale amide coupling reactions were carried out on 5-15 mg scale and subsequently scaled up to give appropriate amounts of conjugates as given below. The concentration of reactants used in the reactions were 8 mM peptide+2.3-2.5 eq. NHS (or TFP) ester+230 mM DIEA in 0.5 mL (depending on scale) DMSO. The reactions were carried at rt for overnight and then purified by directly loading the crude reaction mixture on to preparative reversed phase HPLC columns. Solvents used for purification of the conjugates were: Solvent A: Water+0.1% v/v TFA and Solvent B—acetonitrile+0.1v/v TFA.

For I-3a to I-5a and 1-7 to I-9: column used for purification was Phenomenex Gemini 5 μm, 110 Å, 150×30 mm (part no.: OOF-4435-V0-AX) at a flow rate of 50 mL/min. The gradient used for purification was 30-65% B over 20 min.

For I-6a: column used was Phenomenex Luna 5 μm, 100 Å, 250×50 mm (part no.: OOG-4252-V0-AX) at a flow rate of 110 mL/min. The gradient used for purification was 40-55% over 35 min.

Fractions were analysed by LC-MS using the short method specified above. Pure fractions were pooled and lyophilized to constant weight to give the conjugates as fluffy solids. Purity of the conjugates were determined by LC-MS using a longer method given below. The purified conjugates were analysed using the method below and did not contain any free/unconjugated cytotoxic payload-linker.

| METHOD | | |
|---|---|---|
| Time (min) | % A | % B |
| 0.0 | 95 | 5 |
| 13.0 | 5 | 95 |
| 13.10 | 95 | 5 |
| 15.0 | 95 | 5 |

SUMMARY

Amounts of the compounds (>95% pure by LC-MS) prepared are as follows:
1) I-3a: Amount=33.3 mg
2) 1-7: Amount=31.5 mg
3) I-4a: Amount=25.0 mg
4) 1-8: Amount=9.5 mg and 20.0 mg
5) 1-9: Amount=25.2 mg
6) I-5a: Amount=65.1 mg
7) I-6a: Amount=126.2 mg The HPLC and LC/MS data are as follows:

| Compound | % area | retention time (min) | Mass found (M/2) |
|---|---|---|---|
| I-3a | 95.56 | 5.93 | 1927.39 |
| I-7 | 96.03 | 5.79 | 1898.36 |
| I-4a | 95.36 | 5.74 | 1947.63 |
| I-8 | 96.71 | 5.58 | 1918.9 |
| I-9 | 100 | 6.04 | 1910.38 |
| I-5a | 99.9 | 6.41 | 1982.27 |
| I-6a | 97.78 | 6.67 | 1582.28 |

Based on LC-MS analysis, the final products obtained were free of any unconjugated cytotoxic payload-linker.

Example 13

In vivo efficacy test of I-3a, 1-7, I-4a, and 1-8 in treatment of HT1080 xenograft in BALB/c nude mice Study Objective The objective of the research was to evaluate the in vivo anti-tumor efficacy of I-3a, 1-7, I-4a, and 1-8 in the treatment of HT1080 xenograft in BALB/c nude mice.

Experimental Design

| Gr | n | Treatment | Dosage (mg/kg) | Dosing Volume (ml/g) | Dosing Route | Schedule |
|---|---|---|---|---|---|---|
| 1 | 3 | Vehicle | — | 10 | i.v. | biw*2 weeks |
| 2 | 3 | I-3a | 1 | 10 | i.v. | biw*2 weeks |
| 3 | 3 | I-3a | 3 | 10 | i.v. | biw*2 weeks |
| 4 | 3 | I-3a | 10 | 10 | i.v. | biw*2 weeks |
| 5 | 3 | I-7 | 1 | 10 | i.v. | biw*2 weeks |
| 6 | 3 | I-7 | 3 | 10 | i.v. | biw*2 weeks |
| 7 | 3 | I-7 | 10 | 10 | i.v. | biw*2 weeks |
| 8 | 3 | I-4a | 1 | 10 | i.v. | biw*2 weeks |
| 9 | 3 | I-4a | 3 | 10 | i.v. | biw*2 weeks |
| 10 | 3 | I-4a | 10 | 10 | i.v. | biw*2 weeks |
| 11 | 3 | I-8 | 1 | 10 | i.v. | biw*2 weeks |
| 12 | 3 | I-8 | 3 | 10 | i.v. | biw*2 weeks |
| 13 | 3 | I-8 | 10 | 10 | i.v. | biw*2 weeks |

Materials

Animals and Housing Condition

Animals

Species: *Mus Musculus*

Strain: Balb/c nude

Age: 6-8 weeks

Sex: female

Body weight: 18-22 g

Number of animals: 48 mice plus spare

Housing Condition

The mice were kept in individual ventilation cages at constant temperature and humidity with 3 animals in each cage.

Temperature: 20~26° C.

Humidity 40-70%.

Cages: Made of polycarbonate. The size is 300 mm×180 mm×150 mm. The bedding material is corn cob, which is changed twice per week.

Diet: Animals had free access to irradiation sterilized dry granule food during the entire study period.

Water: Animals had free access to sterile drinking water.

Cage identification: The identification labels for each cage contained the following information: number of animals, sex, strain, the date received, treatment, study number, group number and the starting date of the treatment.

Animal identification: Animals were marked by ear coding.

Test and Positive Control Articles
　Product Identification: I-3a
　　Physical description: Lyophilised powder
　　Molecular weight: 3854.76
　　Package and storage condition: stored at −80° C.
　Product Identification: I-7
　　Physical description: Lyophilised powder
　　Molecular weight: 3796.73
　　Package and storage condition: stored at −80° C.
　Product Identification: I-4a
　　Physical description: Lyophilised powder
　　Molecular weight: 3895.75
　　Package and storage condition: stored at −80° C.
　Product Identification: I-8
　　Physical description: Lyophilised powder
　　Molecular weight: 3837.72
　　Package and storage condition: stored at −80° C.
Experimental Methods and Procedures
Cell Culture The HT1080 tumor cells were maintained in vitro as a monolayer culture in EMEM medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

Tumor Inoculation

Each mouse was inoculated subcutaneously at the right flank with HT1080 tumor cells ($5\times10^6$) in 0.2 ml of PBS for tumor development. The animals were randomized and treatment was started when the average tumor volume reached approximately 150 $mm^3$ for the efficacy study. The test article administration and the animal numbers in each group were shown in the experimental design table.

Testing Article Formulation Preparation

| Treatment | Dosage (mg/ml) | Formulation |
|---|---|---|
| Vehicle | — | 25 mM Histidine pH 7.0, 10% Sucrose |
| I-3a | | Dissolve 9.5 mg I-3a in 4.75 ml formulation buffer to make 2 mg/ml stock |
| | 0.1 | Dilute 45 ul 2 mg/ml I-3a with 855 ul formulation buffer |
| | 0.3 | Dilute 135 ul 2 mg/ml I-3a with 765 ul formulation buffer |
| | 1.0 | Dilute 450 ul 2 mg/ml I-3a with 450 ul formulation buffer |
| I-7 | | Dissolve 9.7 mg I-7 in 4.85 ml formulation buffer to make 2 mg/ml stock |
| | 0.1 | Dilute 45 ul 2 mg/ml I-7 with 855 ul formulation buffer |
| | 0.3 | Dilute 135 ul 2 mg/ml I-7 with 765 ul formulation buffer |
| | 1.0 | Dilute 450 ul 2 mg/ml I-7 with 450 ul formulation buffer |
| I-4a | | Dissolve 8.4 mg I-4a in 4.2 ml formulation buffer to make 2 mg/ml stock |
| | 0.1 | Dilute 45 ul 2 mg/ml I-4a with 855 ul formulation buffer |
| | 0.3 | Dilute 135 ul 2 mg/ml I-4a with 765 ul formulation buffer |
| | 1.0 | Dilute 450 ul 2 mg/ml I-4a with 450 ul formulation buffer |
| I-8 | | Dissolve 9.5 mg I-8 in 4.75 ml formulation buffer to make 2 mg/ml stock |
| | 0.1 | Dilute 45 ul 2 mg/ml I-8 with 855 ul formulation buffer |
| | 0.3 | Dilute 135 ul 2 mg/ml I-8 with 765 ul formulation buffer |
| | 1.0 | Dilute 450 ul 2 mg/ml I-8 with 450 ul formulation buffer |

Observations

All the procedures related to animal handling, care and the treatment in the study were performed following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured every day), eye/hair matting and any other abnormal effect as stated in the protocol. Death and observed clinical signs were recorded on the basis of the numbers of animals within each subset.

Tumor Measurements and the Endpoints

Prior to the onset of drug treatment, mice were measured for tumor size in two dimensions using a caliper, and the tumor volume (mm3) was calculated using formula V=0.5 a×$b^2$ where a and b are the long and short diameters of the tumor in mm, respectively. Mice were randomized into different treatment groups based on the tumor volume.

The tumor size was then used for calculations of T/C value. The T/C value (in percent) is an indication of anti-tumor effectiveness; T and C are the mean volumes of the treated and control groups, respectively, on a given day.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Plasma Collection

At the end of study mice were re-dosed and plasma was collected at 5 min, 15 min, 30 min, 60 min and 120 min post dosing for PK analysis.

Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using Prism. $P<0.05$ was considered to be statistically significant.

Results

Mortality, Morbidity, and Body Weight Gain or Loss

Figure 9:
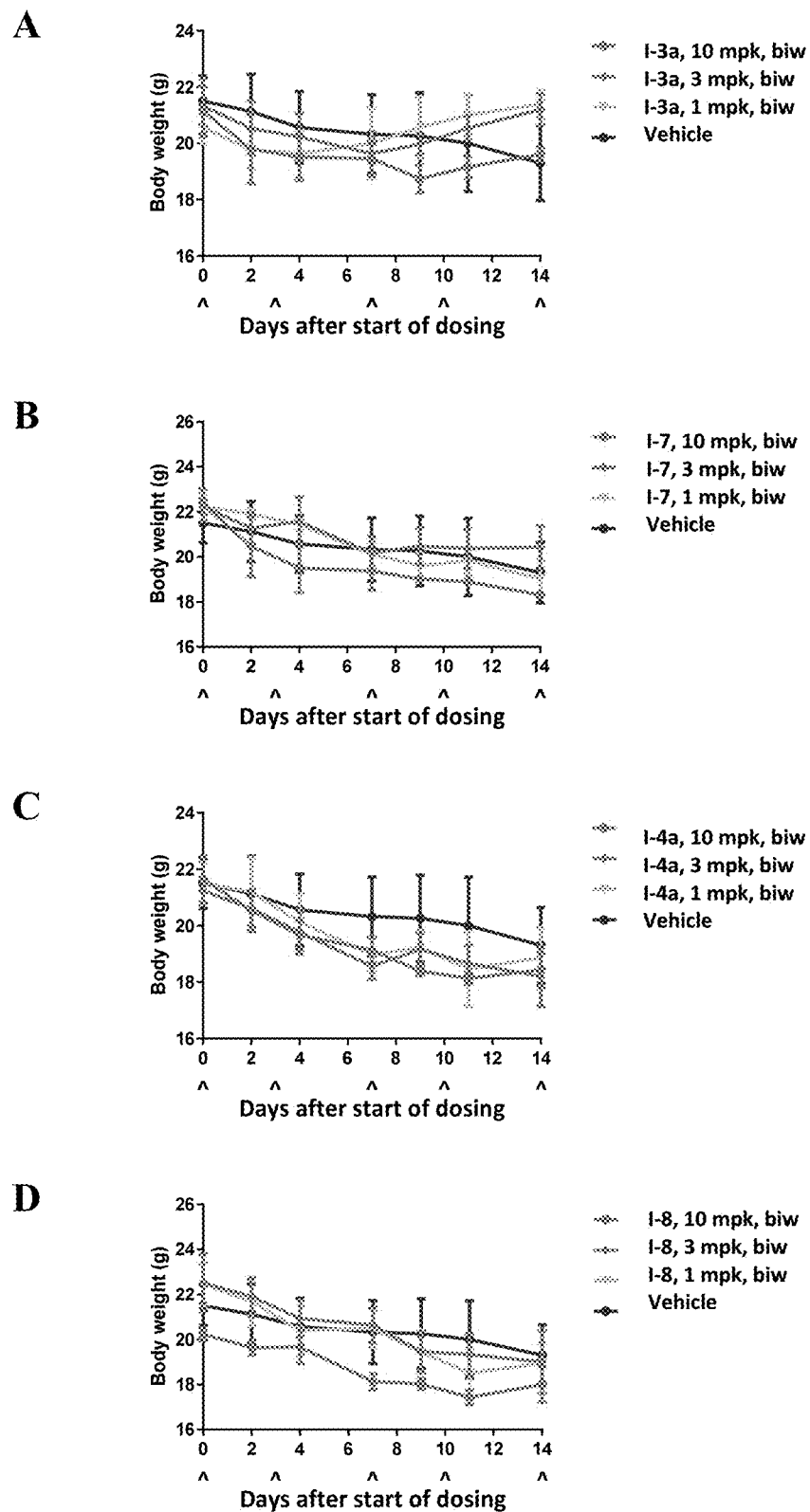
FIG. 9 depicts body weight changes after administering I-3a, I-7, I-4a, and I-8 to female Balb/c nude mice bearing HT1080 xenograft. Data points represent group mean body weight. Error bars represent standard error of the mean (SEM).

Body weight was monitored regularly as an indirect measure of toxicity. Body weight changes in female Balb/c nude mice bearing HT1080 dosed with I-3a, I-7, I-4a, and I-8 are shown in FIG. 9.

Tumor Volume Trace

Mean tumor volume over time in female Balb/c nude mice bearing HT1080 xenograft is shown in Table A.

TABLE A

TUMOR VOLUME TRACE OVER TIME

| | | Days after the start of treatment | | | | | |
|---|---|---|---|---|---|---|---|
| Gr. | Treatment | 0 | 2 | 4 | 7 | 9 | 11 | 14 |
| 1 | Vehicle, biw | 151 ± 31 | 278 ± 69 | 453 ± 105 | 717 ± 235 | 913 ± 281 | 1122 ± 352 | 1468 ± 529 |
| 2 | I-3a, 1 mpk, biw | 146 ± 14 | 176 ± 18 | 147 ± 25 | 72 ± 17 | 46 ± 14 | 15 ± 8 | 0 ± 0 |
| 3 | I-3a, 3 mpk, biw | 146 ± 27 | 102 ± 23 | 46 ± 2 | 18 ± 4 | 13 ± 2 | 5 ± 2 | 0 ± 0 |
| 4 | I-3a, 10 mpk, biw | 146 ± 8 | 74 ± 8 | 28 ± 2 | 12 ± 3 | 9 ± 4 | 2 ± 2 | 0 ± 0 |
| 5 | I-7, 1 mpk, biw | 147 ± 24 | 230 ± 31 | 333 ± 54 | 379 ± 76 | 419 ± 66 | 494 ± 78 | 661 ± 77 |
| 6 | I-7, 3 mpk, biw | 148 ± 7 | 159 ± 3 | 126 ± 8 | 84 ± 23 | 86 ± 26 | 158 ± 75 | 172 ± 75 |
| 7 | I-7, 10 mpk, biw | 148 ± 6 | 116 ± 33 | 44 ± 6 | 31 ± 5 | 5 | 4 | 0 |
| 8 | I-4a, 1 mpk, biw | 150 ± 17 | 226 ± 30 | 302 ± 14 | 434 ± 12 | 518 ± 22 | 621 ± 108 | 837 ± 139 |
| 9 | I-4a, 3 mpk, biw | 150 ± 20 | 200 ± 24 | 244 ± 38 | 277 ± 65 | 319 ± 73 | 385 ± 110 | 468 ± 135 |
| 10 | I-4a, 10 mpk, biw | 154 ± 44 | 208 ± 53 | 235 ± 61 | 221 ± 64 | 165 ± 44 | 160 ± 34 | 194 ± 59 |
| 11 | I-8, 1 mpk, biw | 155 ± 28 | 227 ± 43 | 304 ± 40 | 446 ± 37 | 558 ± 100 | 541 ± 183 | 611 ± 242 |
| 12 | I-8, 3 mpk, biw | 153 ± 25 | 234 ± 47 | 335 ± 38 | 458 ± 33 | 592 ± 80 | 731 ± 96 | 1042 ± 232 |
| 13 | I-8, 10 mpk, biw | 155 ± 45 | 266 ± 58 | 424 ± 71 | 579 ± 92 | 769 ± 140 | 942 ± 154 | 1099 ± 163 |

Figure 10:
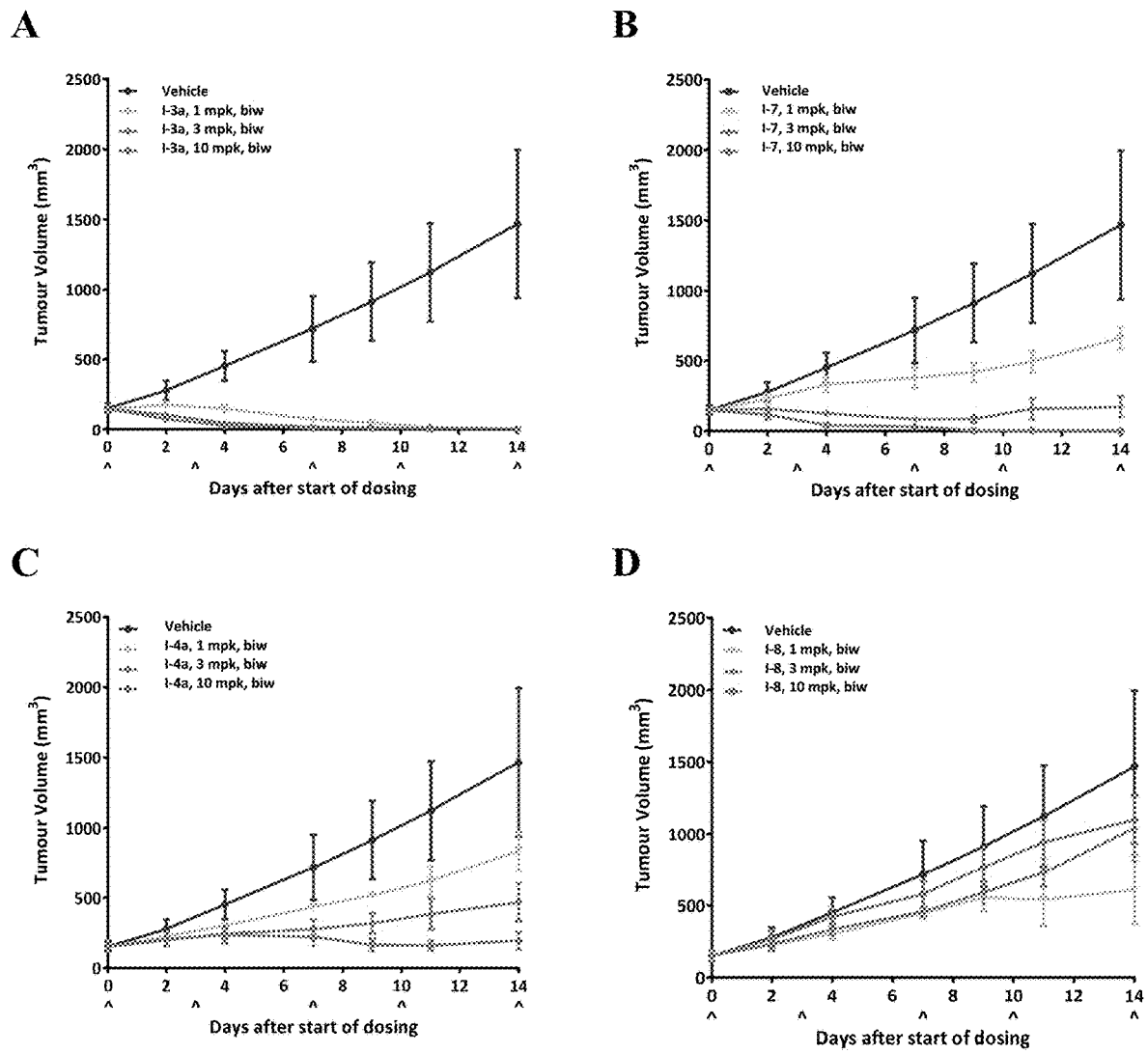
FIG. 10 depicts tumor volume traces after administering I-3a, I-7, I-4a, and I-8 to female Balb/c nude mice bearing HT1080 xenograft. Data points represent group mean, error bars represent standard error of the mean (SEM).

Tumor growth curve is shown in FIG. 10.

Tumor Growth Inhibition Analysis

Tumor growth inhibition rate for I-3a, I-7, I-4a, and I-8 in the HT1080 xenograft model was calculated based on tumor volume measurements at day 14 after the start of treatment.

TABLE B

TUMOR GROWTH INHIBITION ANALYSIS (T/C AND TGI)

| Gr | Treatment | Tumor Volume (mm³)[a] | T/C[b] (%) | TGI (%) | P value |
|---|---|---|---|---|---|
| 1 | Vehicle, biw | 1468 ± 529 | — | — | — |
| 2 | I-3a, 1 mpk, biw | 0 ± 0 | 0.0 | 111.1 | p < 0.001 |
| 3 | I-3a, 3 mpk, biw | 0 ± 0 | 0.0 | 111.1 | p < 0.001 |
| 4 | I-3a, 10 mpk, biw | 0 ± 0 | 0.0 | 111.1 | p < 0.001 |
| 5 | I-7, 1 mpk, biw | 661 ± 77 | 45.0 | 61.0 | p < 0.05 |
| 6 | I-7, 3 mpk, biw | 172 ± 75 | 11.7 | 98.2 | p < 0.001 |
| 7 | I-7, 10 mpk, biw | 0 | 0.0 | 111.3 | — |
| 8 | I-4a, 1 mpk, biw | 837 ± 139 | 57.0 | 47.8 | p > 0.05 |
| 9 | I-4a, 3 mpk, biw | 468 ± 135 | 31.9 | 75.9 | p < 0.01 |
| 10 | I-4a, 10 mpk, biw | 194 ± 59 | 13.2 | 96.9 | p < 0.001 |
| 11 | I-8, 1 mpk, biw | 611 ± 242 | 41.6 | 65.3 | p < 0.05 |
| 12 | I-8, 3 mpk, biw | 1042 ± 232 | 70.9 | 32.5 | p > 0.05 |
| 13 | I-8, 10 mpk, biw | 1099 ± 163 | 74.8 | 28.3 | p > 0.05 |

[a]Mean ± SEM.
[b]Tumor Growth Inhibition is calculated by dividing the group average tumor volume for the treated group by the group average tumor volume for the control group (T/C).

Results Summary and Discussion

In this study, the therapeutic efficacy of I-3a, I-7, I-4a, and I-8 in HT1080 xenograft model was evaluated. The measured body weight changes are shown in the FIG. 9. Tumor volume of all treatment groups at various time points are shown in Tables A, B and FIG. 10.

The mean tumor volume of vehicle treated mice reached 1468 mm³ on day 14. I-3a at 1 mg/kg (TV 0 mm³, TGI=111.1%, p<0.001), 3 mg/kg (TV 0 mm³, TGI=111.1%, p<0.001) and 10 mg/kg (TV 0 mm³, TGI=111.1%, p<0.001) completely eradicated the tumors on day 14.

I-7 at 1 mg/kg (TV 661 mm³, TGI=61.0%, p<0.05), 3 mg/kg (TV 172 mm³, TGI=98.2%, p<0.001) and 10 mg/kg (TV 0 mm³, TGI=111.3%) produced dose-dependent anti-tumor activity. 2/3 mice treated with 1-7 at 10 mg/kg died during the dosing period.

I-4a at 1 mg/kg (TV 837 mm³, TGI=47.8%, p>0.05), 3 mg/kg (TV 468 mm³, TGI=75.9%, p<0.01) and 10 mg/kg (TV 194 mm³, TGI=96.9%, p<0.001) produced dose-dependent antitumor activity.

I-8 at 1 mg/kg, 3 mg/kg and 10 mg/kg didn't show obvious antitumor activity. 1/3 mouse treated with 1-8 at 1 mg/kg showed severe tumor ulceration and 1/3 mouse treated with I-8 at 3 mg/kg died at day 14.

The animal bodyweight loss and death in this study should be due to the combination of BDC treatments and HT1080 tumor burden.

Example 14

In Vivo Efficacy Test of 1-12 and 1-16 in Treatment of HT1080 Xenograft in BALB/C Nude Mice Study Objective The objective of the research was to evaluate the in vivo anti-tumor efficacy of 1-12 and 1-16 in treatment of HT1080 xenograft model in BALB/c nude mice.

Experimental Design

| Gr | Treatment | Dosage (mg/kg) | n | Dosing Volume (ml/g) | Dosing Route | Schedule |
|---|---|---|---|---|---|---|
| 1 | Vehicle | — | 3 | 10 | i.v. | biw*2 weeks |
| 2 | I-12 | 1 | 3 | 10 | i.v. | qw*2 weeks |
| 3 | I-12 | 3 | 3 | 10 | i.v. | qw*2 weeks |
| 4 | I-12 | 10 | 3 | 10 | i.v. | qw*2 weeks |
| 5 | I-16 | 1 | 3 | 10 | i.v. | biw*2 weeks |
| 6 | I-16 | 3 | 3 | 10 | i.v. | biw*2 weeks |
| 7 | I-16 | 10 | 3 | 10 | i.v. | biw*2 weeks |

Note:
n: animal number; Dosing volume: adjust dosing volume based on body weight 10 μl/g.

Materials
Animals and Housing Condition
  Animals
  Species: *Mus Musculus*
  Strain: Balb/c nude
  Age: 6-8 weeks
  Sex: female
  Body weight: 18-22 g
  Number of animals: 21 mice plus spare
Housing Condition
  The mice were kept in individual ventilation cages at constant temperature and humidity with 3 animals in each cage.
  Temperature: 20~26° C.
  Humidity 40-70%.
  Cages: Made of polycarbonate. The size is 300 mm×180 mm×150 mm. The bedding material is corn cob, which is changed twice per week.
  Diet: Animals had free access to irradiation sterilized dry granule food during the entire study period.
  Water: Animals had free access to sterile drinking water.
  Cage identification: The identification labels for each cage contained the following information: number of animals, sex, strain, the date received, treatment, study number, group number and the starting date of the treatment.
  Animal identification: Animals were marked by ear coding.
Test and Positive Control Articles
  Product identification: 1-12
  Physical description: Lyophilised powder
  Molecular weight: 5.3 mg
  Purity: 97.76%
  Package and storage condition: stored at −80° C.
  Product identification: 1-16
  Physical description: Lyophilised powder
  Molecular weight: 7.6 mg
  Purity: 98.36%
  Package and storage condition: stored at −80° C.
Experimental Methods and Procedures
Cell Culture
  The HT1080 tumor cells were maintained in vitro as a monolayer culture in medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.
Tumor Inoculation
  Each mouse was inoculated subcutaneously at the right flank with HT1080 tumor cells ($5\times10^6$) in 0.2 ml of PBS for tumor development. 21 animals were randomized when the average tumor volume reached 174 mm³. The test article administration and the animal numbers in each group were shown in the experimental design table.
Testing Article Formulation Preparation

| Treatment | Dose (mg/ml) | Formulation |
|---|---|---|
| Vehicle | — | 25 mM Histidine pH 7.0, 10% Sucrose(without DMSO) |
| I-12 | 1 | Dissolve 5.3 mg I-12 into 5.181 ml formulation buffer |
| I-12 | 0.3 | Dilute 240 ul 1 mg/ml I-12 into 560 ul formulation buffer |
| I-12 | 0.1 | Dilute 80 ul 1 mg/ml I-12 into 720 ul formulation buffer |
| I-16 | 1 | Dissolve 7.6 mg I-16 into 7.475 ml formulation buffer |
| I-16 | 0.3 | Dilute 240 ul 1 mg/ml I-16 into 560 ul formulation buffer |
| I-16 | 0.1 | Dilute 80 ul 1 mg/ml I-16 into 720 ul formulation buffer |

Observations
  All the procedures related to animal handling, care and the treatment in the study were performed following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss, eye/hair matting and any other abnormal effect as stated in the protocol. Death and observed clinical signs were recorded on the basis of the numbers of animals within each subset.

Tumor Measurements and the Endpoints

The major endpoint was to see if the tumor growth could be delayed or mice could be cured. Tumor volume was measured three times weekly in two dimensions using a caliper, and the volume was expressed in mm$^3$ using the formula: $V=0.5 \text{ a}\times\text{b}^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day.

TGI was calculated for each group using the formula: TGI (%)=[1−(Ti−T0)/(Vi−V0)]×100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start.

Sample Collection

At the end of study plasma was collected at 5 min, 15 min, 30 min, 60 min and 120 min post dosing.

Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using Prism. P<0.05 was considered to be statistically significant.

Results

Body Weight Change and Tumor Growth Curve

Figure 11:
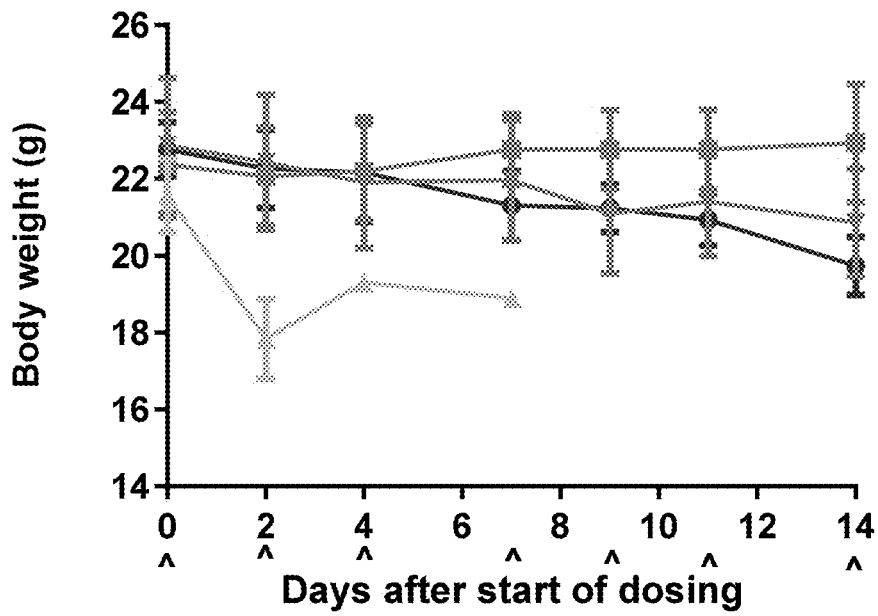
FIG. 11 depicts body weight changes (A) and tumor volume (B) trace after administering I-12 to female BALB/c nude mice bearing HT1080 xenograft. Data points represent group mean body weight. Error bars represent standard error of the mean (SEM).
Figure 11:
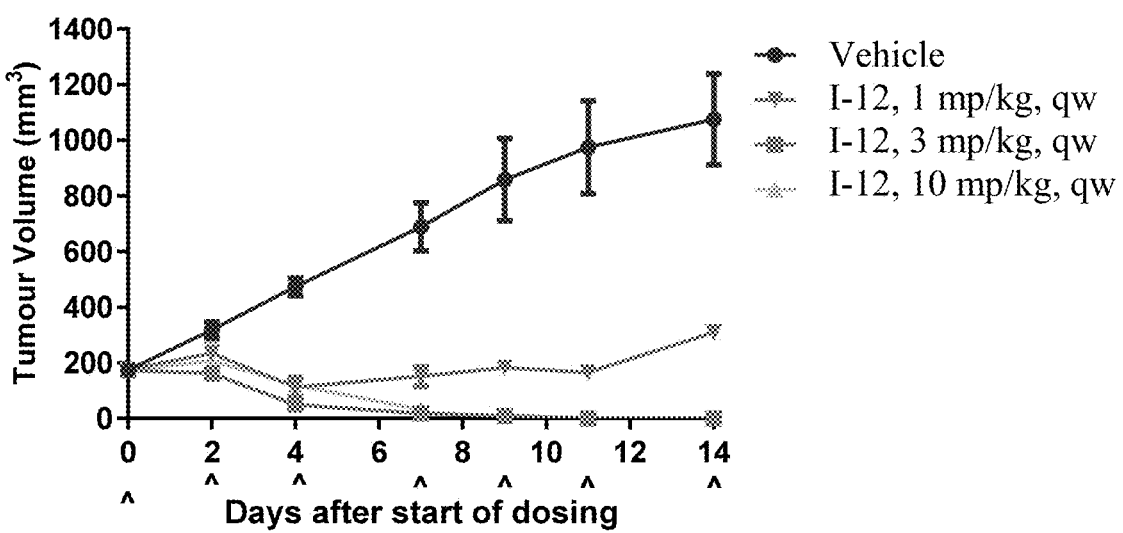
Figure 12:
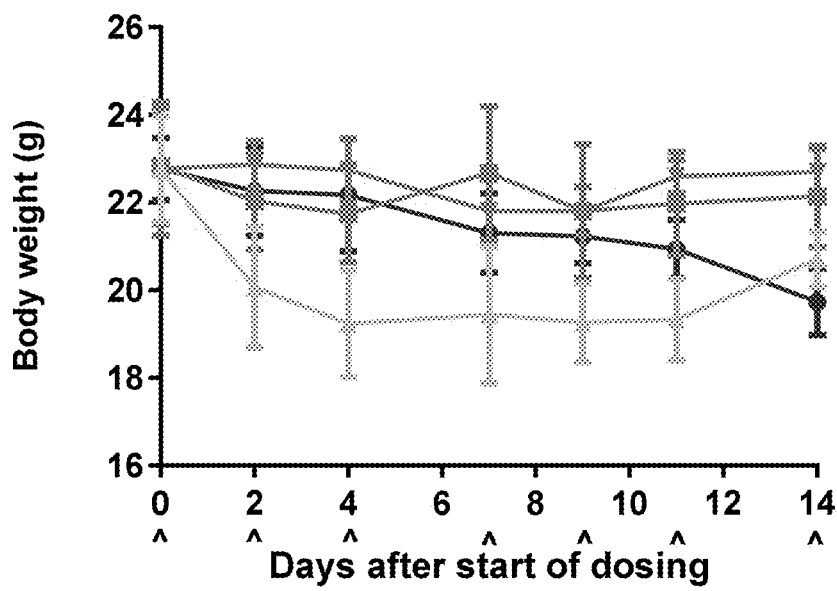
FIG. 12 depicts body weight changes (A) and Tumor volume (B) trace after administering I-16 to female BALB/c nude mice bearing HT1080 xenograft. Data points represent group mean body weight. Error bars represent standard error of the mean (SEM).
Figure 12:
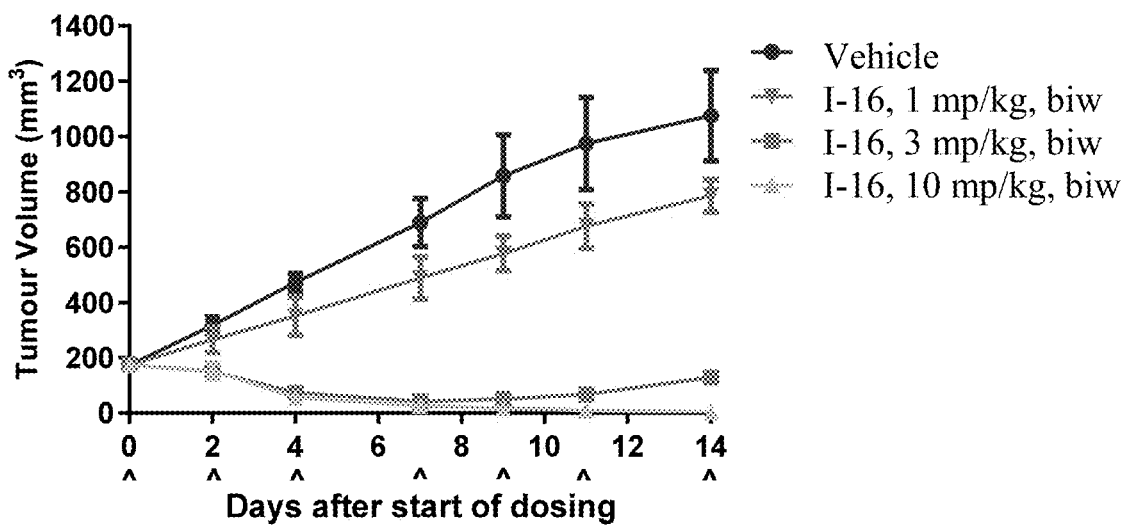

Body weight and tumor growth are shown in FIGS. 11 and 12.

Tumor Volume Trace

Mean tumor volume over time in female Balb/c nude mice bearing HT1080 xenograft is shown in Table C.

Tumor Growth Inhibition Analysis

Tumor growth inhibition rate for I-12, I-16 in the HT1080 xenograft model was calculated based on tumor volume measurements at day 14 after the start of treatment.

TABLE D

TUMOR GROWTH INHIBITION ANALYSIS

| Gr | Treatment | Tumor Volume (mm$^3$)$^a$ | T/C$^b$ (%) | TGI (%) | P value |
|---|---|---|---|---|---|
| 1 | Vehicle, biw | 1075 ± 164 | — | — | — |
| 2 | I-12, 1 mpk, qw | 310 ± 17 | 29 | 85 | p < 0.001 |
| 3 | I-12, 3 mpk, qw | 0 | 0 | 119 | p < 0.001 |
| 4 | I-12, 10 mpk, qw | — | — | — | — |
| 5 | I-16, 1 mpk, biw | 785 ± 58 | 73 | 32 | p > 0.05 |
| 6 | I-16, 3 mpk, biw | 128 ± 16 | 12 | 105 | p < 0.001 |
| 7 | I-16, 10 mpk, biw | 2 ± 2 | 0.2 | 119 | p < 0.001 |

$^a$Mean ± SEM.
$^b$Tumor Growth Inhibition is calculated by dividing the group average tumor volume for the treated group by the group average tumor volume for the control group (T/C).

Results Summary and Discussion

In this study, the therapeutic efficacy of I-12, I-16 in the HT1080 xenograft model was evaluated. The measured body weights and tumor volumes of all treatment groups at various time points are shown in the FIGS. 11 and 12 and Tables C and D.

The mean tumor size of vehicle treated mice reached 1075 mm$^3$ on day 14. I-12 at 1 mg/kg (TV=310 mm$^3$, TGI=85.0%, p<0.001) showed significant anti-tumor activity and completely eradicated the tumors at the dosage of 3 mg/kg (TV=0 mm$^3$, TGI=119.2%, p<0.001), I-12 at 10 mg/kg caused severe body weight loss and death of 3/3 of the animals.

TABLE C

TUMOR VOLUME TRACE OVER TIME

| | | Days after the start of treatment | | | | | |
|---|---|---|---|---|---|---|---|
| Gr. | Treatment | 0 | 2 | 4 | 7 | 9 | 11 | 14 |
| 1 | Vehicle, biw | 174 ± 18 | 318 ± 30 | 473 ± 31 | 688 ± 87 | 859 ± 148 | 975 ± 167 | 1075 ± 164 |
| 2 | I-12, 1 mpk, qw | 175 ± 19 | 234 ± 25 | 112 ± 36 | 151 ± 35 | 182 ± 25 | 165 ± 17 | 310 ± 17 |
| 3 | I-12, 3 mpk, qw | 173 ± 24 | 162 ± 25 | 50 ± 8 | 18 ± 0 | 10 ± 5 | 0 ± 0 | 0 ± 0 |
| 4 | I-12, 10 mpk, qw | 174 ± 23 | 208 ± 61 | 121 ± 0 | 32 ± 0 | | | |
| 5 | I-16, 1 mpk, biw | 174 ± 22 | 265 ± 46 | 351 ± 69 | 488 ± 75 | 577 ± 62 | 676 ± 79 | 785 ± 58 |
| 6 | I-16, 3 mpk, biw | 174 ± 25 | 151 ± 16 | 73 ± 19 | 42 ± 11 | 50 ± 4 | 67 ± 9 | 128 ± 16 |
| 7 | I-16, 10 mpk, biw | 173 ± 25 | 153 ± 29 | 58 ± 20 | 27 ± 1 | 18 ± 4 | 10 ± 1 | 2 ± 2 |

I-16 at 1 mg/kg (TV=785 mm³, TGI=32.2%, p>0.05), 3 mg/kg (TV=128 mm³, TGI=105.1%, p<0.001) and 10 mg/kg (TV=2 mm³, TGI=84.3%, p<0.001) produced dose-dependent antitumor activity. Among them, 1-16 at 10 mg/kg caused complete remission of 2/3 tumors and regressed 1/3 tumor to 7 mm3 on day 14.

```
                        SEQUENCE LISTING

<160> NUMBER OF SEQ ID NOS: 17

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Asn, Cys, Gln, Met, Ser, Thr, Gly, Ala, Ile,
      Leu, Pro or Val
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<223> OTHER INFORMATION: See specification as filed for detailed
      description of substitutions and preferred embodiments

<400> SEQUENCE: 1

Cys Xaa Xaa Xaa Xaa Gly Glu Asp Phe Tyr Xaa Xaa Cys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Tyr Asn Glu Phe Gly Cys Glu Asp Phe Tyr Asp Ile Cys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Tyr Asn Glu Phe Gly Cys Glu Asp Phe Tyr Asp Ile Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: D-Ala

<400> SEQUENCE: 4

Cys Ala Asn Glu Phe Gly Cys Glu Asp Phe Tyr Asp Ile Cys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (5)..(5)
<223> OTHER INFORMATION: 1Nal
<220> FEATURE:
<221> NAME/KEY: MOD_RES
<222> LOCATION: (6)..(6)
<223> OTHER INFORMATION: D-Ala
<220> FEATURE:
<221> NAME/KEY: MOD_RES
<222> LOCATION: (13)..(13)
<223> OTHER INFORMATION: tBuGly

<400> SEQUENCE: 5

Cys Ala Asn Glu Xaa Ala Cys Glu Asp Phe Tyr Asp Xaa Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr, Met, Phe or Val
<220> FEATURE:
<221> NAME/KEY: MOD_RES
<222> LOCATION: (3)..(3)
<223> OTHER INFORMATION: Asn, Cys, Gln, Met, Ser, Thr, Gly, Ala, Ile,
      Leu, Pro or Val
<220> FEATURE:
<221> NAME/KEY: MOD_RES
<222> LOCATION: (4)..(4)
<223> OTHER INFORMATION: Asn, Cys, Gln, Met, Ser, Thr, Asp or Glu
<220> FEATURE:
<221> NAME/KEY: MOD_RES
<222> LOCATION: (5)..(5)
<223> OTHER INFORMATION: Phe, Trp or Tyr
<220> FEATURE:
<221> NAME/KEY: MOD_RES
<222> LOCATION: (12)..(12)
<223> OTHER INFORMATION: Asp or Glu
<220> FEATURE:
<221> NAME/KEY: MOD_RES
<222> LOCATION: (13)..(13)
<223> OTHER INFORMATION: Gly, Ala, Ile, Leu, Pro or Val
<220> FEATURE:
<223> OTHER INFORMATION: See specification as filed for detailed
      description of substitutions and preferred embodiments

<400> SEQUENCE: 6

Cys Xaa Xaa Xaa Xaa Gly Cys Glu Asp Phe Tyr Xaa Xaa Cys
1               5                   10
```

```
<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr, Met, Phe or Val
<220> FEATURE:
<221> NAME/KEY: MOD_RES
<222> LOCATION: (3)..(3)
<223> OTHER INFORMATION: Asn or Gly
<220> FEATURE:
<221> NAME/KEY: MOD_RES
<222> LOCATION: (4)..(4)
<223> OTHER INFORMATION: Glu or Gln

<400> SEQUENCE: 7

Cys Xaa Xaa Xaa Phe Gly Cys Glu Asp Phe Tyr Asp Ile Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr, Met or Phe
<220> FEATURE:
<221> NAME/KEY: MOD_RES
<222> LOCATION: (3)..(3)
<223> OTHER INFORMATION: Asn or Gly
<220> FEATURE:
<221> NAME/KEY: MOD_RES
<222> LOCATION: (4)..(4)
<223> OTHER INFORMATION: Glu or Gln

<400> SEQUENCE: 8

Cys Xaa Xaa Xaa Phe Gly Cys Glu Asp Phe Tyr Asp Ile Cys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr or Met
<220> FEATURE:
<221> NAME/KEY: MOD_RES
<222> LOCATION: (4)..(4)
<223> OTHER INFORMATION: Glu or Gln

<400> SEQUENCE: 9

Cys Xaa Asn Xaa Phe Gly Cys Glu Asp Phe Tyr Asp Ile Cys
1               5                   10

<210> SEQ ID NO 10
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Cys Met Asn Gln Phe Gly Cys Glu Asp Phe Tyr Asp Ile Cys
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Phe Gly Glu Phe Gly Cys Glu Asp Phe Tyr Asp Ile Cys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Val Asn Glu Phe Gly Cys Glu Asp Phe Tyr Asp Ile Cys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Phe Asn Glu Phe Gly Cys Glu Asp Phe Tyr Asp Ile Cys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Tyr Asn Glu Tyr Gly Cys Glu Asp Phe Tyr Asp Ile Cys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Tyr Asn Glu Trp Gly Cys Glu Asp Phe Tyr Asp Ile Cys
1               5                   10
```

```
<210> SEQ ID NO 16
<211> LENGTH: 15
<212> TYPE: PRT
<213> ORGANISM: Artificial Sequence
<220> FE Linker is a bivalent spacer moiety that connects $AA^1$-$AA^2$ moiety with the Toxin moiety; and Toxin is a chemotherapeutic agent.

2. The method of claim 1, wherein the cancer is MT1-positive cancer.

3. The method of claim 1, wherein the cancer is selected from colorectal cancer, non-small cell lung cancer, breast cancer, gastric cancer, sarcoma, myeloma, nasalpharyngeal/laryngeal/oesophageal cancer, ovarian cancer, epithelial cancer, melanoma, glioma, astrocytoma, glioblastoma, neuroblastoma, mesothlioma, bladder cancer, hepatocellular carcinoma, and prostate cancer.

4. The method of claim 1, wherein the polypeptide is -C-X-U/O-X-X-G-C-E-D-F-Y-X-X-C-(SEQ ID NO: 1), wherein X represents any amino acid residue; U represents a polar, uncharged amino acid residue selected from N, C, Q, M, S and T; and O represents a non-polar aliphatic amino acid residue selected from G, A, I, L, P and V.

5. The method of claim 1, wherein the polypeptide is -C(D-Ala)NE(1Nal)(D-Ala)CEDFYD(tBuGly)C- (SEQ ID NO: 5), wherein D-Ala represents D-alanine; 1Nal represents 1-naphthylalanine; and tBuGly represents tert-butylglycine.

6. The method of claim 1, wherein the molecular scaffold is

.

7. The method of claim 1, wherein the Bicycle is of formula II':

II' wherein:

each of $L^1$, $L^2$, and $L^3$ is independently a $C_{1-6}$ bivalent straight or branched saturated or unsaturated hydrocarbon chain wherein 1-2 methylene units of the chain are independently and optionally replaced with —S—, —N(R)—, —C(O)—, —C(O)N(R)—, or —N(R)C(O)—;

each R is independently hydrogen or $C_{1-4}$ alkyl;

Ring A is a 6-membered saturated, partially unsaturated, or aromatic ring having 0-3 heteroatoms independently selected from nitrogen, oxygen, and sulfur;

comprises a polypeptide targeting MT1-MMP, wherein the polypeptide is of SEQ ID NO: 1 or SEQ ID NO: 5; and indicates the site of attachment to the Spacer.

8. The method of claim 7, wherein each of $L^1$, $L^2$, and $L^3$ is $—CH_2—$, or each of $L^1$, $L^2$, and $L^3$ is $—C(O)CH_2CH_2—$.

9. The method of claim 7, wherein Ring A is selected from:

,

,

,

,

, and

.

10. The method of claim 7, wherein the Bicycle is:
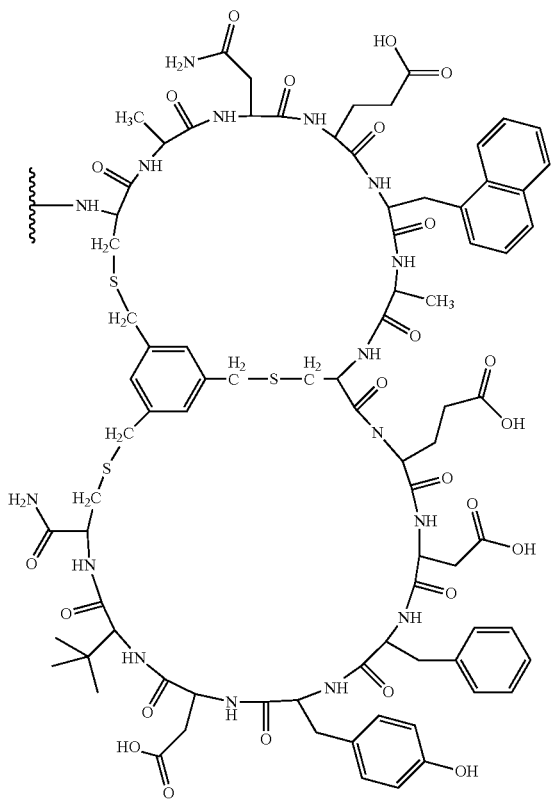 [SMILES: *NC1CSCc2cc3cc(c2)CSCC(NC(=O)C(C)NC(=O)C(Cc2cccc4ccccc24)NC(=O)C(CCC(=O)O)NC(=O)C(CC(N)=O)NC(=O)C(C)NC1=O)C(=O)NC(CCC(=O)O)C(=O)NC(CC(=O)O)C(=O)NC(Cc1ccccc1)C(=O)NC(Cc1ccc(O)cc1)C(=O)NC(CC(=O)O)C(=O)NC(C(C)(C)C)C(=O)NC(C(N)=O)CSC3]
11. The method of claim 1, wherein the AA$^1$-AA$^2$ moiety is
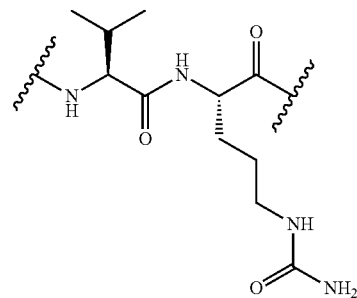
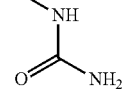 or
-continued
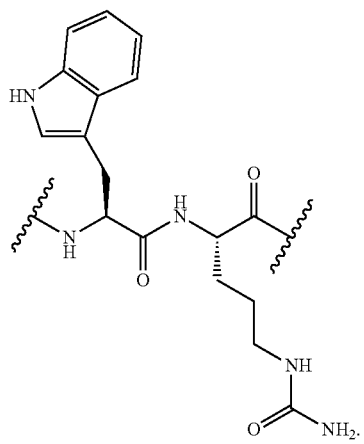
12. The method of claim 1, wherein the Linker moiety is
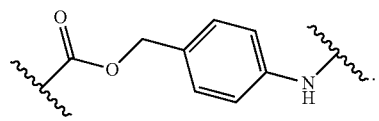 [SMILES: *Nc1ccc(COC(*)=O)cc1]
13. The method of claim 1, wherein the Toxin is selected from the group consisting of MMAE, MMAF, DM1, DM4, SN38, doxorubicin and a duocarmycin analog.
14. The method of claim 1, wherein said compound is
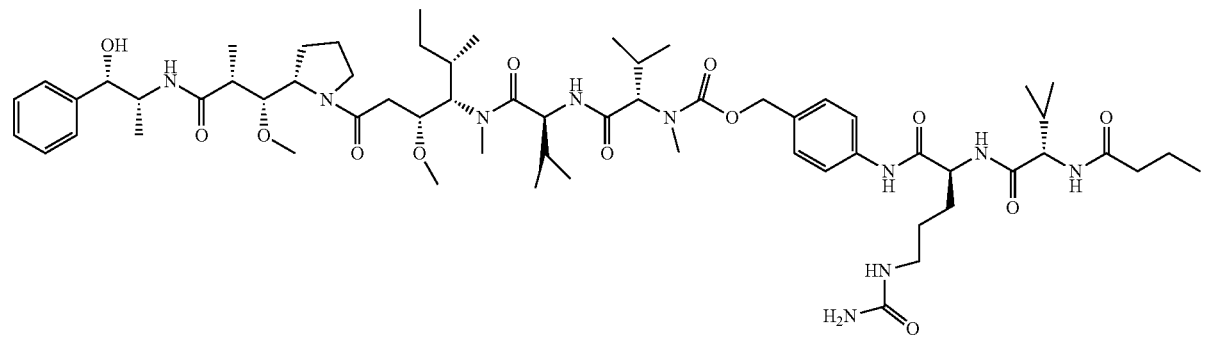

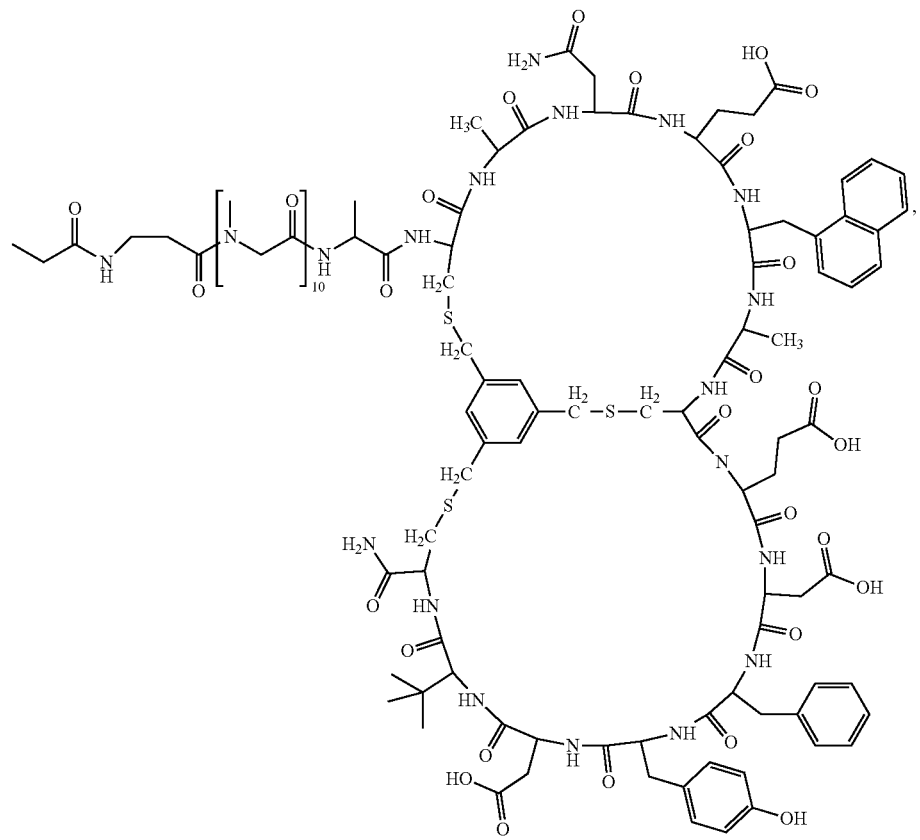

or a pharmaceutically acceptable salt thereof.

15. A method for treating cancer in a patient in need thereof, comprising administering to said patient a compound of formula I:

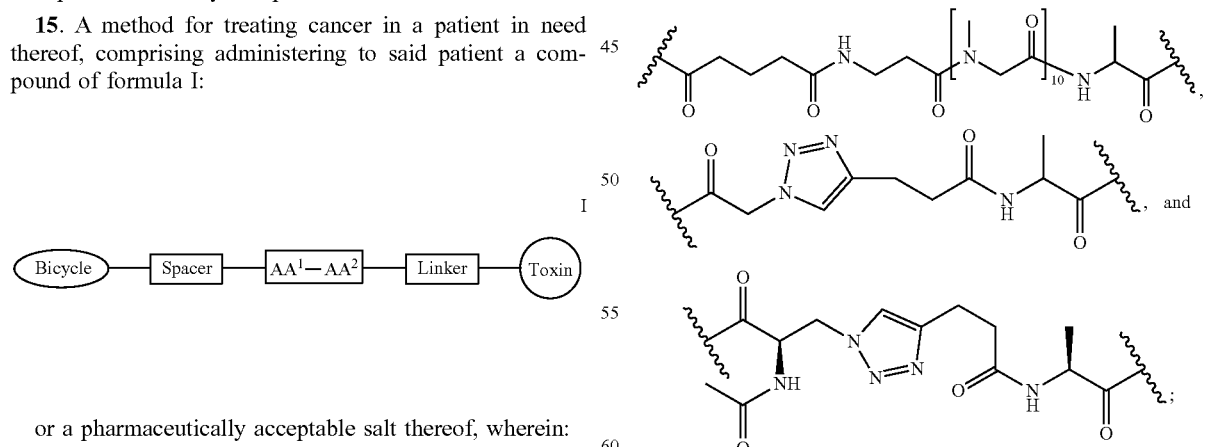

or a pharmaceutically acceptable salt thereof, wherein:
Bicycle is a polypeptide which is covalently bound to a molecular scaffold such that two or more peptide loops are subtended between attachment points to the scaffold;
Spacer is a bivalent moiety that connects the Bicycle moiety with the $AA^1$-$AA^2$ moiety, which is selected from $AA^1$-$AA^2$ is a bivalent moiety comprising at least one citrulline moiety that connects the Spacer moiety with the Linker moiety, wherein each of $AA^1$ and $AA^2$ is an independently selected natural or unnatural amino acid moiety;

Linker is a bivalent spacer moiety that connects AA¹-AA² moiety with the Toxin moiety; and Toxin is a chemotherapeutic agent.

16. The method of claim 15, wherein the polypeptide is -C-X-U/O-X-X-G-C-E-D-F-Y-X-X-C- (SEQ ID NO: 1) wherein X represents any amino acid residue; U represents a polar, uncharged amino acid residue selected from N, C, Q, M, S and T; and O represents a non-polar aliphatic amino acid residue selected from G, A, I, L, P and V.

17. The method of claim 15, wherein the polypeptide is -C(D-Ala)NE(1Nal)(D-Ala)CEDFYD(tBuGly)C- (SEQ ID NO: 5), wherein D-Ala represents D-alanine; 1Nal represents 1-naphthylalanine; and tBuGly represents tert-butylglycine.

18. The method of claim 15, wherein the molecular scaffold is comprises a polypeptide targeting MT1-MMP; and indicates the site of attachment to the Spacer.

20. The method of claim 19, wherein each of $L^1$, $L^2$, and $L^3$ is —CH$_2$—, or each of $L^1$, $L^2$, and $L^3$ is —C(O)CH$_2$CH$_2$—.

21. The method of claim 19, wherein Ring A is selected from:

19. The method of claim 15, wherein the Bicycle is of formula II':

II' wherein:

each of $L^1$, $L^2$, and $L^3$ is independently a $C_{1-6}$ bivalent straight or branched saturated or unsaturated hydrocarbon chain wherein 1-2 methylene units of the chain are independently and optionally replaced with —S—, —N(R)—, —C(O)—, —C(O)N(R)—, or —N(R)C(O)—;

each R is independently hydrogen or $C_{1-4}$ alkyl;

Ring A is a 6-membered saturated, partially unsaturated, or aromatic ring having 0-3 heteroatoms independently selected from nitrogen, oxygen, and sulfur;

22. The method of claim 19, wherein the Bicycle is:
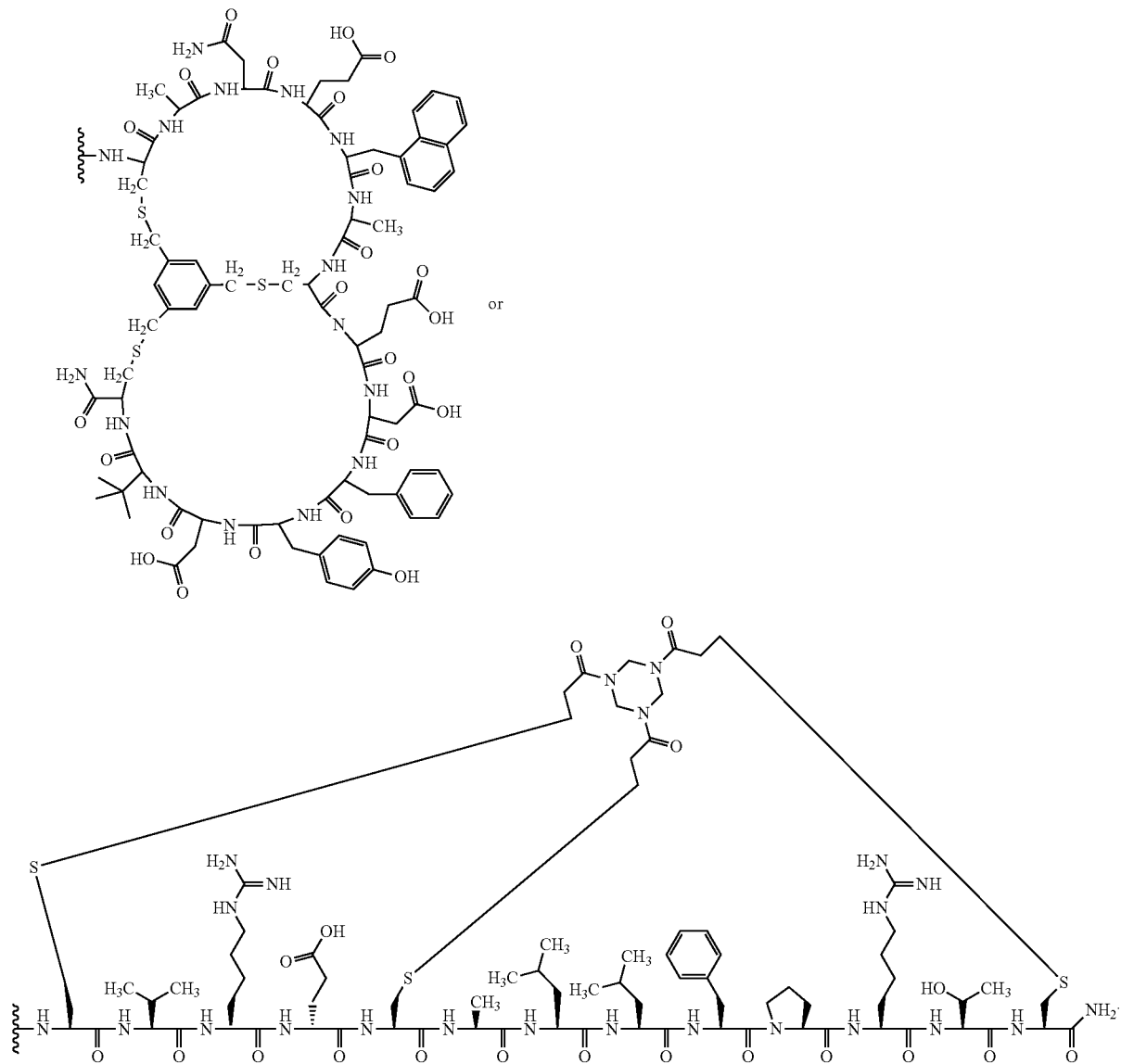
or
23. The method of claim 15, wherein the AA$^1$-AA$^2$ moiety is
-continued
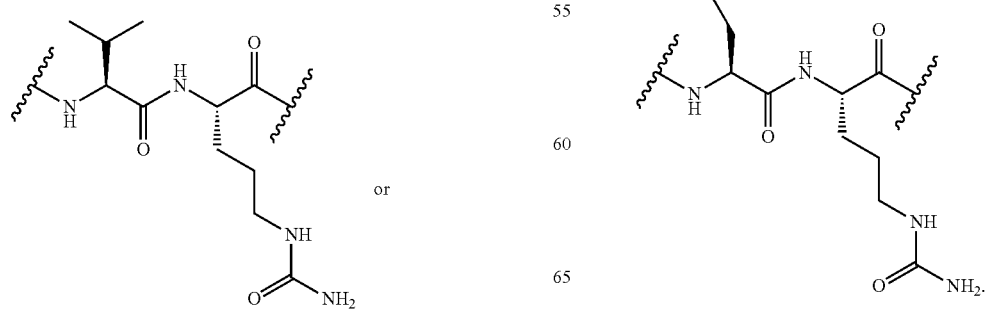

24. The method of claim 15, wherein the Linker moiety is

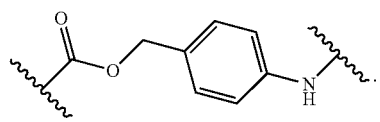 [SMILES: *Nc1ccc(COC(*)=O)cc1]

25. The method of claim 15, wherein the Toxin is selected from the group consisting of MMAE, MMAF, DM1, DM4, SN38, doxorubicin and a duocarmycin analog.

26. The method of claim 15, wherein the cancer is MT1-positive cancer.

27. The method of claim 15, wherein the cancer is selected from colorectal cancer, non-small cell lung cancer, breast cancer, gastric cancer, sarcoma, myeloma, nasalpharyngeal/laryngeal/oesophageal cancer, ovarian cancer, epithelial cancer, melanoma, glioma, astrocytoma, glioblastoma, neuroblastoma, mesothlioma, bladder cancer, hepatocellular carcinoma, and prostate cancer.

28. The method of claim 15, wherein said compound is selected from:

I-1a

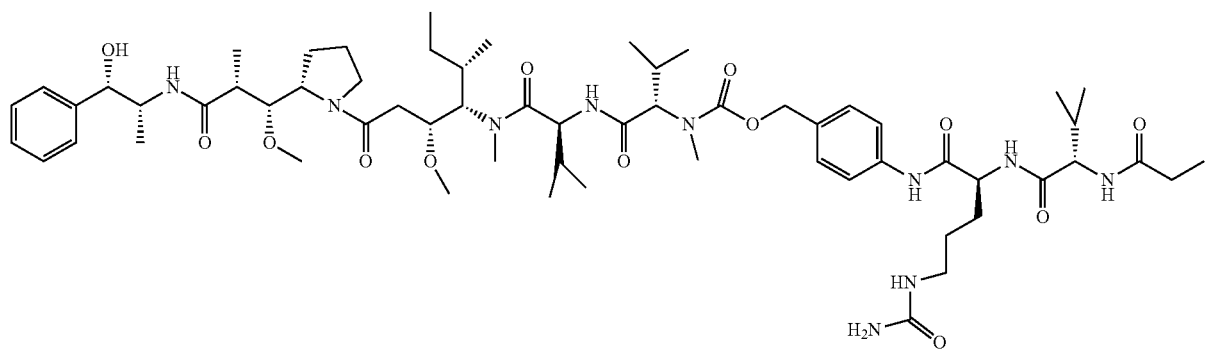

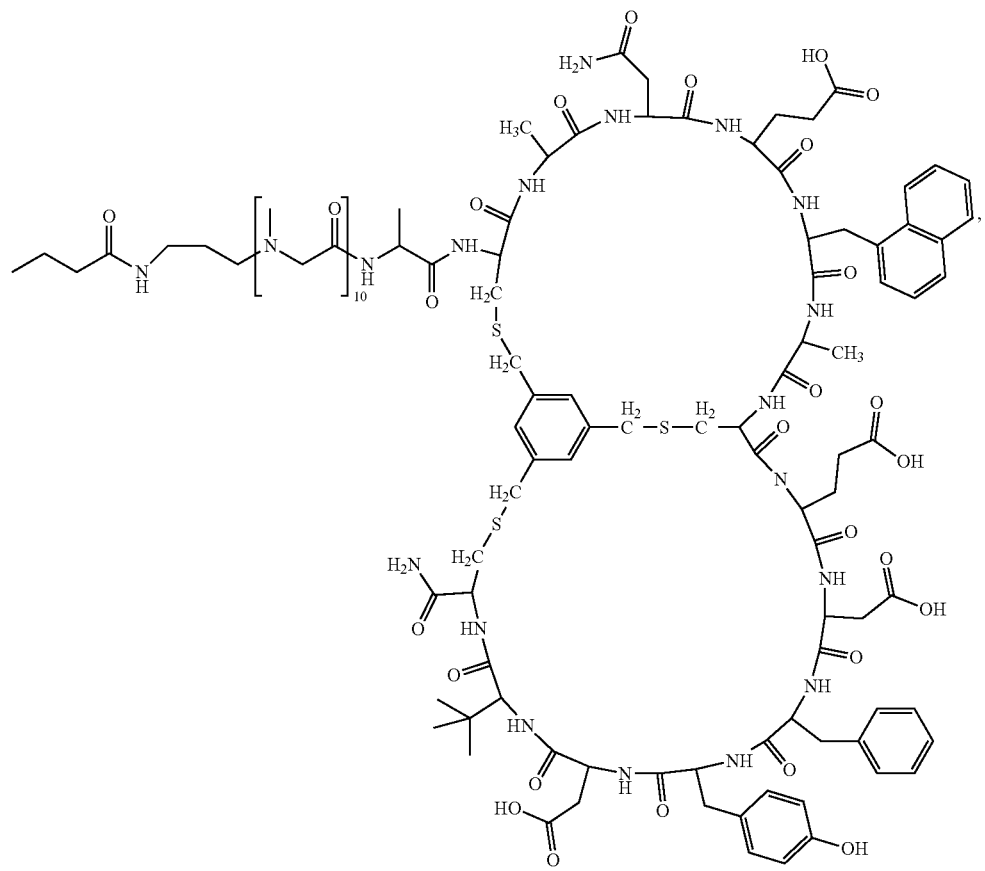

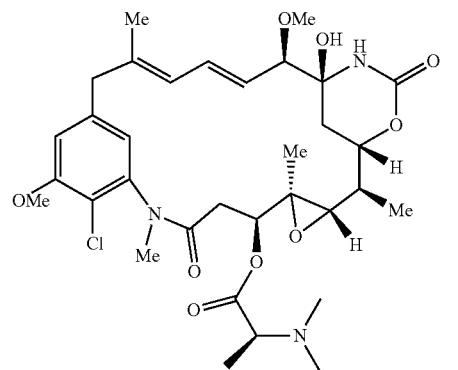
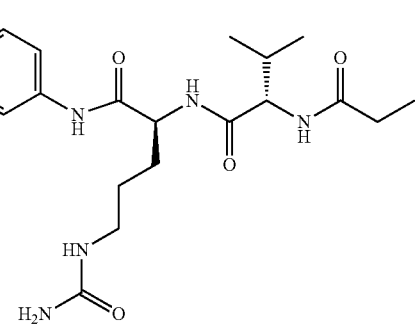
I-3a
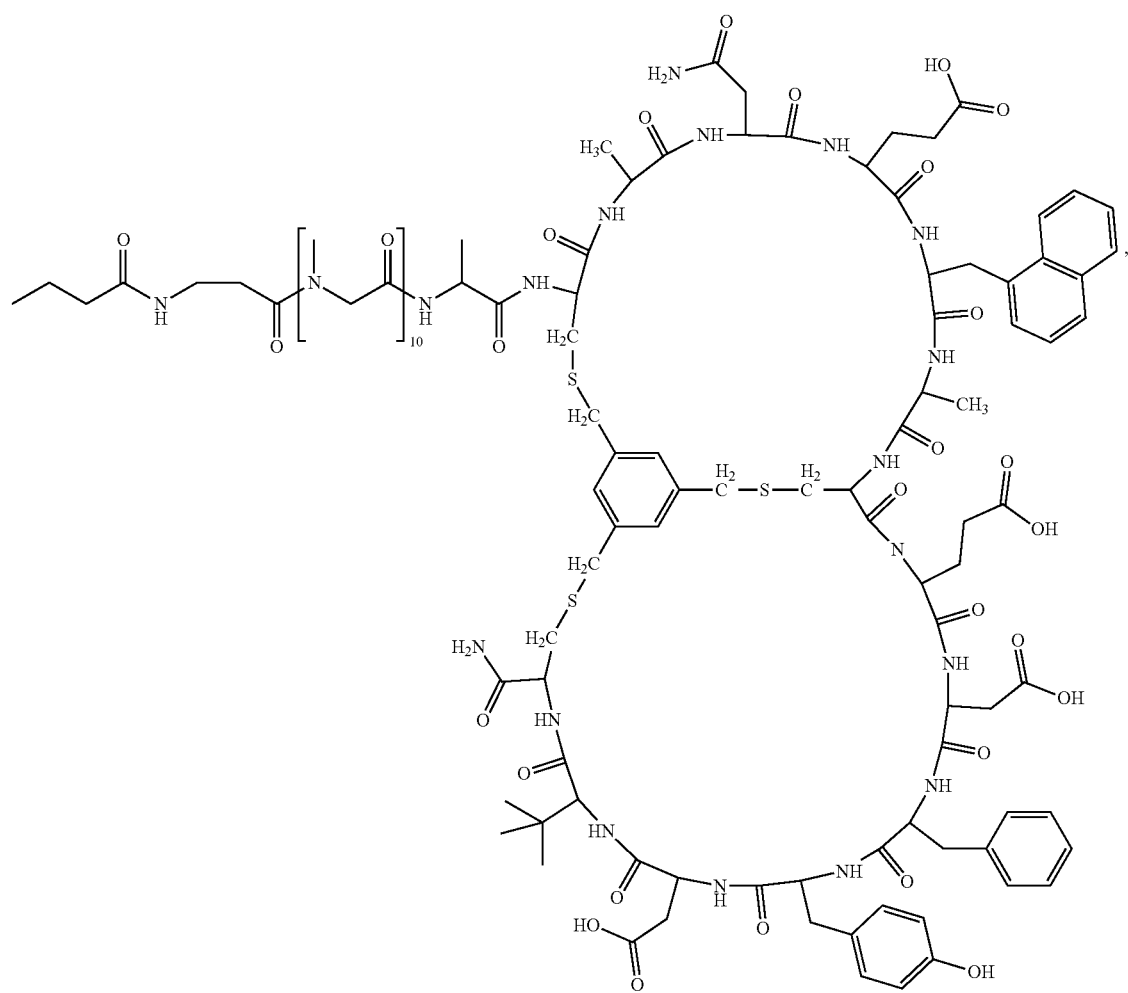

-continued
I-4a
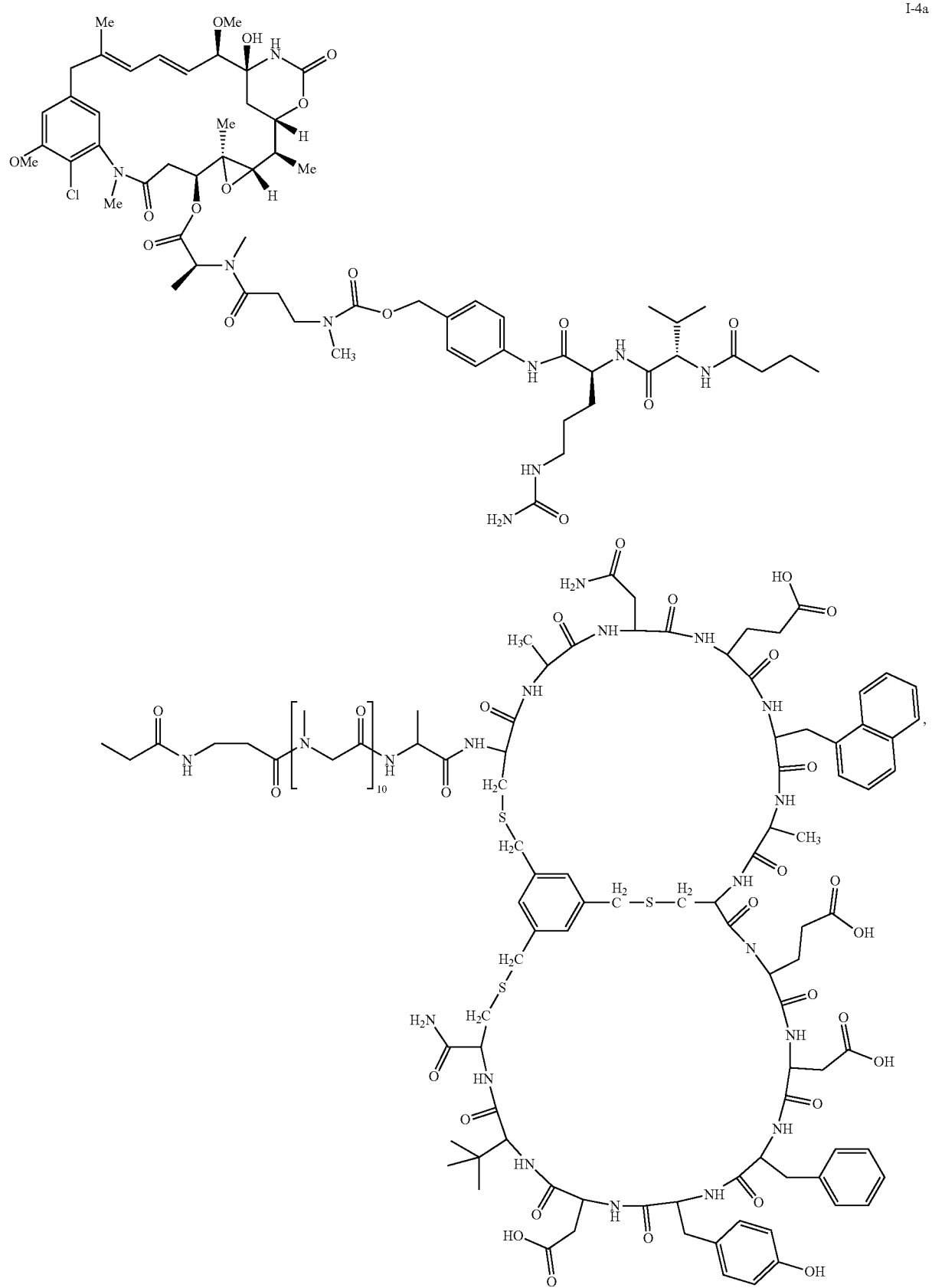

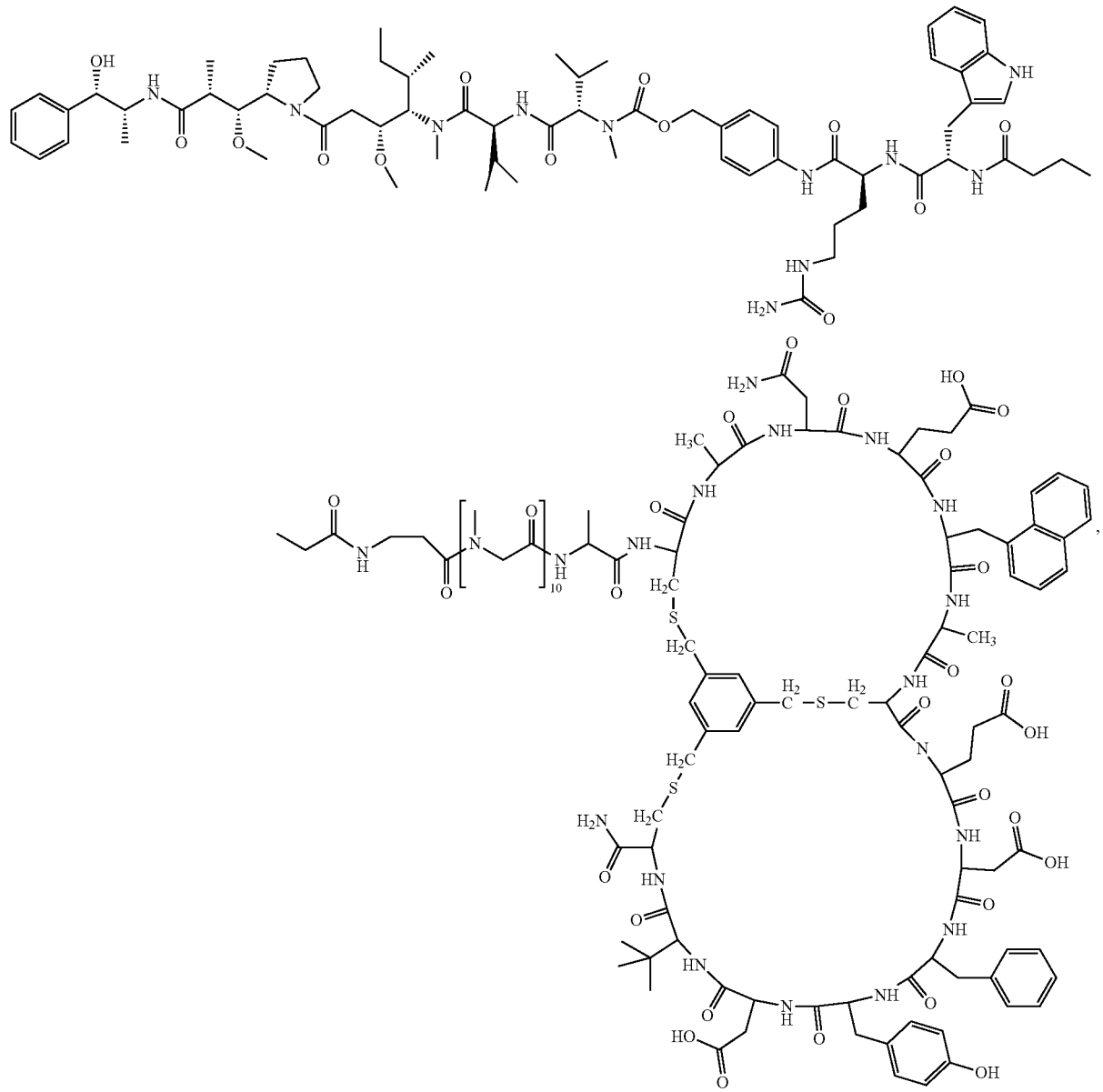
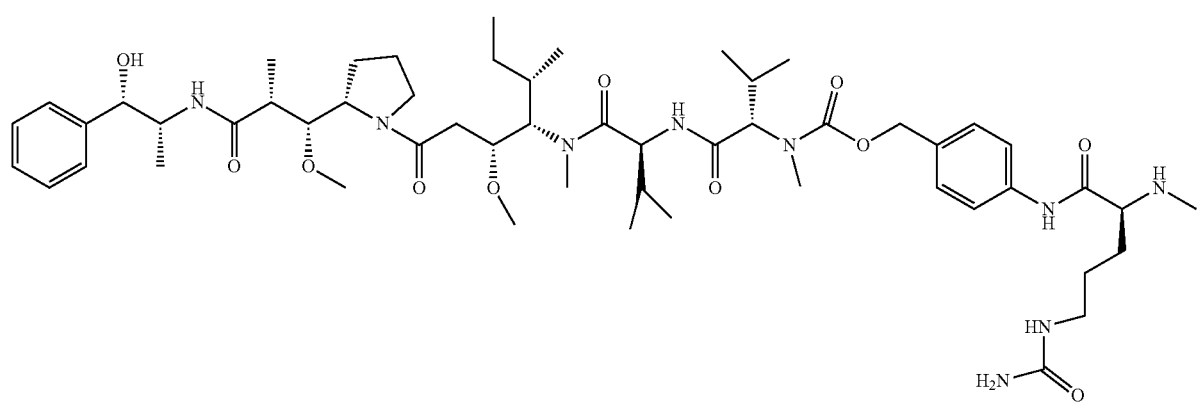

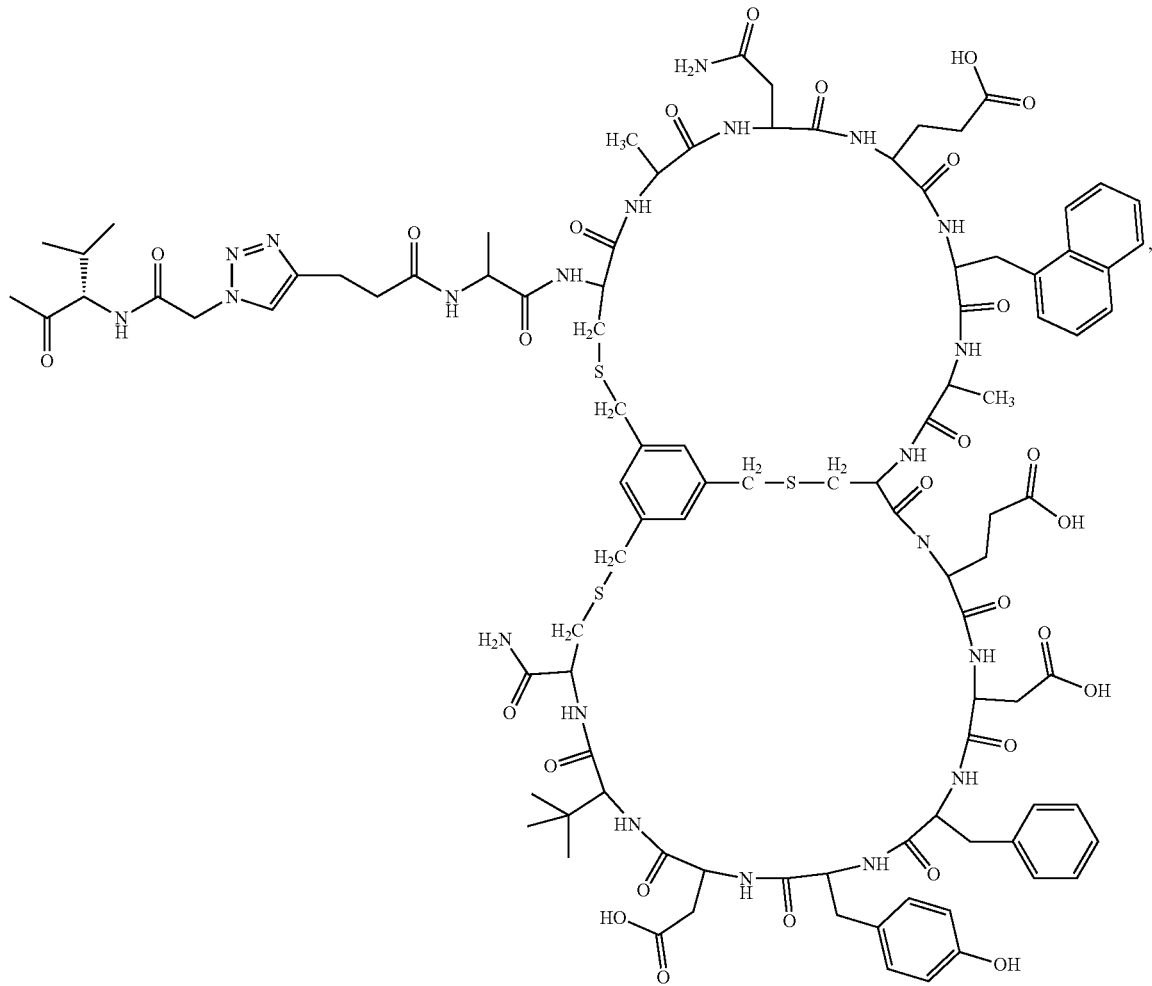
I-7
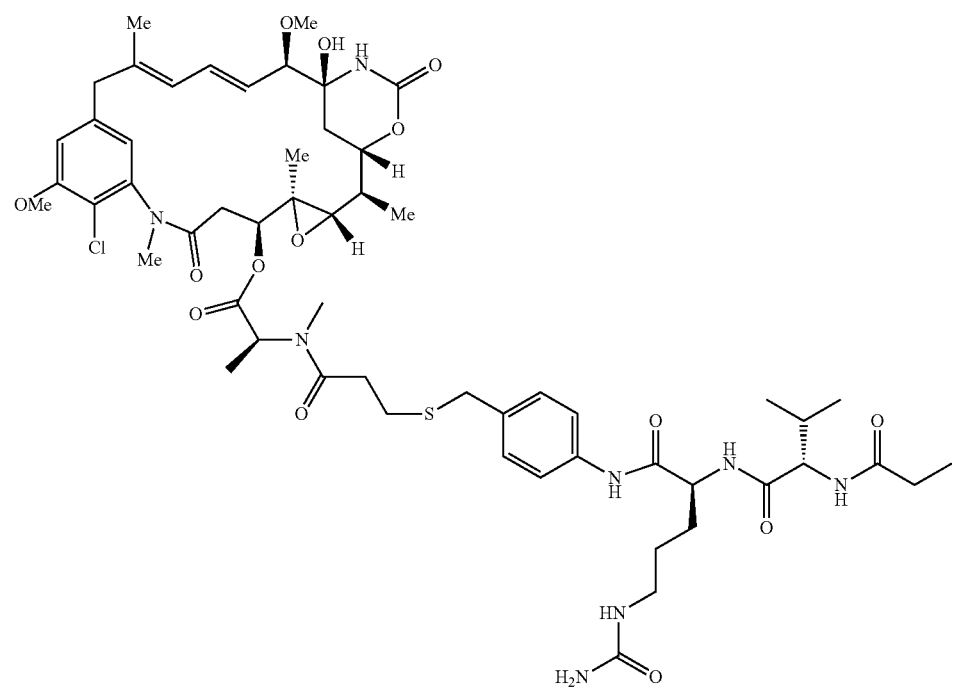

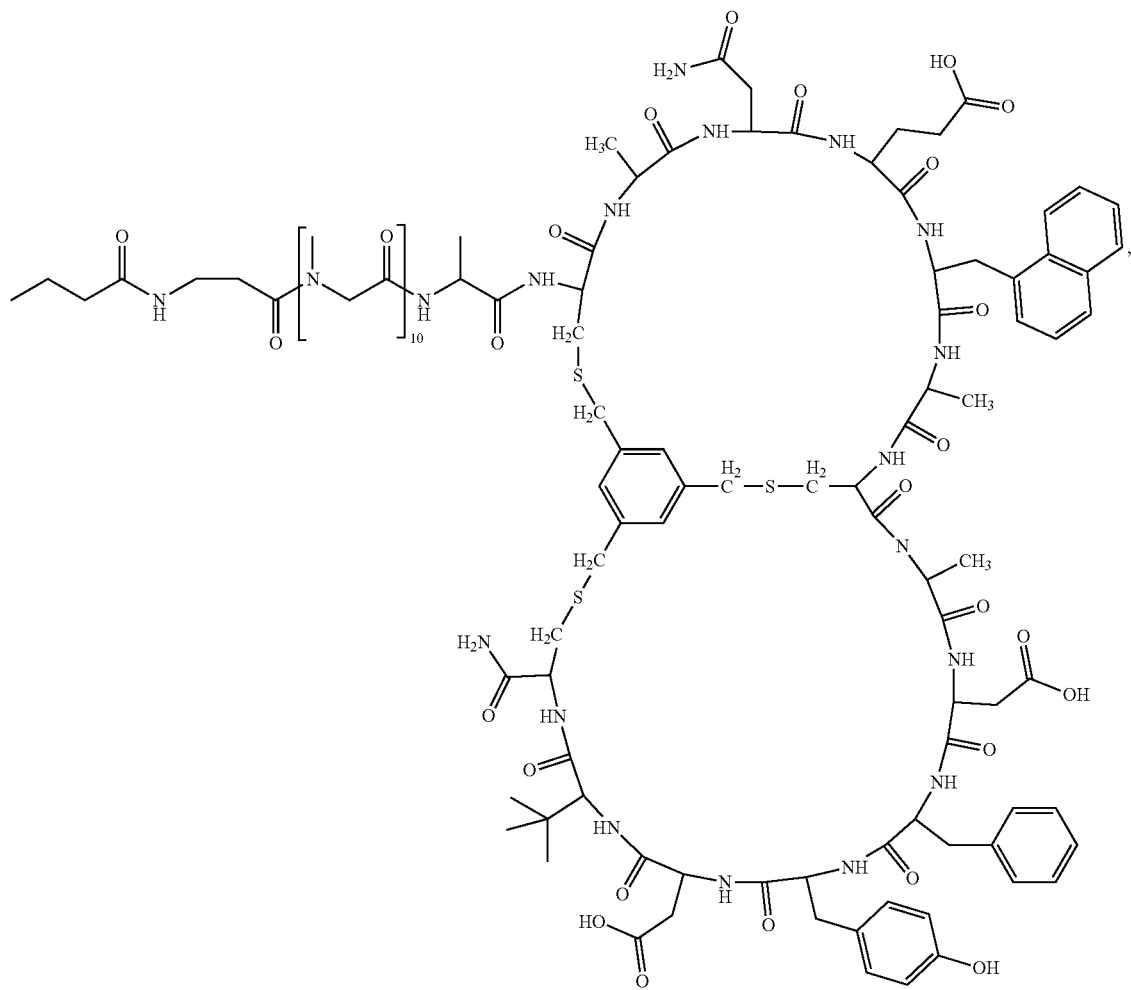
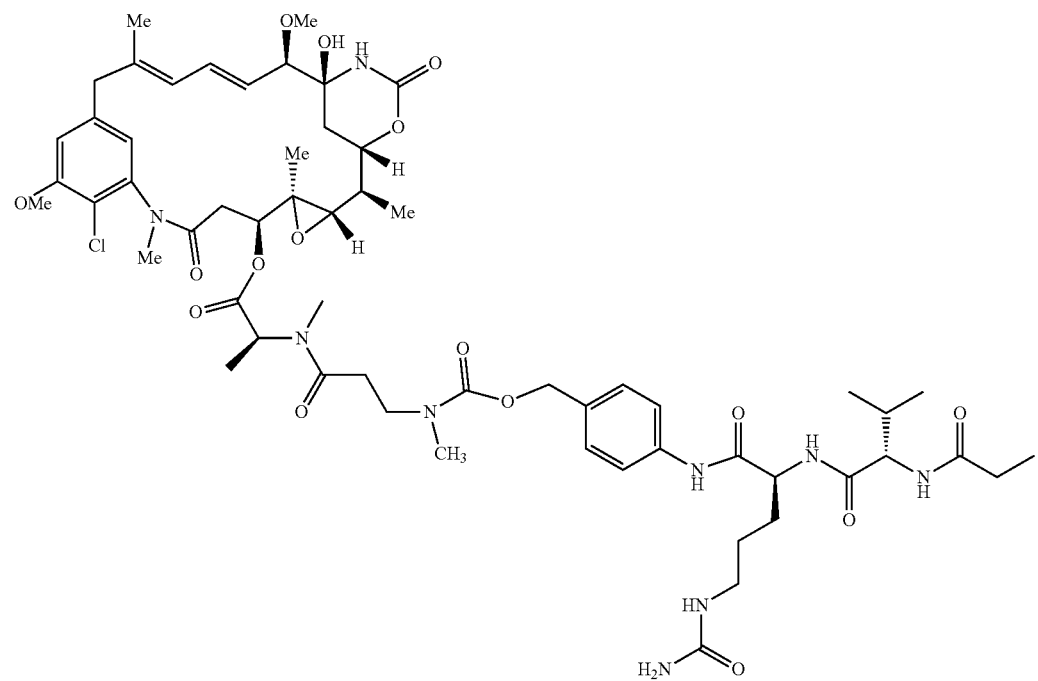
I-8

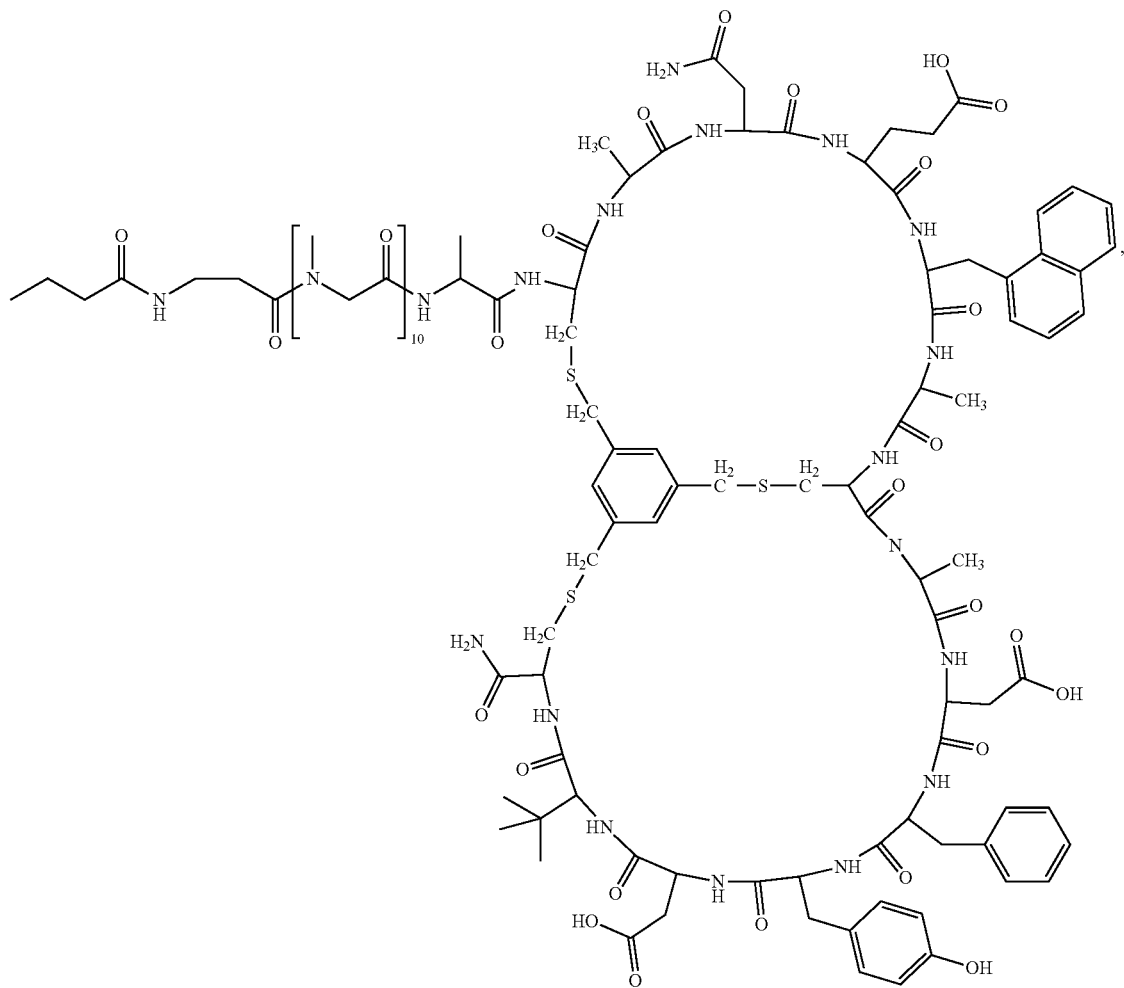
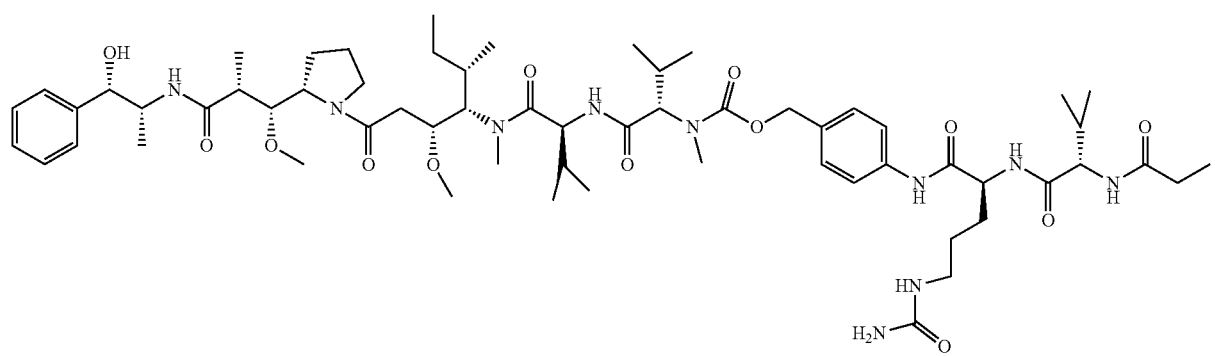
I-9

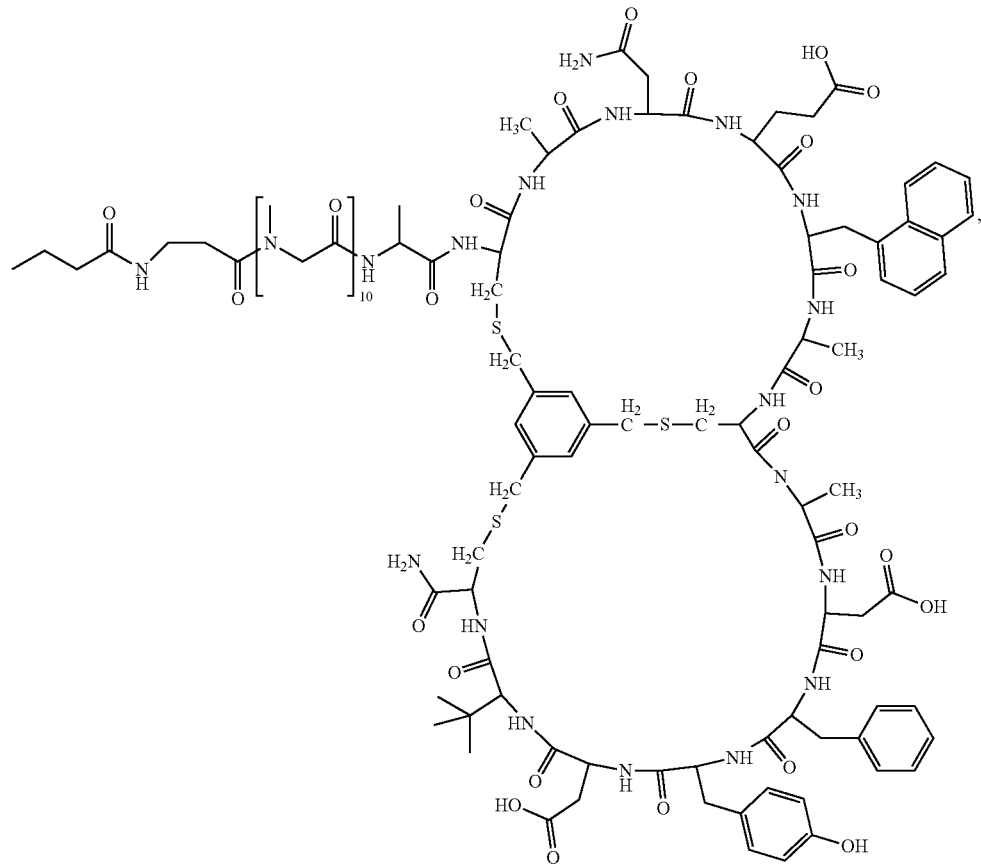
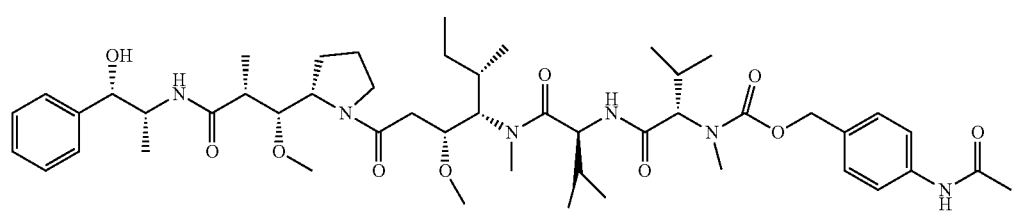
I-11

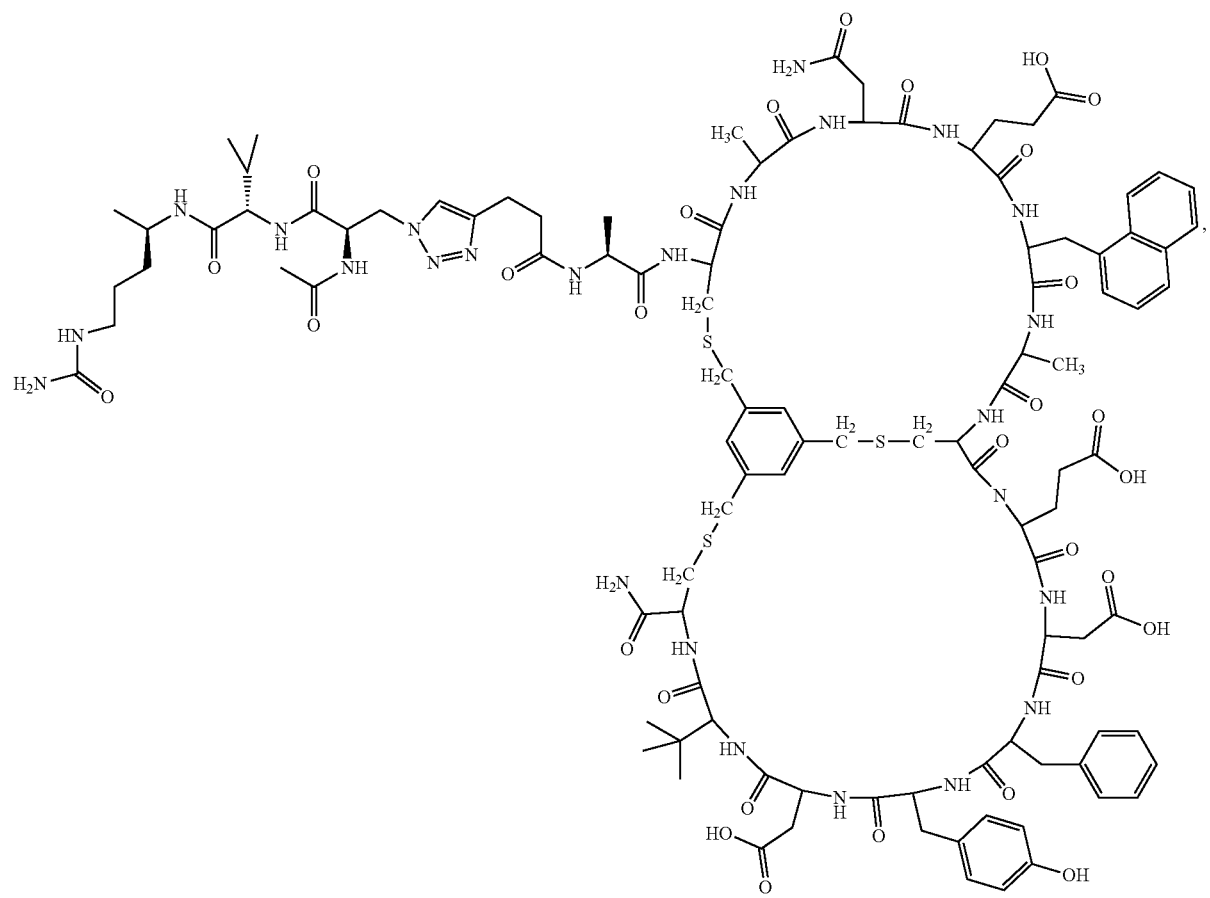
I-16
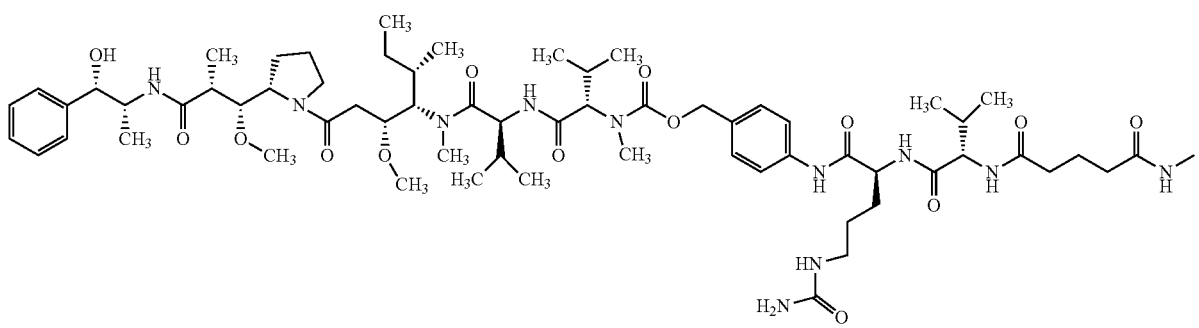
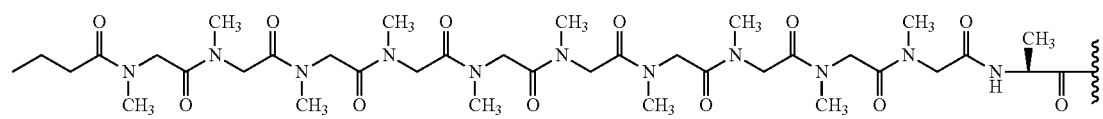
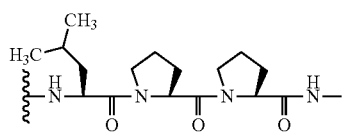

-continued
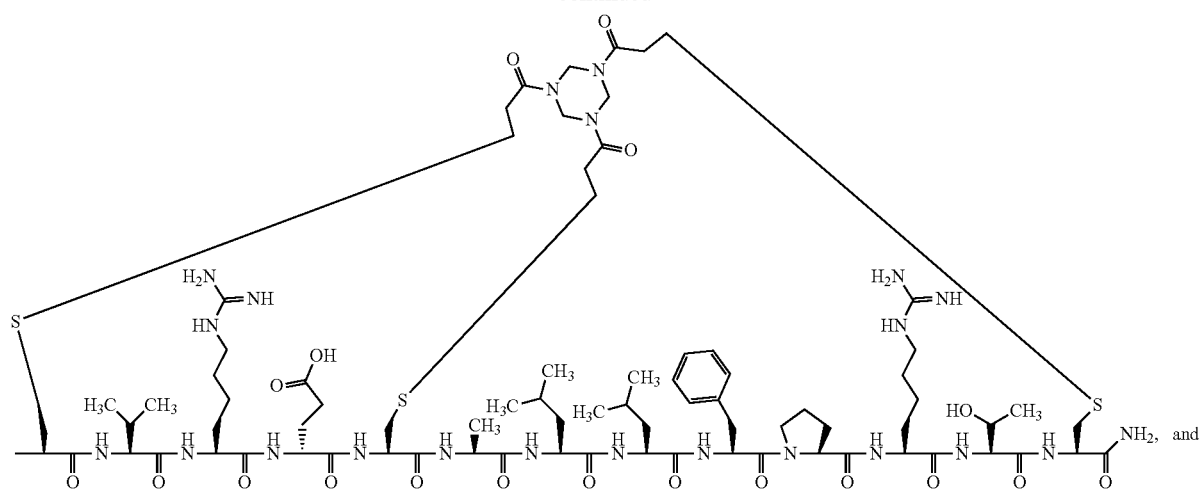
I-17
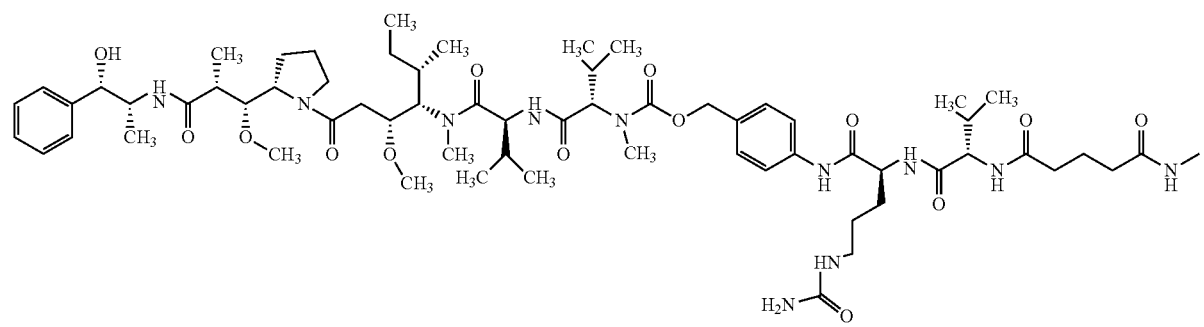
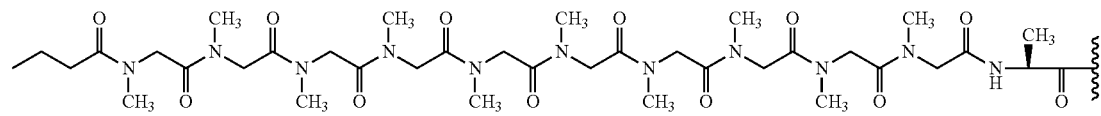
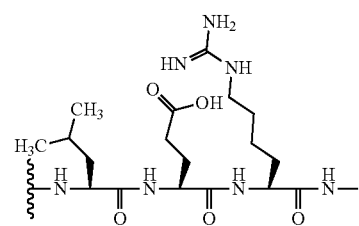

-continued
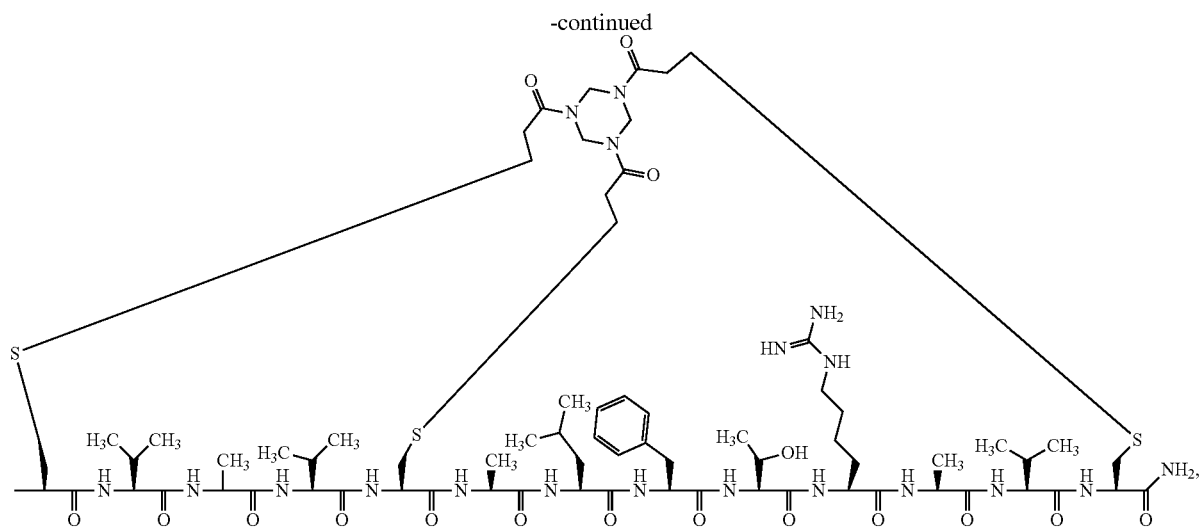
or a pharmaceutically acceptable salt thereof.
* * * * *